US012799529B2

(12) United States Patent
Drmanac et al.

(10) Patent No.: US 12,799,529 B2
(45) Date of Patent: Nov. 17, 2026

(54) MASSIVELY PARALLEL SEQUENCING USING UNLABELED NUCLEOTIDES

(71) Applicant: MGI Tech Co., Ltd., Shenzhen (CN)

(72) Inventors: Snezana Drmanac, Los Altos Hills, CA (US); Handong Li, San Jose, CA (US); Matthew J. Callow, Redwood City, CA (US); Leon Eckhardt, Soquel, CA (US); Scott Gablenz, Santa Clara, CA (US); Radoje Drmanac, Los Altos Hills, CA (US); Ping Zhou, Cupertino, CA (US)

(73) Assignee: MGI Tech Co., Ltd., Shenzhen (CN)

( * ) Notice: Subject to any disclaimer, the term of this patent is extended or adjusted under 35 U.S.C. 154(b) by 1135 days.

(21) Appl. No.: 17/291,962

(22) PCT Filed: Nov. 11, 2019

(86) PCT No.: PCT/US2019/060779
§ 371 (c)(1),
(2) Date: May 6, 2021

(87) PCT Pub. No.: WO2020/097607
PCT Pub. Date: May 14, 2020

(65) Prior Publication Data

US 2022/0162693 A1 May 26, 2022

Related U.S. Application Data

(60) Provisional application No. 62/914,915, filed on Oct. 14, 2019, provisional application No. 62/914,940, filed on Oct. 14, 2019, provisional application No. 62/914,877, filed on Oct. 14, 2019, provisional application No. 62/758,317, filed on Nov. 9, 2018.

(51) Int. Cl.
*C12Q 1/6874* (2018.01)
*C12Q 1/6876* (2018.01)

(52) U.S. Cl.
CPC ......... *C12Q 1/6874* (2013.01); *C12Q 1/6876* (2013.01)

(58) Field of Classification Search
None
See application file for complete search history.

(56) References Cited

U.S. PATENT DOCUMENTS

| | | | |
|---|---|---|---|
| 5,053,336 | A | 10/1991 | Vanderlaan et al. |
| 6,664,079 | B2 | 12/2003 | Ju et al. |
| 10,851,410 | B2 | 12/2020 | Drmanac et al. |
| 11,788,138 | B2 | 10/2023 | Drmanac et al. |
| 2003/0104460 | A1 | 6/2003 | Rabbani et al. |
| 2003/0124560 | A1 | 7/2003 | Makino et al. |
| 2004/0157230 | A1 | 8/2004 | Kallander et al. |
| 2005/0130270 | A1 | 6/2005 | Cupo et al. |
| 2011/0118142 | A1 | 5/2011 | Clarke et al. |
| 2014/0242579 | A1 | 8/2014 | Zhou et al. |
| 2018/0044727 | A1 | 2/2018 | Vijayan et al. |
| 2018/0223358 | A1 | 8/2018 | Drmanac et al. |

FOREIGN PATENT DOCUMENTS

| | | | |
|---|---|---|---|
| CN | 1297058 | A | 5/2001 |
| CN | 104448001 | A | 3/2015 |
| CN | 105001292 | A | 10/2015 |
| CN | 107922968 | A | 4/2018 |
| EP | 1101824 | A2 | 5/2001 |
| EP | 2159285 | | 3/2010 |
| WO | 2002103039 | A1 | 12/2002 |
| WO | 2003003014 | A1 | 1/2003 |
| WO | 03073088 | A2 | 9/2003 |
| WO | 2004070005 | | 8/2004 |
| WO | 2004074503 | | 9/2004 |
| WO | 2013044018 | A1 | 3/2013 |
| WO | 2014114665 | A1 | 7/2014 |
| WO | 2016065248 | A1 | 4/2016 |
| WO | 2016154215 | A1 | 9/2016 |
| WO | 2017185026 | A1 | 10/2017 |
| WO | 2018129214 | A1 | 7/2018 |
| WO | WO 2018/129214 | * | 7/2018 |

OTHER PUBLICATIONS

William Bains, Geoff C. Smith; "A novel method for nucleic acid sequence determination"; J. Theor. Biol (1988) 135, 303-307.*
Guo (Accounts of Chemical Research vol. 43 No. 4 Apr. 10 pp. 551-563).*
European Application No. 19881829.6, Extended European Search Report mailed on Sep. 7, 2022, 8 pages.
Chen et al., The History and Advances of Reversible Terminators Used in New Generations of Sequencing Technology, Genomics Proteomics Bioinformatics, vol. 11, No. 1, Feb. 1, 2013, pp. 34-40.
European Application No. 18736171.2, Communication of Notice of Opposition mailed on Mar. 2, 2023, enclosing Notice of Opposition filed Feb. 23, 2023, 48 pages.
Munns et al., Antibodies Specific for Modified Nucleosides: an Immunochemical Approach for the Isolation and Characterization of Nucleic Acids, Progress in Nucleic Acid Research and Molecular Biology, vol. 24, 1980, pp. 109-165.
European Application No. 18736171.2, Summons to Attend Oral Proceedings mailed on Apr. 11, 2024, 18 pages.
Feederle et al., "Antibodies Specific for Nucleic Acid Modifications", Ribonucleic Acid, vol. 14 No. 9, 2017, pp. 1089-1098.

(Continued)

*Primary Examiner* — Amanda Haney
(74) *Attorney, Agent, or Firm* — Kilpatrick Townsend & Stockton LLP

(57) ABSTRACT

The invention provides compositions and methods for sequencing nucleic acids and other applications. In sequencing by synthesis, unlabeled reversible terminators are incorporated by a polymerase in each cycle, then labeled after incorporation by binding to the reversible terminator a directly or indirectly labeled antibody or other affinity reagent.

8 Claims, 16 Drawing Sheets

Specification includes a Sequence Listing.

(56) References Cited

OTHER PUBLICATIONS

Gonchoroff et al., "A Monoclonal Antibody Reactive with 5-Bromo-2-Deoxyuridine that Does Not Require DNA Denaturation", Cytometry, vol. 6, No. 6, 1985, pp. 506-512.
Johnston et al., "Antibody-Nucleic Acid Interactions. Monoclonal Antibodies Define Different Antigenic Domains in 2', 5'-Oligoadenylates", Biochemistry, vol. 24, 1985, pp. 4710-4718.
Khan et al., "Antibodies Specific to a Deoxyribodinucleotide Sequence", Nucleic Acids Research, vol. 4, No. 9, 1977, pp. 2997-3006.
Munns et al., "Antibody Nucleic Acid Complexes. Lmmunospecific Retention of N6-Methyladenosinecontaining Transfer Ribonucleic Acid", Biochemistry, vol. 17, No. 13, 1978, pp. 2573-2578.
Munns et al., "Characterization of Antibodies Specific for N6-Methyladenosine and for 7-Methylguanosine", Biochemistry, vol. 16, No. 10, 1977, pp. 2163-2168.
Reynaud et al., "Monitoring of Urinary Excretion of Modified Nucleosides in Cancer Patients Using a Set of Six Monoclonal Antibodies", Cancer Letters, 1991, pp. 255-262.
Vold , "Preparation and Specificity of Antibodies Directed Tow a Rd the Ri Base Methylated Nucleotide, 2'-0-Methylguanosine 5'-Monophosphate", Biochimica et Biophysica Acta, vol. 655, 1981, pp. 265-267.
Földesi et al., The Fluoride Cleavable 2-(Cyanoethoxy) Methyl (CEM) Group as Reversible 3'-O-Terminator for DNA Sequencing-by-Synthesis-Synthesis, Incorporation, and Cleavage, Nucleosides, Nucleotides & Nucleic Acids, vol. 26, No. 3, 2007, pp. 271-275.
Guo et al., Four-Color DNA Sequencing With 3'-O-Modified Nucleotide Reversible Terminators and Chemically Cleavable Fluorescent Dideoxynucleotides, Proceedings of the National Academy of Sciences, vol. 105, No. 27, Jul. 8, 2008, pp. 9145-9150.
Hutter et al., Labeled Nucleoside Triphosphates with Reversibly Terminating Aminoalkoxyl Groups, Nucleosides, Nucleotides and Nucleic Acids, vol. 29, Nos. 11-12, Nov. 2010, pp. 879-895.
Knapp et al., Fluoride-Cleavable, Fluorescently Labelled Reversible Terminators: Synthesis and Use in Primer Extension, Chemistry—A European Journal, vol. 17, No. 10, Mar. 1, 2011, pp. 2903-2915.
International Application No. PCT/US2018/012425, International Search Report and Written Opinion mailed on Mar. 26, 2018, 15 pages.
International Application No. PCT/US2019/060779, International Search Report and Written Opinion mailed on Apr. 23, 2020, 20 pages.
European Application No. 22174722.3, Extended European Search Report mailed on Nov. 17, 2022, 7 pages.
Steemers et al., Whole-Genome Genotyping with the Single-Base Extension Assay, Nature Methods, vol. 3, No. 1, Jan. 2006, pp. 31-33.
U.S. Appl. No. 15/862,566, Non-Final Office Action mailed on Dec. 16, 2019, 6 pages.
U.S. Appl. No. 15/862,566, Notice of Allowance mailed on Jul. 29, 2020, 9 pages.
Australian Application No. 2018205472, First Examination Report mailed on Dec. 7, 2021, 3 pages.
European Application No. EP18736171.2, Extended European Search Report mailed on Oct. 6, 2020, 5 pages.
European Application No. EP18736171.2, Notice of Decision to Grant mailed on Apr. 29, 2022, 2 pages.
European Application No. EP18736171.2, Office Action mailed on May 31, 2021, 3 pages.
Japanese Application No. JP2019-536551, Office Action mailed on Jul. 13, 2021, 4 pages (1 page of English translation and 3 pages of Official Copy).
Japanese Application No. JP2019-536551, Office Action mailed on Feb. 9, 2021, 8 pages (5 pages of English translation and 3 pages of Official Copy).
Korean Application No. KR10-2019-7022620, Notice of Decision to Grant mailed on Oct. 25, 2021, 4 pages (1 page of English translation and 3 pages of Official Copy).
International Application No. PCT/US2018/012425, International Preliminary Report on Patentability mailed on Jul. 18, 2019, 12 pages.
International Application No. PCT/US2019/060779, International Preliminary Report on Patentability mailed on May 20, 2021, 15 pages.
International Application No. PCT/US2019/060779, Invitation to Pay Additional Fees and, Where Applicable, Protest Fee mailed on Feb. 10, 2020, 3 pages.
European Application No. 25160087.0, Extended European Search Report mailed on Jun. 10, 2025, 6 pages.

* cited by examiner

FIGURE 1A

N3A light chain

```
BGI_N3A_2C5_L     MDTRAPTQLLGLLLLWLPGATFAQVLTQTPSSVSAAVGGTVTINCQSSPSVYSNYLSWFQ   60
BGI_N3A_3B12_L    MDTRAPTQLLGLLLLWLPGATFAQVLTQTPSPVSAAVGGTVTINCQSSPSVYSNYLSWFQ   60
BGI_N3A_17H7_L    MDTRAPTQLLGLLLLWLPGATFAIKMTQPPASVSAAVGGTVTINCRASEDI-DSYLAWYQ   59
BGI_N3A_18B7_L    MDTRAPTQLLGLLLLWLPGATFAIKMTQTPGSVEVAVGGTVTINCQASQSI-STALAWYQ   59
                  ***********************  :** *. *..**********::* .:  .. *:*:*

BGI_N3A_2C5_L     QKPGQPPKLLIYSASTLASGVPSRFRGSGSGTQFTLTISDVQCDDAANYYCAGGYTYTSD   120
BGI_N3A_3B12_L    QKPGQPPKLLIYSASTLASGVPSRFRGSGSGTQFTLTISDVQCDDAANYYCAGGYTYTSD   120
BGI_N3A_17H7_L    QKPGQPPQLLIYRASTLASGVPSRFSGSGSGTQFTLTISGVQCDDAATYYCQSTYY-SSN   118
BGI_N3A_18B7_L    QKPGQRPKLLIYDASRLASGVPSRFSGSGSGTEFTLTISGVECADAATYYCHQGFG-ASN   118
                  ***** *:**** ** ********* ******:******.*:* ***.***    :  :*:

BGI_N3A_2C5_L     SIWAFGGGTEVVVKGDPVAPTVLIFPPAADQVATGTVTIVCVANKYFPDVTVTWEVDGTT   180
BGI_N3A_3B12_L    SIWAFGGGTEVVVKGDPVAPTVLIFPPAADQVATGTVTIVCVANKYFPDVTVTWEVDGTT   180
BGI_N3A_17H7_L    PEGVFGGGTEVVVKGDPVAPTVLIFPPAADQVATGTVTIVCVANKYFPDVTVTWEVDGTT   178
BGI_N3A_18B7_L    VDNPFGGGTEVVVEGDPVAPTVLIFPPAADQVATGTVTIVCVANKYFPDVTVTWEVDGTT   178
                      *********:**********************************************

BGI_N3A_2C5_L     QTTGIENSKTPQNSADCTYNLSSTLTLTSTQYNSHKEYTCKVTQGTTSVVQSFNRGDC*    238
BGI_N3A_3B12_L    QTTGIENSKTPQNSADCTYNLSSTLTLTSTQYNSHKEYTCKVTQGTTSVVQSFNRGDC*    238
BGI_N3A_17H7_L    QTTGIENSKTPQNSADCTYNLSSTLTLTSTQYNSHKEYTCKVTQGTTSVVQSFNRGDC*    236
BGI_N3A_18B7_L    QTTGIENSKTPQNSADCTYNLSSTLTLTSTQYNSHKEYTCKVTQGTTSVVQSFNRGDC*    236
                  ***********************************************************
```

FIGURE 1B

N3A heavy chain

```
BGI_N3A_2C5_H     METGLRWLLLVAVLKGVQCQEQLEESGGDLVKPEGSLTLTCKASGFDFSSYYYMCWVRQA   60
BGI_N3A_3B12_H    METGLRWLLLVAVLKGVQCQEQLEEAGGDLVKPEGSLRLTCKASGFDFSSYYYMCWVRQA   60
BGI_N3A_17H7_H    METGLRWLLLVAVLKGVQCQQQMEESGGGLVQPEGSLTLTCKASGIDFSSYYYMCWVRQA   60
BGI_N3A_18B7_H    METGLRWLLLVAVLKGVQCQEQLVESGGGLVKPEGSLTLTCTASGFSFSSYYYMCWVRQA   60
                  ********************:*: *:**.**:***** ***.***:.*************

BGI_N3A_2C5_H     PGKGLEWIACIYGGSSGTTYYASWPKGRFTISKTS-STTVTLQMTSLTAADTATYFCMRG   119
BGI_N3A_3B12_H    PGKGLEWIACIYGGASGTTYYASWAKGRFTISKTS-STTVTLQMTSLTAADTATYFCMRG   119
BGI_N3A_17H7_H    PGKGLELIACIYLS-SGSTWYASWVNGRFTISRSTSLNTVTLQMTSLTAADTATYFCARG   119
BGI_N3A_18B7_H    PGKGLELSACIDTG-SGSTWYPSWVNGRFTISRSTSLNTVDLKMTSLTAADTATYFCARE   119
                  ******  ***  . **:*:* ** :******:::  .** *:************** *

BGI_N3A_2C5_H     ANGAGFGD----ANLWGPGTLVTVSSGQPKAPSVFPLAPCCGDTPSSTVTLGCLVKGYLP   175
BGI_N3A_3B12_H    ANGAGFGD----ANLWGPGTLVTVSSGQPKAPSVFPLAPCCGDTPSSTVTLGCLVKGYLP   175
BGI_N3A_17H7_H    GFCTAYSGDGCYFTLWGPGTLVTVSSGQPKAPSVFPLAPCCGDTPSSTVTLGCLVKGYLP   179
BGI_N3A_18B7_H    Y------STAWYFNLWGPGTLVTVSSGQPKAPSVFPLAPCCGDTPSSTVTLGCLVKGYLP   173
                         .     .**********************************************

BGI_N3A_2C5_H     EPVTVTWNSGTLTNGVRTFPSVRQSSGLYSLSSVVSVTSSSQPVTCNVAHPATNTKVDKT   235
BGI_N3A_3B12_H    EPVTVTWNSGTLTNGVRTFPSVRQSSGLYSLSSVVSVTSSSQPVTCNVAHPATNTKVDKT   235
BGI_N3A_17H7_H    EPVTVTWNSGTLTNGVRTFPSVRQSSGLYSLSSVVSVTSSSQPVTCNVAHPATNTKVDKT   239
BGI_N3A_18B7_H    EPVTVTWNSGTLTNGVRTFPSVRQSSGLYSLSSVVSVTSSSQPVTCNVAHPATNTKVDKT   233
                  ************************************************************

BGI_N3A_2C5_H     VAPSTCSKPMCPPPELPGGPSVFIFPPKPKDTLMISRTPEVTCVVVDVSQDDPEVQFTWY   295
BGI_N3A_3B12_H    VAPSTCSKPMCPPPELPGGPSVFIFPPKPKDTLMISRTPEVTCVVVDVSQDDPEVQFTWY   295
BGI_N3A_17H7_H    VAPSTCSKPMCPPPELPGGPSVFIFPPKPKDTLMISRTPEVTCVVVDVSQDDPEVQFTWY   299
BGI_N3A_18B7_H    VAPSTCSKPMCPPPELPGGPSVFIFPPKPKDTLMISRTPEVTCVVVDVSQDDPEVQFTWY   293
                  ************************************************************

BGI_N3A_2C5_H     INNEQVRTARPPLREQQFNSTIRVVSTLPIAHQDWLRGKEFKCKVHNKALPAPIEKTISK   355
BGI_N3A_3B12_H    INNEQVRTARPPLREQQFNSTIRVVSTLPIAHQDWLRGKEFKCKVHNKALPAPIEKTISK   355
BGI_N3A_17H7_H    INNEQVRTARPPLREQQFNSTIRVVSTLPIAHQDWLRGKEFKCKVHNKALPAPIEKTISK   359
BGI_N3A_18B7_H    INNEQVRTARPPLREQQFNSTIRVVSTLPIAHQDWLRGKEFKCKVHNKALPAPIEKTISK   353
                  ************************************************************

BGI_N3A_2C5_H     ARGQPLEPKVYTMGPPREELSSRSVSLTCMINGFYPSDISVEWEKNGKAEDNYKTTPTVL   415
BGI_N3A_3B12_H    ARGQPLEPKVYTMGPPREELSSRSVSLTCMINGFYPSDISVEWEKNGKAEDNYKTTPTVL   415
BGI_N3A_17H7_H    ARGQPLEPKVYTMGPPREELSSRSVSLTCMINGFYPSDISVEWEKNGKAEDNYKTTPTVL   419
BGI_N3A_18B7_H    ARGQPLEPKVYTMGPPREELSSRSVSLTCMINGFYPSDISVEWEKNGKAEDNYKTTPTVL   413
                  ************************************************************

BGI_N3A_2C5_H     DSDGSYFLYSKLSVPTSEWQRGDVFTCSVMHEALHNHYTQKSISRSPGK*   464
BGI_N3A_3B12_H    DSDGSYFLYSKLSVPTSEWQRGDVFTCSVMHEALHNHYTQKSISRSPGK*   464
BGI_N3A_17H7_H    DSDGSYFLYSKLSVPTSEWQRGDVFTCSVMHEALHNHYTQKSISRSPGK*   468
BGI_N3A_18B7_H    DSDGSYFLYSKLSVPTSEWQRGDVFTCSVMHEALHNHYTQKSISRSPGK*   462
                  **************************************************
```

FIGURE 1C

N3C light chain

```
BGI_N3C_1B8_L      MDTRAPTQLLGLLLLWLPGARCALVMTQTPASVEAAVGGTVTIKCQASQSI--SSYLNWY    58
BGI_N3C_2B9_L      MDTRAPTQLLGLLLLWLPGATFAQVLTQTPSPVSAAVGGTVTINCQASQSVFRNNYLAWY    60
BGI_N3C_4C8_L      MDTRAPTQLLGLLLLWLPGATFAQVLTQTPSPVSAAVGSTVTINCQASQSVYKNNYLAWY    60
BGI_N3C_1A10_L     MDTRAPTQLLGLLLLWLPGAICDPVMTQTPSSTSAAVGGTVTISCQSSQSVYNNNYLAWY    60
BGI_N3C_3B7_L      MDTRAPTQLLGLLLLWLPGATFAQVLTQTPSSVSAAVGGTVTISCQSSQSVYNNNYLAWY    60
                   ********************    *:****: ..****.****.**:***:   ..** **

BGI_N3C_1B8_L      QQKSGQPPKNLIYRASTLASGVSSRFKGSGSGTEFTLTINDLECADAATYYCQSYGGYSI    118
BGI_N3C_2B9_L      QQKPGQPPTQLIYLASTLASGVPSRFSGSGSGTQFTLTISDVQCDDAATYYCAGA---TS    117
BGI_N3C_4C8_L      QQKPGQPPKQLIYDASTLASGVPTRFKGSGSGTQFTLTISDVQCDDAATYYCAGA---YS    117
BGI_N3C_1A10_L     QQKPGQPPKRLIYESSKLASGVPSRFRGSGSGAQFTLTISDLECDDAATYYCLGA---YY    117
BGI_N3C_3B7_L      QQKPGQPPKRLIYEASKLASGVPSRFRGSGSGTHFTLTISGVQCDDAATYYCLGA---YF    117
                   *** ****..*** :*.***** :** *****:.*****..::* *******  .

BGI_N3C_1B8_L      YGLVFGGGTEVVVKGDPVAPTVLIFPPAADQVATGTVTIVCVANKYFPDVTVTWEVDGTT    178
BGI_N3C_2B9_L      SIIIFGGGTEVVVKGDPVAPTVLIFPPAADQVATGTVTIVCVANKYFPDVTVTWEVDGTT    177
BGI_N3C_4C8_L      TVVVFGGGTEVVVKGDPVAPTVLIFPPAADQVATGTVTIVCVANKYFPDVTVTWEVDGTT    177
BGI_N3C_1A10_L     TTLDFGGGTEVVVRGDPVAPTVLIFPPAADQVATGTVTIVCVANKYFPDVTVTWEVDGTT    177
BGI_N3C_3B7_L      TTIVFGGGTEVVVRGDPVAPTVLIFPPAADQVATGTVTIVCVANKYFPDVTVTWEVDGTT    177
                     :  *********:**********************************************

BGI_N3C_1B8_L      QTTGIENSKTPQNSADCTYNLSSTLTLTSTQYNSHKEYTCKVTQGTTSVVQSFNRGDC*    236
BGI_N3C_2B9_L      QTTGIENSKTPQNSADCTYNLSSTLTLTSTQYNSHKEYTCKVTQGTTSVVQSFNRGDC*    235
BGI_N3C_4C8_L      QTTGIENSKTPQNSADCTYNLSSTLTLTSTQYNSHKEYTCKVTQGTTSVVQSFNRGDC*    235
BGI_N3C_1A10_L     QTTGIENSKTPQNSADCTYNLSSTLTLTSTQYNSHKEYTCKVTQGTTSVVQSFNRGDC*    235
BGI_N3C_3B7_L      QTTGIENSKTPQNSADCTYNLSSTLTLTSTQYNSHKEYTCKVTQGTTSVVQSFNRGDC*    235
                   ***********************************************************
```

FIGURE 1D

N3C heavy chain

```
BGI_N3C_1B8_H       METGLRWLLLVAVLKGVQCQS-LEESGGDLVKPGASLTLTCKASGIDFSSSYWICWVRQA     59
BGI_N3C_1A10_H      METGLRWLLLVAVLKGVQCQEQLEESGGGLVQPEGSLTLTCTASGFSFSDNAWICWVRQA     60
BGI_N3C_3B7_H       METGLRWLLLVAVLKGVQCQEQLVESGGGLVQPEGSLTLTCTASGFSFSANHWICWVRQA     60
BGI_N3C_2B9_H       METGLRWLLLVAVLKGVQCQEQLEESGGGLVKPEESLTLTCTASGFSFISSDWICWVRQA     60
BGI_N3C_4C8_H       METGLRWLLLVAVLKGVQCQEQLVESGGGLVQPEGSLTLTCKASGFSFSSSYWICWVRQA     60
                    ********************. * ****.**:*  ******.***:.*  .  ********

BGI_N3C_1B8_H       PGKGLEWIACIDTGSSGSTYYASWAKGRFTISKPSSTTVSLQMTSLQAADTATYFCARKG     119
BGI_N3C_1A10_H      PGKGLEWIGCIYIGSS-STYYASWAKGRFTISRTSSTTVNLQMTSLTDADTATYFCGRDP     119
BGI_N3C_3B7_H       PGKGLEWVGCIYIGSG-NTYYASWAKGRFTISKTSSTTVTLQMTSLTDADTAMYFCGRDF     119
BGI_N3C_2B9_H       PGKGLEWIACIYIGGH-TPYYASWARGRFTISKTSSTAVTLQMSSLTAADTATYFCARGI     119
BGI_N3C_4C8_H       PGKGFEWIACIYIGAG-STYYANWAKGRFTISKTSSTTVTLQMTSLTAADTATYFCSRGI     119
                    **** **:.**  *.  . ***.**:******: ***:*.***:**  **** ***.*

BGI_N3C_1B8_H       ---DGTDLWGPGTLVTVSSGQPKAPSVFPLAPCCGDTPSSTVTLGCLVKGYLPEPVTVTW     176
BGI_N3C_1A10_H      TAAWGGGLWGPGTLVTVSSGQPKAPSVFPLAPCCGDTPSSTVTLGCLVKGYLPEPVTVTW     179
BGI_N3C_3B7_H       TAGWGGGLWGPGTLVTVSSGQPKAPSVFPLAPCCGDTPSSTVTLGCLVKGYLPEPVTVTW     179
BGI_N3C_2B9_H       ---AGPALWGPGTLVTVSSGQPKAPSVFPLAPCCGDTPSSTVTLGCLVKGYLPEPVTVTW     176
BGI_N3C_4C8_H       ---AGVALWGPGTLVTVSSGQPKAPSVFPLAPCCGDTPSSTVTLGCLVKGYLPEPVTVTW     176
                        *  *****************************************************

BGI_N3C_1B8_H       NSGTLTNGVRTFPSVRQSSGLYSLSSVVSVTSSSQPVTCNVAHPATNTKVDKTVAPSTCS     236
BGI_N3C_1A10_H      NSGTLTNGVRTFPSVRQSSGLYSLSSVVSVTSSSQPVTCNVAHPATNTKVDKTVAPSTCS     239
BGI_N3C_3B7_H       NSGTLTNGVRTFPSVRQSSGLYSLSSVVSVTSSSQPVTCNVAHPATNTKVDKTVAPSTCS     239
BGI_N3C_2B9_H       NSGTLTNGVRTFPSVRQSSGLYSLSSVVSVTSSSQPVTCNVAHPATNTKVDKTVAPSTCS     236
BGI_N3C_4C8_H       NSGTLTNGVRTFPSVRQSSGLYSLSSVVSVTSSSQPVTCNVAHPATNTKVDKTVAPSTCS     236
                    ************************************************************

BGI_N3C_1B8_H       KPMCPPPELPGGPSVFIFPPKPKDTLMISRTPEVTCVVVDVSQDDPEVQFTWYINNEQVR     296
BGI_N3C_1A10_H      KPMCPPPELPGGPSVFIFPPKPKDTLMISRTPEVTCVVVDVSQDDPEVQFTWYINNEQVR     299
BGI_N3C_3B7_H       KPMCPPPELPGGPSVFIFPPKPKDTLMISRTPEVTCVVVDVSQDDPEVQFTWYINNEQVR     299
BGI_N3C_2B9_H       KPMCPPPELPGGPSVFIFPPKPKDTLMISRTPEVTCVVVDVSQDDPEVQFTWYINNEQVR     296
BGI_N3C_4C8_H       KPMCPPPELPGGPSVFIFPPKPKDTLMISRTPEVTCVVVDVSQDDPEVQFTWYINNEQVR     296
                    ************************************************************

BGI_N3C_1B8_H       TARPPLREQQFNSTIRVVSTLPIAHQDWLRGKEFKCKVHNKALPAPIEKTISKARGQPLE     356
BGI_N3C_1A10_H      TARPPLREQQFNSTIRVVSTLPIAHQDWLRGKEFKCKVHNKALPAPIEKTISKARGQPLE     359
BGI_N3C_3B7_H       TARPPLREQQFNSTIRVVSTLPIAHQDWLRGKEFKCKVHNKALPAPIEKTISKARGQPLE     359
BGI_N3C_2B9_H       TARPPLREQQFNSTIRVVSTLPIAHQDWLRGKEFKCKVHNKALPAPIEKTISKARGQPLE     356
BGI_N3C_4C8_H       TARPPLREQQFNSTIRVVSTLPIAHQDWLRGKEFKCKVHNKALPAPIEKTISKARGQPLE     356
                    ************************************************************

BGI_N3C_1B8_H       PKVYTMGPPREELSSRSVSLTCMINGFYPSDISVEWEKNGKAEDNYKTTPTVLDSDGSYF     416
BGI_N3C_1A10_H      PKVYTMGPPREELSSRSVSLTCMINGFYPSDISVEWEKNGKAEDNYKTTPTVLDSDGSYF     419
BGI_N3C_3B7_H       PKVYTMGPPREELSSRSVSLTCMINGFYPSDISVEWEKNGKAEDNYKTTPTVLDSDGSYF     419
BGI_N3C_2B9_H       PKVYTMGPPREELSSRSVSLTCMINGFYPSDISVEWEKNGKAEDNYKTTPTVLDSDGSYF     416
BGI_N3C_4C8_H       PKVYTMGPPREELSSRSVSLTCMINGFYPSDISVEWEKNGKAEDNYKTTPTVLDSDGSYF     416
                    ************************************************************

BGI_N3C_1B8_H       LYSKLSVPTSEWQRGDVFTCSVMHEALHNHYTQKSISRSPGK*     458
BGI_N3C_1A10_H      LYSKLSVPTSEWQRGDVFTCSVMHEALHNHYTQKSISRSPGK*     461
BGI_N3C_3B7_H       LYSKLSVPTSEWQRGDVFTCSVMHEALHNHYTQKSISRSPGK*     461
BGI_N3C_2B9_H       LYSKLSVPTSEWQRGDVFTCSVMHEALHNHYTQKSISRSPGK*     458
BGI_N3C_4C8_H       LYSKLSVPTSEWQRGDVFTCSVMHEALHNHYTQKSISRSPGK*     458
                    *******************************************
```

FIGURE 1E

```
N3G light chain

BGI_N3G_3G6_L      MDTRAPTQLLGLLLLWLPGATFAAVLTQTPSPVSAAVGGAVTINCQSSKSVYNNNELSWY      60
BGI_N3G_5F6_L      MDTRAPTQLLGLLLLWLPGATFAIVMTQTPASVSAAVGGTVSISCQSSESVYKNNYLSWY      60
BGI_N3G_4B8_L      MDTRAPTQLLGLLLLWLPGARCAADMTQTPSSVSPTVGGTVTINCQSSPSVWNN-YLSWF      59
BGI_N3G_7C8_L      MDTRAPTQLLGLLLLWLPGATFAQVLTQTPSSVSAAVGGTVTINCQSSPSVYRN-YLSWY      59
                   ********************  *  :****: ** :***:*:*.**** **:.*  ***:

BGI_N3G_3G6_L      QQKPGQPPKLLIYLASNLASGVPSRFKGSGSGTQFTLTISDVQCDDAATYYCIGGWSSSS      120
BGI_N3G_5F6_L      QQKPGQPPKRLIYDASTLASGVPSRFKGSGSGTQFTLTISDVVCDDAATYYCAGYKSSAT      120
BGI_N3G_4B8_L      QQKPGQPPKLLIYGASTLASGVPSRFQGSGSGTQFTLTISDVQCDDAATYYCAGGYRSYT      119
BGI_N3G_7C8_L      QQKPGQRPKLLIYHASTLASGVPSRFSASGSGTQFSLTISDAHCDDAATYYCAGGYIGSS      119
                   ****** ** *** **.*********..*******:*****. ********* *   . :

BGI_N3G_3G6_L      DQNGFGGGTEVVVKGDPVAPTVLIFPPAADQVATGTVTIVCVANKYFPDVTVTWEVDGTT      180
BGI_N3G_5F6_L      DGIAFGGGTEVVVKGDPVAPTVLIFPPAADQVATGTVTIVCVANKYFPDVTVTWEVDGTT      180
BGI_N3G_4B8_L      DTFVFGGGTEVVVKGDPVAPTVLIFPPAADQVATGTVTIVCVANKYFPDVTVTWEVDGTT      179
BGI_N3G_7C8_L      DAWAFGGGTEVVVRGDPVAPTVLIFPPAADQVATGTVTIVCVANKYFPDVTVTWEVDGTT      179
                   *   *********:**********************************************

BGI_N3G_3G6_L      QTTGIENSKTPQNSADCTYNLSSTLTLTSTQYNSHKEYTCKVTQGTTSVVQSFNRGDC*       238
BGI_N3G_5F6_L      QTTGIENSKTPQNSADCTYNLSSTLTLTSTQYNSHKEYTCKVTQGTTSVVQSFNRGDC*       238
BGI_N3G_4B8_L      QTTGIENSKTPQNSADCTYNLSSTLTLTSTQYNSHKEYTCKVTQGTTSVVQSFNRGDC*       237
BGI_N3G_7C8_L      QTTGIENSKTPQNSADCTYNLSSTLTLTSTQYNSHKEYTCKVTQGTTSVVQSFNRGDC*       237
                   ***********************************************************
```

FIGURE 1F

N3G heavy chain

```
BGI_N3G_3G6_H    METGLRWLLLVAVLKGVQCQQQLEESGGGLVKPGGTLTLTCRASGIDFSSYYYMCWVRQA    60
BGI_N3G_5F6_H    METGLRWLLLVAVLKGVQCQS-LEESGGGLVQPEGSLTLTCTASGFSFT-MYGIIWVRQA    58
BGI_N3G_4B8_H    METGLRWLLLVAVLKGVQCQEQLVESGGGLVKPGASLALTCKASGIDFNSGYYICWVRQA    60
BGI_N3G_7C8_H    METGLRWLLLVAVLKGVQCQEQLVESGGGLVQPEGSLTLTCKASGLDFLSNYWICWVRQA    60
                 *******************. * *******:* .:*:*** ***:.*    * : *****

BGI_N3G_3G6_H    PGRGLELVACIEPSTV-STWYANWVIGRFTISRTSSTTVTLQMTSLTAADTATYFCATSY    119
BGI_N3G_5F6_H    PGKGLEWIACIDAGRSGSTYYASWAKGRFTISKTSSTTVTLQMTSLTAADTATYFCARG-    117
BGI_N3G_4B8_H    PGKGLEWIACIDTGTAD-TAYATWAKGRFTISKTSSTTVTLQMTSLTGADTATYFCSRDL    119
BGI_N3G_7C8_H    PGKGLEWIACIYIDDGT-TYYANWAKGRFTISRTSSTTVTLQMASLTAADTATYFCARG-    118
                 **:*** :***    .      * **.*. ******:*********:***.********: .

BGI_N3G_3G6_H    SYGRSGYASTTTRLDLWGQGTLVTVSSGQPKAPSVFPLAPCCGDTPSSTVTLGCLVKGYL    179
BGI_N3G_5F6_H    ---G--------AGFTLWGPGTLVTVSSGQPKAPSVFPLAPCCGDTPSSTVTLGCLVKGYL    167
BGI_N3G_4B8_H    GGGG--------YDPDLWGPGTLVTVSSGQPKAPSVFPLAPCCGDTPSSTVTLGCLVKGYL    172
BGI_N3G_7C8_H    ------------NPFTLWGPGTLVTVSSGQPKAPSVFPLAPCCGDTPSSTVTLGCLVKGYL    167
                                *** *****************************************

BGI_N3G_3G6_H    PEPVTVTWNSGTLTNGVRTFPSVRQSSGLYSLSSVVSVTSSSQPVTCNVAHPATNTKVDK    239
BGI_N3G_5F6_H    PEPVTVTWNSGTLTNGVRTFPSVRQSSGLYSLSSVVSVTSSSQPVTCNVAHPATNTKVDK    227
BGI_N3G_4B8_H    PEPVTVTWNSGTLTNGVRTFPSVRQSSGLYSLSSVVSVTSSSQPVTCNVAHPATNTKVDK    232
BGI_N3G_7C8_H    PEPVTVTWNSGTLTNGVRTFPSVRQSSGLYSLSSVVSVTSSSQPVTCNVAHPATNTKVDK    227
                 ************************************************************

BGI_N3G_3G6_H    TVAPSTCSKPMCPPPELPGGPSVFIFPPKPKDTLMISRTPEVTCVVVDVSQDDPEVQFTW    299
BGI_N3G_5F6_H    TVAPSTCSKPMCPPPELPGGPSVFIFPPKPKDTLMISRTPEVTCVVVDVSQDDPEVQFTW    287
BGI_N3G_4B8_H    TVAPSTCSKPMCPPPELPGGPSVFIFPPKPKDTLMISRTPEVTCVVVDVSQDDPEVQFTW    292
BGI_N3G_7C8_H    TVAPSTCSKPMCPPPELPGGPSVFIFPPKPKDTLMISRTPEVTCVVVDVSQDDPEVQFTW    287
                 ************************************************************

BGI_N3G_3G6_H    YINNEQVRTARPPLREQQFNSTIRVVSTLPIAHQDWLRGKEFKCKVHNKALPAPIEKTIS    359
BGI_N3G_5F6_H    YINNEQVRTARPPLREQQFNSTIRVVSTLPIAHQDWLRGKEFKCKVHNKALPAPIEKTIS    347
BGI_N3G_4B8_H    YINNEQVRTARPPLREQQFNSTIRVVSTLPIAHQDWLRGKEFKCKVHNKALPAPIEKTIS    352
BGI_N3G_7C8_H    YINNEQVRTARPPLREQQFNSTIRVVSTLPIAHQDWLRGKEFKCKVHNKALPAPIEKTIS    347
                 ************************************************************

BGI_N3G_3G6_H    KARGQPLEPKVYTMGPPREELSSRSVSLTCMINGFYPSDISVEWEKNGKAEDNYKTTPTV    419
BGI_N3G_5F6_H    KARGQPLEPKVYTMGPPREELSSRSVSLTCMINGFYPSDISVEWEKNGKAEDNYKTTPTV    407
BGI_N3G_4B8_H    KARGQPLEPKVYTMGPPREELSSRSVSLTCMINGFYPSDISVEWEKNGKAEDNYKTTPTV    412
BGI_N3G_7C8_H    KARGQPLEPKVYTMGPPREELSSRSVSLTCMINGFYPSDISVEWEKNGKAEDNYKTTPTV    407
                 ************************************************************

BGI_N3G_3G6_H    LDSDGSYFLYSKLSVPTSEWQRGDVFTCSVMHEALHNHYTQKSISRSPGK*    469
BGI_N3G_5F6_H    LDSDGSYFLYSKLSVPTSEWQRGDVFTCSVMHEALHNHYTQKSISRSPGK*    457
BGI_N3G_4B8_H    LDSDGSYFLYSKLSVPTSEWQRGDVFTCSVMHEALHNHYTQKSISRSPGK*    462
BGI_N3G_7C8_H    LDSDGSYFLYSKLSVPTSEWQRGDVFTCSVMHEALHNHYTQKSISRSPGK*    457
                 ***************************************************
```

FIGURE 1G

N3T light chain

```
BGI_N3T_2D4_L    MDTRAPTQLLGLLLLWLPGATFAAVLTQTPSPVSAAVGGTVTISCQASQSVYNNNWLAWY   60
BGI_N3T_2D10_L   MDTRAPTQLLGLLLLWLPGATFAVVLTQTPSPVSAAVGGTVTISCQASQSVYNNDWLAWY   60
BGI_N3T_1F9_L    MDTRAPTQLLGLLLLWLPGATFAQVLTQTPSSVSAAVGGTVTINCQSSQSVYANNHLSWY   60
BGI_N3T_3B7_L    MDTRAPTQLLGLLLLWLPGAICDPVLTQTPSSVSAVVGGTVTINCQASQSVYNNNHLSWY   60
                 ********************    ******* ***.*******.**:***** *: *:**

BGI_N3T_2D4_L    QQKPGQPPKLLIYWASTLASGVPSRFKGSGSGTQFTLTISDLECDDAATYYCQGGYFRRV   120
BGI_N3T_2D10_L   QQKPGQPPKLLIYWASTLASGVPSRFKGSGSGTQFTLTISDLECDDAATYYCQGGYFRRV   120
BGI_N3T_1F9_L    QQKPGQPPKLLVYRASNLETGVPSRFSGSGSGTQFSLTISGVQCDDAAAYYCGGDVSA--   118
BGI_N3T_3B7_L    QQKAGQPPNLLIYKISTLASGVPSRFSGSGSGTQFTLTISGVQCDDAATYYCGGDFGV--   118
                 *** ****:**:*  *.* :******.********:****.::*****:*** *.

BGI_N3T_2D4_L    DSFPFGGGTEVVVKGDPVAPTVLIFPPAADQVATGTVTIVCVANKYFPDVTVTWEVDGTT   180
BGI_N3T_2D10_L   DSFPFGGGTEVVVKGDPVAPTVLIFPPAADQVATGTVTIVCVANKYFPDVTVTWEVDGTT   180
BGI_N3T_1F9_L    STGGFGGGTEVVVKGDPVAPTVLIFPPAADQVATGTVTIVCVANKYFPDVTVTWEVDGTT   178
BGI_N3T_3B7_L    DVASYGGGTEVVVKGDPVAPTVLIFPPAADQVATGTVTIVCVANKYFPDVTVTWEVDGTT   178
                 .   :*******************************************************

BGI_N3T_2D4_L    QTTGIENSKTPQNSADCTYNLSSTLTLTSTQYNSHKEYTCKVTQGTTSVVQSFNRGDC*   238
BGI_N3T_2D10_L   QTTGIENSKTPQNSADCTYNLSSTLTLTSTQYNSHKEYTCKVTQGTTSVVQSFNRGDC*   238
BGI_N3T_1F9_L    QTTGIENSKTPQNSADCTYNLSSTLTLTSTQYNSHKEYTCKVTQGTTSVVQSFNRGDC*   236
BGI_N3T_3B7_L    QTTGIENSKTPQNSADCTYNLSSTLTLTSTQYNSHKEYTCKVTQGTTSVVQSFNRGDC*   236
                 **********************************************************
```

FIGURE 1H

N3T heavy chain

```
BGI_N3T_2D4_H     METGLRWLLLVAVLKGVQCQS-LEESGGDLVKPGASLTLTCKASGFDLSSSYFMCWVRQA   59
BGI_N3T_2D10_H    METGLRWLLLVAVLKGVQCQS-LEESGGDLVKPGASLTLTCKASGFDLSSSYFMCWVRQA   59
BGI_N3T_1F9_H     METGLRWLLLVAVLKGVQCQEQLKESGGDLVTPGTPLTLTCTVSGFSLSSSY-MSWVRQA   59
BGI_N3T_3B7_H     METGLRWLLLVAVLKGVQCQS-LEESGGRLVTPGTPLTLTCTASGFSLSPTY-MIWVRQA   58
                  ********************. *:**** **.**: *****..***.** :* * *****

BGI_N3T_2D4_H     PGRGLEWIACIDTRNIDTAYATWAKGRFTISKTSSTTVTLQMTSLTAADTAKYFCGRGGN   119
BGI_N3T_2D10_H    PGRGLEWIACIDTRNIDTAYASWAKGRFTISKTSSTTVTLQMTSLTAADTARYFCGRGGN   119
BGI_N3T_1F9_H     PGKGLEWIGIIFAS-GSTYYATWAKGRFTISRTS-TTVDLKMTSLTTEDTATYFCARNSP   117
BGI_N3T_3B7_H     PGKGLEWIGVIYPN-GIPYYATWAKGRFTISKTS-TTVDLRITSPTTEDTATYFCGRNSP   116
                  **:*****. *          **:*********;** *** *;:** *: *** ***.*..

BGI_N3T_2D4_H     INGLATGFALWGPGTLVTVSSGQPKAPSVFPLAPCCGDTPSSTVTLGCLVKGYLPEPVTV   179
BGI_N3T_2D10_H    INGLATGFNLWGPGTLVTVSSGQPKAPSVFPLAPCCGDTPSSTVTLGCLVKGYLPEPVTV   179
BGI_N3T_1F9_H     -----GYGSDIWGPGTLVTVSLGQPKAPSVFPLAPCCGDTPSSTVTLGCLVKGYLPEPVTV  173
BGI_N3T_3B7_H     -----GWGTDMWGPGTLVTVSFGQPKAPSVFPLAPCCGDTPSSTVTLGCLVKGYLPEPVTV  172
                       . *   :********** ************************************

BGI_N3T_2D4_H     TWNSGTLTNGVRTFPSVRQSSGLYSLSSVVSVTSSSQPVTCNVAHPATNTKVDKTVAPST   239
BGI_N3T_2D10_H    TWNSGTLTNGVRTFPSVRQSSGLYSLSSVVSVTSSSQPVTCNVAHPATNTKVDKTVAPST   239
BGI_N3T_1F9_H     TWNSGTLTNGVRTFPSVRQSSGLYSLSSVVSVTSSSQPVTCNVAHPATNTKVDKTVAPST   233
BGI_N3T_3B7_H     TWNSGTLTNGVRTFPSVRQSSGLYSLSSVVSVTSSSQPVTCNVAHPATNTKVDKTVAPST   232
                  ************************************************************

BGI_N3T_2D4_H     CSKPMCPPPELPGGPSVFIFPPKPKDTLMISRTPEVTCVVVDVSQDDPEVQFTWYINNEQ   299
BGI_N3T_2D10_H    CSKPMCPPPELPGGPSVFIFPPKPKDTLMISRTPEVTCVVVDVSQDDPEVQFTWYINNEQ   299
BGI_N3T_1F9_H     CSKPMCPPPELPGGPSVFIFPPKPKDTLMISRTPEVTCVVVDVSQDDPEVQFTWYINNEQ   293
BGI_N3T_3B7_H     CSKPMCPPPELPGGPSVFIFPPKPKDTLMISRTPEVTCVVVDVSQDDPEVQFTWYINNEQ   292
                  ************************************************************

BGI_N3T_2D4_H     VRTARPPLREQQFNSTIRVVSTLPIAHQDWLRGKEFKCKVHNKALPAPIEKTISKARGQP   359
BGI_N3T_2D10_H    VRTARPPLREQQFNSTIRVVSTLPIAHQDWLRGKEFKCKVHNKALPAPIEKTISKARGQP   359
BGI_N3T_1F9_H     VRTARPPLREQQFNSTIRVVSTLPIAHQDWLRGKEFKCKVHNKALPAPIEKTISKARGQP   353
BGI_N3T_3B7_H     VRTARPPLREQQFNSTIRVVSTLPIAHQDWLRGKEFKCKVHNKALPAPIEKTISKARGQP   352
                  ************************************************************

BGI_N3T_2D4_H     LEPKVYTMGPPREELSSRSVSLTCMINGFYPSDISVEWEKNGKAEDNYKTTPTVLDSDGS   419
BGI_N3T_2D10_H    LEPKVYTMGPPREELSSRSVSLTCMINGFYPSDISVEWEKNGKAEDNYKTTPTVLDSDGS   419
BGI_N3T_1F9_H     LEPKVYTMGPPREELSSRSVSLTCMINGFYPSDISVEWEKNGKAEDNYKTTPTVLDSDGS   413
BGI_N3T_3B7_H     LEPKVYTMGPPREELSSRSVSLTCMINGFYPSDISVEWEKNGKAEDNYKTTPTVLDSDGS   412
                  ************************************************************

BGI_N3T_2D4_H     YFLYSKLSVPTSEWQRGDVFTCSVMHEALHNHYTQKSISRSPGK*   463
BGI_N3T_2D10_H    YFLYSKLSVPTSEWQRGDVFTCSVMHEALHNHYTQKSISRSPGK*   463
BGI_N3T_1F9_H     YFLYSKLSVPTSEWQRGDVFTCSVMHEALHNHYTQKSISRSPGK*   457
BGI_N3T_3B7_H     YFLYSKLSVPTSEWQRGDVFTCSVMHEALHNHYTQKSISRSPGK*   456
                  *********************************************
```

FIGURE 5
A.
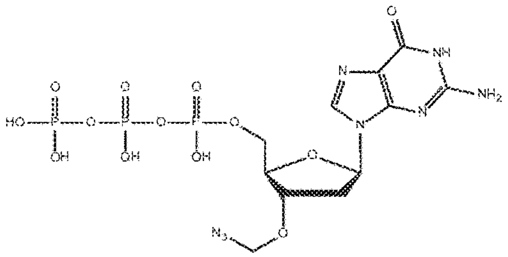
B.
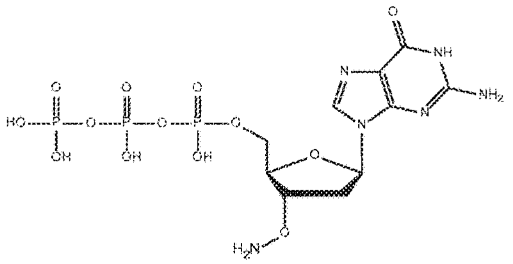
C.
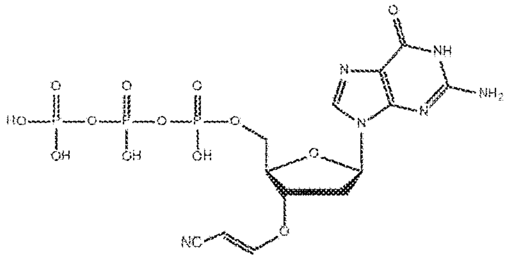
D.
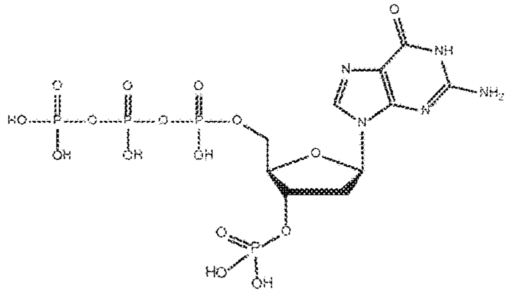
E.
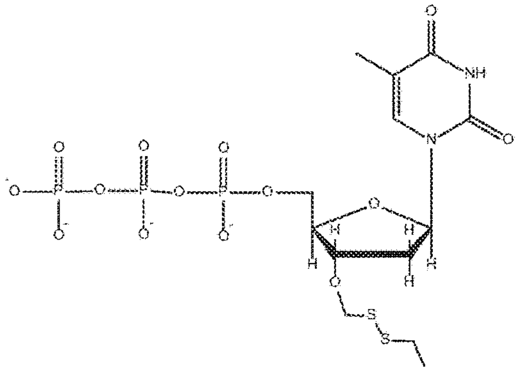

FIGURE 6

Allenyl

Cis or trans-
cyanoethenyl

Cis or trans-
cyanofluoroethenyl

Cis or trans-
Trifluoromethylethenyl

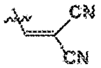

Biscyanoethenyl

Bisfluoroethenyl

Cis or trans propenyl

Nitroethenyl

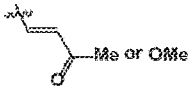

aceto/methylcarbono-
ethenyl

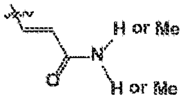

amidoethenyl

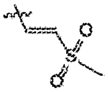

methylsulfonoethenyl

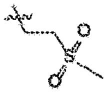

methylsulfonoethyl

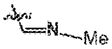

Formimidate

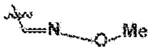

Formhydroxymate

vinyloethenyl

ethylenoethenyl

cyanoethylenyl

nitroethylenyl

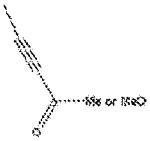

3-oxobut-1-ynyl/
3-methoxy-3-oxoprop-1-ynyl

MASSIVELY PARALLEL SEQUENCING USING UNLABELED NUCLEOTIDES

CROSS-REFERENCE TO RELATED APPLICATIONS

This application claims benefit and is a national phase application of International Patent Application PCT/US2019/060779, filed Nov. 11, 2019, which claims benefit of U.S. provisional application No. 62/758,317, filed Nov. 9, 2018; U.S. provisional application No. 62/914,877, filed Oct. 14, 2019; U.S. provisional application No. 62/914,940, filed Oct. 14, 2019; and U.S. provisional application No. 62/914,915, filed Oct. 14, 2019, each of which is incorporated herein by reference.

This application is related to United States Patent Publication US 2018/0223358 and to International Patent Application No. PCT/US2018/012425, published as WO 2018/129214, both of which are incorporated herein by reference.

FIELD OF THE INVENTION

The invention relates to nucleic acid sequencing and finds use in medicine and biological sciences.

SEQUENCE LISTING

The instant application contains a Sequence Listing which has been submitted electronically in ASCII format and is hereby incorporated by reference in its entirety. Said ASCII copy, created on Nov. 7, 2019, is named 092171-1164247_SL.txt and is 140,686 bytes in size.

BACKGROUND OF THE INVENTION

The need for low cost, high-throughput, methods for nucleic acid sequencing and re-sequencing has led to the development of "massively parallel sequencing" (MPS) technologies. One commonly used method for sequencing DNA is referred to as "sequencing-by-synthesis" (SBS), such as disclosed in Ronaghi et al., Science, 281:363-365, 1998; Li et al., *Proc. Natl. Acad. Sci. USA,* 100:414-419, 2003; Metzker, *Nat Rev Genet.* 11:31-46, 2010; Ju et al., *Proc. Natl. Acad. Sci. USA* 103:19635-19640, 2006; Bentley et al., *Nature* 456:53-59, 2008; and in U.S. Pat. Nos. 6,210,891, 6,828,100, 6,833,246, and 6,911,345, and U.S. Pat. Pub. 2016/0130647.

SBS requires the controlled (i.e., one at a time) incorporation of the correct complementary nucleotide opposite the oligonucleotide being sequenced. This allows for accurate sequencing by adding nucleotides in multiple cycles as each nucleotide residue is sequenced one at a time, thus preventing an uncontrolled series of incorporations occurring. In one approach reversible terminator nucleotides (RTs) are used to determine the sequence of the DNA template. In the most commonly used SBS approach, each RT comprises a modified nucleotide that includes (1) a blocking group that ensures that only a single base can be added by a DNA polymerase enzyme to the 3' end of a growing DNA copy strand, and (2) a fluorescent label that can be detected by a camera. In the most common SBS methods, templates and sequencing primers are fixed to a solid support and the support is exposed to each of four DNA nucleotide analogs, each comprising a different fluorophore attached to the nitrogenous base by a cleavable linker, and a 3'-O-azidomethyl group at the 3'-OH position of deoxyribose, and DNA polymerase. Only the correct, complementary base anneals to the target and is subsequently incorporated at the 3' terminus of primer. Nucleotides that have not been incorporated are washed away and the solid support is imaged. TCEP (tris(2-carboxyethyl)phosphine) is introduced to cleave the linker and release the fluorophores and to remove the 3'-O-azidomethyl group, regenerating a 3'-OH. The cycle can then be repeated (Bentley et al., Nature 456, 53-59, 2008). A different fluorescent color label is used for each of the four bases, so that in each cycle of sequencing, the identity of the RT that is incorporated can be identified by its color.

Despite the widespread use of SBS, improvements are still needed. For example, current SBS methods require expensive reversibly terminated dNTPs (RTs) with a label (e.g., dye) on the base connected with a cleavable linker resulting in a) a chemical scar left on the incorporated bases after label cleavage, b) less efficient incorporation, c) quenching, d) excited dye induced termination of extension, and reduction of signal in each sequencing cycle.

BRIEF SUMMARY OF THE INVENTION

The present invention relates to methods and compositions for nucleic acid analysis and sequencing. Disclosed herein is an SBS sequencing method in which the last incorporated nucleotide base is identified by binding of an affinity reagent (e.g., antibody, aptamer, affimer, knottin, etc.) that recognizes the base, the sugar, a cleavable blocking group or a combination of these components in the last incorporated nucleotide. The binding is directly or indirectly associated with production of a detectable signal.

According to one embodiment, the invention provides methods of sequencing that employ non-labeled reversible terminator (NLRT) nucleotides. A reversible terminator (RT) nucleotide is a modified deoxynucleotide triphosphate (dNTP) or dNTP analog that contains a removable blocking group that ensures that only a single base can be added by a DNA polymerase enzyme to the 3' end of a growing DNA copy strand. As is well known, the incorporation of a dNTP (2'-deoxynucleoside triphosphates) to the 3' end of the growing strand during DNA synthesis involves the release of pyrophosphate, and when a dNTP is incorporated into a DNA strand the incorporated portion is a nucleotide monophosphate (or more precisely, a nucleotide monomer linked by phosphodiester bond(s) to one or two adjacent nucleotide monomers). A reversible terminator (RT) nucleotide is a modified deoxynucleotide triphosphate (dNTP) or dNTP analog that contains a removable blocking group that ensures that only a single base can be added by a DNA polymerase enzyme to the 3' end of a growing DNA copy strand. A non-labeled RT nucleotide does not contain a detectable label. In each cycle of sequencing, the nucleotide or nucleotide analogue is incorporated by a polymerase, extending the 3' end of the DNA copy strand by one base, and unincorporated nucleotides or nucleotide analogues are washed away. An affinity reagent is introduced that specifically recognizes and binds to an epitope(s) of the newly incorporated nucleotides or nucleotide analog. After an image is taken, the blocking group and the labeled affinity reagent are removed from the DNA, allowing the next cycle of sequencing to begin. In some embodiments the epitope recognized by the affinity reagent is formed by the incorporated nucleoside itself (that is, the base plus sugar) or the nucleoside and 3' blocking group. In some embodiments the epitope recognized by the affinity reagent is formed by the reversible terminator itself, the reversible terminator in combination with the deoxyribose, or the reversible terminator in combination with the nucleobase or nucleobase and deoxyribose.

According to one such embodiment, the present invention provides methods for sequencing a nucleic acid, comprising: (a) contacting a nucleic acid template comprising the nucleic acid, a nucleic acid primer complementary to a portion of said template, a polymerase, and an unlabeled RT of Formula I:

Formula I

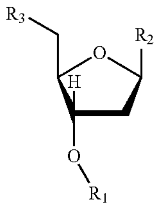

wherein: $R_1$ is a 3'-O reversible blocking group; $R_2$ is a nucleobase selected from adenine (A), cytosine (C), guanine (G), thymine (T), and analogues thereof; and $R_3$ comprises or consists of one or more phosphates; under conditions wherein the primer is extended to incorporate the unlabeled RT into a sequence complementary to the nucleic acid template, thereby producing an unlabeled extension product comprising the incorporated RT; (b) contacting the unlabeled extension product with an affinity reagent under conditions wherein the affinity reagent binds specifically to the incorporated RT to produce a labeled extension product comprising the RT; (c) detecting the binding of the affinity reagent, and (d) identifying the nucleotide incorporated into the labeled extension product to identify at least a portion of the sequence of said extension product, and therefor of the template nucleic acid.

In dNTP analogs commonly used for sequencing by synthesis, the nucleobase is conjugated to a cleavable linker that connects the base to a detectable label such as a fluorophore. See, e.g., US Pat. Pub. 2002/0227131. In contrast, in the dNTP analogs of the present invention generally $R_2$ is not a nucleobase conjugated to a dye or other detectable label by a linker.

According to another embodiment, such a method further comprises (d) removing the reversible blocking group from the RT to produce a 3'-OH; and (e) removing the affinity reagent from the RT.

According to another embodiment, such a method further comprises repeating steps of the method one or more times, that is, performing multiple cycles of sequencing, wherein at least a portion of the sequence of said nucleic acid template is determined.

According to another embodiment, such a method comprises removing the reversible blocking group and the affinity reagent in the same reaction.

According to another embodiment, such a method comprises removing the affinity reagent(s) without removing the reversible blocking group(s) and re-probing with difference affinity reagents.

In such methods, the affinity reagent may include antibodies (including binding fragments of antibodies, single chain antibodies, bispecific antibodies, and the like), aptamers, knottins, affimers, or any other known agent that binds an incorporated NLRT with a suitable specificity and affinity. In one embodiment, the affinity reagent is an antibody.

In another embodiment, the affinity reagent is an antibody comprising detectable label that is a fluorescent label.

According to an embodiment, $R_1$ is selected from the group consisting of allyl, azidomethyl, aminoalkoxyl, 2-cyanoethyl, substituted alkyl, unsubstituted alkyl, substituted alkenyl, unsubstituted alkenyl, substituted alkynyl, unsubstituted alkynyl, substituted heteroalkyl, unsubstituted heteroalkyl, substituted heteroalkenyl, unsubstituted heteroalkenyl, substituted heteroalkynyl, unsubstituted heteroalkynyl, allenyl, cis-cyanoethenyl, trans-cyanoethenyl, cis-cyanofluoroethenyl, trans-cyanofluoroethenyl, cis-trifluoromethylethenyl, trans-trifluoromethylethenyl, biscyanoethenyl, bisfluoroethenyl, cis-propenyl, trans-propenyl, nitroethenyl, acetoethenyl, methylcarbonoethenyl, amidoethenyl, methylsulfonoethenyl, methylsulfonoethyl, formimidate, formhydroxymate, vinyloethenyl, ethylenoethenyl, cyanoethylenyl, nitroethylenyl, amidoethylenyl, amino, cyanoethenyl, cyanoethyl, alkoxy, acyl, methoxymethyl, aminoxyl, carbonyl, nitrobenzyl, coumarinyl, and nitronaphthalenyl.

According to another embodiment, $R_2$ is a nucleobase selected from adenine (A), cytosine (C), guanine (G), and thymine (T).

According to another embodiment, $R_3$ consists of or comprises one or more phosphates.

The term non-labeled reversible terminator (NLRT) may refer to the triphosphate form of the nucleotide analog, or may refer to the incorporated NLRT.

According to another embodiment of the invention, methods are provided for sequencing a nucleic acid, comprising: (a) providing a DNA array comprising (i) a plurality of template DNA molecules, each template DNA molecule comprising a fragment of the nucleic acid, wherein each of said plurality of template DNA molecules is attached at a position of the array, (b) contacting the DNA array with a nucleic acid primer complementary to a portion of each of said template DNA molecules, a polymerase, and an unlabeled RT of Formula I:

Formula I

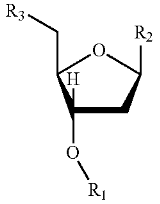

wherein: $R_1$ is a 3'-O reversible blocking group; $R_2$ is a nucleobase selected from adenine (A), cytosine (C), guanine (G), thymine (T), and analogues thereof; and $R_3$ consists of or comprises one or more phosphates; under conditions wherein the primer is extended to incorporate the unlabeled RT into a sequence complementary to at least some of said plurality of said template DNA molecules, thereby producing unlabeled extension products comprising the RT; (c) contacting the unlabeled extension products with an affinity reagent comprising a detectable label under conditions wherein the affinity reagent binds specifically to the RT to produce labeled extension products comprising the RT; and (d) identifying the RT in the labeled extension products to identify at least a portion of the sequence of said nucleic acid.

According to one embodiment of the invention, such a method comprises: (b) contacting the DNA array with a nucleic acid primer complementary to a portion of each of said template DNA molecules, a polymerase, and a set of unlabeled RTs of Formula I that comprises a first RT in which $R_2$ is A, a second RT in which $R_2$ is T, a third RT in which $R_2$ is C, and a fourth RT in which $R_2$ is G, under conditions in which the primer is extended to incorporate the unlabeled RTs into sequences complementary to at least some of said plurality of said template DNA molecules, thereby producing unlabeled extension products comprising the RTs; (c) contacting the unlabeled extension products with a set of affinity reagents under conditions in which the set of affinity reagents binds specifically to the incorporated RTs to produce labeled extension products comprising the RTs, wherein: (i) the set of affinity reagents comprises a first affinity reagent that binds specifically to the first RT, a second affinity reagent that binds specifically to the second RT, a third affinity reagent that binds specifically to the third RT, and, optionally, a fourth affinity reagent that binds specifically to the fourth RT; (ii) each of said first, second, and third affinity reagents comprises a detectable label; and (d) identifying the RTs in the labeled extension products by identifying the label of the affinity reagent bound to the RTs at their respective positions on the array to identify at least a portion (e.g., one base per cycle) of the sequence of said nucleic acid. According to a related embodiment, each of said first, second, third and fourth affinity reagents comprises a detectable label. According to another related embodiment, each of said first, second, and third affinity reagents comprises a different detectable label. According to another related embodiment, each of the first, second, and third affinity reagents comprises the same label (e.g., same fluorophore(s)) in different amounts, resulting in signals of different intensities. According to another embodiment, the affinity reagents bound to incorporated RTs are not directly labeled but are indirectly labeled using secondary affinity reagents.

According to another embodiment of the present invention, DNA arrays are provided. Such arrays comprise: a plurality of template DNA molecules, each DNA molecule attached at a position of the array, a complementary DNA sequence base-paired with a portion of the template DNA molecule at a plurality of the positions, wherein the complementary DNA sequence comprises at its 3' end an incorporated RT; and an affinity reagent attached specifically to at least some of the RTs, the affinity reagent comprising a detectable label that identifies the RT to which it is attached.

According to another embodiment of the invention, kits are provided that comprise: (a) an unlabeled RTs of Formula I:

Formula I

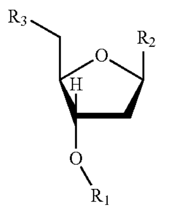

wherein: $R_1$ is a 3'-O reversible blocking group; $R_2$ is a nucleobase selected from adenine (A), cytosine (C), guanine (G), thymine (T), and analogues thereof; and $R_3$ consists of or comprises one or more phosphates; (b) a labeled affinity reagent that is binds specifically to one of the RT; and (c) packaging for the RT and the affinity reagent. According to another embodiment, such a kit comprises: a plurality of the RTs, wherein each RT comprises a different nucleobase, and a plurality of affinity reagents, wherein each affinity reagent binds specifically to one of the RTs.

In any of the foregoing embodiments, the affinity agent may be a monoclonal antibody selected from the group consisting of: 2C5, 3612, 17H7, 1867, 168, 269, 4C8, 1A10, 367, 3G6, 5F6, 468, 7C8, 2D4, 2D10, 1F9, 367 and 4G8 and variants and derivatives thereof.

BRIEF DESCRIPTION OF THE DRAWINGS

FIGS. 1A-H show alignments of heavy and light chain amino acid sequences for monoclonal antibodies specific for: 3'-azidomethyl-dA (N3A): mAbs 2C5, 3B12, 17H7, and 18B7; 3'-azidomethyl-dC (N3C): mAbs 1B8, 2B9, 4C8, 1A10, and 3B7; 3'-azidomethyl-dG (N3G): mAbs 3G6, 5F6, 4B8, and 7C8; and 3'-azidomethyl-dT (N3T): mAbs 2D4, 2D10, 1F9, and 3B7. Specifically, FIG. 1A shows N3A light chain sequences: BGI_N3A_2C5_L (SEQ ID NO: 2), BGI_N3A_3B12_L (SEQ ID NO: 4), BGI_N3A_17H7_L (SEQ ID NO: 6), and BGI_N3A_18B7_L (SEQ ID NO: 8); FIG. 1B shows N3A heavy chain sequences: BGI_N3A_2C5_H (SEQ ID NO: 1), BGI_N3A_3B12_H (SEQ ID NO: 3), BGI_N3A_17H7_H (SEQ ID NO: 5), and BGI_N3A_18B7_H (SEQ ID NO: 7); FIG. 1C shows N3C light chain sequences: BGI_N3C_1B8_L (SEQ ID NO: 12), BGI_N3C_2B9_L (SEQ ID NO: 14), BGI_N3C_4C8_L (SEQ ID NO: 18), BGI_N3C_1A10_L (SEQ ID NO: 10), and BGI_N3C_3B7_L (SEQ ID NO: 16), FIG. 1D shows N3C heavy chain sequences; BGI_N3C_1B8_H (SEQ ID NO: 11), BGI_N3C_1A10_H (SEQ ID NO: 9), BGI_N3C_3B7_H (SEQ ID NO: 15), BGI_N3C_2B9_H (SEQ ID NO: 13), and BGI_N3C_4C8_H (SEQ ID NO: 17); FIG. 1E shows N3G light chain sequences: BGI_N3G 3G6_L (SEQ ID NO: 20), BGI_N3G_5F6_L (SEQ ID NO: 24), BGI_N3G_4B8_L (SEQ ID NO: 22), and BGI_N3G_7C8_L (SEQ ID NO: 26); FIG. 1F shows N3G heavy chain sequences: BGI_N3G_3G6_H (SEQ ID NO: 19), BGI_N3G_5F6_H (SEQ ID NO: 23), BGI_N3G_4B8_H (SEQ ID NO: 21), and BGI_N3G_7C8_H (SEQ ID NO:25); FIG. 1G shows N3T light chain sequences; BGI_N3T 2D4_L (SEQ ID NO: 30), BGI_N3T 2D10_L (SEQ ID NO: 32), BGI_N3T 1F9_L (SEQ ID NO: 28), and BGI_N3T 3B7_L (SEQ ID NO: 34); and FIG. 1H shows N3T heavy chain sequences: BGI_N3T 2D4_H (SEQ ID NO: 29), BGI_N3T 2D10_H (SEQ ID NO: 31), BGI_N3T 1F9_H (SEQ ID NO: 27), and BGI_N3T 3B7_H (SEQ ID NO: 33).

FIG. 5 shows examples of NLRT structures: FIG. 5A 3'-O-azidomethyl-2'-deoxyguanine; FIG. 5B 3'-O-amino-2'-deoxyguanine; FIG. 5C 3'-O-cyanoethylene-2'-deoxyguanine;

FIG. 5D 3'-O-phospho; FIG. 5E: 3'-ethyldisulfide-methylene-2'-deoxythymine.

FIG. 6 illustrates various blocking groups that can be used in the practice of the invention. "~" indicates the attachment point of the molecule to the remainder of the structure.

DETAILED DESCRIPTION OF THE INVENTION

1. Overview

Figure 2A:
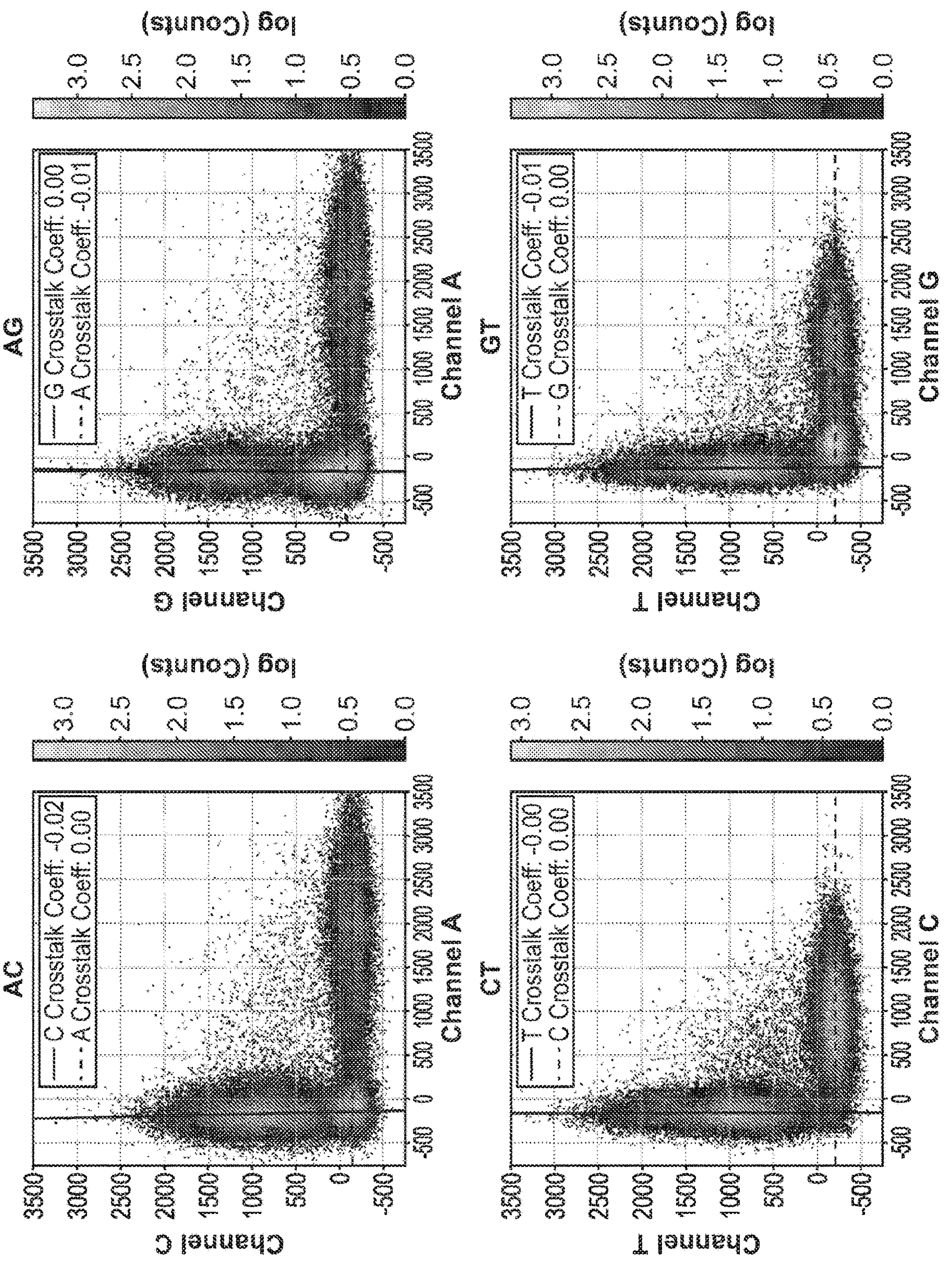
FIG. 2A is a scatter-plot showing the fluorescent intensity for populations of DNBs in two channels within a single imaging field after binding with labeled antibodies.

In certain aspects, the present invention provides methods and compositions for sequencing-by-synthesis (SBS) of nucleic acids that employ unlabeled reversible terminator nucleotides. In one approach, SBS is carried out by producing immobilized single stranded template DNAs at positions on an array. In most approaches, each immobilized single stranded template DNA is at a position with a large number of copies (e.g., amplicons) of like sequence. For example, bridge PCR (e.g, as described in WO1998044151) may be used to generate a cluster of template sequences at a position on an array (Illumina), or rolling circle replication may be used to generate a single-stranded concatemer, or DNA nanoball (DNB) (see, e.g., U.S. Pat. No. 8,445,194), with many copies of the template sequences (Complete Genomics, Inc., San Jose, CA). In one approach SBS is carried out by hybridizing a primer to the template DNA and extending the primer to produce an "extended primer," or "growing DNA strand" (GDS). Extending the primer refers to addition ("incorporation" or "incorporating") of nucleotides at the 3' end of the primer DNA strand while it is hybridized to the template. The nucleotide incorporated at the 3' terminus is complementary to the corresponding nucleotide of the template such that by determining the identity of the incorporated nucleotide at each sequencing cycle the nucleotide sequence of the template may be determined. As used herein, "extended primer" and "growing DNA strand," (GDS) and "growing DNA copy strand" have the same meaning and are used interchangeably.

In one prior art approach, labeled nucleotide analogs are incorporated into the GDS. Generally the labeled nucleotide analogs comprise a blocking group that insures that only a single nucleotide per step can be incorporated and a dye (typically a fluorescent dye) is attached via a cleavable linker to the nucleotide. Each cycle of sequencing encompasses incorporating a labeled nucleotide analog at the end of the GDS, detecting the incorporated labeled nucleotide analog label, removing the label from the incorporated nucleotide analog, and removing the blocking group from the incorporated nucleotide analog to allow incorporation of a new labeled nucleotide analog. In contrast, the present invention does not require labeled nucleotide analogs that include a dye attached, via a cleavable linker, to a base or sugar.

In an alternative approach described in U.S. Pat. Pub. US2017/0240961, which is incorporated herein by reference, a nucleotide analog, when incorporated, comprises an affinity tag attached via a linker to the nucleotide. The affinity tag is one member of a specific binding pair (SBP). In one approach the affinity tag is biotin. After incorporation the incorporated nucleotide is exposed to an affinity reagent comprising the second member of the SBP (e.g., streptavidin) and a detectable label. The detectable label is detected to identify the incorporated nucleotide. Following detection, the incorporated nucleotide analog-affinity reagent complex is treated to cleave the linker and release the detectable label. In one approach the affinity tag is an antigen and the affinity reagent is a fluorescently labeled antibody that specifically binds the antigen. In contrast, the present invention does not require an affinity tag and employs, in some aspects, an affinity reagent that binds the nucleobase, sugar moiety, cleavable blocking group or a combination or sub-combination thereof, rather than to an affinity tag.

According to one aspect of the method disclosed herein, a non-labeled reversible terminator, i.e., a nucleotide analog that includes a reversible terminator or blocking group (Non-Labeled Reversible Terminator, or NLRT), is incorporated at the 3' terminus of the GDS, and then is exposed to an affinity reagent (e.g., antibody) that specifically binds to the incorporated NLRT (the "binding event"). After detection of the binding event, the affinity reagent is removed. In one approach a nucleotide analog comprising a reversible blocking group is incorporated at the 3' terminus of the GDS, and after detection of the binding event, the reversible blocking group and the affinity reagent are removed, optionally in the same step. In this approach, each cycle of sequencing includes: (i) incorporation of an NLRT comprising a blocking group by a DNA polymerase, followed by washing away unincorporated NLRT(s); (ii) contacting the incorporated nucleotide analog with an labeled affinity reagent that recognizes and specifically binds to the incorporated NLRT; (iii) detection of the binding of the affinity reagent; (iv) removal of the blocking group in a fashion that allows incorporation of an additional nucleotide analog (e.g., produces a hydroxyl group at the 3' position of a deoxyribose moiety), and (v) removal of the affinity reagent. This step may be followed by a new cycle or cycles in which a new nucleotide analog is incorporated and detected. The affinity reagent (e.g., antibody) may be directly labeled (e.g., a fluorescent labeled antibody) or may be detected indirectly (e.g., by binding of a labeled anti-affinity reagent secondary affinity reagent). Thus, it will be appreciated that a "labeled affinity reagent" may be directly labeled by, for example, conjugation to a fluorophore, or may be indirectly labeled.

In another approach a nucleotide analog comprising a reversible blocking group is incorporated at the 3' terminus of the GDS, and after detection of the binding event, the reversible blocking group and the affinity reagent are removed. In this approach, each cycle of sequencing includes: (i) incorporation of an NLRT comprising a blocking group by a DNA polymerase, optionally followed by removal (washing away) of unincorporated NLRT(s); (ii) contacting the incorporated nucleotide analog with an labeled affinity reagent that recognizes and specifically binds to the incorporated NLRT; (iii) detection of the binding of the affinity reagent; (iv) removal of the blocking group in a fashion that regenerates a hydroxyl (OH) group at the 3' position of the deoxyribonucleotide, which allows incorporation of an additional nucleotide analog (e.g., produces a hydroxyl group at the 3' position of a deoxyribose moiety), and (v) removal of the affinity reagent. This step may be followed by a new cycle or cycles in which a new nucleotide analog is incorporated and detected. The affinity reagent (e.g., antibody) may be directly labeled (e.g., a fluorescent labeled antibody) or may be detected indirectly (e.g., by binding of a labeled anti-affinity reagent secondary affinity reagent). Thus, it will be appreciated that a "labeled affinity reagent" may be directly labeled by, for example, conjugation to a fluorophore, or indirectly labeled.

SBS involves two or more cycles of primer extension in which a nucleotide is incorporated at the 3' terminus of the extended primer. The present invention makes use of affinity reagents, such as antibodies, to (i) detect the nucleotide incorporated at the 3' terminus of the extended primer ("3' terminal nucleotide") and (ii) identify the nucleobase of that 3' terminal nucleotide and distinguishing one nucleobase from another (e.g., A from G). Without intending to be bound by a specific mechanism, this is possible because each affinity reagent is designed to distinguish a 3' terminal nucleotide from other, "internal" nucleotides of the extended primer, even when the 3' terminal nucleotide and internal nucleotides comprise the same nucleobase. Each affinity reagent (or in some cases combination of affinity reagents) is also designed to detect properties of a 3' terminal nucleotide that identify the nucleobase associated with the 3' terminal nucleotide. A number of strategies, methods, and materials are provided for carrying out these and other steps. This section provides an overview in which many variations are omitted, and should not be considered limiting in any way.

In some approaches the SBS reactions of the invention are carried out using nucleotides with 3' reversible terminator moieties. In these approaches the incorporated 3' terminal nucleotide differs from the internal nucleotides based on the position and presence of the reversible terminator moiety. Thus, an affinity reagent that binds to a reversible terminator moiety in an extended primer is binding to (and thereby detects) the 3' terminal nucleotide, distinguishing it from internal nucleotides. In a different approach the incorporated 3' terminal nucleotide differs from the internal nucleotides based on the presence of a free 3'-OH (hydroxyl) group which is not present on internal nucleotides. Thus, an affinity reagent that binds to a free 3'-OH group in an extended primer is binding to the 3' terminal nucleotide is binding to (and thereby detects) the 3' terminal nucleotide, distinguishing it from internal nucleotides. In some approaches the free 3'-OH group is generated by cleavage of the reversible terminator in an incorporated nucleotide analog. In another approach, the free 3'-OH group results from incorporation of a nucleotide that does not comprise a reversible terminator moiety, such as a naturally occurring nucleotide. In an additional approach, combinable with either of two approaches described above, the incorporated 3' terminal nucleotide differs from the internal nucleotides based on other structural differences characteristic of a 3' terminal nucleotide including, but not limited to, greater accessibility of an affinity reagent to the deoxyribose sugar of a 3' terminal nucleotide relative to deoxyribose of internal nucleotides, greater accessibility of an affinity reagent to the nucleobase of a 3' terminal nucleotide to an affinity reagent relative to deoxyribose of internal nucleotides, and other molecular and conformational differences between the 3' terminal nucleotide and internal nucleosides.

Thus, in an aspect of the present invention affinity reagents are used to detect these structural differences between the 3' terminal nucleotide of an extended primer and other nucleotides.

Also provided are a number of strategies, methods, and materials for detecting properties of the 3' terminal nucleotide that identify the nucleobase of the 3' terminal nucleotide. In one approach, naturally occurring nucleotides, or nucleotide analogs comprising naturally occurring nucleobases (e.g., A, T, C and G), are used in the sequencing reaction and incorporated into the primer extension product. Affinity reagents that specifically bind to one nucleobase (e.g., A) and distinguish that nucleobase from others to which it does not bind (e.g., T, C and G) are used to identify the nucleobase of the 3' terminal nucleotide. In another approach, nucleotide analogs comprising modified (i.e., not naturally occurring) nucleobases are used in the sequencing reaction and incorporated into the primer extension product. Affinity reagents that specifically bind to one modified nucleobase (e.g., modified A) and distinguish that modified nucleobase from other modified or natural nucleobases. An affinity reagent that specifically binds to a modified nucleobase generally recognizes the modification, such that the binding to modified nucleobase differs from binding to a naturally occurring nucleobase without the modification. For example, an affinity reagent that binds to an adenosine analog in which nitrogen at position 7 ($N^7$) is replaced by methylated carbon may not bind to the naturally occurring (unmodified) adenosine nucleobase, or may bind less avidly. Without intending to be bound by a particular mechanism, it is believed that an affinity reagent that specifically recognizes a modified moiety (in this case a modified nucleobase) does so by binding the modified feature (in this case, the portion of modified adenosine comprising the methylated-carbon). Stated differently, the affinity reagent binds an epitope that includes the methylated-carbon. It will be understood that the affinity reagent binds other portions of the incorporated nucleotide as well.

In yet another approach, nucleotides with 3' reversible blocking groups (reversible terminator nucleotides) are incorporated into the primer extension product. The blocking groups are removed at each sequencing cycle so that only the last incorporated nucleotide of the primer extension produce comprises a blocking group. In this approach affinity reagents that bind the blocking groups are used. In one aspect of this approach, at least two nucleotide analogs (i.e., with different nucleobases) used in the sequencing reaction comprise different blocking groups. By, for illustration, using a first blocking group (e.g., 3'-O-azidomethyl) for a nucleotide comprising adenine or an adenine analog, a second, different blocking group (e.g., 3'-O-cyanoethylene) for a nucleotide comprising guanine or a guanine analog, etc., the specificity of the affinity reagent will identify the associated nucleobase. For example, extending the illustration above, if a 3' terminal nucleotide is recognized by an affinity reagent specific for 3'-O-cyanoethylene this indicates that the associated nucleobase is guanine or a guanine analog and the template base at this position is cytosine. In a variation of this approach, blocking groups that differ by only a small feature may be used, and the affinity reagent binds an epitope that includes the distinguishing small feature.

As described herein below, in one aspect of the present invention, affinity reagents that recognize and specifically bind to nucleotides or nucleotide analogs based on a combination of structural features are used (e.g., an affinity reagent that recognizes a particular blocking group and a specific nucleobase, optionally with particular modifications, are used. In this aspect, nucleotides or nucleotide analogs are designed and/or selected for the property of being recognized by a specific affinity reagent. In some cases, an affinity reagent that binds multiple structural features has the advantage of stronger and more specific affinity reagent binding. The table below provides a nonexhaustive collection of examples of structural differences that can be recognized by an affinity reagent to distinguish nucleotides having different nucleobases ($2^{nd}$ column) and the moieties in the last incorporated nucleotide that may be bound by an affinity reagent to provide enough binding efficiency and/or that distinguishes the last incorporated nucleotide from the internal nucleotides based on those features (3rd column).

TABLE 1

| Affinity Reagent Class | Specificity: Distinguishes incorporated nucleotide based on | Elements of Last Incorporated Nucleotide Bound By Affinity Reagent |
|---|---|---|
| A | Differences in natural nucleobases (e.g., A, T, C, G) | 1. Nucleobase and sugar;<br>2. Nucleobase and blocking group;<br>3. Nucleobase and blocking group and sugar; |
| B | Differences in natural nucleobases along with modified features of nucleobase analogs (or "modified nucleobases") | 1. Modified features of nucleobase analogs;<br>2. Modified features of nucleobase analogs and sugar;<br>3. Natural nucleobases, modified features of nucleobase analogs, and blocking group;<br>4. Natural nucleobases, modified features of nucleobase analogs, and blocking group; |
| C | Differences in natural bases combined with differences in blocking groups (in at least some NLRTs) | 1. Nucleobase and variations in blocking group structure or entire blocking group; or<br>2. Nucleobase, variations in blocking group structure or entire blocking group and sugar; |
| D | Differences in blocking groups | 1. Different blocking groups and/or variations in similar blocking groups;<br>2. Different blocking groups and/or variations in similar blocking groups, nucleobase (natural or modified); or<br>3. Different blocking groups and/or variations in similar blocking groups, nucleobase (natural or modified) and sugar; |
| E | Differences in natural nucleobases combined with specific nucleobase modifications of at least some nucleobases and differences in blocking groups of at least some NLRTs | 1. Natural nucleobases, modified features of nucleobase analogs, and blocking group; or<br>2. Natural nucleobases, modified features of nucleobase analogs, and blocking group and sugar. |

As discussed in detail below, the portion of the incorporated nucleotide analog to which the labeled affinity reagent binds may include, for example and not limitation, the nucleobase and the blocking group, or the nucleobase and/or the blocking group in combination with the sugar moiety of the nucleotide analog. See Table 1. Binding of the labeled affinity reagent may depend on the position of the target nucleotide, e.g., distinguishing between a nucleotide analog having a blocking group at the 3' terminus of the GDS, and a similar nucleotide analog (lacking the blocking group) that is located within or internal to the GDS. Binding of the labeled affinity reagent also depends upon the nucleobase itself, such that the affinity reagents binds to one target NLRT (e.g., NLRT-A) incorporated at the end of a GDS at one position on an array but not to other NLRTs (e.g., NLRT-C, -T, or -G) incorporated at the end of a GDS at a different position on an array.

The present invention has several advantages over other SBS methods. Removal of the labeled affinity reagent does not leave behind a chemical "scar" resulting from groups left attached to the dNTP after cleavage of a linker. This is advantageous because such "scars" may reduce the efficiency of dNTP incorporation by polymerase. In addition, in this approach the affinity reagent may include multiple fluorescent moieties and provide a stronger signal than a single fluorescent dye attached to a dNTP according to commonly used methods. This approach also may cause less photodamage, since lower excitation power or shorter exposure times may be used. The approach disclosed herein allows longer high accuracy reads (e.g., reads that are longer than 500 bases, or longer than 1000 bases) and/or more accurate reads longer than 50, 100 or 200 bases, (e.g., with fewer errors than one in 2000 bases or one in 5000 bases). The compositions and methods of the present invention also may be more economical than labeled reversible terminator (RT) methods commonly used for SBS. Unlabeled RTs cost less than labeled RTs. In standard SBS using labeled RTs, high concentrations of labeled RTs are used to drive the incorporation of the RT to completion, and most of the labeled RTs (70-99% or more) are not incorporated by polymerase and are washed away. Using lower cost unlabeled RTs thus reduces this cost. Moreover, in the labeling step of the present invention, in which a labeled affinity reagent is used, it is not necessary that every copy of a target sequence at an array site is bound by the affinity reagent, particularly when the affinity reagent is labeled with multiple dye molecules (e.g., on average 2, 3, 4, 5, at least 2, at least 3, at least 4, at least 5, 2-5 or 3-5 molecules of dye per molecule affinity reagent). For illustration, there may be 50 copies of a template sequence at a site on an array (e.g., a concatemer at a site on an array may contain 50 copies of a template sequence). In one approach one molecule of the affinity reagent is labeled with multiple molecules of dye and less than about 50% of the copies of the template sequence are bound by the affinity reagent. In some embodiments less than about 30%, less than about 25%, less than about 20%, or less than about 15% of the copies of target sequence are bound by the affinity reagent copies. A higher level of binding may be preferred if the affinity reagent bears only a single label molecule (e.g., 50% percent or more or 70%).

2. Definitions and Terms

As used herein, in the context of a nucleotide analog, the terms "unlabeled" and "non-labeled" are used interchangeably.

As used herein, unless otherwise apparent from context, "nonlabled reversible terminator [nucleotide]," "NLRT," "reversible terminator nucleotide," "reversible terminator," "RT," and the like are all used to refer to a sequencing reagent comprising a nucleobase or analog, deoxyribose or analog, and a cleavable blocking group. A nonlabled reversible terminator nucleotide may refer to a dNTP (i.e., a substrate for polymerase) or a reversible terminator nucleotide incorporated to into a primer extension product, initially at the 3' terminus and, following additional incorporation cycles, if any, in an "internal" portion of the primer extension product.

As used herein, a "dNTP" includes both naturally occurring deoxyribonucleotide triphosphates and analogs thereof, including analogs with a 3'-O cleavable blocking group.

As used herein, in the context of a cleavable blocking group of a nucleotide analog, the designation 3'-O-' is sometimes implied rather than explicit. For example, the terms "azidomethyl", "3'-O-azidomethyl" are interchangeable as will be apparent from context.

"Amplicon" means the product of a polynucleotide amplification reaction, namely, a population of polynucleotides that are replicated from one or more starting sequences. Amplicons may be produced by a variety of amplification reactions, including but not limited to polymerase chain reactions (PCRs), linear polymerase reactions, nucleic acid sequence-based amplification, rolling circle amplification and like reactions (see, e.g., U.S. Pat. Nos. 4,683,195; 4,965,188; 4,683,202; 4,800,159; 5,210,015; 6,174,670; 5,399,491; 6,287,824 and 5,854,033; and U.S. Pub. No. 2006/0024711).

"Antigen" as used herein means a compound that can be specifically bound by an antibody. Some antigens are immunogens (see, Janeway, et al., Immunobiology, 5th Edition, 2001, Garland Publishing). Some antigens are haptens that are recognized by an antibody but which do not elicit an immune response unless conjugated to a protein. Exemplary antigens include NLRTs, reversible terminator blocking groups, dNTPs, polypeptides, small molecules, lipids, or nucleic acids.

"Array" or "microarray" means a solid support (or collection of solid supports such as beads) having a surface, preferably but not exclusively a planar or substantially planar surface, which carries a collection of sites comprising nucleic acids such that each site of the collection is spatially defined and not overlapping with other sites of the array; that is, the sites are spatially discrete. The array or microarray can also comprise a non-planar interrogatable structure with a surface such as a bead or a well. The oligonucleotides or polynucleotides of the array may be covalently bound to the solid support, or it may be non-covalently bound. Conventional microarray technology is reviewed in, e.g., Schena, Ed. (2000), Microarrays: A Practical Approach (IRL Press, Oxford). As is wel know, the array is usually contained within a flow cell.

As used herein, "random array" or "random microarray" refers to a microarray where the identity of the oligonucleotides or polynucleotides is not discernable, at least initially, from their location but may be determined by a particular biochemistry detection technique on the array.

The terms "reversible," "removable," and "cleavable" in reference to a blocking group have the same meaning.

The terms "reversible blocking group," of a reversible terminator nucleotide may also be referred to as a "removable blocking group," a "cleavable linker," a "blocking moiety," a "blocking group," "reversible terminator blocking group" and the like. A reversible blocking group is a chemical moiety attached to the nucleotide sugar (e.g., deoxyribose), usually at the 3'-O position of the sugar moiety, which prevents addition of a nucleotide by a polymerase at that position. A reversible blocking group can be cleaved by an enzyme (e.g., a phosphatase or esterase), chemical reaction, heat, light, etc., to provide a hydroxyl group at the 3'-position of the nucleoside or nucleotide such that addition of a nucleotide by a polymerase may occur.

"Derivative" or "analogue" means a compound or molecule whose core structure is the same as, or closely resembles that of, a parent compound, but which has a chemical or physical modification, such as a different or additional side group, or 2' and or 3' blocking groups. For example, the base can be a deazapurine. The derivatives should be capable of undergoing Watson-Crick pairing. "Derivative" and "analogue" also mean a synthetic nucleotide or nucleoside derivative having modified base moieties and/or modified sugar moieties. Such derivatives and analogs are discussed in, e.g., Scheit, Nucleotide Analogs (John Wiley & Son, 1980) and Uhlman et al., Chemical Reviews 90:543-584, 1990. Nucleotide analogs can also comprise modified phosphodiester linkages, including phosphorothioate, phosphorodithioate, alkyl-phosphonate, phosphoranilidate and phosphoramidate linkages. The analogs should be capable of undergoing Watson-Crick base pairing. For example, deoxyadenosine analogues include didanosine (ddl) and vidarabine, and adenosine analogues include, BCX4430; deoxycytidine analogs include cytarabine, gemcitabine, emtricitabine (FTC), lamivudine (3TC), and zalcitabine (ddC); guanosine and deoxyguanosine analogues include abacavir, aciclovir, and entecavir; thymidine and deoxythymidine analogues include stavudine (d4T), telbivudine, and zidovudine (azidothymidine, or AZT); and deoxyuridine analogues include idoxuridine and trifluridine. "Derivative", "analog" and "modified" as used herein, may be used interchangeably, and are encompassed by the terms "nucleotide" and "nucleoside" defined herein. In some approaches the term analog refers to a nucletoide with a 3'OH blocking group and a naturally occurring nucleobase (e.g. adenine, cytosine, guanine, urail or thymine).

"Incorporate" means becoming part of a nucleic acid molecule. In SBS, incorporation of an RT occurs when a polymerase adds an RT to a growing DNA strand through the formation of a phosphodiester or modified phosphodiester bond between the 3' position of the pentose of one nucleotide, that is, the 3' nucleotide on the DNA strand, and the 5' position of the pentose on an adjacent nucleotide, that is, the RT being added to the DNA strand.

"Label," in the context of a labeled affinity reagent, means any atom or molecule that can be used to provide a detectable and/or quantifiable signal. Suitable labels include radioisotopes, fluorophores, chromophores, mass labels, electron dense particles, magnetic particles, spin labels, molecules that emit chemiluminescence, electrochemically active molecules, enzymes, cofactors, and enzyme substrates. In some embodiments, the detection label is a molecule containing a charged group (e.g., a molecule containing a cationic group or a molecule containing an anionic group), a fluorescent molecule (e.g., a fluorescent dye), a fluorogenic molecule, or a metal. Optionally, the detection label is a fluorogenic label. A fluorogenic label can be any label that is capable of emitting light when in an unquenched form (e.g., when not quenched by another agent). The fluorescent moiety emits light energy (i.e., fluoresces) at a specific emission wavelength when excited by an appropriate excitation wavelength. When the fluorescent moiety and a quencher moiety are in close proximity, light energy emitted by the fluorescent moiety is absorbed by the quencher moiety. In some embodiments, the fluorogenic dye is a fluorescein, a rhodamine, a phenoxazine, an acridine, a coumarin, or a derivative thereof. In some embodiments, the fluorogenic dye is a carboxyfluorescein. Further examples of suitable fluorogenic dyes include the fluorogenic dyes commercially available under the Alexa Fluor® product line (Life Technologies, Carlsbad, CA). Alternatively, non-fluorogenic labels may be used, including without limitation, redoxgenic labels, reduction tags, thio- or thiol-containing molecules, substituted or unsubstituted alkyls, fluorescent proteins, non-fluorescent dyes, and luminescent proteins.

"Nucleobase" means a nitrogenous base that can base-pair with a complementary nitrogenous base of a template nucleic acid. Exemplary nucleobases include adenine (A), cytosine (C), guanine (G), thymine (T), uracil (U), inosine (I) and derivatives of these. References to thymine herein should be understood to refer equally to uracil unless otherwise clear from context. As used herein, the terms "nucleobase," "nitrogenous base," add "base" are used interchangeably.

A "naturally occurring nucleobase," as used herein, means adenine (A), cytosine (C), guanine (G), thymine (T), or uracil (U). In some cases, naturally occurring nucleobase refers to A, C, G and T (the naturally occurring bases found in DNA).

A "nucleotide" consists of a nucleobase, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogenous base is a derivative of purine or pyrimidine. The purines are adenine (A) and guanine (G), and the pyrimidines are cytosine (C) and thymine (T) (or in the context of RNA, uracil (U)). The C-1 atom of deoxyribose is bonded to N-1 of a pyrimidine or N-9 of a purine. A nucleotide is also a phosphate ester or a nucleoside, with esterification occurring on the hydroxyl group attached to C-5 of the sugar. Nucleotides are usually mono, di- or triphosphates. A "nucleoside" is structurally similar to a nucleotide, but does not include the phosphate moieties. Common abbreviations include "dNTP" for deoxynucleotide triphosphate.

"Nucleic acid" means a polymer of nucleotide monomers. As used herein, the terms may refer to single- or double-stranded forms. Monomers making up nucleic acids and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like, to form duplex or triplex forms. Such monomers and their internucleosidic linkages may be naturally occurring or may be analogs thereof, e.g., naturally occurring or non-naturally occurring analogs. Non-naturally occurring analogs may include peptide nucleic acids, locked nucleic acids, phosphorothioate internucleosidic linkages, bases containing linking groups permitting the attachment of labels, such as fluorophores, or haptens, and the like. Nucleic acids typically range in size from a few monomeric units, e.g., 5-40, when they are usually referred to as "oligonucleotides," to several hundred thousand or more monomeric units. Whenever a nucleic acid or oligonucleotide is represented by a sequence of letters (upper or lower case), such as "AGCT," it will be understood that the nucleotides are in 5' to 3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually nucleic acids comprise the natural nucleosides (e.g., deoxyadenosine, deoxycytidine, deoxyguanosine, deoxythymidine for DNA or their ribose counterparts for RNA) linked by phosphodiester linkages; however, they may also comprise non-natural nucleotide analogs, e.g., modified bases, sugars, or internucleosidic linkages. To those skilled in the art, where an enzyme has specific oligonucleotide or nucleic acid substrate requirements for activity, e.g., single-stranded DNA, RNA/DNA duplex, or the like, then selection of appropriate composition for the oligonucleotide or nucleic acid substrates is well within the knowledge of one of ordinary skill, especially with guidance from treatises, such as Sambrook et al., Molecular Cloning, Second Edition (Cold Spring Harbor Laboratory, New York, 1989), and like references.

"Primer" means an oligonucleotide, either natural or synthetic, which is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 9 to 40 nucleotides, or in some embodiments, from 14 to 36 nucleotides.

"Polynucleotide" is used interchangeably with the term "nucleic acid" to mean DNA, RNA, and hybrid and synthetic nucleic acids and may be single-stranded or double-stranded. "Oligonucleotides" are short polynucleotides of between about 6 and about 300 nucleotides in length. "Complementary polynucleotide" refers to a polynucleotide complementary to a target nucleic acid.

"Solid support" and "support" are used interchangeably and refer to a material or group of materials having a rigid or semi-rigid surface or surfaces. Microarrays usually comprise at least one substantially planar solid phase support, such as a glass microscope slide. The solid support may comprise an ordered or non-ordered array of immobilization sites or wells.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. For short (e.g., less than 150 amino acid) sequences manual alignment and visual inspection of a pair opf sequences can be carried out to determine percent amino acid sequence identity. Alternatively publicly available computer software such as BLAST, BLAST-2, ALIGN, MEGALIGN (DNASTAR), CLUSTALW, or CLUSTAL OMEGA software. In some embodiments, alignment is performed using the CLUSTAL OMEGA software. Those skilled in the art can determine appropriate parameters for aligning sequences, including any algorithms needed to achieve maximal alignment over the full length of the sequences being compared. Optimal alignment of sequences for comparison can be conducted, for example, by the local homology algorithm of Smith and Waterman (*Adv. Appl. Math.* 2:482, 1970), by the homology alignment algorithm of Needleman and Wunsch (*J. Mol. Biol.* 48:443, 1970), by the search for similarity method of Pearson and Lipman (*Proc. Natl. Acad. Sci. USA* 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

A "conservative substitution" or a "conservative amino acid substitution," refers to the substitution of one or more amino acids with one or more chemically or functionally similar amino acids. Conservative substitution tables providing similar amino acids are well known in the art. Polypeptide sequences having such substitutions are known as "conservatively modified variants." Such conservatively modified variants are in addition to and do not exclude polymorphic variants, interspecies homologs, and alleles. Selected groups of amino acids that are considered conservative substitutions for one another, in certain embodiments. For example, the substitution within the following groups of residues is a conservative substitution: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M). Additional conservative substitutions can be found, for example, in Creighton, Proteins: Structures and Molecular Properties 2nd ed. (1993) W. H. Freeman & Co., New York, N.Y. A protein with conservative substitutions relative to a reference protein can be called a conservatively substituted variant.

As used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and/or methods known to those skilled in the art.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publications and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Although the present invention is described primarily with reference to specific embodiments, it is also envisioned that other embodiments will become apparent to those skilled in the art upon reading the present disclosure, and it is intended that such embodiments be contained within the present inventive methods.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, N.Y., Gait, "Oligonucleotide Synthesis: A Practical Approach" 1984, IRL Press, London, Nelson and Cox (2000), Lehninger, Principles of Biochemistry 3rd Ed., W. H. Freeman Pub., New York, N.Y. and Berg et al. (2002) Biochemistry, 5th Ed., W. H. Freeman Pub., New York, N.Y., all of which are herein incorporated in their entirety by reference for all purposes.

3. Nucleotides and Nucleotide Analogs

In various embodiments SBS according to the invention may use non-labeled reversible terminators ("NLRT") (e.g., a nucleotide analog with a blocking group), non-labeled naturally occurring nucleotides (e.g., dATP, dTTP, dCTP and dGTP), or non-labeled nucleotide analogs that do not include a blocking group.

Non-Labeled Reversible Terminators (NLRT)

Non-labeled reversible terminators ("NLRT") of the invention are nucleotide analogs comprising a removable blocking group at the 3'-OH position of the deoxyribose. Although numerous reversible terminators have been described, and reversible terminators are widely used in SBS, the non-labeled reversible terminators used in accord with the present invention differ from those in commercial use because they are non-labeled and because they are used in conjunction with the affinity reagents described herein below. In an aspect the NLRTs of the invention are non-labeled. In one embodiment, non-labeled means the NLRT does not comprise a fluorescent dye. In one embodiment, non-labeled means the NLRT does not comprise a chemiluminescent dye. In one embodiment, non-labeled means the NLRT does not comprise a light emitting moiety.

In some embodiments, exemplary NLRTs have Structure I, below, prior to incorporation of the NLRT into a DNA strand.

Structure I

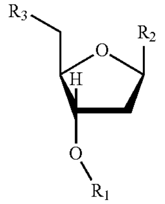

where $R_1$ is a 3'-O reversible blocking group, $R_2$ is, or includes, the nucleobase; and $R_3$ comprises at least one phosphate group or analog thereof.

Reversible blocking groups $R_1$ may be removed after incorporation of the NLRT into a DNA strand. After incorporation of the analog at the 3' terminus of a DNA strand, the removal of the blocking group results in a 3'-OH. Any reversible blocking group may be used. Exemplary reversible blocking groups are described below.

Nucleobases $R_2$ may be, for example, adenine (A), cytosine (C), guanine (G), thymine (T), uracil (U), or inosine (I) or analogs thereof. NLRTs may be referred to according to the nucleobase; for example, an NLRT that has an A nucleobase is referred to as NLRT-A. Thus, the corresponding NLRTs are referred to herein as "NLRT-A," "NLRT-C/" "NLRT-G," "NLRT-T," "NLRT-U," and "NLRT-I," respectively. NLRT-T and NLRT-C may be referred to as NLRT-pyrimidines. NLRT-G and NLRT-A may be referred to as NLRT-purines.

Nucleobase $R_2$ may be any nucleobase or nucleobase analog (e.g., an analog of adenine, cytosine, guanine, thymine, uracil, or inosine). For example, a modification to the naturally occurring nucleobase may be made to increase the immune response to the analog when raising antibodies, or to increase the specificity of the antibody(s) for specific nucleobase.

$R_3$ may be 1-10 phosphate or phosphate analog groups. Phosphate analogs include phosphorothioate (PS), in which the phosphorothioate bond substitutes a sulfur atom for a non-bridging oxygen in the phosphate backbone of the DNA, or any other suitable phosphate analog known in the art. In some cases, $R_3$ may be 1-10 phosphate groups. In some cases, $R_3$ may be 3-12 phosphate groups. In some cases, the nucleotide analogue is a nucleoside triphosphate.

In certain embodiments $R_1$ of Formula I has a MW less than 184, often less than 174, often less than 164, often less than 154, often less than 144, often less than 134, often less than 124, often less than 114, often less than 104, often less than 94, and sometimes less than 84. $R_1$ may act as a hapten and elicit an immune response when conjugated to a larger carrier molecule such as KLH.

It will be appreciated that the unincorporated NLRT nucleotide analogue is suitable as a substrate for an enzyme with DNA polymerase activity and can be incorporated into a DNA strand at the 3' terminus. For example, the reversible blocking group should have a size and structure such that the NLRT is a substrate for at least some DNA polymerases. The incorporation of an NLRT may be accomplished via a terminal transferase, a polymerase or a reverse transcriptase. Any DNA polymerase used in sequencing may be employed, including, for example, a DNA polymerase from *Thermococcus* sp., such as 9° N or mutants thereof, including A485L, including double mutant Y409V and A485L. As is known in the art, polymerases are highly discriminating with regard to the nature of the 3' blocking group. As a result, mutations to the polymerase protein are often needed to drive efficient incorporation. Exemplary DNA polymerases and methods that may be used in the invention include those described in Chen, C., 2014, "DNA Polymerases Drive DNA Sequencing-By-Synthesis Technologies: Both Past and Present" *Frontiers in Microbiology*, Vol. 5, Article 305, Pinheiro, V. et al. 2012 "Polymerase Engineering: From PCR and Sequencing to Synthetic Biology" *Protein Engineering Handbook: Volume* 3:279-302. International patent publications WO2005/024010 and WO2006/120433, each of which is incorporated by reference for all purposes. In some cases the polymerase is DNA polymerase from *Thermococcus* sp., such as 9° N or mutants thereof, including A485L, including double mutant Y409V and A485L. Other examples include KOD polymerase (Kitabayashi et al. 2002. Biosci. Biotechnol. Biochem. 66:10, 2194; Fujii et al. 1999. J. Mol. Biol. 289:835), Taq polymerase, *E. coli* DNA polymerase I, Klenow fragment of DNA polymerase I, T7 or T5 bacteriophage DNA polymerase, HIV reverse transcriptase; Phi29 polymerase, and Bst DNA polymerase.

It will be understood that modifications to the blocking group should not interfere with the reversible terminator function. That is, they should be cleavable to produce a 3'-OH deoxyribonucleotide.

In an embodiment, the RTs have Structure II, below, prior to incorporation of the RT into a DNA strand.

Structure II

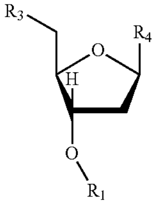

where $R_1$ is a 3'-O reversible blocking group, $R_4$ is a nucleobase selected from adenine (A), cytosine (C), guanine (G), thymine (T), and uracil (U); and $R_3$ comprises at least one (e.g., 1-10) phosphate. In some cases, $R_3$ is triphosphate.

In an embodiment the RTs have Structure III, below, after incorporation of the RT into a DNA strand.

Structure III

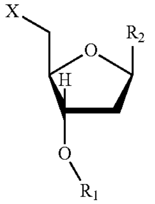

where $R_1$ is a 3'-O reversible blocking group, $R_2$ is a nucleobases such as adenine (A), cytosine (C), guanine (G), thymine (T), uracil (U), or inosine (I) or analogs thereof, and X is a polynucleotide (e.g., GDS) comprising 10-1000 nucleosides linked by phosphate-sugar bonds (e.g., phosphodiester bonds linking the 3' carbon atom of one nucleoside sugar molecule and the 5' carbon atom of another nucleoside sugar molecule).

In another embodiment, the RTs have Structure IV, after incorporation and removal of the reversible blocking group.

Structure IV

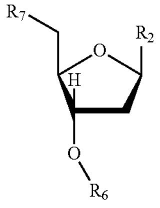

$R_6$ is H and $R_7$ is a polynucleotide (e.g., GDS) comprising 10-1000 nucleosides linked by phosphate-sugar bonds, as defined above, or is $R_3$, as defined above.

In certain embodiments of Structures I, III and IV, $R_2$ is a nucleobase analog (e.g., an analog of A, T, G, C, U) with modifications that do not change the binding specificity of the base (i.e., A analog binds T, T analog binds A, etc.) and (ii) but which may render the analog more immunogenic than the naturally occurring base. In some embodiments the modification may comprise additions of a group comprising no more than 3 carbons. The added group is not removed from nucleosides as they are incorporated into the GDS so that the GDS comprises a plurality of nucleotides comprising the modification. In such embodiments the affinity reagent binds the terminal nucleotide analog, including the modification, but binds internal nucleotides with the modification with much lower affinity.

In applications in which there is more than one terminal nucleotide at a given end (e.g., 3' end), various methods can be used to block ends that are not of interest, e.g. by different blocking groups or attaching the "contaminating" end to a support. For DNB sequencing, for example, there may be 3' ends in addition to the 3' end that is used for sequencing. In PCR clusters produced by bridge PCR, sequencing templates are attached by the 5' end, thus the 3' end of the template is non-extendable with RTs or modified to prevent binding with the molecular binders described here.

Reversible Terminator Blocking Groups

An NLRT used in the present invention can include any suitable blocking group. In some embodiments a suitable blocking group is one that may be removed by a chemical or enzymatic treatment to produce a 3'-OH group. A chemical treatment should not significantly degrade the template or primer extension strand. Various molecular moieties have been described for the 3' blocking group of reversible terminators such as a 3'-O-allyl group (Ju et al., *Proc. Natl. Acad. Sci. USA* 103: 19635-19640, 2006), 3'-O-azidomethyl-dNTPs (Guo et al., *Proc. Nati Acad. Sci. USA* 105, 9145-9150, 2008), aminoalkoxyl groups (Hutter et al., *Nucleosides, Nucleotides and Nucleic Acids,* 29:879-895, 2010) and the 3'-O-(2-cyanoethyl) group (Knapp et al., *Chem. Eur. J.,* 17, 2903-2915, 2011). Exemplary RT blocking groups include —O-azidomethyl and —O-cyanoethenyl. Other exemplary RT blocking groups, for illustration and not limitation, are shown in FIGS. 5 and 6.

In other embodiments, $R_1$ of Formula I (supra) is a substituted or unsubstituted alkyl, substituted or unsubstituted alkenyl, substituted or unsubstituted alkynyl, substituted or unsubstituted heteroalkyl, substituted or unsubstituted heteroalkenyl, or substituted or unsubstituted heteroalkynyl. In some examples, $R_1$ can be selected from the group consisting of allenyl, cis-cyanoethenyl, trans-cyanoethenyl, cis-cyanofluoroethenyl, trans-cyanofluoroethenyl, cis-trifluoromethylethenyl, trans-trifluoromethylethenyl, biscyanoethenyl, bisfluoroethenyl, cis-propenyl, trans-propenyl, nitroethenyl, acetoethenyl, methylcarbonoethenyl, amidoethenyl, methylsulfonoethenyl, methylsulfonoethyl, formimidate, formhydroxymate, vinyloethenyl, ethylenoethenyl, cyanoethylenyl, nitroethylenyl, amidoethylenyl, 3-oxobut-1-ynyl, and 3-methoxy-3-oxoprop-1-ynyl.

A variety of 3'-O reversible blocking groups ($R_1$ in Formula I) may be used in the practice of the invention. According to one embodiment of the methods of the invention, $R_1$ is selected from the group consisting of allyl, azidomethyl, aminoalkoxyl, 2-cyanoethyl, substituted alkyl, unsubstituted alkyl, substituted alkenyl, unsubstituted alkenyl, substituted alkynyl, unsubstituted alkynyl, substituted heteroalkyl, unsubstituted heteroalkyl, substituted heteroalkenyl, unsubstituted heteroalkenyl, substituted heteroalkynyl, unsubstituted heteroalkynyl, allenyl, cis-cyanoethenyl, trans-cyanoethenyl, cis-cyanofluoroethenyl, trans-cyanofluoroethenyl, cis-trifluoromethylethenyl, trans-trifluoromethylethenyl, biscyanoethenyl, bisfluoroethenyl, cis-propenyl, trans-propenyl, nitroethenyl, acetoethenyl, methylcarbonoethenyl, amidoethenyl, methylsulfonoethenyl, methylsulfonoethyl, formimidate, formhydroxymate, vinyloethenyl, ethylenoethenyl, cyanoethylenyl, nitroethylenyl, amidoethylenyl, amino, cyanoethenyl, cyanoethyl, alkoxy, acyl, methoxymethyl, aminoxyl, carbonyl, nitrobenzyl, coumarinyl, and nitronaphthalenyl.

As used herein, the terms "alkyl," "alkenyl," and "alkynyl" include straight- and branched-chain monovalent substituents. Examples include methyl, ethyl, isobutyl, 3-butynyl, and the like. Ranges of these groups useful with the compounds and methods described herein include $C_1$-$C_{10}$ alkyl, $C_2$-$C_{10}$ alkenyl, and $C_2$-$C_{10}$ alkynyl. Additional ranges of these groups useful with the compounds and methods described herein include $C_1$-$C_5$ alkyl, $C_2$-$C_5$ alkenyl, $C_2$-$C_5$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

"Heteroalkyl," "heteroalkenyl," and "heteroalkynyl" are defined similarly as alkyl, alkenyl, and alkynyl, but can contain O, S, or N heteroatoms or combinations thereof within the backbone. Ranges of these groups useful with the compounds and methods described herein include $C_1$-$C_{10}$ heteroalkyl, $C_2$-$C_{10}$ heteroalkenyl, and $C_2$-$C_{10}$ heteroalkynyl. Additional ranges of these groups useful with the compounds and methods described herein include $C_1$-$C_8$ heteroalkyl, $C_2$-$C_8$ heteroalkenyl, $C_2$-$C_5$ heteroalkynyl, $C_1$-$C_6$ heteroalkyl, $C_2$-$C_6$ heteroalkenyl, $C_2$-$C_6$ heteroalkynyl, $C_1$-$C_4$ heteroalkyl, $C_2$-$C_4$ heteroalkenyl, and $C_2$-$C_4$ heteroalkynyl.

The alkyl, alkenyl, alkynyl, heteroalkyl, heteroalkenyl, or heteroalkynyl molecules used herein can be substituted or unsubstituted. As used herein, the term substituted includes the addition of an alkoxy, aryloxy, amino, alkyl, alkenyl, alkynyl, aryl, heteroalkyl, heteroalkenyl, heteroalkynyl, heteroaryl, cycloalkyl, or heterocycloalkyl group to a position attached to the main chain of the alkoxy, aryloxy, amino, alkyl, alkenyl, alkynyl, aryl, heteroalkyl, heteroalkenyl, heteroalkynyl, heteroaryl, cycloalkyl, or heterocycloalkyl, e.g., the replacement of a hydrogen by one of these molecules. Examples of substitution groups include, but are not limited to, hydroxy, halogen (e.g., F, Br, Cl, or I), and carboxyl groups. Conversely, as used herein, the term unsubstituted indicates the alkyl, alkenyl, alkynyl, heteroalkyl, heteroalkenyl, or heteroalkynyl has a full complement of hydrogens, i.e., commensurate with its saturation level, with no substitutions, e.g., linear butane ($-(CH_2)_3-CH_3$).

In other embodiments, the reversible blocking group is an amino-containing blocking group (e.g., $NH_2$—). See, Hutter et al., 2010, *Nucleosides Nucleotides Nucleic Acids* 29(11), incorporated herein by reference, which describes exemplary amino-containing reversible blocking groups. In some embodiments, the reversible blocking group is an allyl-containing blocking group (e.g. $CH_2$═$CHCH_2$—). In some embodiments the reversible blocking group comprises a cyano group (e.g. a cyanoethenyl or cyanoethyl group). In some embodiments, the reversible blocking group is an azido-containing blocking group (e.g., $N_3$—). In some embodiments, the reversible blocking group is azidomethyl ($N_3CH_2$—). In some embodiments, the reversible blocking group is an alkoxy-containing blocking group (e.g., $CH_3CH_2O$—). In some embodiments, the reversible blocking group contains a polyethylene glycol (PEG) moiety with one or more ethylene glycol units. In some embodiments, the reversible blocking group is a substituted or unsubstituted alkyl (i.e., a substituted or unsubstituted hydrocarbon). In some embodiments, the reversible blocking group is acyl. See, U.S. Pat. No. 6,232,465, incorporated herein by reference. In some embodiments, the reversible blocking group is or contains methoxymethyl. In some embodiments, the reversible blocking group is or contains aminoxyl ($H_2NO$—). In some embodiments, the reversible blocking group is or contains carbonyl (O═CH—). In some embodiments, the reversible blocking group comprises an ester or phosphate group.

In some embodiments, the reversible blocking group is nitrobenzyl ($C_6H_4(NO_2)$—$CH_2$—). In some embodiments, the reversible blocking group is coumarinyl (i.e., contains a coumarin moiety or a derivative thereof) wherein, e.g., any one of the CH carbons of the coumarinyl reversible blocking group is covalently attached to the 3'-O of the nucleotide analogue.

In some embodiments, the reversible blocking group is nitronaphthalenyl (i.e., contains a nitronaphthalene moiety or a derivative thereof) wherein, e.g., any one of the CH carbons of the nitronaphthalenyl reversible blocking group is covalently attached to the 3'-O of the nucleoside analogue.

In some embodiments the reversible blocking group is selected from the group:

Structures VI-XIII

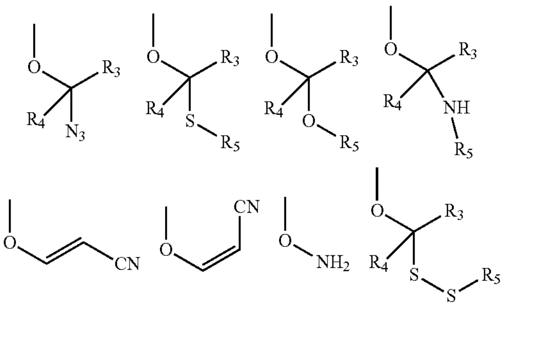

where $R_3$ and $R_4$ are H or alkyl, and $R_5$ is alkyl, cycloalkyl, alkenyl, cycloalkenyl, and benzyl.

Other reversible blocking groups suitable for use in the present invention are described in the literature as a blocking group of a labeled reversible terminator. Generally any suitable reversible blocking group used in sequencing-by-synthesis may be used in the practice of the invention.

Properties of Reversible Terminator Blocking Groups and Nucleotides Containing Them Preferably, for sequencing applications, the blocking group of RTs is removable under reaction conditions that do not interfere with the integrity of the DNA being sequenced. The ideal blocking group will exhibit long term stability, be efficiently incorporated by the polymerase enzyme, cause total blocking of secondary or further incorporation and have the ability to be removed under mild conditions that do not cause damage to the polynucleotide structure, preferably under aqueous conditions.

In certain embodiments of the invention, a blocking group (including the deoxyribose 3' oxygen atom) has a molecular weight (MW) less than 200, often less than 190, often less than 180, often less than 170, often less than 160, often less than 150, often less than 140, often less than 130, often less than 120, often less than 110, and sometimes less than 100). Stated differently, in certain embodiments $R_3$ of Formula I has a MW less than 184, often less than 174, often less than 164, often less than 154, often less than 144, often less than 134, often less than 124, often less than 114, often less than 104, often less than 94, and sometimes less than 84.

The molecular weights of deoxyribonucleotide monophosphates are in the range of about 307 to 322 (dAMP 331.2, dCMP 307.2, dGMP 347.2 and dTMP 322.2). In certain embodiments, the NLRT moiety when incorporated into a GDS (i.e., not including the pyrophosphate of dNTPs) has a molecular weight less than 550, often less than 540, often less than 530, often less than 520, often less than 510, often less than 500, often less than 490, often less than 480, often less than 470, and sometimes less than 460.

Phosphate Containing Moieties

In some embodiments the $R_3$ moiety comprises one or more phosphate and/or phosphate analog moieties. In some embodiments the $R_3$ moiety may have the structure below (Structure V) where n=0 to 12 (usually 0, 1, 3, 4, 5 or 6) and X is H or any structure compatible with incorporation by polymerase in a primer extension reaction. For example, X may be alkyl or any of a variety of linkers described in the art. See, e.g., U.S. Pat. No. 9,702,001, incorporated herein by reference. It will be appreciated that in the process of incorporation of a reversible terminator into a GDS, moiety X is removed from the nucleotide (along with all but the alpha phosphate) such that X is not present in the incorporated reversible terminator deoxyribonucleotide. In certain embodiments X may be a detectable label or affinity tag, with the proviso that affinity reagents of the invention do not bind to moiety X, or discriminate among, reversible terminators based on the presence, absence or structure of moiety X, and that X is not present in the incorporated reversible terminator deoxyribonucleotide.

Structure XIV

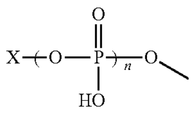

NLRT Sets

In some approaches SBS sequencing according to the invention comprises contacting a sequencing array with multiple NLRTs (e.g., NLRT-A, NLRT-T, NLRT-C and NLRT-G). The contacting may be carried out sequentially, one NLRT at a time. Alternatively, the four NLRTs may be contacted with the sequencing array at the same time, most often as a mixture of the four NLRTs. Together, the four NLRTs make up an "NLRT set." NLRTs of an NLRT set may be packaged as a mixture or may be packaged as a kit comprising each different NLRT is a separate container. In a mixture of the four NLRTs may include each base in equal proportion or may include unequal amounts. I one embodiment members of a NLRT set (NLRT-A, NLRT-T, NLRT-C and NLRT-G) comprise naturally occurring nucleobases and a 3' azidomethyl blocking group.

In one embodiment each NLRT in an NLRT set comprises the same blocking group (e.g. azidomethyl). In one embodiment NLRTs in an NLRT set comprise different blocking groups (e.g. NLRT-A comprises azidomethyl and NLRT-T comprises cyanoethenyl; or NLRT-A and NLRT-G comprise azidomethyl and NLRT-C and NLRT-T comprise cyanoethenyl). If different blocking groups are used, such blocking groups are optionally selected such that the different blocking group can be removed by the same treatment. Alternatively the blocking groups may be selected to be removed by different treatments, optionally at different times. In one embodiment one or more NLRTs in a set comprises a modified (nonnaturally occurring nucleobase).

The NLRTs described herein can be provided or used in the form of a mixture. For example, the mixture can contain two, three, or four (or more) structurally different NLRTs. The structurally different NLRTs can differ in their respective nucleobases. For example, the mixture can contain four structurally different NLRTs each comprising one of the four natural DNA nucleobases (i.e., adenine, cytosine, guanine, and thymine), or derivatives thereof.

For sequencing purposes, different NLRTs in an NLRT set may be separately packaged then mixed on the sequencer itself (e.g., before delivery to a flow cell) or may be packaged together (i.e., premixed). Kits comprising NLRT sets (with different NLRTs packaged in separate containers or as a mixture in the same container) may be provided.

Nucleobase Analogs with Groups that Improve Affinity Reagent Binding

In one embodiment the nucleobase includes a non-removable chemical group that increases the specificity or affinity of the affinity reagent for the nucleobase when present at the 3' terminus of the growing DNA strand (i.e., as the last-incorporated base), but which is not recognized by, or not accessible to, the affinity reagent in nucleotides internal to the primer extension product. In one approach the modification is recognized by or bound by the affinity reagent but with a lower affinity or lower efficiency relative to the same modification in a 3' terminal nucleotide.

For illustration and not limitation, examples of such modified nucleobases include:

STRUCTURES XV-XVIII

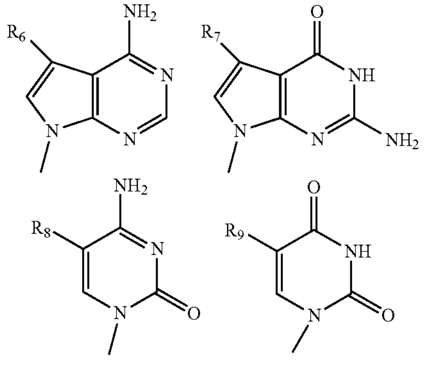

$R_6$, $R_7$, $R_8$, and $R_9$: may be the same or different, each selected from H, I, Br, F, Structures XIX-XXVIII, or any groups that do not interfere with base pairing. Note that when $R_9$ is methyl Structure XVIII in thymidine. In some cases, the modification has the additional benefit of increasing the antigenicity of the nucleotide.

STRUCTURES XIX-XXVIII

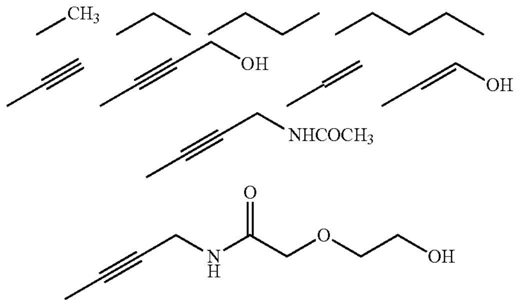

The molecular weights of naturally occurring nucleobases are: adenine 135; guanine 151, thymine 126 and cytosine 111. In some embodiments the nucleobase analog has a molecular weight that does not exceed that of the natural base by more than 10, 20, 30, 40, 50, 60, 70, 80, 90, or 100 Da.

Unblocked dNTPs

In one embodiment, natural dNTPs (e.g., dATP, dGTP, dCTP or dTTP) or dNTP analogs without a 3'-O— blocking group are used for sequencing. In some embodiments, the nucleotides are incorporated one at a time in the sequencing process, as in pyrosequencing or by a polymerase that halts after one base incorporation. Exemplary methods are described in the literature (see, e.g., Ju et al., 2006, *Proc. Natl. Acad. Sci. USA* 103:19635-40, 2006; Guo, *Proc. Nati Acad. Sci. USA* 105, 9145-50, 2008, and Ronaghi et al., *Science,* 281:363-365, 1998) which may be modified for use in the present invention by removal of a label and/or a linker connecting the label to the RT. In some approaches, dNTPs with different nucleobases are added and incorporated sequentially (e.g., A, then G, etc.). Usually nucleobase is separately imaged prior to addition of the next dNTP.

Deoxyribose Analogs

In some embodiments of the invention the sugar (deoxyribose) moiety is modified. For example, an NLRT with the nucleobase adenine, the blocking group azidomethyl, and the sugar deoxyribose can be distinguished from an NLRT with the nucleobase cytosine, the blocking group azidomethyl, and the sugar modified-deoxyribose using an affinity reagent that so that it is recognizes the blocking group and sugar moieties.

Nucleotides Without 3'-O Reversible Terminators

In a different aspect, useful in several applications, a nucleotide with a nonremovable (i.e., not cleavable) 3' blocking group is used in place of a NLRT. In one approach, after detection with the affinity reagent, the last-incorporated base is removed and its position is filed in with a nucleotide that is similar but that has a cleavable blocking group (Koziolkiewicz et al., FEBS Lett. 434:77-82, 1998).

The examples given above include reversible blocking groups attached to the nucleotide via the 3'-O of the deoxyribose sugar moiety. The present invention also includes NLRTs with reversible and non-reversible blocking groups attached to the 2'-O— of the deoxyribose sugar. These embodiments may be used for single base detection (single or a few base primer extension), monitoring gaps and nicks in DNA and other detection methods. Thus, one of ordinary skill in the art will be able to apply the methods and information herein to NLRTs with 2', rather than 3', blocking groups.

4. Affinity Reagents

The present invention uses affinity reagents that specifically bind to NLRTs at the 3' end of a GDS, e.g., after incorporation by a polymerase to the end of a growing DNA chain during SBS. In one embodiment the affinity reagent binds an NLRT of Structure III. In one embodiment the affinity reagent binds an NLRT of Structure IV.

Affinity Reagents Generally

In one aspect the invention relates to affinity reagents used to detect the presence or absence of an NLRT incorporated at the 3' end of a nucleic acid. An affinity reagent is a molecule or macromolecule that specifically binds an NLRT based on a structural feature of the incorporated NLRT. For example, an affinity reagent may specifically bind to an NLRT having, e.g., a particular base and/or particular reversible blocking group.

Exemplary affinity reagents include antibodies (including binding fragments of antibodies, single chain antibodies, etc.), nucleic acid aptamers, affimers, and knottin as described in US Patent Publication 2018/0223358. For illustration, one example of an affinity reagent is a monoclonal antibody (mAb) that binds with high affinity to an incorporated NLRT at the 3' end of a DNA strand when the NLRT comprises the nucleobase adenosine and an azidomethyl reversible blocking group but does not bind with high affinity to an NLRT incorporated at the 3' end of a DNA strand when the NLRT comprises the nucleobase adenosine but has a 3' hydroxyl group rather than an azidomethyl reversible blocker, and does not bind with high affinity to an NLRT incorporated at the 3' terminus of a DNA strand comprising the nucleobase cytosine, guanine, or thymine, each with or without an azidomethyl reversible blocking group. Affinity reagents may be directly or indirectly labeled.

"Specificity" is the degree to the affinity reagent discriminates between different molecules (e.g., NLRTs) as measured, for example, by relative binding affinities of the affinity reagent for the molecules. With respect to the affinity reagents of the present invention, an affinity reagent should have substantially higher affinity for one NLRT (its target RT) than for other NLRTs (for example, the affinity reagent binds to a C nucleoside analogue but not to A, T or G). Also, the affinity reagent binds to its target nucleoside analog at the end of a polynucleotide when incorporated by a polymerase at the 3' end of a growing DNA chain, but not to a nucleotide base elsewhere on the DNA chain. An affinity reagent is specific for a particular NLRT, such as NLRT-A, if in the presence of a plurality (e.g., an array) of template polynucleotides are present in which 3'-termini of GDSs include NLRT-A, NLRT-T, NLRT-C, NLRT-G (e.g., in an array) the affinity reagent binds preferentially to NLRT-A under reaction conditions used in SBS sequencing. As used herein, "preferential binding" of an affinity agent to a first structure compared to a second structure means the affinity agent binds the first structure but does not bind the second structure or binds the second structure less strongly (i.e., with a lower affinity) or less efficiently.

In the context of the binding of an affinity reagent to an incorporated NLRT, the terms "specific binding," "specifically binds," and the like refer to the preferential association of an affinity reagent with a particular NLRT (e.g., NLRT-A having a 3'-O methylazido group) in comparison to an NLRT with a different nucleobase (NLRT-T, -C, or -G), a different blocking group, or no blocking group (e.g., deoxyadenosine with a 3'-OH). Specific binding between an affinity reagent and the NLRT sometimes means an affinity of at least $10^{-6}$ $M^{-1}$ (i.e., an affinity having a lower numerical value than $10^{-6}$ $M^{-1}$ as measured by the dissociation constant $K_d$). Affinities greater than $10^{-8}$ $M^{-1}$ are preferred. Specific binding can be determined using any assay for binding (e.g., antibody binding) known in the art, including Western Blot, enzyme-linked immunosorbent assay (ELISA), flow cytometry, immunohistochemistry, and detection of fluorescently labeled affinity reagent bound to a target NLRT in a sequencing reaction. As discussed herein below, specificity of binding can be determined by positive and negative binding assays.

The specific binding interaction between an affinity reagent, such as an antibody, and an incorporated reversible terminator deoxyribonucleotide can be described in various ways including with reference to the portion, or moiety, of the incorporated reversible terminator deoxyribonucleotide responsible for the specificity. An analogy is useful here: Imagine a protein with two domains, domain 1 and domain 2. Two different antibodies may specifically bind the protein. However, they may recognize different epitopes. For example, one antibody may bind an epitope in domain 1 and the second antibody may bind an epitope in domain 2. In this hypothetical, if modifications are made in domain 1 this may affect the binding of the protein by the first antibody, without changing the binding by the second antibody. In this case the binding of protein by the first antibody may be said to be "dependent on" on domain 1, meaning that a change in domain 1 (e.g., a change in amino acid sequence) will change the binding properties of antibody 1 (e.g., abolish binding, increase binding affinity, reduce binding affinity, etc.). Equivalently, domain 1 may be said to be "responsible for" binding by antibody 1. In the case of an incorporated reversible terminator deoxyribonucleotide specificity of binding may be due to a structural feature of one moiety (e.g., the blocking group) and be unaffected by the structure of other moieties (e.g., the nucleobase) by other moieties. Alternatively, specificity of binding may be due to structural features of multiple moieties (e.g., both the nucleobase and blocking group), etc. Where binding of an affinity reagent to an incorporated reversible terminator deoxyribonucleotide requires the presence of particular structural features of a moiety, the binding by the affinity reagent may "be specific for" or "based on" the presence or absence of a moiety with those structural features. Equivalently, the moiety with those structural features may be "responsible" for binding by the affinity reagent, or binding of the affinity reagent may be "dependent" on the presence of a moiety with those structural features.

It should also be noted that "specificity" may depend on the environment. For example, imagine an affinity reagent that binds both A and A', but does not bind B, C or D. In a reaction or sample containing A, A', B and C, the affinity reagent may bind both A and A', and thus may not be considered to "specifically bind" A. However, in a reaction or sample containing A, B, C and D, the affinity reagent would bind only A, and in that environment would be said to specifically bind A. In another example, in a sample containing A, A', B and C, the affinity reagent may bind A and A' with different affinities, or efficiencies, so that the binding to A and the binding to A' could be distinguished on those bases.

Another related term is "discriminate" (or sometimes "distinguish"). An affinity reagent that binds incorporated reversible terminator deoxyribonucleotides only if particular blocking group (e.g., azidomethyl) is present, but binds to incorporated reversible terminator deoxyribonucleotides with azidomethyl blocking groups without regard to what nucleobase is present, can be said to "discriminate" between incorporated reversible terminator deoxyribonucleotides with and without an azidomethyl blocking group or, more broadly, can be said to "discriminate based on the blocking group."

The specificity of an affinity reagent is a result of the process used to make the affinity reagent. For example, a reagent that recognizes an azidomethyl blocking moiety may be tested empirically with positive and negative binding assays. For illustration, in one approach the reagent is an antibody that binds an NLRT based on the presence of an O-azidomethyl blocking moiety. In one approach antibodies are raised against the hapten O-azidomethyl using azidomethyl conjugated to keyhole limpet hemocyanin. The desired antibody can be selected for binding to 3'-O-azidomethyl-2'-deoxyguanine but against binding to other deoxyguanine nucleotides such as 3'-O-2-(cyanoethoxy)methyl-2'-deoxyguanine; 3'-O-(2-nitrobenzyl)-2'-deoxyguanine; and 3'-O-allyl-2'-deoxyguanine; and against binding other azidomethyl NLRTs such as 3'-O-azidomethyl-2'-deoxyadenosine; 3'-O-azidomethyl-2'-deoxycytosine; and 3'-O-azidomethyl-2'-deoxythymine.

The nature of antibody-hapten interactions can also be determined using art-known methods such as those described in Al Qaraghuli, 2015, "Defining the complementarities between antibodies and haptens to refine our understanding and aid the prediction of a successful binding interaction" *BMC Biotechnology,* 15(1) p.1; Britta et al., 2005, "Generation of hapten-specific recombinant antibodies: Antibody phage display technology: A review" *Vet Med.* 50:231-52; Charlton et al., 2002. "Isolation of anti-hapten specific antibody fragments from combinatorial libraries" *Methods Mol Biol.* 178:159-71; and Hongtao et al., 2014, "Molecular Modeling Application on Hapten Epitope Prediction: An Enantioselective Immunoassay for Ofloxacin Optical Isomers" *J. Agric. Food Chem.* 62 (31) pp 7804-7812. It will be understood that describing an affinity reagent as binding certain moieties (e.g., a nucleobase and a sugar moiety) does not exclude binding to other parts of the incorporated nucleotide. For example, an affinity reagent that binding a nucleobase and a sugar moiety may also bind a blocking group.

The affinity reagent may specifically recognize the nucleobase, the sugar (e.g., deoxyribose), the blocking group, or any other moiety or combination thereof in the target NLRT. In one approach the affinity reagent recognizes an epitope comprising the blocking group. In another approach the affinity reagent recognizes an epitope comprising the nucleobase. In another approach the affinity reagent recognizes an epitope comprising the nucleobase and the blocking group. It will be understood that even if the affinity reagent does not contact a moiety, the moiety may dictate the position of other moieties. For example, for an affinity reagent that discriminates NLRT based on the nucleobase and 3' blocking group, the deoxyribose moiety is required to position a nucleobase and 3' blocking group for recognition.

In the case of affinity reagents that are antibodies, specific binding can be determined using any assay for antibody binding known in the art, including Western Blot, enzyme-linked immunosorbent assay (ELISA), flow cytometry, or column chromatography. In one approach specific binding is demonstrated using an ELISA type assay. For example, serum antibodies raised against 3'-azidomethyl-dC can be serially titrated against a bound substrate of 3'-O-azidomethyl-dC (positive specificity assay) and nucleotide(s) such as 3'-O-azidomethyl-dG or dA or 3'-OH-dC (negative specificity assay).

In some embodiments, the base-specific binding of an affinity reagent for its target nucleoside is 2- to 100-fold higher than binding to other nucleosides or analogs. In some embodiments base-specific binding of an affinity reagent for its target nucleoside is at least 10-fold higher than binding to other nucleosides, or at least 30-fold higher, or at least 100-fold higher The preferred the antibody binding efficiency to the specific base is at the concentration lower than 100 μM, or lower than 1 nM, or lower than 10 nM, or lower than 1 μM.

Affinity reagents with desired specificity can be selected using positive selection (e.g., binds to target molecule) and negative selection (e.g., does not bind to molecules that are not target molecule). In the case of affinity reagents that are monoclonal antibodies, one selection protocol is described below in the section "Screening and selection of monoclonal antibodies."

An affinity reagent may bind both a dNTP in solution and the corresponding nucleotide incorporated at the 3' terminus of a primer extension product. In some embodiments the affinity reagent does not bind an unincorporated NLRT (e.g., an NLRT in solution) or binds with a significantly lower specificity. In general, however, binding of non-incorporated NLRTs by affinity reagents does not occur in the process of sequencing because unincorporated NLRTs are removed (washed away) prior to introduction of the affinity reagents. Alternatively, complexes formed by affinity reagents bound to NLRTs are removed (washed away) prior to imaging.

In one approach, the affinity reagent binds specifically to the nucleobase and distinguishes among different bases (e.g., A, T, G, C) in part based on the presence or absence of a 3'-OH group. In this approach the affinity reagent distinguishes a nucleotide at the 3' end of a GDS with a 3'-OH from incorporated nucleotides interior to the GDS (not at the 3' end). In some cases the affinity reagent that recognizes a specific nucleobase also distinguishes between the presence or absence of a 3'-OH groups, thereby recognizing an incorporated NLRT as a 3' terminal nucleotide with a particular nucleobase.

In one approach the affinity reagent recognizes an epitope comprising the blocking group but does not distinguish between bases. For example, given four RT blocking groups [A. azidomethyl, B. 2-(cyanoethoxy)methyl, C. 3'-O-(2-nitrobenzyl), and D. 3'-O-allyl] affinity reagents can be produced that distinguish the four blocking groups. For illustration, given the deoxyguanine analogs labeled A to D below, an affinity reagent can be selected that recognizes only one, but not the other three, NLRTs.

A. 3'-O— azidomethyl-2'-deoxyguanine

B. 3'-O-2-(cyanoethoxy)methyl-2'-deoxyguanine

C. 3'-O-(2-nitrobenzyl)-2'-deoxyguanine

D. 3'-O-allyl-2'-deoxyguanine

In some embodiments the selected affinity reagent does not distinguish between nucleotides with different nucleobases provided they share the same blocking group. For example, an affinity reagent that recognizes B (3'-O-2-(cyanoethoxy)methyl-2'-deoxyguanine), above, may also recognize 3'-O-2-(cyanoethoxy)methyl-2'-deoxyadenine;

3'-O-2-(cyanoethoxy)methyl-2'-deoxythymine; and 3'-O-2-(cyanoethoxy)methyl-2'-deoxycytosine.

Although the example above described an embodiment in which the four nucleotides had different blocking groups with very distinct structural differences (e.g., azidomethyl vs 2-(cyanoethoxy)methyl, in some embodiments of the present invention there are only small differences between blocking groups bound by distinct affinity reagents. For example, in a blocking group a hydrogen atom may be replaced by a fluorine atom or methyl group to generate three related blocking groups [blocking group, F substitute blocking group, methyl substituted blocking group] that can be distinguished by a set of affinity reagents.

In some embodiments of the invention sequencing is carried out using four NLRT each having a 3'-O-blocking group in which the blocking groups of 2 or more, alternatively 3 or more, alternatively all 4 are structurally similar in the sense that (1) they have the same number of atoms or the number of atoms differs by no more than a small number (e.g., 1, 2, 3, 4, 5, 6, 7, 8, 9, or 10); (2) the molecular formulas of the blocking group moieties differ by 1 to 10 atoms (e.g., single H replaced by $CH_3$ is 3 differences; H replaced by F, O replaced by S), e.g., 1 atom, 2 atoms, 3 atoms, 4 atoms, 6 atoms, 7 atoms, 8 atoms, 9 atoms or 10 atoms. In these and other embodiments the blocking group moiety may have any of the properties described hereinabove in the section captioned "Properties of Reversible Terminator Blocking Groups and Nucleotides Containing Them."

In some embodiments the affinity reagent binds to a NLRT (e.g., 3'-O-azidomethyl-2'-deoxyguanine) but does not bind to the corresponding unblocked nucleotide (e.g., 3'-OH-2'-deoxyguanine).

In one embodiment, the affinity reagent binds to a NLRT (e.g., 3'-O-azidomethyl-2'-deoxyguanine) but disassociates from the nucleotide analog after treatment to remove the blocking group (e.g., after treatment with TCEP (tris(2-carboxyethyl)phosphine)).

An affinity reagent that specifically recognizes NLRT-A is referred to as antiA. An affinity reagent that specifically recognizes NLRT-T is referred to as antiT. An affinity reagent that specifically recognizes NLRT-G is referred to as antiG. An affinity reagent that specifically recognizes NLRT-C is referred to as antiC. An affinity reagent that specifically recognizes NLRT-U is referred to as antiU. Although this nomenclature is similar to that used to describe immunoglobulin specificity, the use of this terminology in the present invention is not intended to indicate that that the affinity reagent is necessarily an antibody.

Affinity reagents may be directly labeled. Alternatively, affinity reagents may be an unlabeled primary affinity reagent detectable using a labeled secondary affinity reagent. For example an unlabeled primary affinity reagent that specifically binds a NLRT may be detected with a labeled secondary affinity reagent that binds the primary affinity reagent (for example, a labeled antibody that binds the primary affinity reagent).

Exemplary Affinity Reagents

In some embodiments, the affinity reagent is an antibody. Any method for antibody production that is known in the art may be employed.

Antibodies

As used herein, "antibody" means an immunoglobulin molecule or composition (e.g., monoclonal and polyclonal antibodies), as well as genetically engineered forms such as chimeric antibodies and other antibodies described herein.

Immunoglobulin G molecules are tetramers with two heavy chains and two light chains. The heavy and light chains contain constant regions and a variable region (VH and VL). The VH and VL regions can be further subdivided into regions of hypervariability (hypervariable regions (HVRs), also called complementarity determining regions (CDRs)) interspersed with regions that are more conserved. The more conserved regions are called framework regions (FRs). Each VH and VL generally comprises three CDRs and four FRs, arranged in the following order (from N-terminus to C-terminus): FR1-CDR1-FR2-CDR2-FR3-CDR3-FR4. The CDRs are involved in antigen binding, and confer antigen specificity and binding affinity to the antibody. See Kabat et al. (1991) Sequences of Proteins of Immunological Interest 5th ed., Public Health Service, National Institutes of Health, Bethesda, MD) CDR sequences on the heavy chain (VH) may be designated as CDRH1, 2, 3, while CDR sequences on the light chain (Vv) may be designated as CDRL1, 2, 3.

The antibody may be from recombinant sources and/or produced in animals, including without limitation transgenic animals. The term "antibody" as used herein includes "antibody fragments," including without limitation Fab, Fab', $F(ab')_2$, scFv, dsFv, ds-scFv, dimers, minibodies, nanobodies, diabodies, and multimers thereof and bispecific antibody fragments. Antibodies can be fragmented using conventional techniques. For example, $F(ab')_2$ fragments can be generated by treating an antibody with pepsin. The resulting $F(ab')_2$ fragment can be treated to reduce disulfide bridges to produce Fab' fragments. Papain digestion can lead to the formation of Fab fragments. Fab, Fab' and $F(ab')_2$, scFv, dsFv, ds-scFv, dimers, minibodies, diabodies, bispecific antibody fragments and other fragments can also be synthesized by recombinant techniques. The antibodies can be in any useful isotype, including IgM and IgG, such as IgG1, IgG2, IgG3 and IgG4.

Antibodies may be chimeric antibodies in which a portion of the heavy and/or light chain is derived from a particular source or species, while the remainder of the heavy and/or light chain is derived from a different source or species. CDR grafted antibodies comprise CDR sequences from one source (e.g., rabbits) and framework residues from a different source (e.g., goat). For example, CDRs from a rabbit IgG can be spliced into a mouse antibody framework or scaffold. For illustration, antibodies may be "humanized" forms of non-human antibodies. Humanized antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies can also comprise residues that are not found in either the recipient antibody or the donor antibody. Such modifications can be made to further refine antibody function. For further details, see Jones et al., Nature, 1986, 321:522-525; Riechmann et al., Nature, 1988, 332:323-329; and Presta, Curr. Op. Struct. Biol., 1992, 2:593-596, each of which is incorporated by reference in its entirety. Humanized antibodies are produced primarily for therapeutic uses and have no unique value in the sequencing context. They are discussed here to illustrate they types of modifications that can be made to antibodies. Similar chimeric antibodies can be made in which both the donor and recipient antibodies are non-human.

In some embodiments, the affinity reagents are minibodies. Other antibody binding moieties include "single-chain Fv" or "sFv" or "scFv" fragments comprise a VH domain and a VL domain in a single polypeptide chain. The VH and VL are generally linked by a peptide linker. See Pluckthun A. (1994). Antibodies from *Escherichia coli* in Rosenberg M. & Moore G. P. (Eds.), The Pharmacology of Monoclonal Antibodies vol. 113 (pp. 269-315). Springer-Verlag, New York, incorporated by reference in its entirety. In some embodiments, the linker can be a single amino acid. In some embodiments, the linker can be a chemical bond.

Minibodies are engineered single chain antibody constructs comprised of the variable heavy (VH) and variable light (VL) chain domains of a native antibody fused to the hinge region and to the CH3 domain of the immunoglobulin molecule. Minibodies are thus small versions of whole antibodies encoded in a single protein chain which retain the antigen binding region, the CH3 domain to permit assembly into a bivalent molecule and the antibody hinge to accommodate dimerization by disulfide linkages. A single domain antibody (sdAb) may also be used. A single domain antibody, or nanobody (Ablynx), is an antibody fragment with a single monomeric variable antibody domain. See Holt et al., Trends in Biotechnol., 2003, 21:484-490, incorporated by reference in its entirety. Single domain antibodies bind selectively to specific antigens and are smaller (MW 12-15 kDa) than conventional antibodies. Other antibody binding moieties include heavy chain antibodies. "Heavy chain antibody" refers to an antibody which comprises at least two heavy chains and lacks light chains. See Harmesen et al., Applied Microbiology and Biotechnology, 77:13-22, 2007; and Hamers-Casterman et al., Nature, 1993, 363:446-448; each of which is incorporated by reference in its entirety. Other antibody binding moieties include antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, rat, guinea, pig, human, camel, llama, fish, shark, goat, rabbit, and bovine. Single domain antibodies are described, for example, in International Application Publication No. WO 94/04678. Other antibody binding moieties include a single light chain antibody is provided in Masat et al., *Proc. Natl. Acad. Sci. USA,* 1994, 91:893-896

Other affinity reagents comprise "alternative scaffolds" such as those derived from fibronectin (e.g., Adnectins™), the β-sandwich (e.g., iMab), lipocalin (e.g., Anticalins), EETI-II/AGRP, BPTI/LACI-D1/ITI-D2 (e.g., Kunitz domains), thioredoxin peptide aptamers, protein A (e.g., Affibody), ankyrin repeats (e.g., DARPins), gamma-B-crystallin/ubiquitin (e.g., Affilins), CTLD3 (e.g., Tetranectins), and (LDLR-A module) (e.g., Avimers). Additional information on alternative scaffolds is provided in Binz et al., Nat. Biotechnol., 2005 23:1257-1268; and Skerra, Current Opin. in Biotech., 2007 18:295-304, each of which is incorporated by reference in its entirety.

Antibody Fusion Affinity Reagents

In addition, fusions directly linking recombinant antibody fragments, e.g., single-chain Fv fragments (scFvs) with reporter proteins (Skerra and Plückthun, Science 240:1038-1041, 1988; Bird et al., Science 242:423-426, 1988; Huston et al., Methods Enzymol 203:46-88, 1991; Ahmad et al., Clin. Dev. Immunol. 2012:1, 2012) may be used. For example, photoproteins with bioluminescent properties, e.g., luciferases and aequorin, may be used as reporter proteins in fusion proteins with antibody fragments, epitope peptides and streptavidin, for example (Oyama et al., Anal Chem 87:12387-12395, 2015; Wang et al., Anal Chim Acta 435: 255-263, 2001; Desai et al., Anal Biochem 294:132-140, 2001; Inouye et al., Biosci Biotechnol Biochem 75:568-571, 2011). For example, Morino et al. (J. Immunol. Methods 257:175-184, 2001) described fusions of single-chain Fv-CL fragments fused with green fluorescent protein (GFP) or red fluorescent protein (RFP), and Luria et al. (mAbs 4:3, 373-384, 2012) described full-length IgG antibodies fused to Superfolder GFP (SFGFP) and mCherry were functional in antigen binding and maintained fluorescent intensity, and additionally linked several SFGFPs in tandem to each IgG, with fluorescence intensity increasing accordingly.

Production of Antibodies

Methods for raising polyclonal antibodies are known and may be used to produce NLRT-specific antibodies. For one approach see Example 2 of WO 2018/129214. According to one method for raising polyclonal antibodies specific for a particular NLRT, e.g., NLRT-A, a rabbit is injected with NLRT-A (conjugated to an immunogen) to raise antibodies, and antibodies are selected to do not bind to: the same structure lacking the blocking group (e.g., having a 3'-OH), and the other NLRTs (NLRT-T, NLRT-G, and NLRT-C). Thus, the polyclonal antibodies produced recognize the specific NLRT that is incorporated at the 3' end of a growing DNA chain at a particular position on a sequencing array, but not that same nucleoside at other interior positions of the growing chain or to other NLRTs that may be incorporated elsewhere on the array. (The polyclonal antibodies may also recognize unincorporated NLRT-A, but unincorporated NLRTs are washed away before incorporated NLRTs are probed using labeled affinity reagents.

It will be recognized that, depending on the needs of the investigator, it is not always necessary to raise antibodies against the entire NLRT. For example, if antibodies specific for the blocking group are desired, the hapten may be deoxyribose with a 3'-O-blocking group (i.e., no nucleobase) or the 3'-O-blocking group alone. In some embodiments antibodies are raised against a polynucleotide with a NLRT of interest at the 3' end. In some embodiments antibodies are raised against a polynucleotide annealed to a template molecule.

For example, to produce monoclonal antibodies, antibody producing cells (lymphocytes) can be harvested from an animal immunized with an immunogen comprising an NLRT and fused with myeloma cells by standard somatic cell fusion procedures thus immortalizing these cells and yielding hybridoma cells. Such techniques are well known in the art (e.g., the hybridoma technique originally developed by Kohler and Milstein (Kohler and Milstein Nature 256:495-497, 1975) as well as other techniques such as the human B-cell hybridoma technique (Kozbor et al., 1983, *Immunol. Today* 4:72), the EBV-hybridoma technique to produce human monoclonal antibodies (Cole et al., 1986, *Methods Enzymol,* 121:140-67), and screening of combinatorial antibody libraries (Huse et al., 1989, *Science* 246: 1275). Hybridoma cells can be screened immunochemically for production of antibodies specifically reactive with a particular RT and the monoclonal antibodies can be isolated. In-vitro production of monoclonal antibodies may be carried out using art-known methods. See, e.g., Li, N. et al., MAbs.

2, 466-477 (2010); Shukla, A. & J. Thömmes, Trends in Biotechnology. 28, 253-261 (2010).

Specific antibodies, or antibody fragments, reactive against particular antigens or molecules, may also be generated by screening expression libraries encoding immunoglobulin genes, or portions thereof, expressed in bacteria with cell surface components. For example, complete Fab fragments, VH regions and FV regions can be expressed in bacteria using phage expression libraries (see for example Ward et al., Nature 341:544-546, 1989; Huse et al. Science 246:1275, 1989; and McCafferty et al. Nature 348:552-554, 1990).

Additionally, antibodies specific for a target NLRT are readily isolated by screening antibody phage display libraries. For example, an antibody phage library is optionally screened by using to identify antibody fragments specific for a target NLRT. Methods for screening antibody phage libraries are well known in the art.

Anti-NLRT antibodies also may be produced in a cell-free system. Nonlimiting exemplary cell-free systems are described, e.g., in Sitaraman et al., Methods Mol. Biol. 498: 229-44, 2009; Spirin, Trends Biotechnol. 22: 538-45, 2004; and Endo et al., Biotechnol. Adv. 21: 695-713, 2003.

Purification of Antibodies:

Anti-NLRT antibodies may be purified by any suitable method. Such methods include, but are not limited to, the use of affinity matrices and/or chromatography (e.g., affinity chromatography, hydrophobic interaction chromatography, size-exclusion chromatography and ion exchange chromatography). In one approach affinity purification using Ig binding proteins such as Protein A, Protein G, Protein A/G, and Protein L are immobilized on resin and used to purify antibodies of interest.

Screening and Selection of Monoclonal Antibodies

The ordinarily skilled artisan guided by this disclosure will be able to produce polyclonal antisera against any desired NLRTs (e.g., NLRT-A, NLRT-T, NLRT-C, NLRT-G) having a blocking moiety at the 3'-OH of deoxyribose). In one approach, as described in the Example 1 and in US 2018/0223358, test animals (e.g., rabbits) are immunized with KLH-antigen every two weeks for 3 months. Serum is collected one week post immunization and is tested by ELISA tested against both target (e.g., NLRT-A) and non-target (e.g., NLRT-T, NLRT-C, NLRT-G) antigens to determine antibody response. Splenocytes are obtained from animals giving a good and specific response. Splenocytes are tested for binding to the target NLRT-A. For example, splenocytes may be sorted by FACS using biotinylated NLRT-A with fluorescent streptavidin detection to create plates of cultured colonies from single cells. Nucleotide analogs with zero or one phosphates may be used in the immunization and/or FACS sorting steps.

Supernatant from these single cell cultures is tested by ELISA against both target and non-target antigens. In one approach, supernatant is tested against target and non-target BSA-NLRTs bound to wells of an ELISA plate (see FIG. 9 of WO 2018/129214). In a second approach, positive and negative ELISA screens are conducted in which the ELISA target antigens are a complex comprising immobilized template DNA hybridized to an extended primer with the target (for positive screening) or non-target (for negative screening) NLRT incorporated at the 3'terminus of the extended primer. The complex is a partial duplex so that the template strand extends beyond the 3' primer terminus mimicking the DNA structure generated in sequencing. In one approach the complex is created for screening by immobilizing a 3' biotinylated DNA template on a streptavidin-coated surface (e.g., well of an ELISA plate), hybridizing a primer, and incorporating an NLRT. The same template may be used screen for different nucleotide specificity by using different primers in the incorporation step. In a related approach, a hairpin oligonucleotide (biotinylated in the loop portion for fluorescent streptavidin detection) has reversible terminator incorporated into the duplex portion of the hairpin at the 3' terminus and is used in a binding assay. In an other approach, a biotinylated primer hybridized to a template may be used to add the 3'-NLRT. The template may be removed (e.g., by denaturation) and the primer captured on streptavidin. This resulting structure may be used for screening to mimic partially denatured DNA ends.

High performing splenocyte clones are selected and IgG-encoding sequences are used to clone and express antibodies. In one approach sequences are cloned into a linear expression module (LEM) for transfection into HEK cell lines (HEK cells) and productive LEM's are cloned into plasmids for transfection and production of purified antibodies. Selected antibodies may be be further altered, for example, to improve affinity for the target, for example, by affinity maturation. See Marks et al. (Bio/Technology, 1992, 10:779-783) which describes affinity maturation by VH and VL domain shuffling. Also see Barbas et al. (Proc. Nat. Acad. Sci. USA., 1994, 91:3809-3813 (describing random mutagenesis of CDR and/or framework residues).

Exemplary Monoclonal Antibodies

Exemplary rabbit anti-NLRT antibodies were produced as described in Examples. A number of monoclonal antibodies that bind specifically to target NLRT5 are discussed herein, including without limitation monoclonal antibodies specific for: 3'-azidomethyl-dA (N3A): mAbs 2C5, 3612, 17H7, and 1867); monoclonal antibodies specific for 3'-azidomethyl-dC (N3C): mAbs 168, 269, 4C8, 1A10, and 367; monoclonal antibodies specific for 3'-azidomethyl-dG (N3G): mAbs 3G6, 5F6, 468, 4G8, and 7C8; and monoclonal antibodies specific for 3'-azidomethyl-dT (N3T): mAbs 2D4, 2D10, 1F9, and 367. The amino acid sequences of heavy and light chains (including the signal peptides) are provided in FIG. 1A-H and in Table 2, below.

TABLE 2

| SEQ ID NO: | Sequence | Name |
|---|---|---|
| 1 | METGLRWLLLVAVLKGVQCQEQLEESGGDLVKPEGSLTLTCKASGEDFSSYYYMCWV RQAPGKGLEWIACIYGGSSGTTYYASWPKGRFTISKTSSTTVTLQMTSLTAADTATYFC MRGANGAGFGDANLWGPGTLVTVSSGQPKAPSVFPLAPCCGDTPSSTVTLGCLVKG YLPEPVTVTWNSGTLTNGVRTFPSVRQSSGLYSLSSVVSVTSSSQPVTCNVAHPATNT KVDKTVAPSTCSKPMCPPPELPGGPSVFIFPPKPKDTLMISRTPEVTCVVVDVSQDDPE VQFTWYINNEQVRTARPPLREQQFNSTIRVVSTLPIAHQDWLRGKEFKCKVHNKALP | N3A_2C5_H |

TABLE 2-continued

| SEQ ID NO: | Sequence | Name |
|---|---|---|
| | APIEKTISKARGQPLEPKVYTMGPPREELSSRSVSLTCMINGFYPSDISVEWEKNGKAE<br>DNYKTTPTVLDSDGSYFLYSKLSVPTSEWQRGDVFTCSVMHEALHNHYTQKSISRSPG<br>K | |
| 2 | MDTRAPTQLLGLLLLWLPGATFAQVLTQTPSSVSAAVGGTVTINCQSSPSVYSNYLSW<br>FQQKPGQPPKLLIYSASTLASGVPSRFRGSGSGTQFTLTISDVQCDDAANYYCAGGYTY<br>TSDSIWAFGGGTEVVVKGDPVAPTVLIFPPAADQVATGTVTIVCVANKYFPDVTVTW<br>EVDGTTQTTGIENSKTPQNSADCTYNLSSTLTLTSTQYNSHKEYTCKVTQGTTSVVQSF<br>NRGDC | N3A_2C5_L |
| 3 | METGLRWLLLVAVLKGVQCQEQLEEAGGDLVKPEGSLRLTCKASGFDFSSYYYMCW<br>VRQAPGKGLEWIACIYGGASGTTYYASWAKGRFTISKTSSTTVTLQMTSLTAADTATY<br>FCMRGANGAGFGDANLWGPGTLVTVSSGQPKAPSVFPLAPCCGDTPSSTVTLGCLV<br>KGYLPEPVTVTWNSGTLTNGVRTFPSVRQSSGLYSLSSVVSVTSSSQPVTCNVAHPAT<br>NTKVDKTVAPSTCSKPMCPPPELPGGPSVFIFPPKPKDTLMISRTPEVTCVVVDVSQD<br>DPEVQFTWYINNEQVRTARPPLREQQFNSTIRVVSTLPIAHQDWLRGKEFKCKVHNK<br>ALPAPIEKTISKARGQPLEPKVYTMGPPREELSSRSVSLTCMINGFYPSDISVEWEKNGK<br>AEDNYKTTPTVLDSDGSYFLYSKLSVPTSEWQRGDVFTCSVMHEALHNHYTQKSISRS<br>PGK | N3A_3B12_H |
| 4 | MDTRAPTQLLGLLLLWLPGATFAQVLTQTPSPVSAAVGGTVTINCQSSPSVYSNYLSW<br>FQQKPGQPPKLLIYSASTLASGVPSRFRGSGSGTQFTLTISDVQCDDAANYYCAGGYTY<br>TSDSIWAFGGGTEVVVKGDPVAPTVLIFPPAADQVATGTVTIVCVANKYFPDVTVTW<br>EVDGTTQTTGIENSKTPQNSADCTYNLSSTLTLTSTQYNSHKEYTCKVTQGTTSVVQSF<br>NRGDC | N3A_3B12_L |
| 5 | METGLRWLLLVAVLKGVQCQQQMEESGGGLVQPEGSLTLTCKASGIDFSSYYYMCW<br>VRQAPGKGLELIACIYLSSGSTWYASWVNGRFTISRSTSLNTVTLQMTSLTAADTATYFH<br>CARGGFCTAYSGDGCYFTLWGPGTLVTVSSGQPKAPSVFPLAPCCGDTPSSTVTLGCL<br>VKGYLPEPVTVTWNSGTLTNGVRTFPSVRQSSGLYSLSSVVSVTSSSQPVTCNVAHPA<br>TNTKVDKTVAPSTCSKPMCPPPELPGGPSVFIFPPKPKDTLMISRTPEVTCVVVDVSQD<br>DPEVQFTWYINNEQVRTARPPLREQQFNSTIRVVSTLPIAHQDWLRGKEFKCKVHNK<br>ALPAPIEKTISKARGQPLEPKVYTMGPPREELSSRSVSLTCMINGFYPSDISVEWEKNGK<br>AEDNYKTTPTVLDSDGSYFLYSKLSVPTSEWQRGDVFTCSVMHEALHNHYTQKSISRS<br>PGK | N3A_17H7_ |
| 6 | MDTRAPTQLLGLLLLWLPGATFAIKMTQPPASVSAAVGGTVTINCRASEDIDSYLAWY<br>QQKPGQPPQLLIYRASTLASGVPSRFSGSGSGTQFTLTISGVQCDDAATYYCQSTYYSS<br>NPEGVFGGGTEVVVKGDPVAPTVLIFPPAADQVATGTVTIVCVANKYFPDVTVTWEV<br>DGTTQTTGIENSKTPQNSADCTYNLSSTLTLTSTQYNSHKEYTCKVTQGTTSVVQSFNR<br>GDC | N3A_17H7_L |
| 7 | METGLRWLLLVAVLKGVQCQEQLVESGGGLVKPEGSLTLTCTASGFSFSSYYYMCWV<br>RQAPGKGLELSACIDTGSGSTWYPSWVNGRFTISRSTSLNTVDLKMTSLTAADTATYF<br>CAREYSTAWYFNLWGPGTLVTVSSGQPKAPSVFPLAPCCGDTPSSTVTLGCLVKGYLP<br>EPVTVTWNSGTLTNGVRTFPSVRQSSGLYSLSSVVSVTSSSQPVTCNVAHPATNTKVD<br>KTVAPSTCSKPMCPPPELPGGPSVFIFPPKPKDTLMISRTPEVTCVVVDVSQDDPEVQF<br>TWYINNEQVRTARPPLREQQFNSTIRVVSTLPIAHQDWLRGKEFKCKVHNKALPAPIE<br>KTISKARGQPLEPKVYTMGPPREELSSRSVSLTCMINGFYPSDISVEWEKNGKAEDNYK<br>TTPTVLDSDGSYFLYSKLSVPTSEWQRGDVFTCSVMHEALHNHYTQKSISRSPGK | N3A_18B7_H |
| 8 | MDTRAPTQLLGLLLLWLPGATFAIKMTQTPGSVEVAVGGTVTINCQASQSISTALAW<br>YQQKPGQRPKLLIYDASRLASGVPSRFSGSGSGTEFTLTISGVECADAATYYCHQGFGA<br>SNVDNPFGGGTEVVVEGDPVAPTVLIFPPAADQVATGTVTIVCVANKYFPDVTVTWE<br>VDGTTQTTGIENSKTPQNSADCTYNLSSTLTLTSTQYNSHKEYTCKVTQGTTSVVQSFN<br>RGDC | N3A_18B7_L |
| 9 | METGLRWLLLVAVLKGVQCQEQLEESGGGLVQPEGSLTLTCTASGFSFSDNAWICW<br>VRQAPGKGLEWIGCIYIGSSSTYYASWAKGRFTISRTSSTTVNLQMTSLTDADTATYFC<br>GRDPTAAWGGGLWGPGTLVTVSSGQPKAPSVFPLAPCCGDTPSSTVTLGCLVKGYLP<br>EPVTVTWNSGTLTNGVRTFPSVRQSSGLYSLSSVVSVTSSSQPVTCNVAHPATNTKVD<br>KTVAPSTCSKPMCPPPELPGGPSVFIFPPKPKDTLMISRTPEVTCVVVDVSQDDPEVQF<br>TWYINNEQVRTARPPLREQQFNSTIRVVSTLPIAHQDWLRGKEFKCKVHNKALPAPIE<br>KTISKARGQPLEPKVYTMGPPREELSSRSVSLTCMINGFYPSDISVEWEKNGKAEDNYK<br>TTPTVLDSDGSYFLYSKLSVPTSEWQRGDVFTCSVMHEALHNHYTQKSISRSPGK | N3C_1A10_H |
| 10 | MDTRAPTQLLGLLLLWLPGAICDPVMTQTPSSTSAAVGGTVTISCQSSQSVYNNNYL<br>AWYQQKPGQPPKRLIYESSKLASGVPSRFRGSGSGAQFTLTISDLECDDAATYYCLGAY<br>YTTLDFGGGTEVVVRGDPVAPTVLIFPPAADQVATGTVTIVCVANKYFPDVTVTWEV<br>DGTTQTTGIENSKTPQNSADCTYNLSSTLTLTSTQYNSHKEYTCKVTQGTTSVVQSFNR<br>GDC | N3C_1A10_L |
| 11 | METGLRWLLLVAVLKGVQCQSLEESGGDLVKPGASLTLTCKASGIDFSSSYWICWVRQ<br>APGKGLEWIACIDTGSSGSTYYASWAKGRFTISKPSSTTVSLQMTSLQAADTATYFCAR<br>KGDGTDLWGPGTLVTVSSGQPKAPSVFPLAPCCGDTPSSTVTLGCLVKGYLPEPVTVT<br>WNSGTLTNGVRTFPSVRQSSGLYSLSSVVSVTSSSQPVTCNVAHPATNTKVDKTVAPS | N3C_1B8_H |

TABLE 2-continued

| SEQ ID NO: | Sequence | Name |
|---|---|---|
| | TCSKPMCPPPELPGGPSVFIFPPKPKDTLMISRTPEVTCVVVDVSQDDPEVQFTWYIN NEQVRTARPPLREQQFNSTIRVVSTLPIAHQDWLRGKEFKCKVHNKALPAPIEKTISKA RGQPLEPKVYTMGPPREELSSRSVSLTCMINGFYPSDISVEWEKNGKAEDNYKTTPTV LDSDGSYFLYSKLSVPTSEWQRGDVFTCSVMHEALHNHYTQKSISRSPGK | |
| 12 | MDTRAPTQLLGLLLLWLPGARCALVMTQTPASVEAAVGGTVTIKCQASQSISSYLNW YQQKSGQPPKNLIYRASTLASGVSSRFKGSGSGTEFTLTINDLECADAATYYCQSYGGY SIYGLVFGGGTEVVVKGDPVAPTVLIFPPAADQVATGTVTIVCVANKYFPDVTVTWEV DGTTQTTGIENSKTPQNSADCTYNLSSTLTLTSTQYNSHKEYTCKVTQGTTSVVQSFNR GDC | N3C_1B8_L |
| 13 | METGLRWLLLVAVLKGVQCQEQLEESGGGLVKPEESLTLTCTASGFSFISSDWICWVR QAPGKGLEWIACIYIGGHTPYYASWARGRFTISKTSSTAVTLQMSSLTAADTATYFCAR GIAGPALWGPGTLVTVSSGQPKAPSVFPLAPCCGDTPSSTVTLGCLVKGYLPEPVTVT WNSGTLTNGVRTFPSVRQSSGLYSLSSVVSVTSSSQPVTCNVAHPATNTKVDKTVAPS TCSKPMCPPPELPGGPSVFIFPPKPKDTLMISRTPEVTCVVVDVSQDDPEVQFTWYIN NEQVRTARPPLREQQFNSTIRVVSTLPIAHQDWLRGKEFKCKVHNKALPAPIEKTISKA RGQPLEPKVYTMGPPREELSSRSVSLTCMINGFYPSDISVEWEKNGKAEDNYKTTPTV LDSDGSYFLYSKLSVPTSEWQRGDVFTCSVMHEALHNHYTQKSISRSPGK | N3C_2B9_H |
| 14 | MDTRAPTQLLGLLLLWLPGATFAQVLTQTPSPVSAAVGGTVTINCQASQSVFRNNYL AWYQQKPGQPPTQLIYLASTLASGVPSRFSGSGSGTQFTLTISDVQCDDAATYYCAGA TSSIIIFGGGTEVVVKGDPVAPTVLIFPPAADQVATGTVTIVCVANKYFPDVTVTWEVD GTTQTTGIENSKTPQNSADCTYNLSSTLTLTSTQYNSHKEYTCKVTQGTTSVVQSFNRG DC | N3C_2B9_L |
| 15 | METGLRWLLLVAVLKGVQCQEQLVESGGGLVQPEGSLTLTCTASGFSFSANHWICW VRQAPGKGLEWVGCIYIGSGNTYYASWAKGRFTISKTSSTTVTLQMTSLTDADTAMY FCGRDPTAGWGGGLWGPGTLVTVSSGQPKAPSVFPLAPCCGDTPSSTVTLGCLVKGY LPEPVTVTWNSGTLTNGVRTFPSVRQSSGLYSLSSVVSVTSSSQPVTCNVAHPATNTK VDKTVAPSTCSKPMCPPPELPGGPSVFIFPPKPKDTLMISRTPEVTCVVVDVSQDDPE VQFTWYINNEQVRTARPPLREQQFNSTIRVVSTLPIAHQDWLRGKEFKCKVHNKALP APIEKTISKARGQPLEPKVYTMGPPREELSSRSVSLTCMINGFYPSDISVEWEKNGKAE DNYKTTPTVLDSDGSYFLYSKLSVPTSEWQRGDVFTCSVMHEALHNHYTQKSISRSPG K | N3C_3B7_H |
| 16 | MDTRAPTQLLGLLLLWLPGATFAQVLTQTPSSVSAAVGGTVTISCQSSQSVYNNNYLA WYQQKPGQPPKRLIYEASKLASGVPSRFRGSGSGTHFTLTISGVQCDDAATYYCLGAY FTTIVFGGGTEVVVRGDPVAPTVLIFPPAADQVATGTVTIVCVANKYFPDVTVTWEVD GTTQTTGIENSKTPQNSADCTYNLSSTLTLTSTQYNSHKEYTCKVTQGTTSVVQSFNRG DC | N3C_3B7_L |
| 17 | METGLRWLLLVAVLKGVQCQEQLVESGGGLVQPEGSLTLTCKASGFSFSSSYWICWV RQAPGKGPEWIACIYIGAGSTYYANWAKGRFTISKTSSTTVTLQMTSLTAADTATYFCS RGIAGVALWGPGTLVTVSSGQPKAPSVFPLAPCCGDTPSSTVTLGCLVKGYLPEPVTV TWNSGTLTNGVRTFPSVRQSSGLYSLSSVVSVTSSSQPVTCNVAHPATNTKVDKTVAP STCSKPMCPPPELPGGPSVFIFPPKPKDTLMISRTPEVTCVVVDVSQDDPEVQFTWYI NNEQVRTARPPLREQQFNSTIRVVSTLPIAHQDWLRGKEFKCKVHNKALPAPIEKTISK ARGQPLEPKVYTMGPPREELSSRSVSLTCMINGFYPSDISVEWEKNGKAEDNYKTTPT VLDSDGSYFLYSKLSVPTSEWQRGDVFTCSVMHEALHNHYTQKSISRSPGK | N3C_4C8_H |
| 18 | MDTRAPTQLLGLLLLWLPGATFAQVLTQTPSPVSAAVGSTVTINCQASQSVYKNNYL AWYQQKPGQPPKQLIYDASTLASGVPTRFKGSGSGTQFTLTISDVQCDDAATYYCAG AYSTVVVFGGGTEVVVKGDPVAPTVLIFPPAADQVATGTVTIVCVANKYFPDVTVTW EVDGTTQTTGIENSKTPQNSADCTYNLSSTLTLTSTQYNSHKEYTCKVTQGTTSVVQSF NRGDC | N3C_4C8_L |
| 19 | METGLRWLLLVAVLKGVQCQQQLEESGGGLVKPGGTLTLTCRASGIDFSSYYYMCW VRQAPGRGLELVACIEPSTVSTWYANWVIGRFTISRTSSTTVTLQMTSLTAADTATYFC ATSYSYGRSGYASTTTRLDLWGQGTLVTVSSGQPKAPSVFPLAPCCGDTPSSTVTLGCL VKGYLPEPVTVTWNSGTLTNGVRTFPSVRQSSGLYSLSSVVSVTSSSQPVTCNVAHPA TNTKVDKTVAPSTCSKPMCPPPELPGGPSVFIFPPKPKDTLMISRTPEVTCVVVDVSQD DPEVQFTWYINNEQVRTARPPLREQQFNSTIRVVSTLPIAHQDWLRGKEFKCKVHNK ALPAPIEKTISKARGQPLEPKVYTMGPPREELSSRSVSLTCMINGFYPSDISVEWEKNGK AEDNYKTTPTVLDSDGSYFLYSKLSVPTSEWQRGDVFTCSVMHEALHNHYTQKSISRS PGK | N3G_3G6_H |
| 20 | MDTRAPTQLLGLLLLWLPGATFAAVLTQTPSPVSAAVGGAVTINCQSSKSVYNNNELS WYQQKPGQPPKLLIYLASNLASGVPSRFKGSGSGTQFTLTISDVQCDDAATYYCIGGW SSSSDQNGFGGGTEVVVKGDPVAPTVLIFPPAADQVATGTVTIVCVANKYFPDVTVT WEVDGTTQTTGIENSKTPQNSADCTYNLSSTLTLTSTQYNSHKEYTCKVTQGTTSVVQ SFNRGDC | N3G_3G6_L |
| 21 | METGLRWLLLVAVLKGVQCQEQLVESGGGLVKPGASLALTCKASGIDFNSGYVICWV RQAPGKGLEWIACIDTGTADTAYATWAKGRFTISKTSSTTVTLQMTSLTGADTATYFC SRDLGGGGYDPDLWGPGTLVTVSSGQPKAPSVFPLAPCCGDTPSSTVTLGCLVKGYLP | N3G_4B8_H |

TABLE 2-continued

| SEQ ID NO: | Sequence | Name |
|---|---|---|
| | EPVTVTWNSGTLTNGVRTFPSVRQSSGLYSLSSVVSVTSSSQPVTCNVAHPATNTKVD KTVAPSTCSKPMCPPPELPGGPSVFIFPPKPKDTLMISRTPEVTCVVVDVSQDDPEVQF TWYINNEQVRTARPPLREQQFNSTIRVVSTLPIAHQDWLRGKEFKCKVHNKALPAPIE KTISKARGQPLEPKVYTMGPPREELSSRSVSLTCMINGFYPSDISVEWEKNGKAEDNYK TTPTVLDSDGSYFLYSKLSVPTSEWQRGDVFTCSVMHEALHNHYTQKSISRSPGK | |
| 22 | MDTRAPTQLLGLLLLWLPGARCAADMTQTPSSVSPTVGGTVTINCQSSPSVWNNYLS WFQQKPGQPPKLLIYGASTLASGVPSRFQGSGSGTQFTLTISDVQCDDAATYYCAGGY RSYTDTFVFGGGTEVVVKGDPVAPTVLIFPPAADQVATGTVTIVCVANKYFPDVTVT WEVDGTTQTTGIENSKTPQNSADCTYNLSSTLTLTSTQYNSHKEYTCKVTQGTTSVVQ SFNRGDC | N3G_4B8_L |
| 23 | METGLRWLLLVAVLKGVQCQSLEESGGGLVQPEGSLTLTCTASGFSFTMYGIIWVRQ APGKGLEWIACIDAGRSGSTYYASWAKGRFTISKTSSTTVTLQMTSLTAADTATYFCAR GGAGFTLWGPGTLVTVSSGQPKAPSVFPLAPCCGDTPSSTVTLGCLVKGYLPEPVTVT WNSGTLTNGVRTFPSVRQSSGLYSLSSVVSVTSSSQPVTCNVAHPATNTKVDKTVAPS TCSKPMCPPPELPGGPSVFIFPPKPKDTLMISRTPEVTCVVVDVSQDDPEVQFTWYIN NEQVRTARPPLREQQFNSTIRVVSTLPIAHQDWLRGKEFKCKVHNKALPAPIEKTISKA RGQPLEPKVYTMGPPREELSSRSVSLTCMINGFYPSDISVEWEKNGKAEDNYKTTPTV LDSDGSYFLYSKLSVPTSEWQRGDVFTCSVMHEALHNHYTQKSISRSPGK | N3G_5F6_H |
| 24 | MDTRAPTQLLGLLLLWLPGATFAIVMTQTPASVSAAVGGTVSISCQSSESVYKNNYLS WYQQKPGQPPKRLIYDASTLASGVPSRFKGSGSGTQFTLTISDVVCDDAATYYCAGYK SSATDGIAFGGGTEVVVKGDPVAPTVLIFPPAADQVATGTVTIVCVANKYFPDVTVTW EVDGTTQTTGIENSKTPQNSADCTYNLSSTLTLTSTQYNSHKEYTCKVTQGTTSVVQSF NRGDC | N3G_5F6_L |
| 25 | METGLRWLLLVAVLKGVQCQEQLVESGGGLVQPEGSLTLTCKASGLDFLSNYWICWV RQAPGKGLEWIACIYIDDGTTYYANWAKGRFTISRTSSTTVTLQMASLTAADTATYFC ARGNPFTLWGPGTLVTVSSGQPKAPSVFPLAPCCGDTPSSTVTLGCLVKGYLPEPVTV TWNSGTLTNGVRTFPSVRQSSGLYSLSSVVSVTSSSQPVTCNVAHPATNTKVDKTVAP STCSKPMCPPPELPGGPSVFIFPPKPKDTLMISRTPEVTCVVVDVSQDDPEVQFTWYI NNEQVRTARPPLREQQFNSTIRVVSTLPIAHQDWLRGKEFKCKVHNKALPAPIEKTISK ARGQPLEPKVYTMGPPREELSSRSVSLTCMINGFYPSDISVEWEKNGKAEDNYKTTPT VLDSDGSYFLYSKLSVPTSEWQRGDVFTCSVMHEALHNHYTQKSISRSPGK | N3G_7C8_H |
| 26 | MDTRAPTQLLGLLLLWLPGATFAQVLTQTPSSVSAAVGGTVTINCQSSPSVYRNYLSW YQQKPGQRPKLLIYHASTLASGVPSRFSASGSGTQFSLTISDAHCDDAATYYCAGGYIG SSDAWAFGGGTEVVVRGDPVAPTVLIFPPAADQVATGTVTIVCVANKYFPDVTVTW EVDGTTQTTGIENSKTPQNSADCTYNLSSTLTLTSTQYNSHKEYTCKVTQGTTSVVQSF NRGDC | N3G_7C8_L |
| 35 | METGLRWLLLVAVLKDIQCQEQLVESGGGLVQPEGSLTLTCTASGFSFSSSHWICWV RQAPGKGLEWIGCIYIGNGRTYYASWAKGRFTISKTSSTTMTLQISSLTDADTATYFSV RDPTAGWGGGLWGPGTLVTVSSGQPKAPSVFPLAPCCGDTPSSTVTLGCLVKGYLPE PVTVTWNSGTLTNGVRTFPSVRQSSGLYSLSSVVSVTSSSQPVTCNVAHPATNTKVDK TVAPSTCSKPMCPPPELPGGPSVFIFPPKPKDTLMISRTPEVTCVVVDVSQDDPEVQFT WYINNEQVRTARPPLREQQFNSTIRVVSTLPIAHQDWLRGKEFKCKVHNKALPAPIEK TISKARGQPLEPKVYTMGPPREELSSRSVSLTCMINGFYPSDISVEWEKNGKAEDNYKT TPTVLDSDGSYFLYSKLSVPTSEWQRGDVFTCSVMHEALHNHYTQKSISRSPGK | 4G8_H |
| 36 | MDTRAPTQLLGLLLLWLPGAICDPVMTQTPSSTSAAVGGTVTISCQSSQSVYNNNYL AWYQQKPGQPPKRLIYEASSLASGVPSRFKGSGSGAQFALTISGVQCDDAATYYCLGA YYTTLVFGGGTEVVVRGDPVAPTVLIFPPAADQVATGTVTIVCVANKYFPDVTVTWEV DGTTQTTGIENSKTPQNSADCTYNLSSTLTLTSTQYNSHKEYTCKVTQGTTSVVQSFNR GDC | 4G8_L |
| 27 | METGLRWLLLVAVLKGVQCQEQLKESGGDLVTPGTPLTLTCTVSGFSLSSSYMSWVR QAPGKGLEWIGIIFASGSTYYATWAKGRFTISRTSTTVDLKMTSLTTEDTATYFCARNS PGYGSDIWGPGTLVTVSLGQPKAPSVFPLAPCCGDTPSSTVTLGCLVKGYLPEPVTVT WNSGTLTNGVRTFPSVRQSSGLYSLSSVVSVTSSSQPVTCNVAHPATNTKVDKTVAPS TCSKPMCPPPELPGGPSVFIFPPKPKDTLMISRTPEVTCVVVDVSQDDPEVQFTWYIN NEQVRTARPPLREQQFNSTIRVVSTLPIAHQDWLRGKEFKCKVHNKALPAPIEKTISKA RGQPLEPKVYTMGPPREELSSRSVSLTCMINGFYPSDISVEWEKNGKAEDNYKTTPTV LDSDGSYFLYSKLSVPTSEWQRGDVFTCSVMHEALHNHYTQKSISRSPGK | N3T_1F9_H |
| 28 | MDTRAPTQLLGLLLLWLPGATFAQVLTQTPSSVSAAVGGTVTINCQSSQSVYANNHL SWYQQKPGQPPKLLVYRASNLETGVPSRFSGSGSGTQFSLTISGVQCDDAAAYYCGG DVSASTGGFGGGTEVVVKGDPVAPTVLIFPPAADQVATGTVTIVCVANKYFPDVTVT WEVDGTTQTTGIENSKTPQNSADCTYNLSSTLTLTSTQYNSHKEYTCKVTQGTTSVVQ SFNRGDC | N3T_1F9_L |
| 29 | METGLRWLLLVAVLKGVQCQSLEESGGDLVKPGASLTLTCKASGFDLSSSYFMCWVR QAPGRGLEWIACIDTRNIDTAYATWAKGRFTISKTSSTTVTLQMTSLTAADTAKYFCG RGGNINGLATGFALWGPGTLVTVSSGQPKAPSVFPLAPCCGDTPSSTVTLGCLVKGYL PEPVTVTWNSGTLTNGVRTFPSVRQSSGLYSLSSVVSVTSSSQPVTCNVAHPATNTKV | N3T_2D4_H |

TABLE 2-continued

| SEQ ID NO: | Sequence | Name |
|---|---|---|
| | DKTVAPSTCSKPMCPPPELPGGPSVFIFPPKPKDTLMISRTPEVTCVVVDVSQDDPEV<br>QFTWYINNEQVRTARPPLREQQFNSTIRVVSTLPIAHQDWLRGKEFKCKVHNKALPA<br>PIEKTISKARGQPLEPKVYTMGPPREELSSRSVSLTCMINGFYPSDISVEWEKNGKAED<br>NYKTTPTVLDSDGSYFLYSKLSVPTSEWQRGDVFTCSVMHEALHNHYTQKSISRSPGK | |
| 30 | MDTRAPTQLLGLLLLWLPGATFAAVLTQTPSPVSAAVGGTVTISCQASQSVYNNNWL<br>AWYQQKPGQPPKLLIYWASTLASGVPSRFKGSGSGTQFTLTISDLECDDAATYYCQGG<br>YFRRVDSFPFGGGTEVVVKGDPVAPTVLIFPPAADQVATGTVTIVCVANKYFPDVTVT<br>WEVDGTTQTTGIENSKTPQNSADCTYNLSSTLTLTSTQYNSHKEYTCKVTQGTTSVVQ<br>SFNRGDC | N3T_2D4_L |
| 31 | METGLRWLLLVAVLKGVQCQSLEESGGDLVKPGASLTLTCKASGFDLSSSYFMCWVR<br>QAPGRGLEWIACIDTRNIDTAYASWAKGRFTISKTSSTTVTLQMTSLTAADTARYFCG<br>RGGNINGLATGFNLWGPGTLVTVSSGQPKAPSVFPLAPCCGDTPSSTVTLGCLVKGYL<br>PEPVTVTWNSGTLTNGVRTFPSVRQSSGLYSLSSVVSVTSSSQPVTCNVAHPATNTKV<br>DKTVAPSTCSKPMCPPPELPGGPSVFIFPPKPKDTLMISRTPEVTCVVVDVSQDDPEV<br>QFTWYINNEQVRTARPPLREQQFNSTIRVVSTLPIAHQDWLRGKEFKCKVHNKALPA<br>PIEKTISKARGQPLEPKVYTMGPPREELSSRSVSLTCMINGFYPSDISVEWEKNGKAED<br>NYKTTPTVLDSDGSYFLYSKLSVPTSEWQRGDVFTCSVMHEALHNHYTQKSISRSPGK | N3T_2D10_H |
| 32 | MDTRAPTQLLGLLLLWLPGATFAVVLTQTPSPVSAAVGGTVTISCQASQSVYNNDWL<br>AWYQQKPGQPPKLLIYWASTLASGVPSRFKGSGSGTQFTLTISDLECDDAATYYCQGG<br>YFRRVDSFPFGGGTEVVVKGDPVAPTVLIFPPAADQVATGTVTIVCVANKYFPDVTVT<br>WEVDGTTQTTGIENSKTPQNSADCTYNLSSTLTLTSTQYNSHKEYTCKVTQGTTSVVQ<br>SFNRGDC | N3T_2D10_L |
| 33 | METGLRWLLLVAVLKGVQCQSLEESGGRLVTPGTPLTLTCTASGFSLSPTYMIWVRQA<br>PGKGLEWIGVIYPNGIPYYATWAKGRFTISKTSTTVDLRITSPTTEDTATYFCGRNSPG<br>WGTDMWGPGTLVTVSFGQPKAPSVFPLAPCCGDTPSSTVTLGCLVKGYLPEPVTVT<br>WNSGTLTNGVRTFPSVRQSSGLYSLSSVVSVTSSSQPVTCNVAHPATNTKVDKTVAPS<br>TCSKPMCPPPELPGGPSVFIFPPKPKDTLMISRTPEVTCVVVDVSQDDPEVQFTWYIN<br>NEQVRTARPPLREQQFNSTIRVVSTLPIAHQDWLRGKEFKCKVHNKALPAPIEKTISKA<br>RGQPLEPKVYTMGPPREELSSRSVSLTCMINGFYPSDISVEWEKNGKAEDNYKTTPTV<br>LDSDGSYFLYSKLSVPTSEWQRGDVFTCSVMHEALHNHYTQKSISRSPGK | N3T_3B7_H |
| 34 | MDTRAPTQLLGLLLLWLPGAICDPVLTQTPSSVSAVVGGTVTINCQASQSVYNNNHLS<br>WYQQKAGQPPNLLIYKISTLASGVPSRFSGSGSGTQFTLTISGVQCDDAATYYCGGDF<br>GVDVASYGGGTEVVVKGDPVAPTVLIFPPAADQVATGTVTIVCVANKYFPDVTVTWE<br>VDGTTQTTGIENSKTPQNSADCTYNLSSTLTLTSTQYNSHKEYTCKVTQGTTSVVQSFN<br>RGDC | N3T_3B7_L |

It will be apparent that antibody chain names may be read as N3X_ABC_Y where X is the nucleobase specificity (e.g., A, T, G or C), ABC is the antibody designation, and Y denotes the heavy (H) or light (L) chain sequence. It will also be recognized that heavy and light chains with a common designation (ABC) may be produced as a heterodimer (H-L) or a H-V dimer optional combined with an antibody constant region. Antibody chain sequences 1-36 include signal peptides. It will be recognized that mature antibodies will not include the signal peptide sequences.

Affinity reagents may be selected from the antibodies disclosed above, or derivatives of such antibodies. In some cases mAb 1867 (A), 4G8 (C), 7C8 (G) and 2D10 (T) are used. All other combinations or subcombinations with the appropriate combination of specificities may be used. Typically mAbs specific for A, T, G and C will be used together. However other combinations may be used; for example in some methods only three affinity reagents or only three labeled affinity reagents are used and one affinity reagent is omitted (so that an absence of signal identifies the 3' terminal base).

Other useful affinity reagents include antibodies (or other affinity reagents) that compete with an affinity reagent selected from mAb 2C5, 3612, 17H7, 1867, 168, 269, 4C8, 1A10, 367, 3G6, 5F6, 468, 7C8, 2D4, 2D10, 1F9, 367 and 4G8 for binding to the target structure. "Target structure" in this context refers to 3' biotinylated DNA template on a streptavidin-coated surface (e.g., well of an ELISA plate), hybridized to a primer having an NLRT nucleotide incorporated at the terminus, as discussed above in the context of antibody screening. Competition assays may be used to identify pairs of antibodies that bind the same epitope (or bind epitopes that overlap or are close together). Thus, when used herein in the context of two or more affinity reagents the term "competes with" indicates that the two or more affinity reagents compete for binding to to the target antigen. Competitive binding assays are well known (see, e.g., Junghans et al., Cancer Res. 50:1495, 1990). In one exemplary assay, one of the "reference mAbs" (mAbs 2C5, 3B12, 17H7, 18B7, 1B8, 2B9, 4C8, 1A10, 3B7, 3G6, 5F6, 4B8, 7C8, 2D4, 2D10, 1F9, 3B7 or 4G8) is allowed to bind to target antigens (e.g., in an ELISA format or sequencing array) and the candidate affinity reagent are added to the target antigen. If the presence of the candidate reduces binding of the reference mAb the candidate affinity reagent competes with the reference mAb. In some embodiments, the presence of the candidate reduces binding by an equimolar amount of the reference mAb to no more than 50% of the binding in the absence of the candidate (i.e., candidate reduces reference binding by half). In some cases the candidate inhibits binding by the reference mAb by at least 50%, and sometimes at least 75% or at least 90%. In another competition assay, the reference mAb is immobilized on the substrate and various concentrations of the candidate along with a soluble target antigen are added to detect and measure competition. In this case the soluble antigen may be a hairpin oligonucleotide (biotinylated in the loop portion for fluorescent streptavidin detection) with a reversible terminator incorporated into the duplex portion of the hairpin at the 3' terminus as discussed above. Thus, in an aspect of the invention sequencing is determined as described herein where the at least one affinity reagent is an affinity reagent (e.g., antibody) that competes with one of mAbs 2C5, 3B12, 17H7, 18B7, 1B8, 2B9, 4C8, 1A10, 3B7, 3G6, 5F6, 4B8, 7C8, 2D4, 2D10, 1F9, 3B7 or 4G8). In some embodiments at least three or at least four of the affinity reagents competes with one of these mAbs.

In some embodiments, the affinity reagent is an antibody or antigen binding portion thereof comprises a heavy chain variable region that comprises an amino acid sequence that is at least 90% identical (for example, at least 90%, 91%, 92%, 93%, 94%, 95%, 96%, 97%, 98% or 99% identical) to any of SEQ ID NOs: 1, 3, 5, 7, 9, 11, 13, 15, 17, 19, 21, 23, 25, 27, 29, 31, 33 (optionally not including the signal peptide, e.g., amino thermal approx. 19 amino acids) and/or a light chain variable region that comprises an amino acid sequence that is at least 90% identical (for example, at least 90%, 91%, 92%, 93%, 94%, 95%, 96%, 97%, 98% or 99%) identical to any of SEQ ID Nos: 2, 4, 6, 8, 10, 12, 14, 16, 18, 20, 22, 24, 26, 28, 30, 32, 34, or 36 (optionally not including the signal peptide, e.g., amino thermal approx. 22 amino acids).

Exemplary CDR Sequences

As noted above, antibody variants may be made using CDR sequences from a donor antibody of known specificity. For example, a monoclonal antibody sequence can be used to produce a chimeric or CDR grafted antibody, e.g., by combining the variable region from one antibody with the constant region of another antibody, or inserting the complementarity determining region (CDR) segments of a donor antibody into an acceptor antibody scaffold by recombinant DNA techniques (reviewed in Almagro and Fransson, Frontiers in Bioscience 13, 1619-1633, 2008), while retaining the specificity of the original monoclonal antibody.

The amino acid sequence boundaries of a CDR can be determined by one of skill in the art using any of a number of known numbering schemes, including those described by Kabat et al., supra ("Kabat" numbering scheme); Al-Lazikani et al., 1997, J. Mol. Biol., 273:927-948 ("Chothia" numbering scheme); MacCallum et al., 1996, J. Mol. Biol. 262:732-745 ("Contact" numbering scheme); Lefranc et al., Dev. Comp. Immunol., 2003, 27:55-77 ("IMGT" numbering scheme); and Honegge and Plückthun, J. Mol. Biol., 2001, 309:657-70 ("AHo" numbering scheme), each of which is incorporated by reference in its entirety.

Table 3, below, provides CDR sequences from the antibody heavy and light chains listed in Table 2. As discussed above CDRs confer antigen specificity and binding affinity to the antibody and these CDR sequences may be incorporated in chimeric, humanized antibodies, single chain antibodies, nanobodies, and other antibodies described above.

The skilled artisan will recognize that Table 3 identifies three CDR sequences for each of 18 light chains and 18 heavy chains, which correspond to 18 four chain antibodies comprising a combination of 2 light and 2 heavy variable regions (a $V_H$-$V_L$ dimer). Each combination of heavy and light chain from the same mAb can be called a "cognate set." The present invention encompasses related affinity reagents (e.g., single chain antibodies) that comprise one or more of the CDR sequences in Table 3. In particular the present invention encompasses affinity reagents that comprise three corresponding CDRs from a heavy or light chain in Table 3. Each group of three CDRs from the same IgG chain is called a "corresponding set." Additionally the present invention encompasses affinity reagents that comprise six CDR sequences from the 18 listed antibodies. Further, the invention comprises the use of such affinity reagents in the sequencing methods described here. In one aspect, the invention comprises use of combinations of 3 or 4 affinity reagents each comprising CDR sequences that confer specificity for a different nucleotide analog (i.e., A, T, G, or C).

In one aspect the invention comprises an affinity reagent (e.g., antibody or antigen binding portion thereof) that comprises: a heavy chain variable region comprising a corresponding set of CDRs including (i) a VH CDR1, (ii) a VH CDR2, (iii) a VH CDR3. For example a heavy chain variable region with CDRs comprising SEQ ID Nos: 37, 74 and 80.

In one aspect the invention comprises an affinity reagent (e.g., antibody or antigen binding portion thereof) that comprises: a light chain variable region comprising a corresponding set of CDRs including (i) a VL CDL1; (ii) a VL CDL2; and (iii) a VL CDL3. For example a light chain variable region with CDRs comprising SEQ ID Nos: 85, 90 and 95.

In one aspect the invention comprises an affinity reagent that contains a heavy chain variable region comprising a corresponding set of CDRs including (e.g., antibody or antigen binding portion thereof) that comprises: a light chain variable region comprising a corresponding set of CDRs including (i) a VL CDL1; (ii) a VL CDL2; and (iii) a VL CDL3. For example a light chain variable region with CDRs comprising SEQ ID Nos: 85, 90 and 95.

TABLE 3

CDR Sequences

A

| | VH | | | | | | VL | | | | | |
|---|---|---|---|---|---|---|---|---|---|---|---|---|
| | CDR1 (29-31) | SEQ ID NO: | CDR2 (49-58) | SEQ ID NO: | CDR3 (95-102) | SEQ ID NO: | CDR1 (28-35) | SEQ ID NO: | CDR2 (49-56) | SEQ ID NO: | CDR3 (91-98) | SEQ ID NO: |
| N3A-2C5-H | FSS | 37 | IACIYGGSSG | 74 | YFCMRGAN | 80 | | | | | | |
| N3A-2C5-L | | | | | | | VYSNYLSW | 85 | YSASTLAS | 90 | GYTYTSDS | 95 |
| N3A-3B12-H | FSS | 37 | IACIYGGASG | 75 | YFCMRGAN | 80 | | | | | | |
| N3A-3B12-L | | | | | | | VYSNYLSW | 85 | YSASTLAS | 90 | GYTYTSDS | 95 |

TABLE 3-continued

| CDR Sequences | | | | | | | | | | | | |
|---|---|---|---|---|---|---|---|---|---|---|---|---|
| N3A-17H7-H | FSS | 37 | IACIYLSSGS | 76 | YFCARGGF | 81 | | | | | | |
| N3A-17H7-L | | | | | | | IDSYLAWY | 86 | RASTLASG | 91 | YYSSNPEG | 96 |
| N3A-6C7-H | SNN | 72 | ACINTGVYDT | 78 | FCARDLTH | 83 | | | | | | |
| N3A-6C7-L | | | | | | | IYNHNYLS | 88 | IYHASTLA | 93 | GAYANTYS | 98 |
| N3A-16D8-H | SSR | 73 | ACIYTGVGST | 79 | CARDYDLW | 84 | | | | | | |
| N3A-16D8-L | | | | | | | VYNNNFSW | 89 | YKPSTLAS | 94 | SSSTDSAF | 99 |
| N3A-1867-H | FSS | 37 | SACIDTGSGS | 77 | YFCAREYS | 82 | | | | | | |
| N3A-1867-L | | | | | | | ISTALAWY | 87 | DASRLASG | 92 | FGASNVDN | 97 |
| C | | | | | | | | | | | | |
| | VH | | | | | | VL | | | | | |
| | CDR1 (29-31) | SEQ ID NO: | CDR2 (49-58) | SEQ ID NO: | CDR3 (95-102) | SEQ ID NO: | CDR1 (28-35) | SEQ ID NO: | CDR2 (49-56) | SEQ ID NO: | CDR3 (91-98) | SEQ ID NO: |
| N3C-1A10-H | FSD | 100 | IGCIYIGSSS | 107 | FCGRDPTA | 118 | | | | | | |
| N3C-1A10-L | | | | | | | SVYNNNYL | 124 | LIYESSKL | 132 | LGAYYTTL | 140 |
| N3C-2B9-H | FIS | 102 | IACIYIGGHT | 109 | FCARGIAG | 120 | | | | | | |
| N3C-2B9-L | | | | | | | SVFRNNYL | 126 | LIYLASTL | 134 | AGATSSII | 142 |
| N3C-3B7-H | FSA | 103 | VGCIYIGSGN | 110 | FCGRDPTA | 118 | | | | | | |
| N3C-3B7-L | | | | | | | SVYNNNYL | 124 | LIYEASKL | 135 | LGAYFTTI | 143 |
| N3C-4C8-H | FSS | 37 | IACIYIGAGS | 111 | FCSRGIAG | 121 | | | | | | |
| N3C-4C8-L | | | | | | | SVYKNNYL | 127 | LIYDASTL | 136 | AGAYSTVV | 144 |
| N3C-4G8-H | FSS | 37 | IGCIYIGNGR | 112 | FSVRDPTA | 122 | | | | | | |
| N3C-4G8-L | | | | | | | SVYNNNYL | 124 | LIYEASSL | 137 | LGAYYTTL | 140 |
| N3C-5E9-H | FSS | 37 | IGCLYVGSGR | 113 | FSVRDPTA | 122 | | | | | | |
| N3C-5E9-L | | | | | | | SLFNNNYL | 128 | LIYEASRL | 138 | LGAFYTTL | 145 |
| N3C-6C12-H | FSR | 104 | IGCIYIGSSG | 114 | FCGRDPTA | 118 | | | | | | |
| N3C-6C12-L | | | | | | | SVYNVNYL | 129 | LIYEASKL | 135 | LGAYYSTL | 146 |
| N3C-7E1-H | FSN | 105 | IGCIYIGSVR | 115 | FCGRDPTA | 118 | | | | | | |
| N3C-7E1-L | | | | | | | NVYSNNYL | 130 | LIYEASRL | 138 | AGAYYTTI | 147 |
| N3C-8H5-H | FSS | 37 | IGCIYIGNGR | 112 | FSVRDPTA | 122 | | | | | | |
| N3C-8H5-L | | | | | | | SVYNNNYL | 124 | LIYEASSL | 137 | LGAYYTTL | 140 |
| N3C-13C7-H | FSS | 37 | IGCIWIGGGG | 116 | YFCGRDPT | 123 | | | | | | |
| N3C-13C7-L | | | | | | | SVYVNNYL | 131 | LIYEASKL | 135 | LGAYYTTL | 140 |
| N3C-13D7-H | ISS | 106 | IGCIYTGSGR | 117 | FSVRDPTA | 122 | | | | | | |
| N3C-13D7-L | | | | | | | SVYNNNYL | 124 | LIYETSKL | 139 | LGAYYTTL | 140 |
| N3C-1B8-H | SSS | 101 | ACIDTGSSGS | 108 | FCARKGDG | 119 | | | | | | |
| N3C-1B8-L | | | | | | | SISSYLNW | 125 | YRASTLAS | 133 | YGGYSIYG | 141 |
| T | | | | | | | | | | | | |
| | VH | | | | | | VL | | | | | |
| | CDR1 (29-31) | SEQ ID NO: | CDR2 (49-58) | SEQ ID NO: | CDR3 (95-102) | SEQ ID NO: | CDR1 (28-35) | SEQ ID NO: | CDR2 (49-56) | SEQ ID NO: | CDR3 (91-98) | SEQ ID NO: |
| N3T-1F9-H | LSS | 148 | GIIFASGSTY | 150 | RNSPGYGS | 153 | | | | | | |
| N3T-1F9-L | | | | | | | VYANNHLS | 156 | VYRASNLE | 160 | GDVSASTG | 163 |
| N3T-2D4-H | SSS | 101 | ACIDTRNIDT | 151 | CGRGGNIN | 154 | | | | | | |
| N3T-2D4-L | | | | | | | VYNNNWLA | 157 | IYWASTLA | 161 | GGYFRRVD | 164 |
| N3T-2D10-H | SSS | 101 | ACIDTRNIDT | 151 | CGRGGNIN | 154 | | | | | | |
| N3T-2D10-L | | | | | | | VYNNDWLA | 158 | IYWASTLA | 161 | GGYFRRVD | 164 |
| N3T-387-H | SPT | 149 | VIYPNGIPYY | 152 | NSPGWGTDG | 155 | | | | | | |
| N3T-387-L | | | | | | | VYNNNHLS | 159 | IYKISTLA | 162 | GDFGVDVA | 165 |

TABLE 3-continued

CDR Sequences

| | VH | | | | | | VL | | | | | |
|---|---|---|---|---|---|---|---|---|---|---|---|---|
| | CDR1 (29-31) | SEQ ID NO: | CDR2 (49-58) | SEQ ID NO: | CDR3 (95-102) | SEQ ID NO: | CDR1 (28-35) | SEQ ID NO: | CDR2 (49-56) | SEQ ID NO: | CDR3 (91-98) | SEQ ID NO: |
| N3G-4B8-H | FNS | 38 | IACIDTGTAD | 43 | FCSRDLGG | 49 | | | | | | |
| N3G-4B8-L | | | | | | | VWNNYLSW | 55 | YGASTLAS | 61 | GYRSYTDT | 67 |
| N3G-5F6-H | TMY | 39 | CIDAGRSGST | 44 | CARGGAGF | 50 | | | | | | |
| N3G-5F6-L | | | | | | | VYKNNYLS | 56 | IYDASTLA | 62 | GYKSSATD | 68 |
| N3G-7C8-H | FLS | 40 | IACIYIDDGT | 45 | FCARGNPF | 51 | | | | | | |
| N3G-7C8-L | | | | | | | VYRNYLSW | 57 | YHASTLAS | 63 | GYIGSSDA | 69 |
| N3G-3G6-H | FSS | 37 | VACIEPSTVS | 42 | FCATSYSY | 48 | | | | | | |
| N3G-3G6-L | | | | | | | VYNNNELS | 54 | IYLASNLA | 60 | GGWSSSSD | 66 |
| N3G-9F11-H | SGY | 41 | AIDRGSYGTT | 46 | CVRGGAGF | 52 | | | | | | |
| N3G-9F11-L | | | | | | | VYNNYLSW | 58 | YDTSTLAS | 64 | YKSSTTDG | 70 |
| N3G-18D3-H | FSS | 37 | IACIYHFSGR | 47 | FCARDGIG | 53 | | | | | | |
| N3G-18D3-L | | | | | | | LYNYNQLS | 59 | IYSASTLA | 65 | GTYITSHN | 71 |

5. Labeled Affinity Reagents

Fluorescent Detectable Labels

The affinity reagents used in the practice of the invention, including antibodies, aptamers, affimers, knottins and other affinity reagents described herein, can be detectably labeled. For example the affinity reagents described herein can be detectably labeled with fluorescent dyes or fluorophores. “Fluorescent dye” means to a fluorophore (a chemical compound that absorbs light energy of a specific wavelength and re-emits light at a longer wavelength). Fluorescent dyes typically have a maximal molar extinction coefficient at a wavelength between about 300 nm to about 1,000 nm or of at least about 5,000, more preferably at least about 10,000, and most preferably at least about 50,000 cm-1 M-1, and a quantum yield of at least about 0.05, preferably at least about 0.1, more preferably at least about 0.5, and most preferably from about 0.1 to about 1. Labeling strategies for labeling affinity reagents that accommodate multiple dye molecules are described below.

There is a great deal of practical guidance available in the literature for selecting appropriate detectable labels for attachment to an affinity reagent, as exemplified by the following references: Grimm et al., *Prog. Mol. Biol. Transl. Sci.* 113:1-34, 2013; Oushiki et al., Anal. Chem. 84:4404-4410, 2012; Medintz & Hildebrandt, editors, 2013, “FRET—Förster Resonance Energy Transfer: from theory to applications,” (John Wiley & Sons); and the like. The literature also includes references providing lists of fluorescent molecules, and their relevant optical properties for choosing fluorophores or reporter-quencher pairs, e.g., Haugland, Handbook of Fluorescent Probes and Research Chemicals (Molecular Probes, Eugene, 2005); and the like. Further, there is extensive guidance in the literature for derivatizing reporter molecules for covalent attachment via common reactive groups that can be added to an RT or portion thereof, as exemplified by: Ullman et al., U.S. Pat. No. 3,996,345; Khanna et al., U.S. Pat. No. 4,351,760; and the like. Each of the aforementioned publications is incorporated herein by reference in its entirety for all purposes.

Exemplary fluorescent dyes include, without limitation, acridine dyes, cyanine dyes, fluorone dyes, oxazine dyes, phenanthridine dyes, and rhodamine dyes. Exemplary fluorescent dyes include, without limitation, fluorescein, FITC, Texas Red, ROX, Cy3, an Alexa Fluor dye (e.g., Alexa Fluor 647 or 488), an ATTO dye (e.g., ATTO 532 or 655), and Cy5. Exemplary fluorescent dyes can further include dyes that are used in, or compatible with, two- or four-channel SBS chemistries and workflows. Exemplary label molecules may be selected from xanthene dyes, including fluoresceins, and rhodamine dyes. Many suitable forms of these compounds are widely available commercially with substituents on their phenyl moieties which can be used as the site for linking to an affinity reagent. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate, and 2-p-toluidinyl-6-naphthalene sulfonate. Other labels include 3-phenyl-7-isocyanatocoumarin; acridines, such as 9-isothiocyanatoacridine and acridine orange; N-(p-(2-benzoxazolyl)phenyl)maleimide; benzoxadiazoles; stilbenes; pyrenes; and the like. In some embodiments, labels are selected from fluorescein and rhodamine dyes. These dyes and appropriate linking methodologies are described in many references, e.g., Khanna et al. (cited above); Marshall, *Histochemical J.,* 7:299-303 (1975); Menchen et al., U.S. Pat. No. 5,188,934; Menchen et al., European Pat. App. No. 87310256.0; and Bergot et al., International Application PCT/US90/05565. Fluorophores that can be used as detectable labels for affinity reagents or nucleoside analogues include, but are not limited to, rhodamine, cyanine 3 (Cy 3), cyanine 5 (Cy 5), fluorescein, Vic™, Liz™, Tamra™, 5-Fam™, 6-Fam™, 6-HEX, CAL Fluor Green 520, CAL Fluor Gold 540, CAL Fluor Orange 560, CAL Fluor Red 590, CAL Fluor Red 610, CAL Fluor Red 615, CAL Fluor Red 635, and Texas Red (Molecular Probes).

By judicious choice of labels, analyses can be conducted in which the different labels are excited and/or detected at different wavelengths in a single reaction. See, e.g., Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 1972; and Haugland, Handbook of Fluorescent Probes and Research Chemicals, Molecular Probes, Eugene (2005).

Enzymatically Labeled Affinity Reagents

In one approach the affinity reagent (e.g., antibody or affimer) is enzymatically labeled and, in the presence of substrate, the enzyme associated with an affinity reagent bound to a primer extension product produces a detectable signal. For example and without limitation, enzymes include peroxidase, phosphatase, luciferase, etc. In one approach the enzyme is a peroxidase. In one approach the affinity reagent (e.g., antibody or affimer) is directly labeled enzymatically. In one approach, for example, an antibody or other affinity reagent is labeled using peroxidase, such as horseradish peroxidase (HRP) or a phosphatase, such as an alkaline phosphatase (Beyzavi et al., Annals Clin Biochem 24:145-152, 1987). In one approach, the affinity reagent is coupled to (or is part of a fusion protein with) luciferase or other protein that can be used to produce a chemiluminescent signal (for example, from 2,2'-azino-bis(3-ethylbenzothiazoline-6-sulphonic acid (ABTS) or luminol). In another approach, the affinity reagent can be coupled/fused to an enzyme system that is selected to produce a non-optical signal, such as a change in pH where protons can be detected, for example, by ion semiconductor sequencing (e.g., Ion Torrent sequencers; Life Technologies Corporation, Grand Island, NY). Use of enzyme labeled affinity reagents has certain advantages, including high sensitivity resulting from signal amplification and the ability to tailor the sequencing method to a variety of instruments. Enzyme reporter systems are reviewed in Rashidian et al., *Bioconjugate Chem.* 24:1277-1294, 2013.

Indirect and Direct Detection Methods

An affinity reagent may be directly labeled (e.g., by conjugation to the label, e.g., via a covalent bond, to a fluorophore) or indirectly labeled, e.g., by binding of a labeled secondary affinity reagent that binds a primary affinity reagent directly bound to the extended primer with a 3' NLRT. Unlabeled primary affinity reagents bind the target nucleotide and labeled secondary affinity reagents (e.g., antibodies, aptamers, affimers or knottins) bind the primary affinity reagents. In some approaches the primary and/or secondary affinity reagent is an antibody. For example, in one approach the affinity reagent is a "primary" antibody (e.g., rabbit anti-NLRT-C antibody) and the secondary binder is a labeled anti-primary antibody (e.g., dye-labeled goat anti-rabbit antibody). In some approaches, use of a secondary affinity reagent provides advantageous signal amplification.

In the case of indirect detection, the assay may comprise two distinct parts: first, there is a period of incubation (usually one hour) with the unlabeled primary antibody, during the antibody binds to the antigen (assuming of course that the antigen is present). Excess unbound primary antibody is then washed away and a labeled secondary reagent is added. After a period of incubation (again one hour), excess secondary reagent is washed away and the amount of label associated with the primary antibody (i.e., indirectly via the secondary reagent) is quantified. The label usually results in the production of a colored substance or an increase in the amount of light emitted at a certain wavelength, if the antigen is present. In the absence of antigen there is no binding of the primary antibody and no binding of the secondary reagent, and thus no signal. With direct detection, the prior covalent attachment of the label to the primary antibody means that only a single incubation step with the antigen is required and only a single round of wash steps, as opposed to two rounds of incubation and wash steps with indirect detection.

Secondary Antibody Specificity

Primary and secondary antibodies may be selected to distinguish multiple antigens (e.g., to distinguish RT-A, RT-C, RT-G and RT-T from each other). Unlabeled primary antibodies (typically monoclonal or engineered antibodies) may have different isotypes and/or have sequences characteristic of different species (e.g., polyclonal antibodies raised in different animals or corresponding monoclonal antibodies or other affinity reagents). In such cases, labeled secondary (i.e., anti-primary) antibodies for each antigen be specific for the appropriate isotype or species sequence. For example, primary antibodies of isotypes IgG1, IgG2a, IgG2b, and IgG3 can be used with isotype-specific secondary antibodies.

Precombined Primary and Secondary Antibodies

Primary and secondary antibodies or other agents may be added to a sequencing array, equentially, simultaneously, or may be precombined under conditions in which the secondary antibody(s) bind to the primary antibody and added to the array as a complex.

Methods for Labeling Antibodies and Other Affinity Reagents

Labeled affinity reagents can be used to sequence a template nucleic acid by a variety of methods. Any method of labeling antibodies and other affinity reagents of the invention may be used. Methods for linking of antibodies and other affinity reagents to reporter molecules, e.g., signal-generating proteins including enzymes and fluorescent/luminescent proteins are well known in the art (Wild, *The Immunoassay Handbook,* $4^{th}$ ed.; Elsevier: Amsterdam, the Netherlands, 2013; Kobayashi and Oyama, Analyst 136: 642-651, 2011). Enzymes, biotin, fluorophores and radioactive isotopes are all commonly used to provide a detection signal in biological assays and may be linked or conjugated to affinity reagents such as antibodies.

Most antibody labeling strategies use one of three targets: (1) Primary amines (—NH2): these occur on lysine residues and the N-terminus of each polypeptide chain. They are numerous and distributed over the entire antibody. (2) Sulfhydryl groups (—SH): these occur on cysteine residues and exist as disulfide bonds that stabilize the whole-molecule structure. Hinge-region disulfides can be selectively reduced to make free sulfhydryls available for targeted labeling. (3) Carbohydrates (sugars): glycosylation occurs primarily in the Fc region of antibodies (IgG). Component sugars in these polysaccharide moieties that contain cis-diols can be oxidized to create active aldehydes (—CHO) for coupling. The four main chemical approaches for antibody labeling are summarized below:

1. NHS esters. In the case of fluorescent dye labels it is usual to purchase an activated form of the label with an inbuilt NHS ester (also called a 'succinimidyl ester'). The activated dye can be reacted under appropriate conditions with antibodies (all of which have multiple lysine groups). Excess reactive dye is removed by one of several possible methods (often column chromatography) before the labeled antibody can be used in an immunoassay.
2. Heterobifunctional reagents. If the label is a protein molecule (e.g. horseradish peroxidase [HRP], alkaline phosphatase, or phycoerythrin) the antibody labeling procedure is complicated by the fact that the antibody and label have multiple amines. In this situation it is usual to modify some of the lysines on one molecule (e.g. the antibody) to create a new reactive group (X) and lysines on the label to create another reactive group (Y). A 'heterobifunctional reagent' is used to introduce the Y groups, which subsequently react with X groups when the antibody and label are mixed, thus creating heterodimeric conjugates. There are many variations on this theme and you will find hundreds of examples in the literature on the use of heterobifunctional reagents to create labeled antibodies and other labeled biomolecules.

3. Carbodiimides. These reagents (EDC is one very common example) are used to create covalent links between amine- and carboxyl-containing molecules. Carbodiimides activate carboxyl groups, and the activated intermediate is then attacked by an amine (e.g. provided by a lysine residue on an antibody). Carbodimides are commonly used to conjugate antibodies to carboxylated particles (e.g. latex particles, magnetic beads), and to other carboxylated surfaces, such as microwell plates or chip surfaces. Carbodiimides are rarely used to attach dyes or protein labels to antibodies, although they are important in the production of NHS-activated dyes (see above).
4. Sodium periodate. This chemical cannot be employed with the vast majority of labels but is quite an important reagent in that it is applicable to HRP, the most popular diagnostic enzyme. Periodate activates carbohydrate chains on the HRP molecule to create aldehyde groups, which are capable of reacting with lysines on antibody molecules. Since HRP itself has very few lysines it is relatively easy to create antibody-HRP conjugates without significant HRP polymerization.

For any particular antibody clone, lysines (primary amines) might occur prominently within the antigen binding site. Thus, the lone drawback to this labeling strategy is that it occasionally causes a significant decrease in the antigen-binding activity of the antibody. The decrease may be particularly pronounced when working with monoclonal antibodies or when attempting to add a high density of labels per antibody molecule.

Random Labeling

In one approach antibodies are specifically labeled (e.g., at specific sites on the antibody) with a defined number of dye molecules (e.g., 1, 2, 3, 4 or 5 dye molecules per antibody). In another approach, antibodies are randomly labeled, for example by reaction of available free amines on the protein with NHS ester activated fluorescent dyes (Mattson et al., A practical approach to crosslinking. Mol. Biol. Rep. 17, 167-183 (1993), incorporated by reference herein). In one approach NHS ester activated fluorophores are diluted in anhydrous DMSO and reacted at concentrations (10-100 μM) that provide strong signals without adversely affecting antibody binding or specificity. The random labeling process may be used to produce antibodies labeled with multiple dye molecules per antibody. Likewise, specific labeling methods may be may be used to produce antibodies labeled with multiple dye molecules per antibody. Where there are multiple dye molecules per antibody the dyes on a given antibody protein (e.g., tetramer) may be the same or different (e.g., two different dyes). Thus, in one approach, antibodies in an antibody group (where an antibody group comprises antibodies with the same nucleobase specificity, such as a nucleobase-specific monoclonal antibody) are labeled with 2 or more dye molecules that are the same dye (e.g., two fluorescein molecules). In one approach, antibodies in an antibody group are labeled with 2 or more dye molecules that are not the same (e.g., one fluorescein molecule and one rhodamine molecule).

Labeling Without Removal of Dye Purification of Free Dye

In one approach antibody are labeled by reaction of available free amines on the antibody protein with NHS ester activated fluorescent dyes. For example, NHS ester activated fluorophores are diluted in anhydrous DMSO and reacted at concentrations (10-100 uM). Relatively low concentrations of antibody are adjusted to pH 8 in bicarbonate buffer and reacted with the NHS ester dyes. The antibody concentration at this stage may be about (1 mg/ml) or, in various embodiments, may be e.g., 0.1 to 0.5 mg/ml, 0.5 to 5 mg/ml. 0.3-1 mg/ml, or 0.3 to 2 mg/ml. Incubation wis continued for 45 min at room temperature. Optionally quenching of unreacted dye in tris-buffered saline (pH 7.4) is carried out. This labeling approach provides strong signals without adversely affecting antibody binding or specificity.

For antibody binding in the final sequencing reactions, the labeled antibody composition(s) are diluted (usually 30-300-fold, e.g., more than 50-fold, often more than 100-fold, and sometimes more than 500-fold. In the final sequencing reaction mixture incubated on the nucleic acid array, an excess of antibodies may be used, for example at a concentration of about 1 to about 10 ug/ml. This results in a final dye concentration in the antibody binding reaction on the order of 0.2 uM compared with greater than 1 uM typically used of highly purified base-labeled labeled nucleotides.

Surprisingly, we have found that these labeled antibodies may be stored at −20C and used without purification of free unreacted dye from antibody and, surprisingly, we have found that it is not necessary to remove free unreacted dye from the labeled antibody preparation prior to use in sequencing reactions.

In one aspect the invention provides a composition comprising fluorescent dye labeled anti-NLRT antibodies and free (i.e., not conjugated to protein) dye, where the composition comprises greater than 10 nanomoles free dye per 1 mg antibody, often greater than 20 nanomoles, and often greater than 50 nanomoles per 1 mg antibody, where usually the antibodies are labeled on average with more than one dye molecule. In one embodiment the dyes are NHS ester activated fluorophores. After optional "quenching" of unused dye molecules, labeled antibodies may be stored even without glycerol at −4 C or −20 or −80 C. Four labeled antibodies can be mixed and stored or the pool may be be stored at concentrations in the range 1 ug/ml to 10 ug/ul.

Thus, one aspect of the invention comprises: (1) Labeling affinity reagents (e.g., a protein, such as an antibody) with dyes (e.g., fluorescent dyes, such as NHS ester activated fluorescent dyes) to produce a composition comprising labeled affinity reagents and unreacted dyes; (2) using the composition in affinity reagent-based sequencing as described herein, without removal of the unreacted dye molecules (without purification). Affinity reagent (antibody) based sequencing by synthesis is carried out using NLRTs where base-specific labeled antibodies are used in the binding reaction in the presence of a non-incorporated dye at a concentration greater than 10 nanomole per mg of the labeled antibody protein, sometimes greater than 20 nanomole, and sometimes greater than 50 nanomole.

6. Sequencing Systems

Array-Based Sequencing

Various SBS methods can be used with the NLRTs and antibodies of the present application, for example as disclosed in PCT Pat. Pub. WO 1999/019341; WO 2005/082098; WO 2006/073504; WO 2018/129214, and Shendure et al., 2005, Science, 309: 1728-1739. SBS methods can employ the ordered DNA nanoball arrays that are described, for example, in U.S. Pat. Pubs. 2010/0105052, 2007/099208, and US 2009/0264299) and PCT Pat. Pubs. WO 2007/120208, WO 2006/073504, WO 2007/133831, incorporated by reference in their entirety for all purposes. In some embodiments, the nucleic acid template is immobilized on a solid surface (e.g., silicon, glass, gold, a polymer, PDMS, bead), often within wells. In some embodiments, the nucleic acid template is immobilized or contained within a droplet (optionally immobilized on a bead or other substrate within the droplet). Generally the array (sometimes called an array chi) is contained in a flow cell, a fluidic device that delivers reagent solutions to the arrayed templates. Generally the reagent solutions are delivered to a reaction chamber formed between the surface of the array and a coverslip. See US Pat. Pub. 2013/0281305, incorporated by reference.

In some embodiments, the nucleic acid template is an immobilized DNA concatemer comprising multiple copies of a target sequence. In some embodiments, the template nucleic acid is represented as a DNA concatemer, such as a DNA nanoball (DNB) comprising multiple copies of a target sequence and an "adaptor sequence". In some embodiments, the DNA templates are DNA concatemers and there is a single concatemer at each position. See PCT Pat. Pub. WO 2007/133831, the content of which is hereby incorporated by reference in its entirety for all purposes.

In some embodiments, the nucleic acid template at each position of the array is a clonal population of DNA fragments. In some embodiments, the clonal population of DNA fragments are produced by bridge PCR. In some embodiments the template is a single polynucleotide molecule. In some embodiments the template is present as a clonal population of template molecules (e.g., a clonal population produced by bridge amplification or Wildfire amplification).

Suitable template nucleic acids, including DNBs, clusters, polonys, and arrays or groups thereof, are further described in U.S. Pat. Nos. 8,440,397; 8,445,194; 8,133,719; 8,445,196; 8,445,197; 7,709,197; 12/335,168, 7,901,891; 7,960,104; 7,910,354; 7,910,302; 8,105,771; 7,910,304; 7,906,285; 8,278,039; 7,901,890; 7,897,344; 8,298,768; 8,415,099; 8,671,811; 7,115,400; 8,236,499, and U.S. Pat. Pub. Nos. 2015/0353926; 2010/0311602; 2014/0228223; and 2013/0338008, all of which are hereby incorporated by reference in their entirety.

In one aspect the invention provides a DNA array comprising: a plurality of template DNA molecules, each DNA molecule attached at a position of the array, a complementary DNA sequence base-paired with a portion of the template DNA molecule at a plurality of the positions, wherein the complementary DNA sequence comprises at its 3' end an incorporated first reversible terminator deoxyribonucleotide; and a first affinity reagent bound specifically to at least some of the first reversible terminator deoxyribonucleotides. In one approach the DNA array comprises primer extension products with 3' terminal nucleotides comprising A, T, G or C nucleobases or analogs thereof, and affinity reagents bound to the primer extension products.

Methods for detecting binding of the antibody to the incorporated RT will vary with the nature of the detectable label(s) being used. Numerous methods are known in the art and are commercially available. For fluorescent labels, one approach is to pass laser light over the array to activate the fluorescent label. Fluorescence is detected using a camera (e.g., a CCD- or CMOS-based camera) and recorded on a computer, e.g., as sets of tiled fluorescence or luminescence images of the recorded after each iterative sequencing step. (or, as discussed below, collected more than once in each full cycle. Different dyes emit light at different wavelengths (or different colors) and intensities. In one approach each color results in a separate image (acquiring signals at different wavelengths) and the images are compared. using various techniques and algorithms that can be performed on one or more computer systems. Dyes of different colors can be distinguished using a variety of art-known approaches. One common approach uses multiple lasers that activate dyes with different excitation wavelengths and/or optical filters to capture light of different wavelengths. Such filters and methods usually capture light over a spectrum of wavelengths that can be called a "color" (e.g. red or green) "band" or "detection channel." In an approach each channel produce a different image such that images may be compared to determine the nature of the signal at each array position. Commercially available sequencers may be adapted for 1-color, 2-color, or 4 color based on the presence or absence of filters, illumination sources, and software.

One color sequencing is particularly adapted to methods in which chemiluminescent (rather than fluorescent) labels are used or non-light generating labels are used, and affinity reagents labeled with chemiluminescent dyes and alternative labels may be used in the methods disclosed herein.

7. Removal of Blocking Groups and Removal of Affinity Reagents

Removal of blocking groups and affinity reagents can occur simultaneously or can be uncoupled and occur at different times. In one approach an array is exposed to conditions in which of blocking groups and affinity reagents are removed simultaneously. In one the array is contacted with a solution with a combination of agents some of which result in removal of the affinity reagents (e.g., high salt, small molecule competitors, protease, etc.) combined with agents that cleave the blocking group.

In some cases, removal of the 3' blocking group results in removal of the affinity reagent. Without intending to be bound by a particular mechanism, it is believed that in these cases, removal of the blocking moiety destroys the epitope required for binding of the antibody or other affinity reagent.

In a different approach, the removal of the affinity reagent and blocking group is uncoupled, such that the affinity reagent is removed but the blocking group is not cleaved from the nucleotide sugar. In one aspect of the invention, SBS is carried out on DNA arrays using NLRTs wherein base-specific labeled antibodies are removed after imaging before removing blocking group is removed. The antibodies are generally removed at high temperature (greater than 50C, sometimes greater than 60C) and removal is substantially complete within 40 seconds after introduction of the removal conditions (some of which are discussed below.

It will be appreciated that conditions for removal conditions for removal of affinity reagents and/or blocking groups will be selected to preserve the integrity of the DNA being sequenced.

Removal of Blocking Groups

Nucleoside analogues or NLRTs include those that are 3'-O reversibly blocked. In some aspects, the blocking group provides for controlled incorporation of a single 3'-O reversibly blocked NLRT at the 3'-end of a primer, e.g., a GDS extended in a previous sequencing cycle.

Generally, in each sequencing cycle in which NLRTs are used, the blocking group is removed and the affinity reagent is disassociated from the NLRT. These steps may be carried our concurrently. For example, a azidomethyl blocking group can be removed by treatment with phosphine (a widely used process) and an antibody affinity reagent can be removed by treatment with a low pH (e.g., 100 mM glycine pH 2.8) or high pH (e.g., 100 mM glycine pH 10), high salt, or chaotropic stripping buffer. In an embodiment, a single treatment or condition can be used to remove both the NLRT and the affinity reagent (e.g., phosphine in a high salt buffer). In some embodiments, removal of the blocking group results in disassociation of the affinity reagent if, for example, the blocking group is required for affinity reagent binding.

The 3'-O reversible blocking group can be removed by enzymatic cleavage or chemical cleavage (e.g., hydrolysis). The conditions for removal can be selected by one of ordinary skill in the art based on the descriptions provided herein, the chemical identity of the blocking group to be cleaved, and nucleic acid chemistry principles known in the art. In some embodiments, the blocking group is removed by contacting the reversibly blocked nucleoside with a reducing agent such as dithiothreitol (DTT), or a phosphine reagent such as tris(2-carboxyethyl)phosphine (TCEP), tris(hydroxymethyl)phosphine (THP), or tris(hydroxypropyl) phosphine. In some cases, the blocking group is removed by washing the blocking group from the incorporated nucleotide analogue using a reducing agent such as a phosphine reagent. In some cases, the blocking group is photolabile, and the blocking group can be removed by application of, e.g., UV light. In some cases, the blocking group can be removed by contacting the nucleoside analogue with a transition metal catalyzed reaction using, e.g., an aqueous palladium (Pd) solution. In some cases, the blocking group can be removed by contacting the nucleoside analogue with an aqueous nitrite solution. Additionally, or alternatively, the blocking group can be removed by changing the pH of the solution or mixture containing the incorporated nucleotide analogue. For example, in some cases, the blocking group can be removed by contacting the nucleoside analogue with acid or a low pH (e.g., less than 4) buffered aqueous solution. As another example, in some cases, the blocking group can be removed by contacting the nucleoside analogue with base or a high pH (e.g., greater than 10) buffered aqueous solution.

3'-O reversible blocking groups that can be cleaved by a reducing agent, such as a phosphine, include, but are not limited to, azidomethyl. 3'-O reversible blocking groups that can be cleaved by UV light include, but are not limited to, nitrobenzyl. 3'-O reversible blocking groups that can be cleaved by contacting with an aqueous Pd solution include, but are not limited to, allyl. 3'-O reversible blocking groups that can be cleaved with acid include, but are not limited to, methoxymethyl. 3'-O reversible blocking groups that can be cleaved by contacting with an aqueous buffered (pH 5.5) solution of sodium nitrite include, but are not limited to, aminoalkoxyl.

Removal of Affinity Reagents

Antibody-based affinity reagents can be removed by low pH, high pH, high or low salt, or denaturing agents such as a chaotropic stripping buffer. Other classes of affinity reagents (e.g., aptamers) can be removed by any means known in the art. In addition, affinity reagents, such as antibodies, can be removed by introducing an agent that competes with the bound epitope for affinity reagent binding, for example as illustrated in Example 10 below.

In one approach, high temperature (e.g. 50-60C or 55C-65C or 60-70C), or a combination of high temperature (e.g. 60-65C) with high pH (8.5-9.5) may also be used to quantitatively remove antibodies in less than 30s or less than 20s or less than 10s. Fast complete or near complete removal of antibodies without cleaving the 3' blocking group allows i) optimal cleavage condition or ii) fast sequential binding/detection/removal of each antibody or two antibodies at a time.

As noted above, affinity reagents may also be removed by disrupting the ability of the agent to bind the incorporated NLRT. Typically this occurs when the 3' blocking group is cleaved from the incorporated nucleotide analog. In cases in which the affinity reagent binding depends on the presence of the blocking group (for example, in cases in which an epitope recognized by a 1° antibody includes the blocking group or a portion thereof) removal of the blocking group results in release of the affinity reagent as well.

Simultaneous removal of affinity reagents and blocking groups may also be effected by addition of a solution comprising a blocking group cleaving component (e.g., a phosphine reagent) and an affinity reagent releasing agent (e.g., high salt).

Simultaneous Second Incorporation and Antibody Removal

In an aspect of the invention SBS is used to incorporate NLRTs into a growing primer strand (“first incorporation”) and affinity reagents (e.g., monoclonal antibodies) are used to detect incorporation. In one approach, after detection, the affinity reagents are removed and the reversible blocking group is removed (“deblocking”). In one approach, following detection and prior to deblocking, a second NLRT incorporation step is carried out concurrently with, or after, removal of the affinity reagents. The second incorporation addresses the problem of asynchrony (out of phase incorporation). SBS is often carried out using a large clonal population of templates of a position on an array. Exemplary large clonal populations of templates include DNBs and template clusters (which may be generated by bridge PCR or similar methods). In some cases, for some of the DNA template copies at a position on an array, DNA polymerase may fail to incorporate complementary RTs into the GDS, so that sequencing reactions on the large number of DNA templates on a DNA array can be incomplete or asynchronous (out of phase). That is to say, not all primers hybridized to all templates are extended at equal efficiency, and this disparity increases as the cycle number increases resulting in lower quality sequencing data. The second incorporation step provides a second opportunity in each sequencing cycle for DNA polymerases to incorporate RTs when there is complementarity between the RT and the base on the DNA template, increasing the proportion of templates are extended during each sequencing cycle. Antibody removal and second incorporation may occur at the same time under the same conditions. This dispenses the need to take steps to change conditions in order to accommodate two different types of reactions and significantly reduces cost and cycle time.

In one approach, after detection of signal from the labeled extension products and prior to deblocking, the DNA array (and the labeled extension products immobilized thereon) are subjected to a dissociation condition under which (1) labeled affinity reagents are dissociated from the extension products and (2) further incorporation (“second incorporation”) of NLRT’s occurs at any template location in which a blocked nucleotide was not incorporated in the first incorporation step. The second incorporation comprises adding additional polymerase and, optionally, additional NLRT(s) under the antibody disassociation conditions. The addition of polymerase and NLRTs and removal of affinity reagents may occur simultaneously (i.e., both under the disassociation conditions). Alternatively, the affinity reagents may be removed, or partially removed, under disassociation conditions and the polymerase/NLRTs added subsequently under the same or similar disassociation conditions, generally, without an intervening wash step (removing disassociated affinity reagents). It will be recognized by the careful reader that the second incorporation step is carried out under disassociation conditions.

Following the second incorporation, the blocking groups of both the NLRTs incorporated through the first incorporation and the NLRTs incorporated through the second incorporation are removed, which permits the next cycle of extension of the growing DNA copy strands and identification of subsequently incorporated NLRTs.

Sequencing methods disclosed herein use reagents that allow second incorporation to be performed under the same condition as the antibody dissociation step. The condition results in disassociation of labeled antibodies from their target RTs on the array, and yet is suitable for polymerases properly carry out the polymerization reaction (e.g., the second incorporation).

As used herein, “first incorporation” or “second incorporation” refers to incorporation of a RT at the 3' end of a nucleic acid primer or a growing DNA strand. The RT incorporated by first incorporation will be identified through antibody binding, while the RT incorporated by second incorporation will not be subjected to antibody binding. The second incorporation occurs after the first incorporation, antibody binding and detection.

The NLRT’s used in the first incorporation and second incorporation steps generally have the same blocking group(s). However, different blocking groups may be used. When multiple different blocking groups are used it is preferable that the groups can all be cleaved under the same conditions, e.g., at a common temperature, pH and salt concentration and with compatable cleavage agents.

In one approach, one cycle of the sequencing reaction include following steps: i) forming unlabeled extension products by incorporating RTs at the 3' end of nucleic acid primers or growing DNA copy strands that are hybridized to the plurality of DNA templates on the array (“first incorporation”), ii) forming labeled extension products by binding of a labeled affinity reagnet (e.g., antibody) to the extension products, iii) detecting the labeled extension products, iv) removing the bound labeled antibodies and incorporating an additional quantity of RTs (“second incorporation”) under conditions that allow for both processes to occur (simultaneously or under the same conditions). After removal of a blocking group these steps may be repeated to carry out additional cycles of sequencing reaction.

First Incorporation

As described above, the first incorporation step involves extension of a nucleic acid primer hybridized to a template nucleic acid on the DNA array or extension of a primer extension product generated in an earlier sequencing cycle. The reaction includes a DNA polymerase, NLRTs, and a buffer that is suitable for primer extension. In one approach, NLRTs used in the methods disclosed herein are a mixture of A, G, C, and T (i.e., NLRT-A, NLRT-G, NLRT-C, and NLRT-T). Alternatively, individual NLRTs, or combinations of NLRTs, can be separately incorporated in separate steps (for example, in certain two-color protocols described herein). In each cycle, NLRTs are incorporated into the growing DNA strand of one of the template DNA molecules to form an unlabeled extension product. In some cases, following the first incorporation, unincorporated NLRTs are washed away and removed from the sequencing reaction.

Antibody Binding And Detection

Unlabeled extension products formed by first incorporation are then combined with labeled antibodies. Each of the antibodies used in the methods can specifically bind to one nucleobase (e.g., A) and distinguish that nucleobase from others to which it does not bind at all or bind inefficiently (e.g., T, C and G). For example, if a 3' terminal nucleotide is recognized by an antibody specific for a guanosine nucleobase (e.g., a 3'-OH blocked guanosine nucleotide incorporated into a growing strand of a template primer duplex), this indicates that the associated nucleobase is guanine and that the template base at this position is cytosine. The binding of the labeled antibody to an unlabeled extension product to form a labeled extension product, and the labeled extension product is then detected, using methods known in the art. Optionally, unbound labeled antibodies are washed away before the detection step.

Binding of the antibody to the RT incorporated in growing DNA strands are typically performed at a condition (“binding condition”) that is suitable for antibody-antigen interaction. For example, in some embodiments, binding occurs at a temperature that in the ranges of 30 to 45° C. or 35-50° C. In some embodiments, binding occurs in an environment having a pH that ranges from 7 to 8.5, often 7 to 7.5. In some embodiments, binding is performed binding conditions include a temperature in the range from 3-45° C. and/or an environment having a pH that ranges from 7 to 7.5. Under certain conditions on DNB arrays, low salt (e.g. 30-70 mM) Tris buffer with EDTA (~1-20 mM) and no Mg++ was found to promote binding, indicating that the composition of good binding reaction is enabling more efficient end-breathing of extended primer.

After binding excess (unbound) antibody may be removed under removal conditions, often at relatively high salt concentration that ranges from 150 mM to 1000 mM, e.g., from 150 mM to 400 mM from 150 mM to 350 mM, and at near neutral pH (e.g., pH ranging from 6 to 8, from 6.5 to 7.5, e.g., about 7). The wash may be performed under a temperature that ranges from 20 to 50° C., e.g., from 25 to 40° C., or about 30° C. In an other approach low salt (30-100 or 50-150 mM) in near neutral buffer (e.g., pH 6.8 to 7.2) is another possibility.

Antibody Dissociation And Second Incorporation

After detection, the DNA array is subjected to dissociation conditions (e.g., by raising temperature and/or pH) under which the bound, labeled antibodies are dissociated from the DNA templates. The DNA polymerase(s) used in the second incorporation step should retain their polymerase activity under these dissociation conditions, such that incorporation of additional RTs can occur under the conditions of antibody disassociation. Typically additional NLRTs and additional polymerase are added to the sequencing reaction after detection.

The same incorporation reaction composition (usually pH 9, with enzyme and NLRTs) used for the first incorporation may be used at proper temperature for 10-60s for a simultaneous second incorporation and antibody removal. Multiple aliquots of incorporation reaction can be pushed through the flow cell, e.g. 2-3 aliquots each incubated 10-20 seconds. The presence of the NLRTs in solution favors complete or near complete labeled antibody removal at lower temperature (e.g. less than 60C) or shorter time (e.g. 20-50% shorter) than reactions omitting the NLRTs, likely due to competition for antibody binding.

Depending on the selection of wash steps prior to second incorporation in some embodiments only additional NLRT's may be added (relying on residual polymerase from the first incorporation step) or additional polymerase (relying on residual NLRTS from the first incorporation) may be added. The additional polymerase may be the same or different as the polymerase used in the first incorporation and the additional NLRTs may be the same or different (e.g., different blocking moieties) as used in the first incorporation.

Exemplary dissociation conditions comprise a high temperature, such as temperature in the range from 50° C. to 75° C., and sometimes 55° C. to 75° C., e.g., 60° C. to 70° C. In some embodiments, the high pH is greater than 7, greater than 8, e.g., about 9. Exemplary dissociation conditions comprise a high pH environment (pH in the range from pH 8 to 10). In preferred embodiments the dissociation conditions comprise high temperature and high pH. Additionally, in some embodiments, removal of the antibody and second incorporation occurs in a reaction mixture that contains salt at a concentration that is less than 100 mM, such as less than 90 mM, or less than 80 mM. Under preferred disassociation conditions the antibody removal or dissociation generally can be carried out within less than 60 seconds, e.g., less than 40 seconds, or less than 30 seconds. In some embodiments, the dissociation conditions are those under which at least about 90%, sometimes at least about 95%, and sometimes at least about 99% of the bound labeled antibodies are dissociated from the template DNA molecules in less than 5 minutes, less than 60 seconds, e.g., less than 40 seconds, or less than 30 seconds, less than 20s, or less than 10s.

For the second incorporation it is preferred that a DNA polymerases are used that retain at least 90% polymerase activity under dissociation conditions, as compared to the activity for that polymerase under an known, optimal condition. Optimal conditions for each DNA polymerase are generally available in manufacturer's instructions.

Non-limiting examples of suitable DNA polymerases that can be used in methods disclosed herein include, a DNA polymerase from *Thermococcus* sp., such as 9° N or mutants thereof, including A485L, including double mutant Y409V and A485L, as described in, e.g., WO2018/129214. Other non-limiting examples of DNA polymerases include Taq polymerase, Bst DNA polymerase, and KOD polymerase.

The desired dissociation conditions generally result, at least in part, from a change in the buffer in contact with the array (e.g., by supplementing the prior buffer (e.g., binding buffer) with addition reagents (e.g., NLRTs) or by buffer exchange. That is, disassociation conditions generally result from introduction of a disassociation buffer that is introduced to the DNA array (e.g., injected into a flow cell), optionally with direct heating or cooling of the flow cell.

Timing

In some embodiments, antibody dissociation and second incorporation occur essentially simultaneously (e.g., under the same conditions in the same reaction buffer). In some embodiments a disassociation buffer without polymerase and/or without reversible terminator nucleotides is introduced in an initial set and rapidly supplemented by addition of polymerase and/or reversible terminator nucleotides to the buffer, or buffer exchange in which the second buffer comprises polymerase and/or reversible terminator nucleotides. However, antibody dissociation and second incorporation may occur in any order, for example, antibody dissociation may occur before, after, or substantially the same time as second incorporation.

The duration during which the DNA array is subjected to high temperature and high pH condition is brief (typically less than 60 seconds or less than 30 seconds). These relatively mild dissociation conditions advantageously minimize negative effects on the incorporated RT and on the subsequent extension reaction. Antibody removal and second incorporation can occur under the same condition according to the methods disclosed herein means no actions are required to change conditions to accommodate the two different reactions. The methods thus significantly improve efficiency and reduces sequencing cost and cycle time.

Wash

After the antibody removal following the second incorporation step, the array may be washed to remove antibodies and unincorporated RTs. The removable blocking groups of the RTs are then removed to permit the next cycle of primer extension, antibody binding, and detection.

Cycle

In some approaches, each cycle of the sequencing reaction on the DNA array comprises (i) incorporating an RT comprising a removable blocking group to at least some of the plurality of template DNA molecules on the array to form unlabeled extension products; (ii) contacting the incorporated RT on the unlabeled extension products with a labeled antibody that specifically binds to the incorporated RT, and the binding event forms labeled extension products; (iii) detecting the binding of the antibody, optionally followed by washing away the unbound antibodies; (iv) subjecting the labeled extension products, which are hybridized to the DNA array, to a condition that enables both disassociation of bound antibody and incorporation of additional RTs, (v) removal of the blocking group in a fashion that allows incorporation of an additional nucleotide analog (e.g., produces a hydroxyl group at the 3' position of a deoxyribose moiety). This step may be followed by a new cycle or cycles in which a new RT is incorporated and detected. The antibody may be directly labeled (e.g., a fluorescent labeled antibody) or may be detected indirectly (e.g., by binding of a labeled secondary antibodies).

In the context of concurrent removal of blocking groups and affinity reagents, a DNA polymerase used to incorporate NLRTs can mediate polymerization under conditions that are also suitable for dissociation of the labeled antibody from its target, i.e., the incorporated RT at the 3' end of the primer extension product. As disclosed above, these conditions, referred to as dissociation conditions, generally involve relatively high temperature (e.g., between 50-75° C., between 55-75° C., or between 60-70° C.), high pH (ranging pH 8 to 10, e.g., pH 9), and low salt condition (salt is present in the reaction in a concentration that is less than 100 mM). In some embodiments, polymerases used in the invention are capable of retaining at least 80%, at least 85%, or at least 90% of its polymerase activity. Using DNA polymerases possessing these properties allows antibody removal and second incorporation of RTs to occur the same condition, which improves sequencing efficiency and reduces costs.

TABLE 4

| Step | Action | Conditions |
|---|---|---|
| $1^{st}$ incorporation | Add 3' blocked unlableled dNTP + polymerase | pH 8-10 (e.g., pH 9), 50-75° C. (e.g., 60°) |
| Wash | Remove unincorporated dNTPs | Preferably pH ~7, 40-60° C. |
| Binding buffer | Add and bind labeled mAb | pH 7-7.5, 30-45° |

TABLE 4-continued

| Step | Action | Conditions |
|---|---|---|
| Wash Buffer | Remove excess of antibodies | 150-1000 mM salt, pH ~7, ~30° C. |
| Imaging buffer | | |
| Disassociation buffer | removal of mAb & second incorporation. less than 100 mM salt | pH 8-10 (e.g., pH 9), 50-75° C. (e.g., 60° C.), |
| Deblocking buffer | Cleave 3' protecting group with a cleavage reagent (e.g. THPP) | For THPP pH 8-10 (preferably pH 9), 50-75° C. (e.g., 60°), 150-1000 mM |

8. Sequencing with Fewer Than Four Channels or Images

General Approaches

Imagers with two or one detection channels (detecting one or two wave-length bands) are more efficient (e.g. more light detected, no dye-cross-talk) and less expensive than 4-channel imagers. Some of these imagers may provide electronic or other detection equivalent to one channel detection. It is advantageous to use these imagers for SBS on DNA arrays by generating 1, 2, 3, 4 or more images per cycle (per DNA position). However, sequencing that requires fewer than than 4 images per position is faster and results in less data to process. Using NLRTs and labeled base-specific antibodies provides many benefits in these types of sequencing processes, especially i) more accurate sequencing using less than 4 images or ii) efficient generation of 4 or more images with two or more separate antibody binding and imaging (including re-probing) steps to achieve exceptional accuracy. In some approaches these methods may use only three labeled antibodies with one unlabeled or absent) labeled or all four labeled antibodies, and use only one or two or more different dyes or other labels detectable in the one or two channels available per imager. For example, by attaching different number of dye molecules per antibody, especially in combination with using dyes of different brightness, four antibodies can generate 4 distinct intensities (e.g. in relative numbers 0.5, 1, 2, 4) to differentiate 4 incorporated nucleotides in one image. An alternative for such single channel imager, is to generate two images each for detecting two antibodies with two distinct intensities (e.g. 1 and 4) using two consecutive antibody binding, imaging and removal steps.

In contrast to labeled dNTP, it is feasible economically and chemically, to attach multiple dye molecules to antibodies of the invention. Attaching multiple dye molecules per antibody provides stronger signal than one dye molecule attached to the base for more efficient high quality imaging with less illumination light. Additionally, we have recognized that this enables development of new detection strategies. For example, Attaching multiple dye molecules per antibody allows us to balance signal intensities in 2-color MPS sequencing previously described where one nucleotide has to be detected at two distinct wavelength channels. See U.S. Pat. No. 8,617,811. More dye molecules can be attached to the antibody where 50% of antibody molecules have to be labeled with one dye and 50% with a different dye.

Methods are provided for antibody/NLRT sequencing and detection using antibodies or other affinity reagents directly or indirectly labeled for one-, two-, three-, or four-color detection. In some embodiments one affinity reagent is unlabeled.

As used herein, dyes with similar emission wavelengths are considered the “same color” if they are detected in the same channel of an automated sequencing system, where detects emissions in a 200 nm wavelength band, preferably a 100 nm band, sometimes a 50 nm or narrower band. It will be understood by the skilled practitioner that dyes of different colors can be selected to avoid or minimize cross-talk or overlapping emission spectra. Sequencing using methods of the invention may be two-, three-, or four-color sequencing. In one approach (four-color sequencing) each affinity reagent is directly or indirectly labeled with a different detectable label (e.g., a fluorescent dye) or combination of labels producing a unique signal. It will be appreciated that when a single antigen is recognized with two or more dyes (or other labels) it is possible, but not necessary, to label a single affinity reagent molecule with both (or all) of the dyes or other labels. Rather, a portion (e.g., 50%) of the affinity reagent molecules specific for the single antigen can be labeled with one dye and another portion (e.g., 50%) of the affinity reagent molecules specific for the single antigen can be labeled with the other dye.

According to one such method, an array is provided that comprises single-stranded nucleic acid templates disposed at positions on a surface. Sequencing by extension, or SBS, is performed in order to determine the identity of nucleotides at detection positions in nucleic acid templates in multiple sequencing cycles by: (i) binding (or incorporating) an unlabeled complementary nucleotide (NLRT) to a nucleotide at a detection position, (ii) labeling the NLRT by binding to it a directly or indirectly labeled affinity reagent that specifically binds to such an NLRT; (iii) detecting the presence or absence of a signal(s) associated with the complementary NLRT at the detection position, the signal resulting from the label (e.g., a fluorescent signal); wherein (1) detecting a first signal and not a second signal at the detection position identifies the complementary NLRT as selected from NLRT-A, NLRT-T, NLRT-G and NLRT-C; (2) detecting the second signal and not the first signal at the detection position identifies the complementary NLRT as an NLRT selected from NLRT-A, NLRT-T, NLRT-G or NLRT-C that is different from the NLRT selected in (1); (3) detecting both the first signal and the second signal at the detection position identifies the complementary NLRT as an NLRT selected from NLRT-A, NLRT-T, NLRT-G and NLRT-C that is different from nucleotides selected in (1) and (2); and (4) detecting neither the first signal nor the second signal at the position identifies the complementary NLRT as an NLRT selected from NLRT-A, NLRT-T, NLRT-G and NLRT-C that is different from the nucleotides selected in (1), (2) and (3); and (iii) deducing the identity of the nucleotide at the detection position in the nucleic acid template based on the identity of the complementary NLRT.

Another such method comprises: providing a plurality of nucleic acid templates each comprising a primer binding site and, adjacent to the primer binding site, a target nucleic acid sequence; performing sequencing reactions on the plurality of different nucleic acid templates by hybridizing an primer to the primer binding site and extending individual primers by one nucleotide per cycle in one or more cycles of sequencing-by-synthesis using a set of NLRTs and a corresponding set of affinity reagents, e.g.: (i) first NLRTs and first affinity reagents that specifically bind to the first NLRTs and that comprise a first label; (ii) second NLRTs and second affinity reagents that specifically bind to the second NLRTs and that comprise a second label; (iii) third NLRTs and third affinity reagents that specifically bind to the third NLRTs and that comprise both the first label and the second label; and (iv) fourth NLRTs and fourth affinity reagents that specifically bind to the fourth NLRTs and that comprise neither the first label nor the second label, wherein the first label and the second label are distinguishable from each other; and in each cycle of sequencing-by-synthesis, determining the identities of NLRTs at the detection positions by detecting the presence or absence of the first label and the presence or absence of the second label to determine the target nucleic acid sequences. An alternative to the foregoing method is to use a mixture of third affinity reagents that specifically bind to the third NLRTs, some of which comprise the first label and some of which comprise the second label (e.g., an equal mixture).

In a one-color sequencing method, the affinity reagents include a detectable label that is present at distinguishable intensities. For example, according to one such embodiment, such a method comprises: such method comprises: providing a plurality of nucleic acid templates each comprising a primer binding site and, adjacent to the primer binding site, a target nucleic acid sequence; performing sequencing reactions on the plurality of different nucleic acid templates by hybridizing a primer to the primer binding site and extending individual primers by one nucleotide per cycle in one or more cycles of sequencing-by-synthesis using a set of NLRTs and a corresponding set of affinity reagents, e.g.: (i) first NLRTs and first affinity reagents that specifically bind to the first NLRTs and that comprise a label at a first intensity; (ii) second NLRTs and second affinity reagents that specifically bind to the second NLRTs and that comprise the label at a second intensity; (iii) third NLRTs and third affinity reagents that specifically bind to the third NLRTs and that comprise the label at a third intensity; and (iv) fourth NLRTs and fourth affinity reagents that specifically bind to the fourth NLRTs and that are unlabeled (or, alternatively, the affinity reagent set includes only the first, second and third affinity reagent and does not include a fourth affinity reagent that binds to the fourth NLRT); and in each cycle of sequencing-by-synthesis, determining the identities of NLRTs at the detection positions by detecting the presence and intensity (or absence) of the label to determine the target nucleic acid sequences.

In another approach, affinity affinity reagents are used that are labeled with one or the same number of molecules of a single dye yet discriminate among the four NLRTs as a result of different binding efficiencies (i.e., the average number of affinity reagents that are bound to a single spot on an array, e.g., 10% of all copies of the target DNA molecule for NLRT-A, 30% for NLRT-T, and 60% for NLRT-C (and zero percent or little detectable binding for NLRT-G). In one approach, the targets have the same blocking group and affinity reagents are selected that have different affinities for their target. In another one approach blocking groups may be modified with small chemical changes to tune the efficiency of binding of the same affinity reagent, thus generating base specific levels of signal. For example, an unmodified blocking group may produce the highest signal (100% of signal), a blocking group with modification 1 may produce a lower level of signal (e.g. 50%),), a blocking group with modification 2 may produce a still lower signal with even less (25%), etc.

In another approach, only one affinity reagent is used. Nucleotide mixtures with different proportions of the blocking group recognized by the affinity reagent are used to generate distinguishable levels of signal. The balance of nucleotides in the mixtures have a blocking group with no corresponding affinity reagent. For illustration:

| | |
|---|---|
| dA | 0% Blocking group 1, 100% blocking group 2 |
| dG | 25% Blocking group 1, 75% blocking group 2 |
| dC | 50% Blocking group 1, 50% blocking group 2 |
| dT | 100% Blocking group 1, 0% blocking group 2 |

In another embodiment the antibody could recognize two bases (a nucleotide dimer) where the downstream base is modified with the addition of a cleavable or un-cleavable group.

In another embodiment the last-incorporated base is identified by the binding of two affinity reagents in combination: one affinity reagent specifically recognizes and binds to the nucleobase, and the second affinity reagent specifically recognizes and binds to the blocking group. Only when both affinity reagents bind and/or are in spatial proximity, can a determination of the identity of the terminal base be made such as when the two affinity reagents include a FRET donor-acceptor pair as their respective "labels." Alternatively, the binding of one of the affinity reagents could lead to a conformational change that allows or enhances binding of the second affinity reagent.

The nucleoside analogues described herein can be used in a variety of sequencing methods. For example, the analogues can be used in one label (sometimes called "no-label"), two-label, three-label, or four-label sequencing methods, in which unlabeled analogues are paired with affinity reagents directly or indirectly labeled according to a one-, two-, three-, or four-label scheme.

Exemplary one-label sequencing methods include, but are not limited to, methods in which nucleoside analogues having different nucleobases (e.g., A, C, G, T) are delivered in succession and incorporation is detected by detecting the presence or absence of the same signal or label for each different nucleobase. Thus, one-label methods are sometimes known as one-color methods because the detection signal and/or label is the same for all nucleobases, even though it may differ in intensity (or be absent) for each nucleoside analogue. For example, incorporation of a nucleoside into a primer by DNA polymerase mediated template directed polymerization can be detected by detecting a pyrophosphate cleaved from the nucleoside pyrophosphate. Pyrophosphate can be detected using a coupled assay in which ATP sulfurylase converts pyrophosphate to ATP, in the presence of adenosine 5' phosphosulfate, which in turn acts as a substrate for luciferase-mediated conversion of luciferin to oxyluciferin, generating visible light in amounts proportional to ATP generation.

According to another embodiment, two-label, or two-color (also called "two channel"), sequencing can be performed using the RTs and affinity reagents described herein, using two distinguishable signals in a combinatorial fashion to detect incorporation of four different RTs. Exemplary two-label systems, methods, and compositions include, without limitation, those described in U.S. Pat. No. 8,617,811, the contents of which are hereby incorporated by reference in the entirety for all purposes and particularly for disclosure related to two-label sequencing. Briefly, in two-label sequencing, incorporation of a first RT (e.g., RT-A) is detected by labeling the newly incorporated RT by specific binding of a first affinity reagent that includes a first label, then detecting the presence of the first label. Incorporation of a second RT (e.g., RT-C) is detected by labeling the second RT by specific binding of a second affinity reagent that includes a second label, then detecting the presence of the second label. Incorporation of a third RT (e.g., RT-T) is detected by labeling the third RT by specific binding of a third affinity reagent that includes both the first and the second label (e.g., an affinity reagent in which individual molecules are conjugated to two different labels), then detecting the presence of both the first and second label; and, incorporation of a fourth RT (e.g., RT-G) is detected by detecting the absence of both first and second labels, whether this results from binding of a fourth affinity reagent that is unlabeled, or from the fact that no fourth affinity reagent is included in the affinity reagent set that is used. In two-color sequencing the first label is distinguishable from the second label and the combination of the first and second label can be distinguished from the first and second label taken alone.

According to another embodiment, three-label sequencing can be performed using a first RT labeled by specific binding of an first affinity reagent that includes a first label, a second RT labeled by specific binding of an second affinity reagent that includes a second label, a third RT labeled by specific binding of a third affinity reagent that includes a third label. For the fourth RT, the corresponding affinity reagent is omitted from the affinity reagent set, or is unlabeled, or includes a combination of two or more of the first, second, and third labels (or a mixture of affinity reagents that are labeled with a different one of the labels and that specifically bind to the fourth RT). The first, second and third labels are distinguishable from each other.

Similarly, four-label sequencing can employ a first NLRT that is labeled by specific binding of a first affinity reagent that includes a first label, a second NLRT that is labeled by specific binding of a second affinity reagent that includes a second label, a third NLRT that is labeled by specific binding of a third affinity reagent that includes a third label, and a fourth NLRT that is labeled by specific binding of a fourth affinity reagent that includes a fourth label. Again, the first, second, third and fourth labels are distinguishable from each other.

Two Color Sequencing in which Three Classes of Affinity Reagents are Labeled

In one approach the extended primers on an array are labeled by contacting the array with a set of at least three different affinity reagents (hereinafter referred to as antibodies for clarity but not for limitation) that include the following:

(a) a composition comprising a first antibody specific for one of the four nucleotide analogs, bearing a first label that fluoresces or produces a product that fluoresces at a first wavelength;

(b) a composition comprising a second antibody specific for another of the four nucleotide analogs, bearing a second label that fluoresces or produces a product that fluoresces at a second wavelength; and (c) a composition comprising a third antibody specific for one of the two remaining nucleotide analogs, bearing both the first and second labels. The fourth antibody may be absent or unlabeled.

In one approach the composition in (c) comprises a mixture of antibodies, some of which (e.g., 50%) comprise a first label and some of which (e.g., 50%) comprise a second label. In this embodiment the density of first label (dye molecules per antibody labeled with the first label) in composition (c) is greater than the density of first label in composition (a) and the density of second label (dye molecules per antibody labeled with the second label) in composition (c) is greater than the density of second label in composition (b). For example, the antibodies in composition (a) may comprise 2 molecules of first label, or comprise on average 2 molecules of first label, and the antibodies in composition (c) that are labeled with the first label may comprise 3 or 4 or more molecules of first label, or comprise on average 3 or 4 or more molecules of first label, and likewise the antibodies in composition (b) may comprise 2 molecules of second label, or comprise on average 2 molecules of second label and the antibodies in composition (c) that are labeled with the second label may comprise 3 or 4 or more molecules of second label, or comprise on average 3 or 4 or more molecules of second label. An antibody specific for a nucleotide identified based on emissions at two wavelengths may be more densely labeled More dye molecules can be attached to the antibody where 50% of antibody molecules have to be labeled with one dye and 50% with a different dye.

TABLE 5

| Ab specificity | Label | Dye molecules per antibody | Proportion of nucleobase-specific antibodies so labeled | Intensity of signal (arbitrary units) |
|---|---|---|---|---|
| A | First | 2 | 100% | 2 |
| T | Second | 2 | 100% | 2 |
| C | First | 4 | 50% | 2 |
| C | Second | 4 | 50% | 2 |
| G | neither | n/a | n/a | 0 |

Table 4 above shows balancing when the affinity reagent labeled with two different dyes is divided into two equal portions and there is equal incorporation of each of the 4 nucleotides. It will be apparent to the reader that the general principle illustrated can be adapted to situations in which affinity reagents are divided into unequal proportions.

In another approach the composition in (c) comprises antibodies in which individual antibodies (e.g., tetramers) with both the first and second labels attached thereto where the density of first label in composition (c) antibodies is greater than the density of first label in composition (a) antibodies and the density of first label in composition (c) antibodies is greater than the density of first label in composition (b) antibodies. For example, the antibodies in composition (a) may comprise 1 molecule of first label, or comprise on average 1 molecules of first label and the antibodies in composition (c) may comprise 2 molecules of first label and or comprise on average 2 molecules of first label and 2 molecules of second label or comprise on average 2 molecules of second label.

The compositions in (a), (b), and (c) may be a combined as a single composition, for example, allowing the affinity reagents to be added at the same time. Alternatively the compositions may be different and may be combined on the array at about the same time (simultaneously). Alternatively the compositions may be added to the array one at a time, sequentially.

Optionally, the set of affinity reagents further includes a fourth affinity reagent that specifically binds to the fourth nucleotide analog, but does not detectably fluoresce or produce a product that fluoresces at either the first or the second wavelength. In this context, the term “detectable” means fluorescence that scores a negative, being below the threshold for scoring as a positive, when the detection apparatus is adjusted to accurately discriminate positive and negative signals from the first affinity reagent and the second affinity reagent Following binding of the affinity reagents to the extended primer, unreacted affinity reagent is washed away, and nucleotide analog that has been incorporated in the extended primers is determined by detecting or measuring the label at individual sites on an array. Fluorescence at only the first wavelength indicates that the first nucleotide analog has been incorporated, fluorescence at only the second wavelength indicates that the second nucleotide analog has been added, fluorescence at both the first and the second wavelength indicates that the third nucleotide analog has been incorporated; and fluorescence at neither wavelength indicates that the fourth nucleotide analog has been incorporated. This is shown in the following table:

TABLE 6

| nucleotide in target | analog in primer | affinity reagent | Image 1 ($1^{st}$ wavelength) | Image 2 ($2^{nd}$ wavelength) |
|---|---|---|---|---|
| A | (1) T | (a) anti-T | + | absent |
| T | (2) A | (b) anti-A | absent | + |
| C | (3) G | (c) anti-G | + | + |
| G | (4) C | (d) anti-C | absent | absent |

Table 6 is provided by way of illustration only. Any combination of affinity agent specificity in column 3 and labeling in cols. 4 and 5 may be used so that interpretation of the nucleotide in the target nucleic acid in column 1 can be in any order.

As described above, to accomplish the two-color method, the third affinity reagent is labeled so as to be detectable or imaged concurrently with both the first affinity reagent and the second affinity reagent. As discussed above, intensity of signal at each of the wavelengths by the third affinity reagent can be matched in intensity with the first and second affinity reagents. Possible techniques for matching intensity include the following:

(1) The third affinity reagent includes one specific antibody or its equivalent that bears a combination of two different labels that fluoresce or produce products that respectively fluoresce at the first and second wavelengths. The two different labels on the antibody in the third affinity reagent can be the same as the label used for the antibodies in the first and second affinity regents, respectively. To match the same intensity, the antibody in the third affinity reagents bears the same density of each label as each of the antibodies in the first and second reagents, for a total of twice the density.

(2) As an alternative, the third affinity reagent can be labeled with one or a plurality of labels that are different from the labels on the first and second affinity reagents. The intensity of fluorescence of the third affinity reagent at each of the two wavelengths can be matched to the first and second affinity reagents by selecting label(s) for the third affinity reagent that fluoresce at a higher intensity (perhaps double the intensity) at the wavelengths used to detect each of the labels on the first and second affinity reagents when excited at the same wavelengths.

(3) In another alternative, the third affinity reagent includes a mixture of at least two specific antibodies or their equivalents, the first of which bears a label that fluoresces or produces a product that fluoresces at the first wavelength, the second of which bears a label that fluoresces or produces a product that fluoresces at the second wavelength. For example, the first antibody bears the same label as the antibody in the first affinity reagent at about twice the density, and the second antibody bears the same label as the antibody in the second affinity regent at about twice the density.

To facilitate detection, it is helpful to match the intensity of the two labels on the third affinity reagent with the labels on each of the first and the second regent, when measured separately. When two different antibodies are present in the third reagent bearing labels that fluoresce at the first and second wavelength respectively, the intensity can be matched by doubling the density of labeling on each antibody, by doubling the total amount of antibody in the reagent. In this way, extended primers labeled with the third reagent fluoresce at the first wavelength at an intensity that is comparable to the intensity of first analogs labeled with the first reagent; and fluoresce at the second wavelength at an intensity that matches or is comparable to the intensity of second analogs labeled with the second reagent. Intensity that “matches” or is “comparable” in this context means that the intensity of each of the labels in the double-labeled reagent is at least about 75% and typically not more than about 135% or 150% of the intensity of the labels in either of the single-labeled reagents.

Two Color Sequencing in which Two or More Binding Reactions are Carried Out

In some approaches for detecting which nucleotide has been incorporated into the extended primer on a one- or two-channel instrument, multiple separate labeling reactions are carried out.

In approach, a total of four images (one for each base), are acquired as follows:

In the first reaction, the extended primers containing comprising four incorporated nucleotides (e.g., A, T, G and C) at the 3' terminus are contacted with affinity reagents to form first reaction products under conditions wherein a first affinity reagent bearing a label that fluoresces or produces a product that fluoresces at a first wavelength binds specifically to the first nucleotide analog, and a second affinity reagent bearing a second label that fluoresces or produces a product that fluoresces at a second wavelength binds specifically to the second nucleotide analog. After optionally removing unbound reagents, the newly incorporated nucleotide added in each of the two first reaction products is determined by detecting and/or measuring fluorescence at the first and second wavelengths. The first and second affinity reagents (or the labels thereupon) are then removed (or modified so that they no longer emit signal) and the second labeling reaction can be performed and interpreted. In one approach labels are attached to affinity reagents via a cleavable linker and affinity reagents are modified so they no longer emit associated with a signal by cleavage of the label.

In the second reaction, the extended primers are contacted with affinity reagents to form second reaction products under conditions wherein a third affinity reagent comprising a label that fluoresces or produces a product that fluoresces at the first wavelength binds specifically to the third nucleotide analog, and a fourth affinity reagent comprising a label that fluoresces or produces a product that fluoresces at the second wavelength binds specifically to the fourth nucleotide analog. After optionally removing unreacted reagent, the nucleotide analog that has been added in each of the second reaction products is determined by measuring fluorescence at the first and second wavelengths.

Thus, the four affinity reagents are as follows:

(a) a first affinity reagent specific for one of the nucleotide analogs, bearing a label that fluoresces or produces a fluorescent product that fluoresces at a first wavelength;

(b) a second affinity reagent specific for another of the nucleotide analogs, bearing a label that fluoresces or produces a fluorescent product that fluoresces at a second wavelength;

(c) a third affinity reagent specific for one of the two remaining nucleotide analogs, bearing a label that fluoresces or generates a product that fluoresces at the same wavelength as the first affinity reagent, and (d) a fourth affinity reagent specific for the fourth nucleotide analog, bearing a label that fluoresces or generates a product that fluoresces at the same wavelength as the second affinity reagent.

In certain embodiments the first and third affinity reagents comprise the same label (e.g., the same dye) and the second and fourth affinity reagents comprise the same label (e.g., the same dye) which is different from the label on the first and third affinity reagents. In other embodiments the dyes/labels detected in the same channel are different with similar or different brightness.

The results of the labeling and detection are interpreted as follows: fluorescence at the first wavelength in the first reaction product indicates that the first nucleotide analog has been incorporated, fluorescence at the second wavelength in the first reaction product indicates that the second nucleotide analog has been incorporated, fluorescence at the first wavelength in the second reaction product indicates that the third nucleotide analog has been incorporated, and fluorescence at the second wavelength in the second reaction product indicates that the fourth nucleotide analog has been incorporated. This is shown in the following table:

TABLE 7

| nucleotide in target | analog in primer | affinity reagent | Image 1 ($1^{st}$ wavelength) | Image 2 ($2^{nd}$ wavelength) |
|---|---|---|---|---|
| Reaction 1: | | | | |
| A | (1) T | (a) anti-T | 1 | 0 |
| T | (2) A | (b) anti-A | 0 | 1 |
| C | (3) G | none | 0 | 0 |
| G | (4) C | none | 0 | 0 |
| Reaction 2: | | | | |
| A | (1) T | none | 0 | 0 |
| T | (2) A | none | 0 | 0 |
| C | (3) G | (c) anti-G | 1 | 0 |
| G | (4) C | (d) anti-C | 0 | 1 |

Table 7 is provided by way of illustration only. As before, any combination of affinity agent specificity in column 3 and labeling in cols. 4 and 5 may be used so that interpretation of the nucleotide in the target nucleic acid in column 1 can be in any order.

As discussed above, in applying the labeling and detecting schemes put forth above, the exemplary affinity reagent is a monoclonal antibody (or antigen binding fragment derived therefrom) having the requisite specificity. As discussed elsewhere herein and affinity reagent may be labeled directly or indirectly. For example, where the affinity reagent is an unlabeled antibody, it may bind to the corresponding nucleotide analog directly, and subsequently be labeled using a secondary antibody that binds specifically to a primary antibody.

Exemplary labels are fluorescent moieties that can be distinguished under different conditions (emission wavelength), attached directly to the respective antibody or affinity reagent. This disclosure also includes two-color detection using labels that are not fluorescent themselves, but produce a product that fluoresces. Labels in this category include enzymes that convert a small-molecule substrate that does not substantially fluoresce at the detection wavelength to a product that emits fluorescence at the detection wavelength. Such substrates include L-Alanine 4-methoxy-β-naphthylamide hydrochloride, 3-Amino-9-ethylcarbazole, Dansylcadaverine, Dihydrorhodamine, Fluorescein di(β-D-galactopyranoside, L-Methionine 7-amido-4-methylcoumarin trifluoroacetate, 4-Methylumbelliferyl α-D-galactopyranoside, Resorufin ethyl ether, Tyramine, available from Sigma Aldrich and Thermofisher Scientific. The reader is referred to the most recent edition of "The Molecular Probes" handbook, invitrogen.

To practice the two color method, two enzymes may be used to label the first, second, and third affinity agents in the detection system. The two enzymes respectively convert substrates to two different products that emit florescence at two different wavelengths. Under some reaction conditions, a plurality of fluorescent molecules will be produced per enzyme moiety. This may intensify the signal, whereupon the user will typically time the reaction to obtain the intensity desired. The binary detection scheme of this invention may also be practiced by labeling the antibody or affinity reagent with a label that is detectable by other means, mutatis mutandis, be it conjugation, measurement of bioluminescence, or other suitable technique.

Discussion of labels in the description above does not necessarily require that each antibody or other affinity reagent be labeled with a single labelling moiety (such as a fluorescent dye or enzyme). More typically, affinity reagents are labeled so as to place a plurality of labeling moieties on each of the affinity reagent molecules (for example, in a Poisson distribution), whereby the labeling intensity is determined by the average number of entities per affinity reagent (i.e., the total number of moieties in an aliquot divided by the total number of affinity reagents in the aliquot). An aliquot of affinity reagent may have some molecules that are not labeled. This generally doesn't interfere with the efficacy of detection, since nucleic acid molecules to be sequenced on an array are typically amplicons of DNA fragments, presenting a plurality of binding sites.

Unless explicitly stated or required, labels that fluoresce at the same wavelengths are not necessarily the same label. Intensity of emission of a fluorescent label at a particular wavelength can be adjusted by adjusting the number of labels per affinity reagent, and/or by selecting different labels that emit fluorescence at the same detection wavelength at different intensities per labeling moiety.

In the labeling and detection methods put forth above, the reactions can be performed in any effective order. For example, target nucleic acids are typically contacted with all nucleotide analogs at the same time, and then contacted with the affinity reagent at the same time. Nevertheless, it is permissible to contact the target nucleic acids with the analogs and then with the affinity reagents in a sequential fashion. It is also permissible to intermesh different steps in the protocol in an effective manner: for example, reacting the hybrid with some but not all of the analogs, and detecting the analogs incorporated, and then reacting the hybrid with the other analogs and detecting the analogs subsequently.

The methods put forth above can be adopted in a two-color method of sequencing a DNA molecule as follows: A sequencing primer is hybridized to the DNA molecule. Subsequently, the user performs multiple cycles of:

A. contacting the sequencing primer with a nucleotide analog to form an extended primer and B. determining the nucleotide analog incorporated into the extended primer; then C. removing the labeled affinity reagent and fluorescent label and D. converting the terminator nucleotide on each extended primer to a non-terminator nucleotide, thereby permitting further extension of the primer in subsequent cycles of the sequencing.

Optionally steps B and C are repeated (in two half-cycles) using two pairs of antibodies with different specificities, as discussed above.

Any desired number of cycles can be performed, such as 5 or 10 cycles, with more than 25, 50, 100, or 200 cycles being more typical.

This disclosure also provides kits or sets of reagents for sequencing a DNA molecule. For example, to supply reagents of sequencing using the first detection scheme described above, the set of reagents may comprise: (1) four different nucleotide analogs that will extend a sequencing primer hybridized to the DNA molecule depending on whether the complementary nucleotide on the DNA is adenine, thymine, cytosine, or guanine; and (2) at least three affinity reagents, wherein (a) a first affinity reagent specific for one of the four nucleotide analogs, bearing a label that fluoresces or produces a product that fluoresces at a first wavelength;

(b) a second affinity reagent specific for another of the four nucleotide analogs, bearing a label that fluoresces or produces a product that fluoresces at a second wavelength;

(c) a third affinity reagent specific for one of the two remaining nucleotide analogs, bearing one or more labels that fluoresce at both the first and second wavelength; and optionally (d) a fourth reagent specific for the fourth nucleotide analog, which does not bear a label or produce a product that fluoresces at either the first or the second wavelength.

To supply reagents for sequencing using the second detection scheme described above, the set of reagents may comprise: (1) four different nucleotide analogs that will extend a sequencing primer hybridized to the DNA molecule depending on whether the complementary nucleotide on the DNA is adenine, thymine, cytosine, or guanine; and (2) four affinity reagents, wherein:

(a) a first affinity reagent specific for one of the nucleotide analogs, bearing a label that fluoresces or produces a fluorescent product that fluoresces at a first wavelength;

(b) a second affinity reagent specific for another of the nucleotide analogs, bearing a label that fluoresces or produces a fluorescent product that fluoresces at a second wavelength;

(c) a third affinity reagent specific for one of the two remaining nucleotide analogs, bearing a label that fluoresces or generates a product that fluoresces at the same wavelength as the first affinity reagent (optionally the same label as used with the first affinity reagent), and (d) a fourth affinity reagent specific for the fourth nucleotide analog, bearing a label that fluoresces or generates a product that fluoresces at the same wavelength as the second affinity reagent (optionally the same label as used with the second affinity reagent).

In another approach, two binding reactions are used, first bound antibodies are not removed. Second pair of images detects two nucleotides each.

In another approach, four binding reactions are performed for obtaining 4 images on a single-channel imager. In the first reaction, one affinity agent is bound. In the second reaction, a second affinity agent is bound without removing the first affinity agent. Third and fourth affinity agents are similarly bound and the results are interpreted as illustrated in the table below. This approach may be used on a one channel (single color) sequencer.

| | 1st Image | 2nd Image | 3rd Image | 4th Image |
|---|---|---|---|---|
| A | + | + | + | + |
| T | | + | + | + |
| G | | | + | + |
| C | | | | + |

Similar schema using three labeled antibodies can be used on a single-channel imager by obtaining two consecutive images. For example: Image 1: dye 1 labeled antibodies A, C. Image 2: dye 2 labeled antibodies T, C:

| | Image 1 | Image 2 |
|---|---|---|
| A | + | null |
| C | + | + |
| T | null | + |
| G | Null or absent | Null or absent |

In yet another approach, four binding reactions are performed for obtaining 4 images on a single-channel imager by using substrates to change signals. Two binding reactions may be used on a single-channel imager to obtained four images (one for each base) if after binding these two antibodies detectable signal is generated from one antibody first and than from the second bound antibody. For example, if each antibody is bound to a different luciferase, where each luciferase acts on a different substrate for emitting bioluminescence, by adding first substrate the first antibody would be detected. The substrate could then be removed and replaced with a second substrate to detect the second antibody.

Re-Probing

As noted Section 8, above, it is possible according to the invention to uncouple removal of affinity reagents (e.g., antibodies) and the 3' protecting group(s). Because affinity reagents can be removed without removing the blocking moiety, it is advantageously possible to reprobe some or all base positions to increase accuracy of base calling, test the integrity of the chip, or for other reasons. Any given base position can be probed once and reprobed 0, 1, 2 or more than 2 times. Usually, a single round of reprobing is considered sufficient. Solely for convenience, in a case in which a base position is probed two times, the first round of probing can be referred to as the first-halfcycle and the second round of probing can be referred to as the second-halfcycle.

When reprobing, it is possible to probe each position twice with the same affinity reagent, e.g., same primary antibody. More often, a different affinity reagent is used, such as a different antibody preparation (e.g., a different monoclonal antibody), a different class of affinity reagent (e.g., probing with an antibody in the first-halfcycle and with an aptamer in the second-halfcycle), or an affinity reagent with a different specificity. For example, in the first-halfcycle an array may be probed with anti-A, anti-T, anti-C and anti-G, and in the second-halfcycle the array may be probed with anti-purine and anti-pyrimidine used.

In one approach four NLRTs are blocked using two blocking groups, e.g., azidomethyl-T, azidomethyl-G, cyanoethenyl-C and cyanoethenyl-A and the array is probed once with two affinity reagents (one specific for 3'-O-azidomethyl-2'-deoxyribose and the other specific for 3'-O-cyanoethenyl-2'-deoxyribose) and probed a second time with a different pair of affinity reagents (one specific for purines and one specific for pyrimidines). An address on an array that shows signal characteristic of 3'-O-azidomethyl-2'-deoxyribose and purine would be identified as having a guanine base, and so forth.

9. Affinity Reagent Sets

"Affinity reagent sets" are used to label NLRTs used in SBS. For example, in one embodiment, for an NLRT set that includes four NLRTs (NLRT-A, NLRT-T, NLRT-C and NLRT-G), there could be a corresponding affinity reagent set of four affinity reagents, each specifically recognizing and binding to one of the RTs (antiA, antiT, antiC and antiG). Affinity reagent sets describe combinations of affinity reagents that can be (i) provided in kit form, as a mixture or in separate containers and/or (ii) contacted with, or combined on, a sequencing array (e.g., within a sequencing flow cell). It is contemplated that affinity reagents of the present invention include at least one affinity reagent described above that includes one or more (e.g. 3 of 6) CDRs set forth in Table 3. It will be appreciated that this contemplated set will include affinity reagents that include at least one (e.g., 2) antibody chain as described in Table 2.

According to one embodiment, each member of an affinity reagent set has a different, distinguishable detectable label, as in four-color SBS. According to another embodiment, one member of an affinity reagent set is unlabeled, while the other members are labeled. Alternatively, the affinity reagent set could simply exclude the unlabeled affinity reagent and include only the labeled affinity reagents.

For example, according to one embodiment, one affinity reagent is labeled with a first label (e.g., antiA); a second affinity reagent is labeled with a second label (e.g., antiT); a third affinity reagent is labeled with a third label (e.g., antic); and a fourth affinity reagent is unlabeled or simply excluded from the affinity reagent set (e.g., antiG). Such an affinity reagent set would be useful for three-color sequencing.

According to another embodiment, one affinity reagent (e.g., antiA) is labeled with a first label; a second affinity reagent (e.g., antiT) is labeled with a second label; a third affinity reagent (e.g., antic) is labeled with both the first label and the second label; and a fourth affinity reagent (e.g., antiG) is unlabeled (or excluded from the affinity reagent set). Alternatively, the third affinity reagent may include a mixture of affinity reagent molecules, all of which specifically bind to a particular base (e.g., all are antic), but some include the first label and some include the second label. Such affinity reagent sets would be useful for two-color sequencing.

According to another embodiment, only a single detectable label is used (or a single combination of two or more labels), but differs in intensity among members of the set, such as when the affinity reagent includes differing amounts of the label (or of at least one label of a combination of two or more labels). For example, in one embodiment, a first affinity reagent (e.g., antiA) is labeled with a label at a first intensity; a second affinity reagent (e.g., antiT) is labeled with the same label but at a second intensity; a third affinity reagent (e.g., antic) is labeled with the same label but at a third intensity; and a fourth affinity reagent (e.g., antiG) is unlabeled (or the fourth affinity reagent is excluded from the affinity reagent set). In another embodiment, a first affinity reagent (e.g., antiA) is labeled with a first label at a first intensity and a second label; a second affinity reagent (e.g., antiT) is labeled with the same first label but at a second intensity and the same second label; a third affinity reagent (e.g., antiC) is labeled with the same first label but at a third intensity and the same second label; and a fourth affinity reagent (e.g., antiG) is unlabeled, is labeled only with the second label, or is excluded from the affinity reagent set.

10. Reaction Mixtures and Kits

Reaction Mixtures

Nucleoside analogues (e.g., NLRTs) and oligo- or polynucleotides containing such nucleoside analogues or reaction products thereof can be used as a component of a reaction mixture. For example, such components can be used in reaction mixtures for nucleic acid sequencing (e.g., SBS). Exemplary reaction mixtures include, but are not limited to, those containing (a) template nucleic acid; (b) polymerase; (c) oligonucleotide primer; (d) a 3'-O reversibly blocked nucleoside analogue, or a mixture of 3'-O reversibly blocked nucleoside analogues having structurally different nucleobases; and (e) a labeled affinity reagent. Exemplary sequencing reaction mixtures of the invention include, but are not limited to, arrays comprising a plurality of different template nucleic acids immobilized at different locations on the array; (b) polymerase; (c) oligonucleotide primer; (d) and one or a mixture of NLRTs. Exemplary sequencing reaction mixtures of the invention include, but are not limited to, arrays comprising a plurality of different template nucleic acids immobilized at different locations on the array; (b) growing DNA strands (GDS) (which may comprise a 3' NLRT; and (c) one or more affinity reagents (e.g., an affinity reagent set as described hereinabove).

Affinity reagents that recognize different epitopes of a single NLRT may be used in combination. For example a first affinity reagent that recognizes the nucleobase portion of the incorporated NLRT may be used with a second affinity reagent that recognizes a blocking group. Staining may be done simultaneously or sequentially. In sequential staining the second affinity reagent may be applied while the first affinity reagent remains bound to the NLRT or after removal of the first affinity reagent in the case of re-probing (discussed below).

Components described in this application can be used in reaction mixtures for nucleic acid sequencing. Exemplary reaction mixtures include, but are not limited to, those containing (a) a nucleic acid array comprising a plurality of clonal populations of nucleic acid template molecules at positions on the array substrate; (b) a polymerase; (c) a primer extension product; (d) a mixture of 3'-O reversibly blocked nucleoside analogues (e.g., 3'-O-reversible terminator deoxyribonucleotides) having structurally different nucleobases; and (e) one or more labeled antibodies that can specifically bind to one or more of the 3'-O reversibly blocked nucleoside analogues having structurally different nucleobases, wherein at least 95% of the antibody molecules are free in solution (i.e., dissociated from the nucleic acid templates), and wherein the reaction mixture is at elevated temperature and pH (i.e., disassociation conditions as discussed above) and generally a salt concentration of less than 100 mM.

In some embodiments, the reaction mixture comprises (a) a DNA polymerase, wherein the polymerase is capable of mediating polymerization under a temperature of 60° C., pH 9, and 50 mM salt; (c) a oligonucleotide primer; (d) a 3'-O-reversible terminator deoxyribonucleoide, or a mixture of 3'-O reversibly blocked nucleoside analogues having structurally different nucleobases; and (e) one or more labeled antibodies that can specifically bind to one or more of the 3'-O reversibly blocked nucleoside analogues having structurally different nucleobases, and at least 95% of the labeled antibody molecules ain the reaction mixture are not associated with their target 3'-O reversibly blocked nucleoside analogues.

Exemplary sequencing reaction mixtures of the invention may also include wash buffers, and/or arrays comprising a plurality of template nucleic acids immobilized at different locations on the array. The template nucleic acids on the array may have different sequences.

Kits

Kits may be provided for practicing the invention. As described above, NLRTs and NLRT sets may be provided in kit form. Also as described, above, affinity reagents and affinity reagent sets may be provided in kit form. Also contemplated are kits comprising both NLRTs and NLRT sets and affinity reagents or affinity reagent sets. For example, the invention provides kits that include, without limitation (a) a reversible terminator nucleotide (RT) or RT set that includes one, two, three, four or more different individual RTs; (b) a corresponding affinity reagent or affinity reagent set that includes one, two, three, four or more affinity reagents, each of which is specific for one of the RTs; and (c) packaging materials and or instructions for use. It is contemplated that kits of the present invention include at least one affinity reagent described above that includes one or more (e.g. 3 of 6) CDRs set forth in Table 3. It will be appreciated that this contemplated set will include affinity reagents that include at least one (e.g., 2) antibody chain as described in Table 2.

According to another embodiment, such a kit comprises a plurality of the RTs, wherein each RT comprises a different nucleobase, and a plurality of affinity reagents, wherein each affinity reagent binds specifically to one of the RTs. It will be recognized that kits of the present invention include at least one affinity reagent described above that includes one or more (e.g. 3 of 6) CDRs set forth in Table 3. It will be appreciated that this contemplated set will include affinity reagents that include at least one (e.g., 2) antibody chain as described in Table 2.

In one example, the invention provide a kit comprising (a) a reversible terminator nucleotide as herein described that may be incorporated into a primer extension product; (b) a first affinity reagent that is binds specifically to the reversible terminator nucleotide when incorporated at the 3' terminus of a primer extension product; and (c) packaging for (a) and (b). In one approach, the kit contains a plurality of reversible terminator deoxyribonucleotides, wherein each reversible terminator deoxyribonucleotide comprises a different nucleobase, and a plurality of first affinity reagents, wherein each first affinity reagent binds specifically a different one of the reversible terminator deoxyribonucleotides. In some embodiments the first affinity reagents are detectably labeled and can be distinguished from each other. In some embodiments the kit comprises secondary affinity reagents. In some embodiments the first and/or second affinity reagents are antibodies.

Kits may include one or more of the NLRTs, DNA polymerases, and antibodies as described above. For example, the invention provides kits that include, without limitation (a) a NLRT) or NLRT set that includes one, two, three, four or more NLRTs having different structural nucleobases; (b) a corresponding affinity agents, each of which can bind to one of the NLRTs in a nucleobase-specific manner; (c) a DNA polymerase that is capable of mediating polymerization at 50-75° C. (e.g., 60° C.), pH 8-10 (e.g., pH 9); (c) packaging materials and or instructions for use (a)-(c). In some embodiments the affinity agent or the set of affinity agents are detectably labeled and can be distinguished from each other. In some embodiments the kit comprises secondary affinity reagents. In some embodiments the first and/or second affinity reagents are antibodies. In some embodiments, the kit further comprises a first wash buffer, wherein the first wash buffer has a pH in the range of 6-8 (e.g., pH 6.5-7.5) and can be used to wash away unbound NLRTs. In some embodiments, the kit further comprises a second wash buffer, wherein the second buffer comprises 150 mM-1000 mM, or 150 mM-400 mM of salt.

Unlabeled Reversible Terminator Nucleotides (RTs)

In various embodiments sequencing methods according to the invention comprise contacting a DNA array with multiple unlabeled RTs (e.g., RT-A, RT-T, RT-C and RT-G). The contacting may be carried out sequentially, one RT at a time. Alternatively, the four RTs may be contacted with the sequencing array at the same time, most often as a mixture of the four RTs. In some embodiments, the four RTs are provided together as an "RT set." In one embodiment, the RT set comprises RT-A, RT-T, RT-C, and RT-G. In one embodiment, the RT set comprises RT-A, RT-U, RT-C, and RT-G. In one embodiment, one or more RTs in a set comprises a modified (non-naturally occurring) nucleobase conjugated to a removable blocking group.

RTs of an RT set may be packaged as a mixture or may be packaged as a kit comprising each different RT is a separate container. In a mixture of the four RTs may include each base in equal proportion or may include unequal amounts.

In some embodiments, the 3'-O removable blocking groups of the RTs used in the invention can be cleaved by a reducing agent, such as a phosphine, include, but are not limited to, azidomethyl and tris(hydroxypropyl)phosphine (THPP). In some embodiments, the 3'-O reversible blocking groups of the RTs used in the invention can be cleaved by UV light including, but not limited to, nitrobenzyl. In some embodiments, the 3'-O reversible blocking groups of the RTs used in the invention can be cleaved by contacting with an aqueous Pd solution. The aqueous Pd solutions include, but are not limited to, allyl. In some embodiments, the 3'-O reversible blocking groups can be cleaved with acid. Suitable acids include, but are not limited to, methoxymethyl. 3'-O reversible blocking groups that can be cleaved by contacting with an aqueous buffered (pH 5.5) solution of sodium nitrite include, but are not limited to, aminoalkoxyl.

In one embodiment each RT in an RT set comprises the same blocking group (e.g. azidomethyl). In one embodiment RTs in an RT set comprise different blocking groups (e.g. RT-A comprises azidomethyl and RT-T comprises cyanoethenyl; or RT-A and RT-G comprise azidomethyl and RT-C and RT-T comprise cyanoethenyl). If different blocking groups are used, such blocking groups are optionally selected such that the different blocking group can be removed by the same treatment. Alternatively the blocking groups may be selected to be removed by different treatments, optionally at different times.

11. Examples

WO 2018/129214 provides examples that are useful for understanding the present inventions and as antecedents to the examples below. Preparation of conjugated 3'-O-azidomethyl-2'-dG, -dC, -dA and -dT antigens is described in Example 1 of WO 2018/129214. Polyclonal antibodies against non-labeled reversible terminator (NLRT) antigens were prepared as described in Example 2 of WO 2018/

129214. DNA nanoball (DNB) arrays of an *E. coli* genomic DNA library were used in sequencing experiments. These arrays are described in Example 3 of WO 2018/129214. Briefly, circular library constructs were made from fragments of *E. coli* genomic DNA, and the library constructs were amplified by rolling circle amplification (RCA) to produce DNBs comprising genomic DNA inserts with adjacent primer binding sites. The DNBs were arrayed in a DNA sequencing flow-cell (e.g., a BGISEQ-500 flow-cell or BGISEQ-1000 flow-cell). See Drmanac et al., 2010, *Science* 327:78-81 and Huang et al., 2017, *Gigascience* 6:1-9. Example 4 of WO 2018/129214. describes using dN-azidomethyl-specific rabbit polyclonal antibodies and labeled goat anti rabbit secondary antibodies to detect incorporated NLRTs in a DNB array. Example 5 of WO 2018/129214. described DNA Sequencing Using Fluorescently Labeled RT-A, —C and -T and Unlabeled RT-G. Example 6 of WO 2018/129214. describes DNA sequencing using four unlabeled RTs and unlabeled anti-NLRT polyclonal antibodies. Example 7 of WO 2018/129214 describes 50 cycles of sequencing in which unlabeled rt-g is detected using an anti-RT-G rabbit primary antibody and a labeled goat anti-rabbit secondary antibody. Example 8 of WO 2018/129214 describes antibodies that bind NLRT with sufficient specificity to generate signal-to-noise-ratio (snr) values suitable for base calling analysis. Example 9 of WO 2018/129214 describes sequencing for 25 cycles using labeled anti NLRT polyclonal antibodies. Example 11 of WO 2018/129214 describes removal of anti-NLRT antibody without removing 3' blocking group. As discussed elsewhere herein, antibody removal (disassociation from primer extension product) can be decoupled from the cleavage and removal of the 3' blocking group. In one approach antibody was removed by specific competition. Primer extension was performed on a DNB array comprising an *E. coli* library using four non-labeled 3'-azidomethyl-base nucleotides. Staining was simultaneously incubating all four anti-3'-azidomethyl-base antibodies directly labeled with the Color Set 1 fluorophores. Specific competition was used to remove the detecting affinity reagents by incubating in the presence of 20 μM free antigen (3'-O-azidomethyl-2'-deoxyguanine, deoxyadenine, deoxycytosine, deoxythymine, each in triphosphate form) at 57° C. for 2 min in 50% WB1, 50% Ab buffer. The Ab removal procedure was (1) WB1, 55° C.; (2) removal solution; (3) WB1, 20° C.; (4) WB2; (5) SRE. WB1: NaCl 0.75 M, sodium citrate 0.075M, Tween 20 0.05%, pH 7.0; WB2 NaCl 50 mM, Tris-HCl pH9 50 mM, Tween 20 0.05%, EDTA 1 mM. pH 9.0; SRE NaCl 400 mM, Tris HCl pH7 1000 mM, Sodium L ascorbate 100 mM, Tween 20 0.05%, pH 7.0.

Example 1: Rabbit Anti-NLRT Monoclonal Antibodies (mAbs) and Sequence

Rabbit monoclonal antibodies were raised against KLH-conjugated 3'-azidomethyl-dA (N3A), 3'-azidomethyl-dC (N3C), 3'-azidomethyl-dG (N3G), or 3'-azidomethyl-dT (N3T) (Yurogen Biosystems, Worcester, MA). Briefly, 8 rabbits were immunized with four different KLH-conjugated NLRTs, two rabbits for each of the four molecules. Bleed analysis by ELISA was performed using each NLRT. On day 63 post-immunization, rabbits were sacrificed and peripheral blood mononuclear cells (PBMC) or splenocytes were isolated. Rabbits were selected for cell sorting and culturing antibody-secreting B-cells. The co-culture supernatants were screened using the NLRTs. Five or ten different clones of the anti-NLRT antibodies (depending on the target) were prepared for each of the four NLRTs, resulting in >30 mAb preparations.

Rabbit IgG genes were cloned from specific B-cells identified by antigen screening. Heavy- and light-chain IgG antibody sequences were obtained for selected monoclonal antibodies that bind to each target antigen. FIG. 1A-H shows aligned heavy and light chain sequences for monoclonal antibodies specific for each of the four NLRTs.

Linear expression modules were constructed. The recombinant rabbit mAbs were expressed by mini-scale transient expression in human embryonic kidney (HEK) 293T cells. Supernatant from the transfected 293T cells was screened by ELISA.

Heavy- and light-chain sequences were subcloned into separate expression vectors and expressed in HEK293 cells. The expressed recombinant rabbit mAbs were validated by binding to antigen by indirect ELISA.

Example 2: Using dN-Azidomethyl-Specific Rabbit Monoclonal Antibodies and Labeled Goat Anti-Rabbit Secondary Antibodies to Detect Incorporated NLRTs in a DNB Array Rabbit monoclonal antibodies N3A, N3T, N3G and N3C were used in this experiment. DNB arrays containing *E. coli* genomic DNA inserts were primed, and primers were extended using BG9 DNA polymerase (BGI, Shenzhen, China). Thirty antibody preparations were individually applied to separate lanes on the DNB arrays at 3 μg/mL or 25% culture supernatant as indicated and incubated at 35° C. for 5 min (30 separate incubations). At the end of the incubation unbound primary antibody was removed by washing the array with antibody buffer (AbB) (Tris buffered saline pH 7.4+0.1% BSA and 0.05% Tween-20) at 35° C. The array was then incubated with a Cy3-labeled goat anti-rabbit secondary antibody (Fab fragment) obtained from Jackson Immune Research (West Grove, PA, USA) for 5 min at 35° C. The array was washed with AbB to remove unbound secondary antibody and imaged using a BGISEQ-1000 sequencing system. As mentioned above, each of the 30 antibody preparations stained with a single primary antibody would be expected to bind to incorporated NLRTs at approximately 25% of DNA sites.

An initial screen was performed to determine whether ELISA-positive clones were also positive in a functional assay, i.e., sequencing. Control lanes (lanes 1, 8) in the sequencing arrays were generated by priming the DNBs and extending the primers using all four 3'-azidomethyl dNTPs labeled by a fluorophore attached to the base via a cleavable linker. Control values shown for ACG are Cy3. T antibody data is using a ROXtra labeled secondary and control values are for ROX. The results are shown in TABLE 7.

TABLE 8

| Row | Average of mean signal (Cy3) | Background subtracted | Clone |
|---|---|---|---|
| 8846 N3A purified @ 3 μg/ml | | | |
| 1 | 13893.71 | 10343.71 | |
| 2 | | | Blank |
| 3 | 3559.27 | 9.27 | 1E8 |
| 4 | 3573.80 | 23.80 | 3F8 |
| 5 | 3573.19 | 23.19 | 2B1 |

TABLE 8-continued

| Row | Average of mean signal (TxR) | Background subtracted | Clone |
|---|---|---|---|
| 6 | 20794.12 | 17244.12 | 3B12 |
| 7 | 9246.02 | 5696.02 | 2C5 |
| 8 | 12237.50 | 8687.50 | |
| | 8955 N3C 25% supernatant in AbB | | |
| 1 | 12565.93 | 8026.93 | |
| 2 | 4539.76 | 0.76 | Blank |
| 3 | 23470.84 | 18931.84 | 2B9 |
| 4 | 10930.90 | 6391.90 | 2B5 |
| 5 | 35030.09 | 30491.09 | 1B8 |
| 6 | 17198.75 | 12659.75 | 1A10 |
| 7 | 6931.59 | 2392.59 | 1A9 |
| 8 | | | |
| | 8839 N3C 25% supernatant in AbB | | |
| 1 | 13010.32 | 8490.32 | |
| 2 | 4520.55 | 0.55 | Neg. control |
| 3 | 4911.82 | 391.82 | 4D6 |
| 4 | 28031.66 | 23511.66 | 4C6 |
| 5 | 5725.85 | 1205.85 | 3C1 |
| 6 | 7488.84 | 2968.84 | 3B4 |
| 7 | 25278.45 | 20758.45 | 3B7 |
| 8 | 12668.26 | 8148.26 | |
| | 8954 N3G purified @ 3 μg/ml | | |
| 1 | 12480.22 | 7960.22 | |
| 2 | 26886.42 | 22366.42 | Poly100X [c] |
| 3 | 31874.67 | 27354.67 | 7C8 |
| 4 | 29543.70 | 25023.70 | 5F6 |
| 5 | 9335.82 | 4815.82 | 4B8 |
| 6 | 5115.09 | 595.09 | 3F12 |
| 7 | 27935.02 | 23415.02 | 3G6 |
| 8 | 12629.10 | 8109.10 | |

| Row | Average of mean signal (TxR) | Background subtracted | Clone |
|---|---|---|---|
| | 8945 N3T 25% supernatant in AbB | | |
| 1 | 9072.58 | 6382.58 | |
| 2 | 2691.67 | 1.67 | Blank |
| 3 | 17297.50 | 14607.50 | 2D10 |
| 4 | 16091.69 | 13401.69 | 2D4 |
| 5 | 4187.58 | 1497.58 | 1D10 |
| 6 | 12185.74 | 9495.74 | 1F9 |
| 7 | 5987.59 | 3297.59 | 1H4 |
| 8 | 9569.79 | 6879.79 | |
| | 8811 N3T 25% supernatant in AbB | | |
| 1 | 7918.82 | 5228.82 | |
| 2 | 2690.49 | 0.49 | Blank |
| 3 | 2694.17 | 4.17 | Neg. control |
| 4 | 2740.63 | 50.63 | 3B11 |
| 5 | 4509.58 | 1819.58 | 3B9 |
| 6 | 2891.12 | 201.12 | 3B7 |
| 7 | 2726.76 | 36.76 | 3A3 |
| 8 | 9085.29 | 6395.29 | |

The signal varied from clone to clone, even using a given concentration of antibody. Some antibodies that were positive by ELISA did not perform well on the DNB array.

Example 3: Sequencing-by-Synthesis Using Labeled Anti-NLRT Monoclonal Antibodies An *E. coli* genomic DNA library was made as described previously and arrayed on a BGISEQ-500 flow-cell. Primers were added and sequencing-by-synthesis was performed by primer extension using one target unlabeled nucleotide 3'-azidomethyl reversible terminators (dATP, dCTP, dGTP, dTTP) and three conventionally labeled reversible terminators at a ratio of: A-AF532 25% labeled, C-IF700 40% labeled, G-Cy5 35% labeled, and T-ROX 35% labeled (in one experiment, two of the RTs, RT-A and RT-C, are conventionally labeled, and two of the RTs, RT-G and RT-T, are detected by labeled monoclonal antibodies.) The 3'-blocked dNTPs were present at a concentration of 1 μM total for each nucleotide and were incorporated using BG9 DNA at 55° C. for 1 min per cycle. After incorporation and washing to remove unincorporated nucleotides, the target 3'-azidomethyl-base nucleotides were detected by incubating the array with a mixture of four directly labeled anti-3'-azidomethyl-base antibodies (range of 1-3 μg/mL). The antibodies were incubated on the array at 35° C. 2×2 min per cycle, where "2×2" refers to incubation with antibody for two minutes, followed by further two minute incubation after adding additional antibody. The array was washed two times to remove any unbound antibodies and then incubated with an appropriately fluorescent dye labeled secondary at 35° C. 2×2 min per cycle. The array was washed two times to remove any unbound antibodies. Table 9 shows shows the identity of the fluorophore directly conjugated to each secondary antibody.

TABLE 9

| Rabbit mAb Specificity | Fluorescent Dye |
|---|---|
| 3'-O-azidomethyl-2'-deoxyguanine | Cy5 |
| 3'-O-azidomethyl-2'-deoxyadenine | AF532 (Invitrogen, Carlsbad, CA) |
| 3'-O-azidomethyl-2'-deoxycytosine | IF700 (AAT Bioquest, Sunnyvale, CA) |
| 3'-O-azidomethyl-2'-deoxythymine | 6-ROXtra ™ (AAT Bioquest, Sunnyvale, CA) |

The fluorescence signal at each position on the DNB array was determined by scanning for 40 ms during laser excitation of the fluorophore. After the identity of the DNB base was determined, the 3' blocking group was removed by reduction with THPP (26 mM) for two minutes at 57° C., allowing for the regeneration of 3'-OH group and permitting further extension of the nascent DNA strand. Removal of the 3' blocking group also resulted in disassociation of the antibody from the primer extension product.

This series of steps (extension, antibody incubation, detection, and unblocking) was repeated for a total of 25 cycles of DNA sequencing.

Table 10 shows the results from 25-30 cycles of sequencing using labeled anti-NLRT monoclonal antibodies (using the *E. coli* genome as the reference genome).

TABLE 10

| | Exp423 N3A (3B12) | | Exp 425 N3G (5F6) | | Exp 426 N3T 1(F9) | | Exp 427 N3C (2B9) | |
|---|---|---|---|---|---|---|---|---|
| | 20 min | 30 min | 20 min | 30 min | 20 min | 30 min | 20 min | 30 min |
| Cycle # | 25 | 25 | 25 | 25 | 30 | 30 | 30 | 30 |
| Total Reads (M) | 44.117 | 41.263 | 22.339 | 22.337 | 32.674 | 31.538 | 32.679 | 32.683 |
| Mapped Reads (M) | 35.458 | 33.374 | 21.346 | 21.190 | 30.958 | 29.545 | 29.527 | 29.017 |

TABLE 10-continued

| | Exp423 N3A (3B12) | | Exp 425 N3G (5F6) | | Exp 426 N3T 1(F9) | | Exp 427 N3C (2B9) | |
|---|---|---|---|---|---|---|---|---|
| | 20 min | 30 min | 20 min | 30 min | 20 min | 30 min | 20 min | 30 min |
| Mapping Rate (%) | 80.37 | 80.88 | 95.56 | 94.87 | 94.75 | 93.68 | 90.35 | 88.78 |
| Avg Error Rate (%) | 3.23 | 3.10 | 0.33 | 0.40 | 0.30 | 0.31 | 1.33 | 1.34 |

These data demonstrate that multiple cycles of DNA sequencing can be carried out using unlabeled reversible terminators and monoclonal antibodies that bind to the blocking group and base.

Example 4: Obtaining and Labeling Monoclonal Antibody-MPS Antibodies

As discussed above, to demonstrate Antibody-MPS we used natural unlabeled adenosine, cytosine, guanosine and thymidine, azidomethyl-3'-modified monophosphate nucleotides. Nucleotides were linked via the monophosphate to an NHS which was then linked to KLH protein for the immunization of rabbits every two weeks. Sera was collected from immunized rabbits over a three-month period and screened by ELISA to determine immune response. Antigen for the ELISA screen was azidomethyl-3'-blocked nucleotides linked to BSA coated onto wells of a microtiter plate.

Splenocyte screening: Splenocytes collected from seropositive rabbits were FACS sorted for positive antibody expression using antigen bound via biotin to fluorescently labeled streptavidin. FACS selected single cells with positive expression for immunogen reactive surface bound IgG for further growth in 384-well plates. This allowed confirmative screening of expressed antibodies.

Antibody screening: After splenocyte expansion, supernatant from each single cell derived clonal culture was screened against all 4 nucleotide variants (A, C, G and T) to identify clones giving high reactivity against the specific nucleobase antigen, and low or non-detectable reactivity to the 3 non-targeted bases. For this ELISA screen we used antigens that mimic DNA structure generated in sequencing. Four biotinylated DNA templates with hybridized primer were used to incorporate unlabeled azido-methyl RTs and bound to streptavidin plates for positive and negative ELISA screening. Those antibodies with high non-specific binding (>20%), as indicated by high ELISA positive signal to the non-targeted bases were excluded from further consideration.

Antibody cloning and expression: Selected splenocyte cultures had coding regions for antibody heavy and light chains cloned into a plasmid expression system. These plasmids were used to transiently transfect a 293 cell-line for monoclonal antibody production. Expressed antibodies were purified by protein A capture columns and eluted in low pH buffer before buffer exchange into phosphate buffered saline.

Antibodies were labeled by reaction of available free amines on the protein with NHS ester activated fluorescent dyes (14). NHS ester activated fluorophores were diluted in anhydrous DMSO and reacted at concentrations (10-100 uM) that provide strong signals without adversely affecting antibody binding or specificity. Relatively low and easy to obtain concentrations of antibody (1 mg/ml) were adjusted to pH 8 in bicarbonate buffer and reacted with the NHS ester dyes. Incubation was continued for 45 min at room temperature before quenching of unreacted dye in tris-buffered saline (pH 7.4). Without any purification, these labeled antibodies were aliquoted and stored at −20 C. The random labeling process under these conditions balances the number of fluorophores per antibody and antibody inactivation. Antibody-MPS antibodies can be labeled with multiple dye molecules per antibody molecule potentially providing stronger sequencing signal.

Example 5: Characterization of Antibody-MPS Antibodies in Sequencing Assays

Sequencing Platform

DNBSEQ-G400 was used for testing and implementing the Antibody-MPS process. The DNBSEQ platform utilizes PCR-free nanoarrays of DNA nanoballs (DNBs); linear concatamers of DNA copies generated by rolling circle replication that are bound to defined positions of a patterned nanoarray (4). For popular pair-end (PE) or second-end sequencing we used a controlled multiple displacement amplification (MDA) process on DNB arrays described in US20160237488, incorporated by reference for all purposes. After the first read is generated on DNBs, extended products (optionally using an additional primer) are further extended using natural unblocked nucleotides in a controlled and sufficiently synchronized way by a strand displacement polymerase such as Phi29. The process generates single-stranded (ss) DNA branches complementary to original DNBs and still bound to DNBs through regions that are not displaced (FIG. 3) The resulting "branched DNBs" usually comprise 1-3 template copies per branch providing more priming sites and stronger signal in the second end-read than in the first end-read.

Complementary Strand Making and Pair-End Sequencing on the DNBSEQ MPS Platform.

See U.S. Pat. No. 10,227,647 describes methods for paired-end sequencing. In the approach used in examples, a DNA nanoball (DNB), as a concatemer, containing copies of adaptor sequence and inserted genomic DNA, is hybridized with a primer for the first-end sequencing. After generating the first-end read, controlled, continued extension is performed by a strand displacing DNA polymerase to generate a plurality of complementary strands. When the 3' ends of the newly synthesized strands reach the 5' ends of the downstream strands, the 5' ends are displaced by the DNA polymerase generating ssDNA overhangs creating a "branched DNB". A second-end sequencing primer is hybridized to the adaptor copies in the newly-created branches to generate a second-end read.

For sequencing we used a standard MPS kits modified to implement the Antibody-MPS process. Labeled RTs were replaced by unlabeled RTs with a natural nucleobase and a cocktail of the four labeled antibodies (specific for each natural nucleobase) in binding buffer was added to the cartridge. The antibodies were labeled with fluorescent dyes of similar excitation and emission spectra as used in labeled RTs to enable imaging on the current sequencers. Each cycle of sequencing included reversible terminator incorporation with a modified polymerase, followed by binding of antibody. After washing excess, un-bound antibodies, standard imaging was performed, followed by bound antibody removal and standard 3' de-blocking as either one combined, or two separate steps.

Example 6: Antibody Evaluation in Sequencing Assays on the DNBSEQ Platform

Specificity

In the initial DNBSEQ screening of several ELISA positive antibodies for each of the four nucleotides, we found that up to 50% had relatively weak positive signals. A possible explanation was unsuccessful clonal expansion or false positive ELISA. We selected a set of four antibodies with good signal and low background. We then evaluated critical properties of these antibodies required for sequencing. Primary splenocyte supernatant from promising clones was also.

Accurate sequence determination requires that the antibodies are specific for the base associated with the 3' reversible terminated ribose. To demonstrate that each antibody species is specific for each individual base, arrays of DNA nanoballs were created and hybridized with primers that were then extended one nucleotide with a reversible terminator.

FIG. 2A shows the fluorescent intensity for populations of DNBs in two channels within a single imaging field after binding with fluorescent antibodies. Pairs of channels that do not have spectral dye cross-talk such as A-G, A-C, T-G, T-C do not show any antibody cross binding. DNBs are either negative in both channels or positive in one but not in the other channel (DNB clusters on the x and y axis). Positive and negative antibody selection using oligonucleotide constructs that mimics incorporated RTs during sequencing contributes to high antibody specificity.

Antibody-MPS generated DNB intensities from one cycle are plotted in pairs of imaging channels. A random selection of 100,000 DNBs in an FOV are represented. Background subtracted intensities without dye cross-talk correction are presented. Only pairs of channels without dye cross talk are shown. For each pair, three clusters of DNBs are expected if there is no antibody cross binding on an X-Y co-ordinate representation: −/−; low X and Y intensities, +/−; high X and low Y intensities, −/+; low X and high Y intensities. If there is cross-binding, +/− or −/+ clusters would shift from X or Y at an angle. In all four pairs, strong binding (relative signal in the range of 1000 counts) of only one antibody is observed without detectable cross-binding.

Example 7: Antibodies Used in these Examples Recognize the 3' Blocking Group

Our immunogens use nucleotides with a 3' azidomethyl blocking group. After confirming base specificity, we next determined if the azidomethyl is required for strong binding.

Figure 2B:
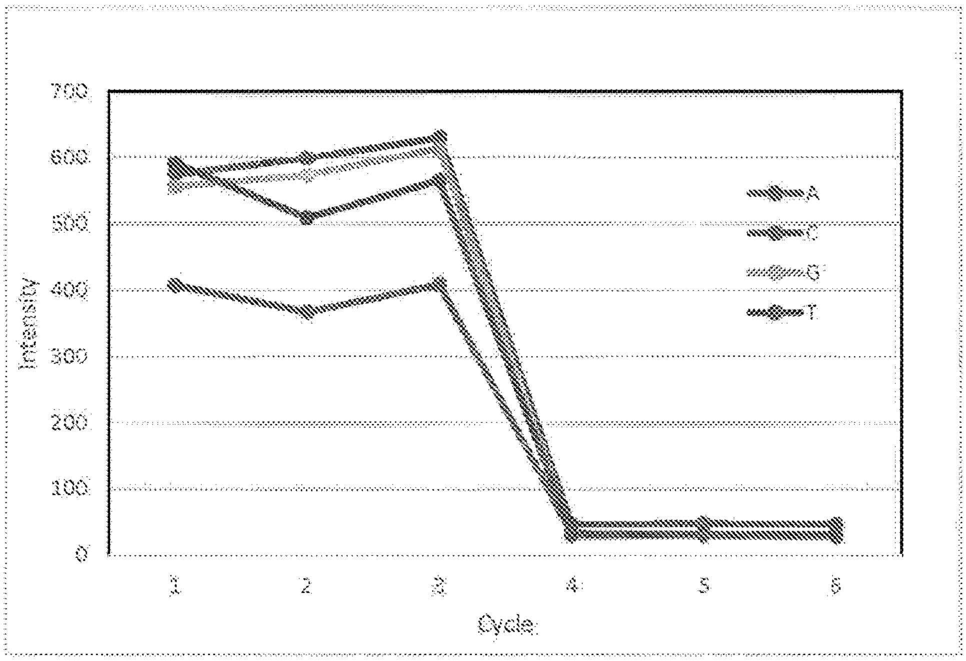
FIG. 2B is a plot of detected fluorescence, showing that antibody binding is dependent on both the base and the sugar with a 3' azidomethyl block.

FIG. 2B is a plot of detected fluorescence, showing that antibody binding is dependent on both the base and the sugar with a 3' azidomethyl block. Three regular sequencing cycles in which the 3' blocking group is removed after antibody binding and imaging, were followed by three cycles in which the 3' azido-methyl group was cleaved before antibody binding and imaging. Background subtracted, phase corrected and spectral cross-talk corrected intensities are shown and or each imaging channel (corresponding to each base), an average intensity of DNBs with highest intensities in that channel are depicted.

In the first 3 cycles, the intensity of fluorescence achieved when individual antibodies were incubated with the surface associated DNBs. Here, we report intensity as a background subtracted and spectral cross-talk corrected measure of the average population intensity for DNBs assigned to a fluorophore channel (having the strongest intensities in that channel) within an imaging field.

All four antibodies produce strong signal (400-600 counts) when the azidomethyl was present during antibody binding. In cycle 4 onward, each cycle had a cleavage step before antibody binding. No signal detection was evident after removal of the 3' azidomethyl blocking group suggesting that in addition to the base this chemical moiety is important for strong antibody binding potentially preventing antibody to bind to other target bases in DNA. Bases on non-terminal nucleotides can also be discriminate by other spatial or chemical features because they have a stacking base and phosphate on 5' and 3' side.

Example 8: Fast Binding Kinetics

In optimizing antibody-binding conditions we found that low salt (50 mM) Tris buffer (pH7.6) provided efficient binding at 35-40° C.

Figure 2C:
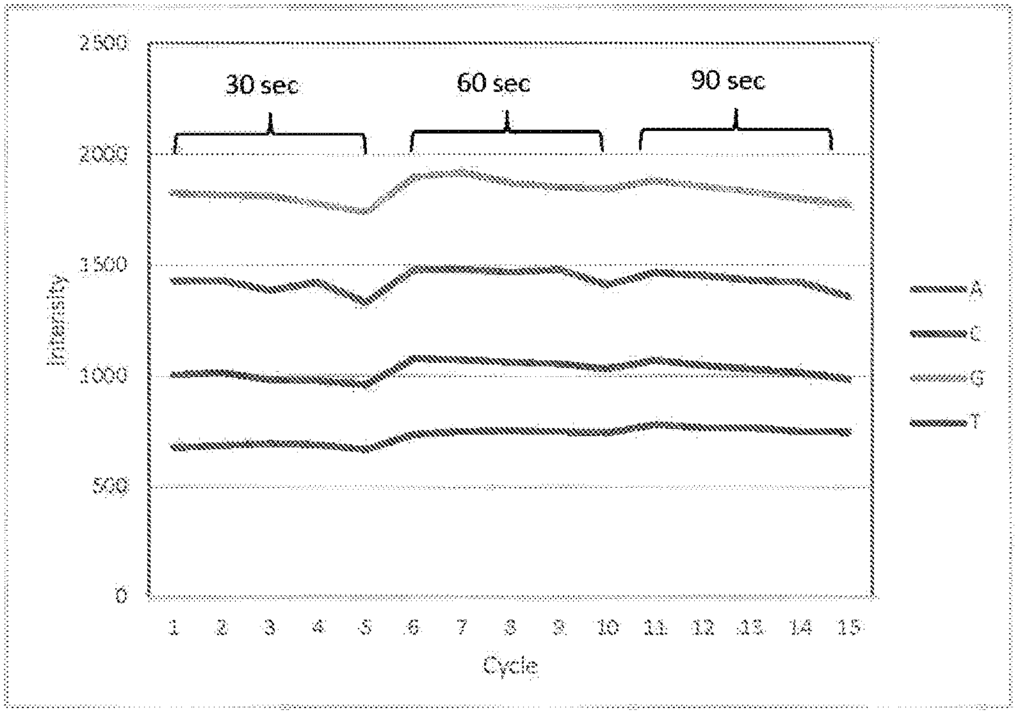
FIG. 2C is a plot of data showing the rapid kinetics of antibody binding to detect primer extensions in DNA Nanoball (DNB) sequencing. Labeled antibody binding in 30, 60 or 90 seconds to unlabeled RT nucleotides is shown.

Referring to FIG. 2C, the effect of 30, 60 or 90 seconds of labeled antibody binding to unlabeled RT nucleotides is shown, incorporated by DNBSEQ sequencing. Minimal increase in fluorescent intensity was observed with increasing times of incubation. Although this suggests shorter incubation time than 30 seconds is possible, it must be remembered that this represents the behavior of the population average and specific sequence contexts could behave differently.

The same concentration of antibodies (~4 ug/ml, providing excess of antibodies) were allowed to bind to DNBs for the three incubation times at 35° C. A 30 second incubation already generates >90% of maximal signal demonstrating fast binding kinetics of all 4 selected antibodies. Background subtracted, phase corrected and spectral cross-talk corrected intensities are shown. For each imaging channel (corresponding to each base) an average intensity of DNBs with highest intensities in that channel are depicted.

Example 9: Efficient Removal of Bound Antibodies

Sufficient removal (e.g., at least 95% or complete removal) of the bound antibodies after imaging and before the next cycle of nucleotide incorporation is important for high quality sequencing. In some cases, antibody removal and 3' block cleavage are performed at the same time. In some cases, antibody removal and second incorporation is performed at the same time, see above.

Figure 2D:
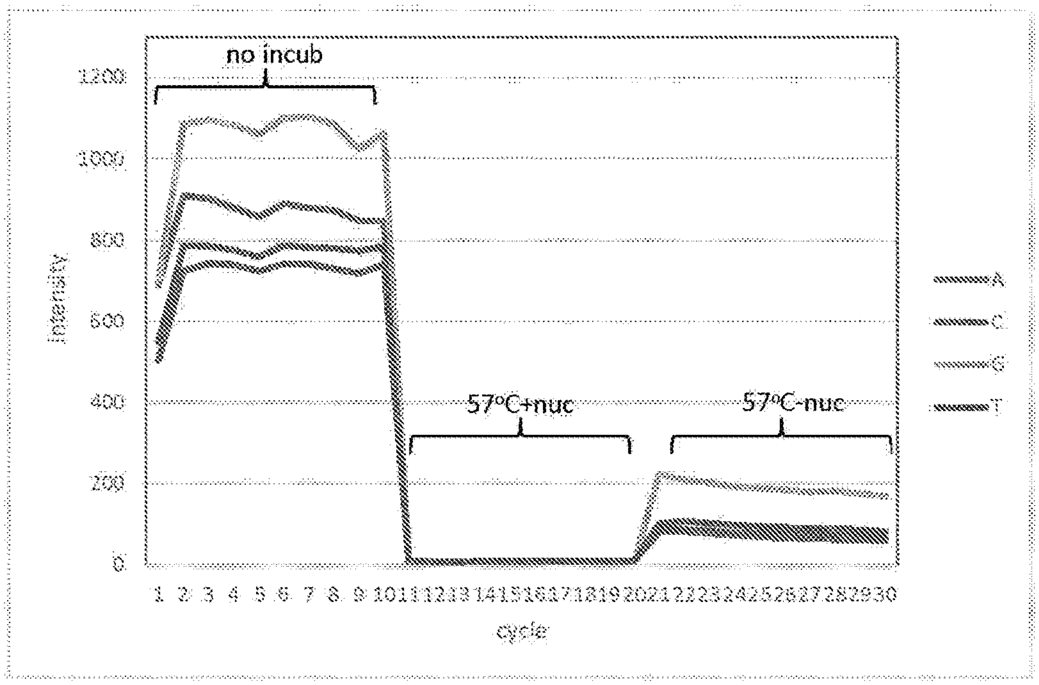
FIG. 2D compares intensity data showing the effect of removing fluorescent antibodies after binding to RTs under several reaction conditions.

FIG. 2D is a plot of intensity data showing the effect of removing fluorescent antibodies after binding to RTs. In cycles 1-10 flow cells were washed briefly with pH 7 SSC buffer at 40° C. before imaging at 20° C. In cycles 11-20 flow cells were incubated at 57° C. for 1 minute in 50 mM Tris pH 9 buffer including RTs, for 60 sec before imaging. Cycles 21-30 show intensities after incubation for 60 seconds in the same buffer without nucleotides before imaging. Background subtracted and spectral cross-talk corrected intensities are used and or each imaging channel (corresponding to each base) an average intensity of DNBs with highest intensities in that channel are depicted.

We found that high pH (>pH 8) and temperatures over 55° C. were efficient in quantitative antibody removal. We also found that including unlabeled RTs in the removal buffer speeds up the dissociation. Buffer conditions without including RTs are compatible with the azidomethyl cleavage reaction.

Example 10 Labeled Antibodies Generate Stronger Signal than Labeled RTs

Labeled RTs can have only one dye attached to a base due to proximity quenching. To minimize negative impact of base scar, usually only 60-70% are labeled. Antibody-MPS antibodies can be labeled with multiple dye molecules per antibody molecule potentially providing stronger sequencing signal.

We tested the signal strength provided by the current random labeling process that balances the number of fluorophores per antibody and antibody inactivation. We find that in a composition comprising labeled antibodies, individual antibody molecules are typically labeled with 1-5 fluorophores or are unlabeled. In some embodiments at least 50% (mole %) of the antibodies are labeled with more than one fluorophore molecule (e.g., 2-5 fluorophore molecules). In some embodiments at least 75% of the antibodies are labeled with more than one fluorophore molecule (e.g., 2-5 fluorophore molecules). Exemplary dyes are described, for illustration and not limitation, in Drmanac et al. ¶¶[0059], [0171]-[0174].

Figure 2E:
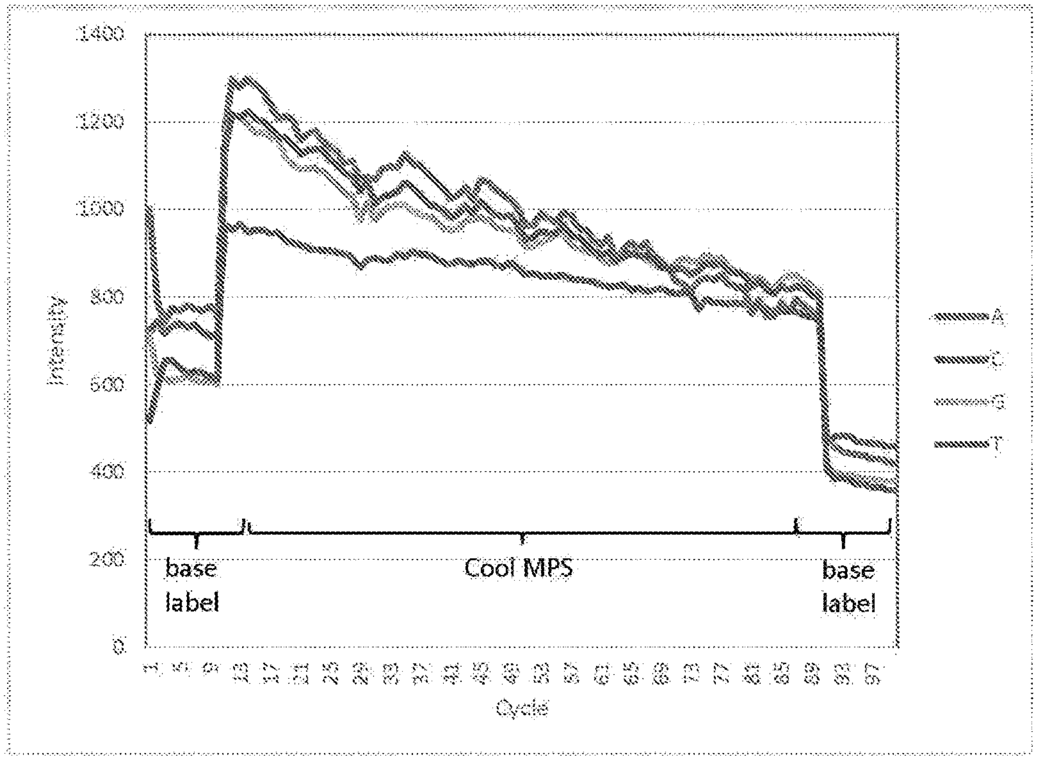
FIG. 2E compares the relative intensities of base-labeled nucleotides over the first 10 cycle positions followed by an additional 80 cycle positions with antibody labeled detection, before returning to base-labeled RTs.

FIG. 2E is a plot that compares the relative intensities of base-labeled nucleotides over the first 10 cycle positions followed by an additional 80 cycle positions with antibody labeled detection, before returning to base-labeled RTs. Relative to base-labeling of nucleotides, antibody detection generated much stronger signal with some fluorophores producing an over 200% increase in intensity relative to its base-labeled counterpart. The range of responses by different fluorophores may reflect labeling efficiency of the dyes to the specific antibodies, antibody binding affinities, or fluorophore quenching. The benefits of increased intensity include preservation of sufficient signal in low copy DNBs throughout long sequencing runs, shorter exposure times or more rapid imaging.

Ten cycles of base-labeled sequencing were performed before switching to Antibody-MPS sequencing (cycles 10-90), and then back to standard direct base labeled. sequencing. Background subtracted, phase corrected and spectral cross-talk corrected intensities are shown or each imaging channel (corresponding to each base). An average intensity of DNBs with highest intensities in that channel are depicted for each cycle Example 11 No Signal Suppression We observed that labeled RTs generate some signal suppression (e.g. quenching) in the following cycle which most likely was due to modified ("scarred") bases. Because Antibody-MPS uses unlabeled RTs we expected no such effect.

Figure 2F:
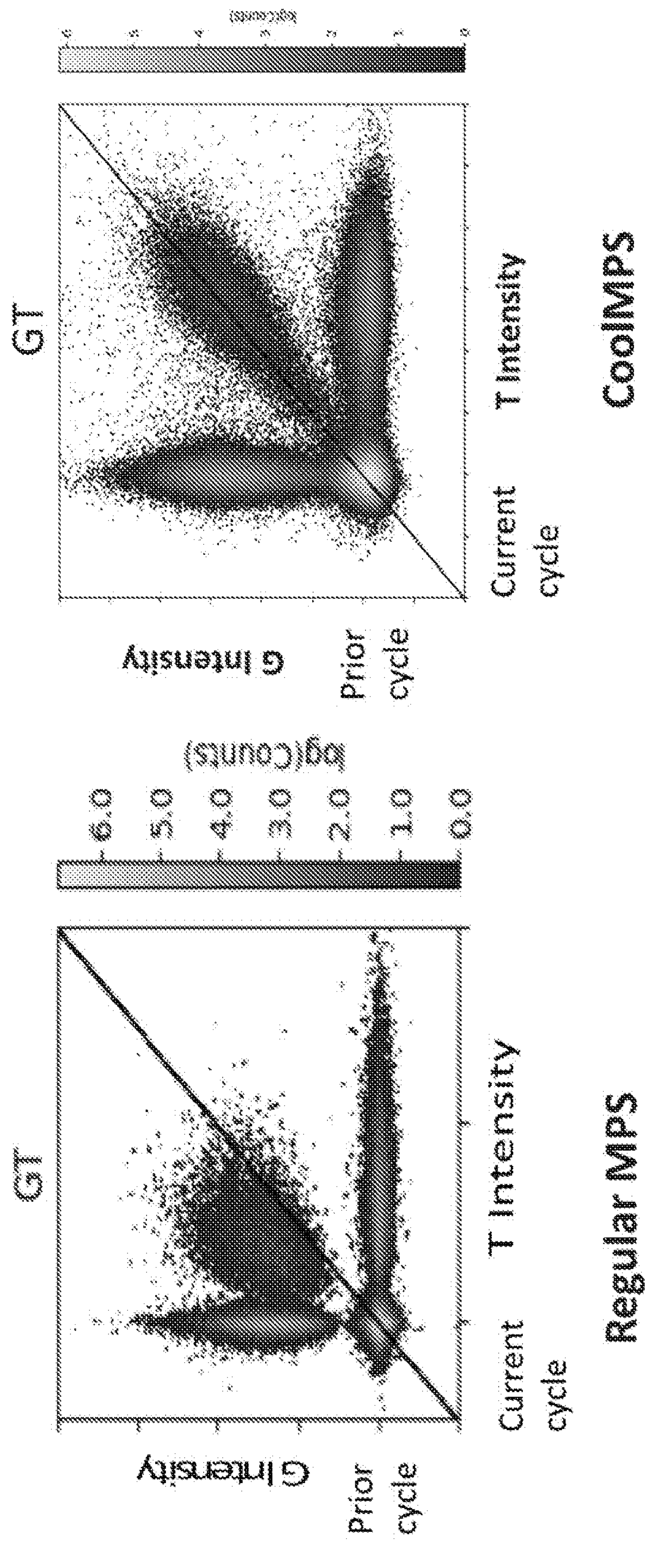
FIG. 2F is a scatter-plot comparing signals in a set of DNBs in two consecutive cycles, showing independent labeling of different bases.

FIG. 2F provides data comparing signals in a set of DNBs (from one field-of-view) in two consecutive cycles and demonstrates that DNBs that have G at the prior cycle and T in the current cycle have a suppressed T signal when labeled RTs are used. Lower than expected T signal causes the GT cluster to move from the diagonal toward the Y axis, representing G signals. No suppression was observed in Antibody-MPS using unlabeled RTs with a natural base without any scar. Furthermore, dyes on the T antibody are further from the G base avoiding quenching.

These data show that the antibody-MPS technology eliminates signal suppression. DNB signals in a set of DNBs are compared in channel G for the prior cycle (Y axes) and channel T for the current cycle (X axes). Labeled RTs chemistry and Antibody-MPS chemistry (natural unlabeled bases, labeled base-specific antibodies) are shown. Each point on the plot is a DNB forming 4 clusters: nonG/nonT, G/nonT, T/nonG and G/T. Lower than expected T signal is observed in the case of labeled RTs (the cluster of GT DNBs is shifted toward Y axes). No suppression was observed in Antibody-MPS.

Example 12: Full Sequencing Tests of Antibody-MPS Chemistry

Generating 200 Base Reads: SE200 Sequencing

MPS reads longer that 100 bases are very useful. As an initial demonstration test of Antibody-MPS potential we obtained 200-base reads. Two hundred cycles of sequencing was performed on DNBs loaded into the lanes of a flow cell of a DNBSEQ-G400 sequencer. DNBs were prepared from standard 300-base libraries of *E. coli* DNA using MGI's protocols.

Figure 3A:
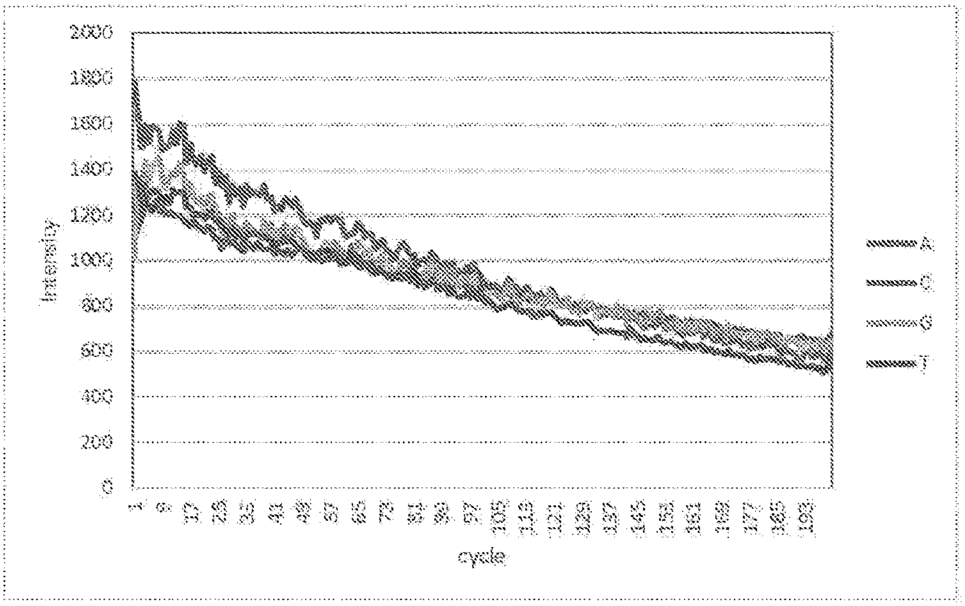
FIG. 3A shows the average called-base intensity of DNBs in a selected region of the array, showing change in label intensity over 200 cycles of single-end read.

FIG. 3A shows the average called-base intensity of DNBs in a selected region of the array with optimal fluidics and optics to highlight potential of this new chemistry. The change in label intensity is shown over 200 cycles of single-end read. Background subtracted, phase corrected and spectral cross-talk corrected intensities are shown and for each imaging channel (corresponding to each base) an average intensity of DNBs with highest intensities in that channel are depicted.

As previously observed with directly labeled nucleotides, a decline of intensity was observed as cycles progressed. Several factors contribute to this including: i) out-of-phase signal, ii) irreversible termination in part due to impure RTs and, DNA damage in imaging; or ii) DNA loss. We found similar signal loss even without antibody binding and imaging, just cycles of incorporation of unlabeled RTs (data no shown). This excludes the impact of antibody binding, imaging or removal. Differences in decline rates between the bases are presumed to be due to the influence of changing background or efficiency of illumination of light collection during cycles. Although declines in dye intensity could be occurring in the cartridge during the run, this is a minor contributor since minimal increase in intensity is observed when fresh reagents are added through the course of a run (data not shown). Nevertheless, the remaining signal after 200 cycles is still high supporting the possibility of much longer Antibody-MPS reads.

Positional discordance is increasing over cycles as in the standard MPS with reversible terminators. This is due to i) accumulation of out-phase signal that become confused with dye-cross talk and ii) signal loss relative to background, especially affecting DNBs with low template copy number. Lag (−1 signal) and runon (+1 signal) are relatively low per cycle (<0.1%) but still accumulates to ~30% combined out-of-phase in 200 cycles.

Figure 3B:
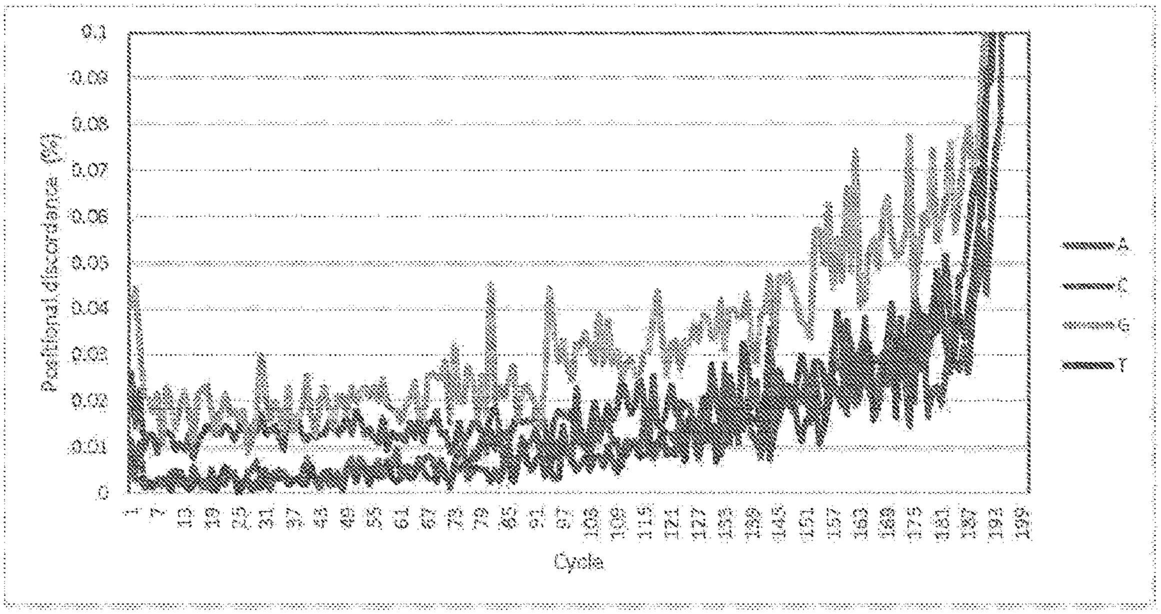
FIG. 3B is a plot of positional discordance for 200 cycles of sequencing. The data demonstrate high accuracy and 94% sequencing yield.

FIG. 3B shows positional discordance for 200 cycles of SE sequencing. Note; the high rate of discordance increase after cycle 185 is due to short inserts and reading into the adapter region not matching the human reference. After filtering out 5% of empty spots and mixed DNBs from all binding spots in the array, the mapping rate of the remaining 95% of DNBs is 99% with an overall discordance of 0.11% which is further reduced to 0.06% in base calls with a quality score >Q10. This is a very promising result for 200 base reads showing high accuracy and 94% sequencing yield (0.95 filtered reads x 0.99 mapping rate).

We further evaluated sequence discordance in 100-base reads in a PCR free *E. coli* library. We obtained overall discordance of 0.029% (1 difference from the reference in 3,500 called bases). We then calculated discordance at different base-call quality filters. Base calls with quality score >20 (close to 99.8% of all base calls) have five to six fold less errors (discordance close to 0.0005% or one mismatch in 20,000 bases). The remaining high quality discordances can be caused by replication errors in DNA, DNA damage or real sequencing errors. This indicates great potential of Antibody-MPS for high quality sequencing with very low overall error rate and extremely rare high quality errors.

TABLE 11

| Reference | *Ecoli* |
|---|---|
| CycleNumber | 200 |
| ESR % | 95.09 |
| >Q30% | 95.23 |
| MappingRate % | 97.83 |
| AvgDiscordanceRate % | 0.11 |
| <=Q10_Percent | 0.21 |
| >Q10_DiscordanceRate % | 0.06 |
| Lag % per cycle | 0.07 |
| Runon % per cycle | 0.07 |

Example 13 High Quality 150-Base Pair-End Reads: PE150 Sequencing

Pair-end (PE) sequencing provides very useful MPS reads that bridge repeats longer than reads and minimize needs for long continuous reads. PE150 (150 bases from both ends of 300-600b inserts) is most frequently used.

Figure 4A:
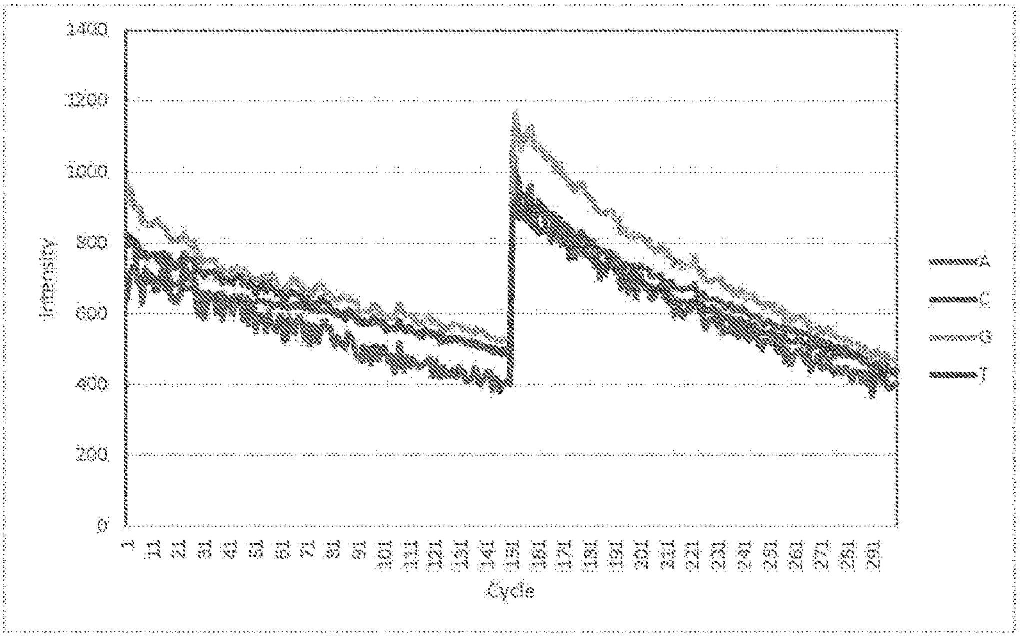
FIG. 4A is a plot showing the PE150 intensity for a human DNA library, with the background subtracted and spectral cross-talk corrected.

We tested Antibody-MPS PE150 to demonstrate that using antibodies does not interfere with the DNBSEQ PE process of controlled MDA. FIG. 4A shows the change in intensity over the 150 cycles of the first strand, then good recovery of intensity on the second strand as the complementary template and corresponding sequencing primer is used for extension. In this test, the concentration of antibodies used for the second strand was twice that of the first strand. Overall there was about a 30-50% decline in intensity values over the 150 positions of the first strand and a 40-50% decline on the second strand in part due to higher incorporation incompletion (lag) in the second strand.

Figure 4B:
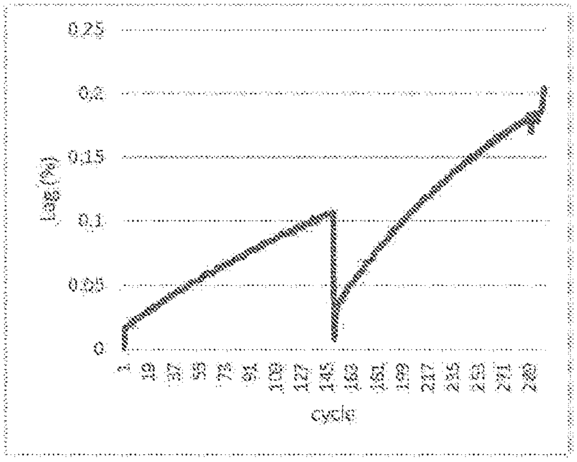
FIGS. 4B and 4C show the PE150 Lag for the same DNA library, and the PE100 Lag for an *E. coli* library with optimized Ph29 removal.

After filtering about 11-13% of empty and low quality array spots mapping rates were >99% with a discordance rate of 0.08% and 0.26% on the first strand of *E. coli* (300b inserts) and Human (400b inserts) DNA libraries, respectfully (FIG. 4B). For the second strand, mapping rate is about 99% with a discordance rate of 0.22% and 0.62%%. After filtering 0.4% and 0.8% of base calls with quality score <10, the combined discordance is reduced from to 0.06% and 0.24% respectively in *E. coli* and Human DNA library. Part of discordance is due to PCR errors introduced in library preparation. Human library is expected to have higher discordance due to polymorphisms in the sample relative to the human reference.

Figure 4C:
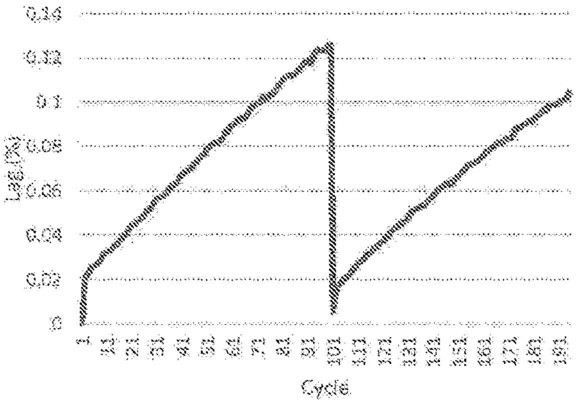

In spite of higher signal, the higher discordance rate in the second read is due to higher lag and lower quality threshold used for DNB filtering. Higher lag (−1 out-of-phase) in the second read is probably due to incomplete removal of Phi 29 polymerase used in high concentration for the complementary strand making. This was confirmed in a PE100 run using optimized Phi29 removal, reducing accumulated lag from about 15% to about 11% (FIGS. 4B and 4C). Furthermore, the lag accumulation is more linear indicating less of −2 phase. This results illustrates the complexities (many biochemical steps with multiple interdependences) of MPS process that require carefully balanced optimizations.

Referring to FIG. 4A, the PE150 intensity for a human DNA library is shown, with the background subtracted and spectral cross-talk corrected or each imaging channel (corresponding to each base) an average intensity of DNBs with highest intensities in that channel are depicted.

TABLE 12

| Reference | *E. coli* | *E. coli* | Human |
|---|---|---|---|
| CycleNumber | 200 | 300 | 300 |
| ESR % | 90.73 | 89.1 | 86.51 |
| >Q30% | 94.78 | 93.37 | 89.88 |
| MappingRate1% | 99.93 | 99.71 | 99.32 |
| MappingRate2% | 99.85 | 99.54 | 98.72 |
| AvgDiscordanceRate1% | 0.06 | 0.08 | 0.26 |
| AvgDiscordanceRate2% | 0.14 | 0.22 | 0.62 |
| <=Q10_Percent | 0.247 | 0.387 | 0.814 |
| >Q10_DiscordanceRate % | 0.049 | 0.063 | 0.235 |
| Lag1 c100% | 12.62 | 9.21 | 8.16 |
| Lag2 c100% | 11.28 | 13.13 | 15.11 |

FIG. 4B shows the PE150 Lag (−1 out of phase incorporation) in the same run as FIG. 4A. Lag represents intensity contributions of the prior (−1) base to the current cycle.

FIG. 4C shows the PE100 Lag in a PE100 run (*E. coli* library) with optimized Ph29 removal. There are many developed tools to further optimize Antibody-MPS process, including replacing full antibodies with smaller versions such as ScFv or nanobodies expressed in bacterial host. and efficiently labeled at targeted sites. Binding times of antibodies was demonstrated to be relatively quick compared to many common procedures utilizing antibodies for detection (e.g. western blot, ELISA) with just 30 seconds proving effective for generating enough intensity to provide low-error base calling. Increased antibody binding time had minimal effect on increasing intensity suggesting most available target sites were occupied within 30 seconds. Furthermore, about 4 ug/ml of antibodies is enough to bind most of incorporated RTs.

This is surprising, because the target nucleotide is present in dsDNA and the immunogen used was single monophosphate reversibly terminated nucleotide. Most likely there is some temporary dsDNA end-melting allowing antibody to bind. Preferred binding buffer with low salt and no Mg++ (that helps breathing of DNA ends) supports this explanation.

A special benefit of Antibody-MPS is the possibility of stepwise base detection after single reaction incorporation of all unlabeled RTs. This is enabled by fast binding and removal of labeled antibodies without removing 3' blocking group. Each base can be detected in a separate image using a more efficient and cost-effective 2- or 1-color imagers without dye crosstalk present at 4-color imagers. For a 2-color imagers two antibodies labeled with different dyes would be bound first and two images generated. After quick removal of bound antibodies, two other antibodies labeled with the same pair of dyes would be bound to generate two more images one for each base. For the fast imagers the entire process will take slightly longer but the sequence quality is expected to be much higher because 2-color imagers collect 2-3 more light (wider filter band) without any dye cross talk.

In addition to PCR-free DNBSEQ MPS platform, Antibody-MPS can be use on any MPS platform including PCR-based clonal arrays (PCR clusters on the support or beads) or single molecule array. The combination of higher quality and lower cost of Antibody-MPS chemistry and PCR-free cost-effective DNB nanoarrays creates a novel advanced MPS platform to drive implementation of genomics based health monitoring requiring comprehensive, accurate and affordable sequencing based screening tests.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

We claim:

1. A method for detecting incorporation of unlabeled 3'-O-reversible terminator deoxyribonucleotides (RTs) at the 3' end of a plurality of primer extension products, wherein the plurality of primer extension products are hybridized to a plurality of template nucleic acids immobilized on a surface to form a plurality of primer-template complexes, wherein each RT comprises a nucleobase selected from adenine (A), cytosine (C), guanine (G), thymine (T), and analogues thereof, a sugar moiety, and a cleavable blocking group, in one sequencing cycle, said method comprising (a) providing the plurality of primer-template complexes generated through a first incorporation with a first DNA polymerase and a first set of RTs, wherein the first set of RTs comprise one or more RTs selected from RT-A, RT-G, RT-C, RT-T, and analogues thereof;

(b) combining the plurality of primer-template complexes from (a) with a plurality of affinity reagents, wherein one or more of the plurality of affinity reagents bind to the nucleobase and/or the cleavable blocking group of the one or more incorporated RTs;

(c) detecting binding of the one or more affinity reagents to the incorporated RTs; and (d) combining the plurality of primer-template complexes from (b) with a second DNA polymerase and a second set of RTs to conduct a second incorporation, wherein the second set of RTs is the same as the first set of RTs, and wherein the second incorporation occurs concurrently with dissociation of the one or more affinity reagents from the primer-template complexes but does not remove the cleavable blocking group.

2. The method of claim 1, wherein the second DNA polymerase in step (d) is the same as the first DNA polymerase.

3. The method of claim 1, further comprising (e) removing the cleavable blocking group to produce a 3'-OH deoxyribonucleotide.

4. The method of claim 3, wherein the primer extension products are on a DNA array comprising a plurality of primer extension products hybridized to a plurality of different template DNA molecules, the method further comprising:

(f) contacting the DNA array with a polymerase and unlabeled RTs of Formula I:

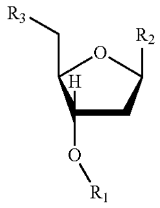

wherein $R_1$ is a 3'-O reversible blocking group;

$R_2$ is a nucleobase selected from adenine (A), cytosine (C), guanine (G), thymine (T), and analogues thereof; and $R_3$ comprises of one or more phosphates;

under conditions wherein, at least some of the primer extension products are extended to incorporate the unlabeled RTs;

(g) contacting the primer extension products with affinity reagents comprising a detectable label under conditions wherein the affinity reagents bind specifically to the reversible terminators to produce labeled extension products comprising the RTs; and (h) identifying the RTs in the labeled extension products.

5. The method of claim 1, wherein binding is detected in step (c) by detecting a fluorescence or chemiluminescence signal.

6. The method of claim 1, wherein the second set of RTs disassociate the one or more affinity reagents from the plurality of primer-template complexes.

7. The method of claim 1, wherein the one or more affinity reagents are antibodies.

8. The method of claim 1, wherein the first set of RTs comprises multiple RTs selected from RT-A, RT-G, RT-C, RT-T, and analogues thereof, wherein the one or more affinity reagents comprises multiple affinity reagents, and wherein each affinity reagent binds to one or more incorporated RTs.

* * * * *

SEQUENCE LISTING

```
<160> NUMBER OF SEQ ID NOS: 165

<210> SEQ ID NO 1
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Asp Leu Val Lys
            20                  25                  30

Pro Glu Gly Ser Leu Thr Leu Thr Cys Lys Ala Ser Gly Phe Asp Phe
        35                  40                  45

Ser Ser Tyr Tyr Tyr Met Cys Trp Val Arg Gln Ala Pro Gly Lys Gly
    50                  55                  60

Leu Glu Trp Ile Ala Cys Ile Tyr Gly Gly Ser Ser Gly Thr Thr Tyr
65                  70                  75                  80

Tyr Ala Ser Trp Pro Lys Gly Arg Phe Thr Ile Ser Lys Thr Ser Ser
                85                  90                  95

Thr Thr Val Thr Leu Gln Met Thr Ser Leu Thr Ala Ala Asp Thr Ala
            100                 105                 110

Thr Tyr Phe Cys Met Arg Gly Ala Asn Gly Ala Gly Phe Gly Asp Ala
        115                 120                 125

Asn Leu Trp Gly Pro Gly Thr Leu Val Thr Val Ser Ser Gly Gln Pro
    130                 135                 140

Lys Ala Pro Ser Val Phe Pro Leu Ala Pro Cys Cys Gly Asp Thr Pro
145                 150                 155                 160

Ser Ser Thr Val Thr Leu Gly Cys Leu Val Lys Gly Tyr Leu Pro Glu
                165                 170                 175

Pro Val Thr Val Thr Trp Asn Ser Gly Thr Leu Thr Asn Gly Val Arg
            180                 185                 190

Thr Phe Pro Ser Val Arg Gln Ser Ser Gly Leu Tyr Ser Leu Ser Ser
        195                 200                 205

Val Val Ser Val Thr Ser Ser Ser Gln Pro Val Thr Cys Asn Val Ala
    210                 215                 220

His Pro Ala Thr Asn Thr Lys Val Asp Lys Thr Val Ala Pro Ser Thr
225                 230                 235                 240

Cys Ser Lys Pro Met Cys Pro Pro Pro Glu Leu Pro Gly Gly Pro Ser
                245                 250                 255

Val Phe Ile Phe Pro Pro Lys Pro Lys Asp Thr Leu Met Ile Ser Arg
            260                 265                 270
```

Thr Pro Glu Val Thr Cys Val Val Val Asp Val Ser Gln Asp Asp Pro
275 280 285

Glu Val Gln Phe Thr Trp Tyr Ile Asn Asn Glu Gln Val Arg Thr Ala
290 295 300

Arg Pro Pro Leu Arg Glu Gln Gln Phe Asn Ser Thr Ile Arg Val Val
305 310 315 320

Ser Thr Leu Pro Ile Ala His Gln Asp Trp Leu Arg Gly Lys Glu Phe
325 330 335

Lys Cys Lys Val His Asn Lys Ala Leu Pro Ala Pro Ile Glu Lys Thr
340 345 350

Ile Ser Lys Ala Arg Gly Gln Pro Leu Glu Pro Lys Val Tyr Thr Met
355 360 365

Gly Pro Pro Arg Glu Glu Leu Ser Ser Arg Ser Val Ser Leu Thr Cys
370 375 380

Met Ile Asn Gly Phe Tyr Pro Ser Asp Ile Ser Val Glu Trp Glu Lys
385 390 395 400

Asn Gly Lys Ala Glu Asp Asn Tyr Lys Thr Thr Pro Thr Val Leu Asp
405 410 415

Ser Asp Gly Ser Tyr Phe Leu Tyr Ser Lys Leu Ser Val Pro Thr Ser
420 425 430

Glu Trp Gln Arg Gly Asp Val Phe Thr Cys Ser Val Met His Glu Ala
435 440 445

Leu His Asn His Tyr Thr Gln Lys Ser Ile Ser Arg Ser Pro Gly Lys
450 455 460

<210> SEQ ID NO 2
<211> LENGTH: 238
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

Met Asp Thr Arg Ala Pro Thr Gln Leu Leu Gly Leu Leu Leu Leu Trp
1 5 10 15

Leu Pro Gly Ala Thr Phe Ala Gln Val Leu Thr Gln Thr Pro Ser Ser
20 25 30

Val Ser Ala Ala Val Gly Gly Thr Val Thr Ile Asn Cys Gln Ser Ser
35 40 45

Pro Ser Val Tyr Ser Asn Tyr Leu Ser Trp Phe Gln Gln Lys Pro Gly
50 55 60

Gln Pro Pro Lys Leu Leu Ile Tyr Ser Ala Ser Thr Leu Ala Ser Gly
65 70 75 80

Val Pro Ser Arg Phe Arg Gly Ser Gly Ser Gly Thr Gln Phe Thr Leu
85 90 95

Thr Ile Ser Asp Val Gln Cys Asp Asp Ala Ala Asn Tyr Tyr Cys Ala
100 105 110

Gly Gly Tyr Thr Tyr Thr Ser Asp Ser Ile Trp Ala Phe Gly Gly Gly
115 120 125

Thr Glu Val Val Val Lys Gly Asp Pro Val Ala Pro Thr Val Leu Ile
130 135 140

Phe Pro Pro Ala Ala Asp Gln Val Ala Thr Gly Thr Val Thr Ile Val
145 150 155 160

Cys Val Ala Asn Lys Tyr Phe Pro Asp Val Thr Val Thr Trp Glu Val

```
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235


<210> SEQ ID NO 3
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Glu Thr Gly Leu Arg Trp Leu Leu Leu Val Ala Val Leu Lys Gly
1               5                   10                  15

Val Gln Cys Gln Glu Gln Leu Glu Glu Ala Gly Gly Asp Leu Val Lys
            20                  25                  30

Pro Glu Gly Ser Leu Arg Leu Thr Cys Lys Ala Ser Gly Phe Asp Phe
        35                  40                  45

Ser Ser Tyr Tyr Tyr Met Cys Trp Val Arg Gln Ala Pro Gly Lys Gly
    50                  55                  60

Leu Glu Trp Ile Ala Cys Ile Tyr Gly Gly Ala Ser Gly Thr Thr Tyr
65                  70                  75                  80

Tyr Ala Ser Trp Ala Lys Gly Arg Phe Thr Ile Ser Lys Thr Ser Ser
                85                  90                  95

Thr Thr Val Thr Leu Gln Met Thr Ser Leu Thr Ala Ala Asp Thr Ala
            100                 105                 110

Thr Tyr Phe Cys Met Arg Gly Ala Asn Gly Ala Gly Phe Gly Asp Ala
        115                 120                 125

Asn Leu Trp Gly Pro Gly Thr Leu Val Thr Val Ser Ser Gly Gln Pro
    130                 135                 140

Lys Ala Pro Ser Val Phe Pro Leu Ala Pro Cys Cys Gly Asp Thr Pro
145                 150                 155                 160

Ser Ser Thr Val Thr Leu Gly Cys Leu Val Lys Gly Tyr Leu Pro Glu
                165                 170                 175

Pro Val Thr Val Thr Trp Asn Ser Gly Thr Leu Thr Asn Gly Val Arg
            180                 185                 190

Thr Phe Pro Ser Val Arg Gln Ser Ser Gly Leu Tyr Ser Leu Ser Ser
        195                 200                 205

Val Val Ser Val Thr Ser Ser Ser Gln Pro Val Thr Cys Asn Val Ala
    210                 215                 220

His Pro Ala Thr Asn Thr Lys Val Asp Lys Thr Val Ala Pro Ser Thr
225                 230                 235                 240

Cys Ser Lys Pro Met Cys Pro Pro Pro Glu Leu Pro Gly Gly Pro Ser
                245                 250                 255

Val Phe Ile Phe Pro Pro Lys Pro Lys Asp Thr Leu Met Ile Ser Arg
            260                 265                 270

Thr Pro Glu Val Thr Cys Val Val Val Asp Val Ser Gln Asp Asp Pro
        275                 280                 285
```

-continued

```
Glu Val Gln Phe Thr Trp Tyr Ile Asn Asn Glu Gln Val Arg Thr Ala
    290                 295                 300

Arg Pro Pro Leu Arg Glu Gln Gln Phe Asn Ser Thr Ile Arg Val Val
305                 310                 315                 320

Ser Thr Leu Pro Ile Ala His Gln Asp Trp Leu Arg Gly Lys Glu Phe
                325                 330                 335

Lys Cys Lys Val His Asn Lys Ala Leu Pro Ala Pro Ile Glu Lys Thr
            340                 345                 350

Ile Ser Lys Ala Arg Gly Gln Pro Leu Glu Pro Lys Val Tyr Thr Met
        355                 360                 365

Gly Pro Pro Arg Glu Glu Leu Ser Ser Arg Ser Val Ser Leu Thr Cys
    370                 375                 380

Met Ile Asn Gly Phe Tyr Pro Ser Asp Ile Ser Val Glu Trp Glu Lys
385                 390                 395                 400

Asn Gly Lys Ala Glu Asp Asn Tyr Lys Thr Thr Pro Thr Val Leu Asp
                405                 410                 415

Ser Asp Gly Ser Tyr Phe Leu Tyr Ser Lys Leu Ser Val Pro Thr Ser
            420                 425                 430

Glu Trp Gln Arg Gly Asp Val Phe Thr Cys Ser Val Met His Glu Ala
        435                 440                 445

Leu His Asn His Tyr Thr Gln Lys Ser Ile Ser Arg Ser Pro Gly Lys
    450                 455                 460


<210> SEQ ID NO 4
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Gly Thr Val Thr Ile Asn Cys Gln Ser Ser
        35                  40                  45

Pro Ser Val Tyr Ser Asn Tyr Leu Ser Trp Phe Gln Gln Lys Pro Gly
    50                  55                  60

Gln Pro Pro Lys Leu Leu Ile Tyr Ser Ala Ser Thr Leu Ala Ser Gly
65                  70                  75                  80

Val Pro Ser Arg Phe Arg Gly Ser Gly Ser Gly Thr Gln Phe Thr Leu
                85                  90                  95

Thr Ile Ser Asp Val Gln Cys Asp Asp Ala Ala Asn Tyr Tyr Cys Ala
            100                 105                 110

Gly Gly Tyr Thr Tyr Thr Ser Asp Ser Ile Trp Ala Phe Gly Gly Gly
        115                 120                 125

Thr Glu Val Val Val Lys Gly Asp Pro Val Ala Pro Thr Val Leu Ile
    130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190
```

Asn Ser Ala Asp Cys Thr Tyr Asn Leu Ser Ser Thr Leu Thr Leu Thr
195 200 205

Ser Thr Gln Tyr Asn Ser His Lys Glu Tyr Thr Cys Lys Val Thr Gln
210 215 220

Gly Thr Thr Ser Val Val Gln Ser Phe Asn Arg Gly Asp Cys
225 230 235

<210> SEQ ID NO 5
<211> LENGTH: 468
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

Met Glu Thr Gly Leu Arg Trp Leu Leu Leu Val Ala Val Leu Lys Gly
1 5 10 15

Val Gln Cys Gln Gln Gln Met Glu Glu Ser Gly Gly Gly Leu Val Gln
20 25 30

Pro Glu Gly Ser Leu Thr Leu Thr Cys Lys Ala Ser Gly Ile Asp Phe
35 40 45

Ser Ser Tyr Tyr Tyr Met Cys Trp Val Arg Gln Ala Pro Gly Lys Gly
50 55 60

Leu Glu Leu Ile Ala Cys Ile Tyr Leu Ser Ser Gly Ser Thr Trp Tyr
65 70 75 80

Ala Ser Trp Val Asn Gly Arg Phe Thr Ile Ser Arg Ser Thr Ser Leu
85 90 95

Asn Thr Val Thr Leu Gln Met Thr Ser Leu Thr Ala Ala Asp Thr Ala
100 105 110

Thr Tyr Phe Cys Ala Arg Gly Gly Phe Cys Thr Ala Tyr Ser Gly Asp
115 120 125

Gly Cys Tyr Phe Thr Leu Trp Gly Pro Gly Thr Leu Val Thr Val Ser
130 135 140

Ser Gly Gln Pro Lys Ala Pro Ser Val Phe Pro Leu Ala Pro Cys Cys
145 150 155 160

Gly Asp Thr Pro Ser Ser Thr Val Thr Leu Gly Cys Leu Val Lys Gly
165 170 175

Tyr Leu Pro Glu Pro Val Thr Val Thr Trp Asn Ser Gly Thr Leu Thr
180 185 190

Asn Gly Val Arg Thr Phe Pro Ser Val Arg Gln Ser Ser Gly Leu Tyr
195 200 205

Ser Leu Ser Ser Val Val Ser Val Thr Ser Ser Ser Gln Pro Val Thr
210 215 220

Cys Asn Val Ala His Pro Ala Thr Asn Thr Lys Val Asp Lys Thr Val
225 230 235 240

Ala Pro Ser Thr Cys Ser Lys Pro Met Cys Pro Pro Pro Glu Leu Pro
245 250 255

Gly Gly Pro Ser Val Phe Ile Phe Pro Pro Lys Pro Lys Asp Thr Leu
260 265 270

Met Ile Ser Arg Thr Pro Glu Val Thr Cys Val Val Val Asp Val Ser
275 280 285

Gln Asp Asp Pro Glu Val Gln Phe Thr Trp Tyr Ile Asn Asn Glu Gln
290 295 300

Val Arg Thr Ala Arg Pro Pro Leu Arg Glu Gln Gln Phe Asn Ser Thr 305 310 315 320

Ile Arg Val Val Ser Thr Leu Pro Ile Ala His Gln Asp Trp Leu Arg
325 330 335

Gly Lys Glu Phe Lys Cys Lys Val His Asn Lys Ala Leu Pro Ala Pro
340 345 350

Ile Glu Lys Thr Ile Ser Lys Ala Arg Gly Gln Pro Leu Glu Pro Lys
355 360 365

Val Tyr Thr Met Gly Pro Pro Arg Glu Glu Leu Ser Ser Arg Ser Val
370 375 380

Ser Leu Thr Cys Met Ile Asn Gly Phe Tyr Pro Ser Asp Ile Ser Val
385 390 395 400

Glu Trp Glu Lys Asn Gly Lys Ala Glu Asp Asn Tyr Lys Thr Thr Pro
405 410 415

Thr Val Leu Asp Ser Asp Gly Ser Tyr Phe Leu Tyr Ser Lys Leu Ser
420 425 430

Val Pro Thr Ser Glu Trp Gln Arg Gly Asp Val Phe Thr Cys Ser Val
435 440 445

Met His Glu Ala Leu His Asn His Tyr Thr Gln Lys Ser Ile Ser Arg
450 455 460

Ser Pro Gly Lys
465

<210> SEQ ID NO 6
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

Met Asp Thr Arg Ala Pro Thr Gln Leu Leu Gly Leu Leu Leu Leu Trp
1 5 10 15

Leu Pro Gly Ala Thr Phe Ala Ile Lys Met Thr Gln Pro Pro Ala Ser
20 25 30

Val Ser Ala Ala Val Gly Gly Thr Val Thr Ile Asn Cys Arg Ala Ser
35 40 45

Glu Asp Ile Asp Ser Tyr Leu Ala Trp Tyr Gln Gln Lys Pro Gly Gln
50 55 60

Pro Pro Gln Leu Leu Ile Tyr Arg Ala Ser Thr Leu Ala Ser Gly Val
65 70 75 80

Pro Ser Arg Phe Ser Gly Ser Gly Ser Gly Thr Gln Phe Thr Leu Thr
85 90 95

Ile Ser Gly Val Gln Cys Asp Asp Ala Ala Thr Tyr Tyr Cys Gln Ser
100 105 110

Thr Tyr Tyr Ser Ser Asn Pro Glu Gly Val Phe Gly Gly Gly Thr Glu
115 120 125

Val Val Val Lys Gly Asp Pro Val Ala Pro Thr Val Leu Ile Phe Pro
130 135 140

Pro Ala Ala Asp Gln Val Ala Thr Gly Thr Val Thr Ile Val Cys Val
145 150 155 160

Ala Asn Lys Tyr Phe Pro Asp Val Thr Val Thr Trp Glu Val Asp Gly
165 170 175

Thr Thr Gln Thr Thr Gly Ile Glu Asn Ser Lys Thr Pro Gln Asn Ser
180 185 190

Ala Asp Cys Thr Tyr Asn Leu Ser Ser Thr Leu Thr Leu Thr Ser Thr
195 200 205

Gln Tyr Asn Ser His Lys Glu Tyr Thr Cys Lys Val Thr Gln Gly Thr
210 215 220

Thr Ser Val Val Gln Ser Phe Asn Arg Gly Asp Cys
225 230 235

<210> SEQ ID NO 7
<211> LENGTH: 462
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Met Glu Thr Gly Leu Arg Trp Leu Leu Leu Val Ala Val Leu Lys Gly
1 5 10 15

Val Gln Cys Gln Glu Gln Leu Val Glu Ser Gly Gly Gly Leu Val Lys
20 25 30

Pro Glu Gly Ser Leu Thr Leu Thr Cys Thr Ala Ser Gly Phe Ser Phe
35 40 45

Ser Ser Tyr Tyr Tyr Met Cys Trp Val Arg Gln Ala Pro Gly Lys Gly
50 55 60

Leu Glu Leu Ser Ala Cys Ile Asp Thr Gly Ser Gly Ser Thr Trp Tyr
65 70 75 80

Pro Ser Trp Val Asn Gly Arg Phe Thr Ile Ser Arg Ser Thr Ser Leu
85 90 95

Asn Thr Val Asp Leu Lys Met Thr Ser Leu Thr Ala Ala Asp Thr Ala
100 105 110

Thr Tyr Phe Cys Ala Arg Glu Tyr Ser Thr Ala Trp Tyr Phe Asn Leu
115 120 125

Trp Gly Pro Gly Thr Leu Val Thr Val Ser Ser Gly Gln Pro Lys Ala
130 135 140

Pro Ser Val Phe Pro Leu Ala Pro Cys Cys Gly Asp Thr Pro Ser Ser
145 150 155 160

Thr Val Thr Leu Gly Cys Leu Val Lys Gly Tyr Leu Pro Glu Pro Val
165 170 175

Thr Val Thr Trp Asn Ser Gly Thr Leu Thr Asn Gly Val Arg Thr Phe
180 185 190

Pro Ser Val Arg Gln Ser Ser Gly Leu Tyr Ser Leu Ser Ser Val Val
195 200 205

Ser Val Thr Ser Ser Ser Gln Pro Val Thr Cys Asn Val Ala His Pro
210 215 220

Ala Thr Asn Thr Lys Val Asp Lys Thr Val Ala Pro Ser Thr Cys Ser
225 230 235 240

Lys Pro Met Cys Pro Pro Pro Glu Leu Pro Gly Gly Pro Ser Val Phe
245 250 255

Ile Phe Pro Pro Lys Pro Lys Asp Thr Leu Met Ile Ser Arg Thr Pro
260 265 270

Glu Val Thr Cys Val Val Val Asp Val Ser Gln Asp Asp Pro Glu Val
275 280 285

Gln Phe Thr Trp Tyr Ile Asn Asn Glu Gln Val Arg Thr Ala Arg Pro
290 295 300

Pro Leu Arg Glu Gln Gln Phe Asn Ser Thr Ile Arg Val Val Ser Thr
305 310 315 320

Leu Pro Ile Ala His Gln Asp Trp Leu Arg Gly Lys Glu Phe Lys Cys
325 330 335

Lys Val His Asn Lys Ala Leu Pro Ala Pro Ile Glu Lys Thr Ile Ser
340 345 350

Lys Ala Arg Gly Gln Pro Leu Glu Pro Lys Val Tyr Thr Met Gly Pro
355 360 365

Pro Arg Glu Glu Leu Ser Ser Arg Ser Val Ser Leu Thr Cys Met Ile
370 375 380

Asn Gly Phe Tyr Pro Ser Asp Ile Ser Val Glu Trp Glu Lys Asn Gly
385 390 395 400

Lys Ala Glu Asp Asn Tyr Lys Thr Thr Pro Thr Val Leu Asp Ser Asp
405 410 415

Gly Ser Tyr Phe Leu Tyr Ser Lys Leu Ser Val Pro Thr Ser Glu Trp
420 425 430

Gln Arg Gly Asp Val Phe Thr Cys Ser Val Met His Glu Ala Leu His
435 440 445

Asn His Tyr Thr Gln Lys Ser Ile Ser Arg Ser Pro Gly Lys
450 455 460

<210> SEQ ID NO 8
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Met Asp Thr Arg Ala Pro Thr Gln Leu Leu Gly Leu Leu Leu Leu Trp
1 5 10 15

Leu Pro Gly Ala Thr Phe Ala Ile Lys Met Thr Gln Thr Pro Gly Ser
20 25 30

Val Glu Val Ala Val Gly Gly Thr Val Thr Ile Asn Cys Gln Ala Ser
35 40 45

Gln Ser Ile Ser Thr Ala Leu Ala Trp Tyr Gln Gln Lys Pro Gly Gln
50 55 60

Arg Pro Lys Leu Leu Ile Tyr Asp Ala Ser Arg Leu Ala Ser Gly Val
65 70 75 80

Pro Ser Arg Phe Ser Gly Ser Gly Ser Gly Thr Glu Phe Thr Leu Thr
85 90 95

Ile Ser Gly Val Glu Cys Ala Asp Ala Ala Thr Tyr Tyr Cys His Gln
100 105 110

Gly Phe Gly Ala Ser Asn Val Asp Asn Pro Phe Gly Gly Gly Thr Glu
115 120 125

Val Val Val Glu Gly Asp Pro Val Ala Pro Thr Val Leu Ile Phe Pro
130 135 140

Pro Ala Ala Asp Gln Val Ala Thr Gly Thr Val Thr Ile Val Cys Val
145 150 155 160

Ala Asn Lys Tyr Phe Pro Asp Val Thr Val Thr Trp Glu Val Asp Gly
165 170 175

Thr Thr Gln Thr Thr Gly Ile Glu Asn Ser Lys Thr Pro Gln Asn Ser
180 185 190

Ala Asp Cys Thr Tyr Asn Leu Ser Ser Thr Leu Thr Leu Thr Ser Thr
195 200 205

Gln Tyr Asn Ser His Lys Glu Tyr Thr Cys Lys Val Thr Gln Gly Thr

```
    210                 215                 220

Thr Ser Val Val Gln Ser Phe Asn Arg Gly Asp Cys
225                 230                 235


<210> SEQ ID NO 9
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Gly Leu Val Gln
            20                  25                  30

Pro Glu Gly Ser Leu Thr Leu Thr Cys Thr Ala Ser Gly Phe Ser Phe
        35                  40                  45

Ser Asp Asn Ala Trp Ile Cys Trp Val Arg Gln Ala Pro Gly Lys Gly
    50                  55                  60

Leu Glu Trp Ile Gly Cys Ile Tyr Ile Gly Ser Ser Ser Thr Tyr Tyr
65                  70                  75                  80

Ala Ser Trp Ala Lys Gly Arg Phe Thr Ile Ser Arg Thr Ser Ser Thr
                85                  90                  95

Thr Val Asn Leu Gln Met Thr Ser Leu Thr Asp Ala Asp Thr Ala Thr
            100                 105                 110

Tyr Phe Cys Gly Arg Asp Pro Thr Ala Ala Trp Gly Gly Gly Leu Trp
        115                 120                 125

Gly Pro Gly Thr Leu Val Thr Val Ser Ser Gly Gln Pro Lys Ala Pro
    130                 135                 140

Ser Val Phe Pro Leu Ala Pro Cys Cys Gly Asp Thr Pro Ser Ser Thr
145                 150                 155                 160

Val Thr Leu Gly Cys Leu Val Lys Gly Tyr Leu Pro Glu Pro Val Thr
                165                 170                 175

Val Thr Trp Asn Ser Gly Thr Leu Thr Asn Gly Val Arg Thr Phe Pro
            180                 185                 190

Ser Val Arg Gln Ser Ser Gly Leu Tyr Ser Leu Ser Ser Val Val Ser
        195                 200                 205

Val Thr Ser Ser Ser Gln Pro Val Thr Cys Asn Val Ala His Pro Ala
    210                 215                 220

Thr Asn Thr Lys Val Asp Lys Thr Val Ala Pro Ser Thr Cys Ser Lys
225                 230                 235                 240

Pro Met Cys Pro Pro Pro Glu Leu Pro Gly Gly Pro Ser Val Phe Ile
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Asp Asp Pro Glu Val Gln
        275                 280                 285

Phe Thr Trp Tyr Ile Asn Asn Glu Gln Val Arg Thr Ala Arg Pro Pro
    290                 295                 300

Leu Arg Glu Gln Gln Phe Asn Ser Thr Ile Arg Val Val Ser Thr Leu
305                 310                 315                 320

Pro Ile Ala His Gln Asp Trp Leu Arg Gly Lys Glu Phe Lys Cys Lys
                325                 330                 335
```

```
Val His Asn Lys Ala Leu Pro Ala Pro Ile Glu Lys Thr Ile Ser Lys
            340                 345                 350

Ala Arg Gly Gln Pro Leu Glu Pro Lys Val Tyr Thr Met Gly Pro Pro
        355                 360                 365

Arg Glu Glu Leu Ser Ser Arg Ser Val Ser Leu Thr Cys Met Ile Asn
    370                 375                 380

Gly Phe Tyr Pro Ser Asp Ile Ser Val Glu Trp Glu Lys Asn Gly Lys
385                 390                 395                 400

Ala Glu Asp Asn Tyr Lys Thr Thr Pro Thr Val Leu Asp Ser Asp Gly
                405                 410                 415

Ser Tyr Phe Leu Tyr Ser Lys Leu Ser Val Pro Thr Ser Glu Trp Gln
            420                 425                 430

Arg Gly Asp Val Phe Thr Cys Ser Val Met His Glu Ala Leu His Asn
        435                 440                 445

His Tyr Thr Gln Lys Ser Ile Ser Arg Ser Pro Gly Lys
    450                 455                 460


<210> SEQ ID NO 10
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Asp Thr Arg Ala Pro Thr Gln Leu Leu Gly Leu Leu Leu Leu Trp
1               5                   10                  15

Leu Pro Gly Ala Ile Cys Asp Pro Val Met Thr Gln Thr Pro Ser Ser
            20                  25                  30

Thr Ser Ala Ala Val Gly Gly Thr Val Thr Ile Ser Cys Gln Ser Ser
        35                  40                  45

Gln Ser Val Tyr Asn Asn Asn Tyr Leu Ala Trp Tyr Gln Gln Lys Pro
    50                  55                  60

Gly Gln Pro Pro Lys Arg Leu Ile Tyr Glu Ser Ser Lys Leu Ala Ser
65                  70                  75                  80

Gly Val Pro Ser Arg Phe Arg Gly Ser Gly Ser Gly Ala Gln Phe Thr
                85                  90                  95

Leu Thr Ile Ser Asp Leu Glu Cys Asp Asp Ala Ala Thr Tyr Tyr Cys
            100                 105                 110

Leu Gly Ala Tyr Tyr Thr Thr Leu Asp Phe Gly Gly Gly Thr Glu Val
        115                 120                 125

Val Val Arg Gly Asp Pro Val Ala Pro Thr Val Leu Ile Phe Pro Pro
    130                 135                 140

Ala Ala Asp Gln Val Ala Thr Gly Thr Val Thr Ile Val Cys Val Ala
145                 150                 155                 160

Asn Lys Tyr Phe Pro Asp Val Thr Val Thr Trp Glu Val Asp Gly Thr
                165                 170                 175

Thr Gln Thr Thr Gly Ile Glu Asn Ser Lys Thr Pro Gln Asn Ser Ala
            180                 185                 190

Asp Cys Thr Tyr Asn Leu Ser Ser Thr Leu Thr Leu Thr Ser Thr Gln
        195                 200                 205

Tyr Asn Ser His Lys Glu Tyr Thr Cys Lys Val Thr Gln Gly Thr Thr
    210                 215                 220

Ser Val Val Gln Ser Phe Asn Arg Gly Asp Cys
225                 230                 235
```

<210> SEQ ID NO 11
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Lys Ala Ser Gly Ile Asp Phe Ser
        35                  40                  45

Ser Ser Tyr Trp Ile Cys Trp Val Arg Gln Ala Pro Gly Lys Gly Leu
    50                  55                  60

Glu Trp Ile Ala Cys Ile Asp Thr Gly Ser Ser Gly Ser Thr Tyr Tyr
65                  70                  75                  80

Ala Ser Trp Ala Lys Gly Arg Phe Thr Ile Ser Lys Pro Ser Ser Thr
                85                  90                  95

Thr Val Ser Leu Gln Met Thr Ser Leu Gln Ala Ala Asp Thr Ala Thr
            100                 105                 110

Tyr Phe Cys Ala Arg Lys Gly Asp Gly Thr Asp Leu Trp Gly Pro Gly
        115                 120                 125

Thr Leu Val Thr Val Ser Ser Gly Gln Pro Lys Ala Pro Ser Val Phe
    130                 135                 140

Pro Leu Ala Pro Cys Cys Gly Asp Thr Pro Ser Ser Thr Val Thr Leu
145                 150                 155                 160

Gly Cys Leu Val Lys Gly Tyr Leu Pro Glu Pro Val Thr Val Thr Trp
                165                 170                 175

Asn Ser Gly Thr Leu Thr Asn Gly Val Arg Thr Phe Pro Ser Val Arg
            180                 185                 190

Gln Ser Ser Gly Leu Tyr Ser Leu Ser Ser Val Val Ser Val Thr Ser
        195                 200                 205

Ser Ser Gln Pro Val Thr Cys Asn Val Ala His Pro Ala Thr Asn Thr
    210                 215                 220

Lys Val Asp Lys Thr Val Ala Pro Ser Thr Cys Ser Lys Pro Met Cys
225                 230                 235                 240

Pro Pro Pro Glu Leu Pro Gly Gly Pro Ser Val Phe Ile Phe Pro Pro
                245                 250                 255

Lys Pro Lys Asp Thr Leu Met Ile Ser Arg Thr Pro Glu Val Thr Cys
            260                 265                 270

Val Val Val Asp Val Ser Gln Asp Asp Pro Glu Val Gln Phe Thr Trp
        275                 280                 285

Tyr Ile Asn Asn Glu Gln Val Arg Thr Ala Arg Pro Pro Leu Arg Glu
    290                 295                 300

Gln Gln Phe Asn Ser Thr Ile Arg Val Val Ser Thr Leu Pro Ile Ala
305                 310                 315                 320

His Gln Asp Trp Leu Arg Gly Lys Glu Phe Lys Cys Lys Val His Asn
                325                 330                 335

Lys Ala Leu Pro Ala Pro Ile Glu Lys Thr Ile Ser Lys Ala Arg Gly
            340                 345                 350

Gln Pro Leu Glu Pro Lys Val Tyr Thr Met Gly Pro Pro Arg Glu Glu
```

```
        355                 360                 365

Leu Ser Ser Arg Ser Val Ser Leu Thr Cys Met Ile Asn Gly Phe Tyr
    370                 375                 380

Pro Ser Asp Ile Ser Val Glu Trp Glu Lys Asn Gly Lys Ala Glu Asp
385                 390                 395                 400

Asn Tyr Lys Thr Thr Pro Thr Val Leu Asp Ser Asp Gly Ser Tyr Phe
                405                 410                 415

Leu Tyr Ser Lys Leu Ser Val Pro Thr Ser Glu Trp Gln Arg Gly Asp
            420                 425                 430

Val Phe Thr Cys Ser Val Met His Glu Ala Leu His Asn His Tyr Thr
        435                 440                 445

Gln Lys Ser Ile Ser Arg Ser Pro Gly Lys
    450                 455


<210> SEQ ID NO 12
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Asp Thr Arg Ala Pro Thr Gln Leu Leu Gly Leu Leu Leu Leu Trp
1               5                   10                  15

Leu Pro Gly Ala Arg Cys Ala Leu Val Met Thr Gln Thr Pro Ala Ser
            20                  25                  30

Val Glu Ala Ala Val Gly Gly Thr Val Thr Ile Lys Cys Gln Ala Ser
        35                  40                  45

Gln Ser Ile Ser Ser Tyr Leu Asn Trp Tyr Gln Gln Lys Ser Gly Gln
    50                  55                  60

Pro Pro Lys Asn Leu Ile Tyr Arg Ala Ser Thr Leu Ala Ser Gly Val
65                  70                  75                  80

Ser Ser Arg Phe Lys Gly Ser Gly Ser Gly Thr Glu Phe Thr Leu Thr
                85                  90                  95

Ile Asn Asp Leu Glu Cys Ala Asp Ala Ala Thr Tyr Tyr Cys Gln Ser
            100                 105                 110

Tyr Gly Gly Tyr Ser Ile Tyr Gly Leu Val Phe Gly Gly Gly Thr Glu
        115                 120                 125

Val Val Val Lys Gly Asp Pro Val Ala Pro Thr Val Leu Ile Phe Pro
    130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235


<210> SEQ ID NO 13
<211> LENGTH: 458
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 13

Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Gly Leu Val Lys
            20                  25                  30

Pro Glu Glu Ser Leu Thr Leu Thr Cys Thr Ala Ser Gly Phe Ser Phe
        35                  40                  45

Ile Ser Ser Asp Trp Ile Cys Trp Val Arg Gln Ala Pro Gly Lys Gly
    50                  55                  60

Leu Glu Trp Ile Ala Cys Ile Tyr Ile Gly Gly His Thr Pro Tyr Tyr
65                  70                  75                  80

Ala Ser Trp Ala Arg Gly Arg Phe Thr Ile Ser Lys Thr Ser Ser Thr
                85                  90                  95

Ala Val Thr Leu Gln Met Ser Ser Leu Thr Ala Ala Asp Thr Ala Thr
            100                 105                 110

Tyr Phe Cys Ala Arg Gly Ile Ala Gly Pro Ala Leu Trp Gly Pro Gly
        115                 120                 125

Thr Leu Val Thr Val Ser Ser Gly Gln Pro Lys Ala Pro Ser Val Phe
    130                 135                 140

Pro Leu Ala Pro Cys Cys Gly Asp Thr Pro Ser Ser Thr Val Thr Leu
145                 150                 155                 160

Gly Cys Leu Val Lys Gly Tyr Leu Pro Glu Pro Val Thr Val Thr Trp
                165                 170                 175

Asn Ser Gly Thr Leu Thr Asn Gly Val Arg Thr Phe Pro Ser Val Arg
            180                 185                 190

Gln Ser Ser Gly Leu Tyr Ser Leu Ser Ser Val Val Ser Val Thr Ser
        195                 200                 205

Ser Ser Gln Pro Val Thr Cys Asn Val Ala His Pro Ala Thr Asn Thr
    210                 215                 220

Lys Val Asp Lys Thr Val Ala Pro Ser Thr Cys Ser Lys Pro Met Cys
225                 230                 235                 240

Pro Pro Pro Glu Leu Pro Gly Gly Pro Ser Val Phe Ile Phe Pro Pro
                245                 250                 255

Lys Pro Lys Asp Thr Leu Met Ile Ser Arg Thr Pro Glu Val Thr Cys
            260                 265                 270

Val Val Val Asp Val Ser Gln Asp Asp Pro Glu Val Gln Phe Thr Trp
        275                 280                 285

Tyr Ile Asn Asn Glu Gln Val Arg Thr Ala Arg Pro Pro Leu Arg Glu
    290                 295                 300

Gln Gln Phe Asn Ser Thr Ile Arg Val Val Ser Thr Leu Pro Ile Ala
305                 310                 315                 320

His Gln Asp Trp Leu Arg Gly Lys Glu Phe Lys Cys Lys Val His Asn
                325                 330                 335

Lys Ala Leu Pro Ala Pro Ile Glu Lys Thr Ile Ser Lys Ala Arg Gly
            340                 345                 350

Gln Pro Leu Glu Pro Lys Val Tyr Thr Met Gly Pro Pro Arg Glu Glu
        355                 360                 365

Leu Ser Ser Arg Ser Val Ser Leu Thr Cys Met Ile Asn Gly Phe Tyr
    370                 375                 380

```
Pro Ser Asp Ile Ser Val Glu Trp Glu Lys Asn Gly Lys Ala Glu Asp
385                 390                 395                 400

Asn Tyr Lys Thr Thr Pro Thr Val Leu Asp Ser Asp Gly Ser Tyr Phe
                405                 410                 415

Leu Tyr Ser Lys Leu Ser Val Pro Thr Ser Glu Trp Gln Arg Gly Asp
            420                 425                 430

Val Phe Thr Cys Ser Val Met His Glu Ala Leu His Asn His Tyr Thr
        435                 440                 445

Gln Lys Ser Ile Ser Arg Ser Pro Gly Lys
    450                 455
```

<210> SEQ ID NO 14
<211> LENGTH: 235
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Gly Thr Val Thr Ile Asn Cys Gln Ala Ser
        35                  40                  45

Gln Ser Val Phe Arg Asn Asn Tyr Leu Ala Trp Tyr Gln Gln Lys Pro
    50                  55                  60

Gly Gln Pro Pro Thr Gln Leu Ile Tyr Leu Ala Ser Thr Leu Ala Ser
65                  70                  75                  80

Gly Val Pro Ser Arg Phe Ser Gly Ser Gly Ser Gly Thr Gln Phe Thr
                85                  90                  95

Leu Thr Ile Ser Asp Val Gln Cys Asp Asp Ala Ala Thr Tyr Tyr Cys
            100                 105                 110

Ala Gly Ala Thr Ser Ser Ile Ile Ile Phe Gly Gly Gly Thr Glu Val
        115                 120                 125

Val Val Lys Gly Asp Pro Val Ala Pro Thr Val Leu Ile Phe Pro Pro
    130                 135                 140

Ala Ala Asp Gln Val Ala Thr Gly Thr Val Thr Ile Val Cys Val Ala
145                 150                 155                 160

Asn Lys Tyr Phe Pro Asp Val Thr Val Thr Trp Glu Val Asp Gly Thr
                165                 170                 175

Thr Gln Thr Thr Gly Ile Glu Asn Ser Lys Thr Pro Gln Asn Ser Ala
            180                 185                 190

Asp Cys Thr Tyr Asn Leu Ser Ser Thr Leu Thr Leu Thr Ser Thr Gln
        195                 200                 205

Tyr Asn Ser His Lys Glu Tyr Thr Cys Lys Val Thr Gln Gly Thr Thr
    210                 215                 220

Ser Val Val Gln Ser Phe Asn Arg Gly Asp Cys
225                 230                 235
```

<210> SEQ ID NO 15
<211> LENGTH: 461
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Gln
            20                  25                  30

Pro Glu Gly Ser Leu Thr Leu Thr Cys Thr Ala Ser Gly Phe Ser Phe
        35                  40                  45

Ser Ala Asn His Trp Ile Cys Trp Val Arg Gln Ala Pro Gly Lys Gly
    50                  55                  60

Leu Glu Trp Val Gly Cys Ile Tyr Ile Gly Ser Gly Asn Thr Tyr Tyr
65                  70                  75                  80

Ala Ser Trp Ala Lys Gly Arg Phe Thr Ile Ser Lys Thr Ser Ser Thr
                85                  90                  95

Thr Val Thr Leu Gln Met Thr Ser Leu Thr Asp Ala Asp Thr Ala Met
            100                 105                 110

Tyr Phe Cys Gly Arg Asp Pro Thr Ala Gly Trp Gly Gly Gly Leu Trp
        115                 120                 125

Gly Pro Gly Thr Leu Val Thr Val Ser Ser Gly Gln Pro Lys Ala Pro
    130                 135                 140

Ser Val Phe Pro Leu Ala Pro Cys Cys Gly Asp Thr Pro Ser Ser Thr
145                 150                 155                 160

Val Thr Leu Gly Cys Leu Val Lys Gly Tyr Leu Pro Glu Pro Val Thr
                165                 170                 175

Val Thr Trp Asn Ser Gly Thr Leu Thr Asn Gly Val Arg Thr Phe Pro
            180                 185                 190

Ser Val Arg Gln Ser Ser Gly Leu Tyr Ser Leu Ser Ser Val Val Ser
        195                 200                 205

Val Thr Ser Ser Ser Gln Pro Val Thr Cys Asn Val Ala His Pro Ala
    210                 215                 220

Thr Asn Thr Lys Val Asp Lys Thr Val Ala Pro Ser Thr Cys Ser Lys
225                 230                 235                 240

Pro Met Cys Pro Pro Pro Glu Leu Pro Gly Gly Pro Ser Val Phe Ile
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Asp Asp Pro Glu Val Gln
        275                 280                 285

Phe Thr Trp Tyr Ile Asn Asn Glu Gln Val Arg Thr Ala Arg Pro Pro
    290                 295                 300

Leu Arg Glu Gln Gln Phe Asn Ser Thr Ile Arg Val Val Ser Thr Leu
305                 310                 315                 320

Pro Ile Ala His Gln Asp Trp Leu Arg Gly Lys Glu Phe Lys Cys Lys
                325                 330                 335

Val His Asn Lys Ala Leu Pro Ala Pro Ile Glu Lys Thr Ile Ser Lys
            340                 345                 350

Ala Arg Gly Gln Pro Leu Glu Pro Lys Val Tyr Thr Met Gly Pro Pro
        355                 360                 365

Arg Glu Glu Leu Ser Ser Arg Ser Val Ser Leu Thr Cys Met Ile Asn
    370                 375                 380

Gly Phe Tyr Pro Ser Asp Ile Ser Val Glu Trp Glu Lys Asn Gly Lys
385                 390                 395                 400
```

```
Ala Glu Asp Asn Tyr Lys Thr Thr Pro Thr Val Leu Asp Ser Asp Gly
                405                 410                 415

Ser Tyr Phe Leu Tyr Ser Lys Leu Ser Val Pro Thr Ser Glu Trp Gln
            420                 425                 430

Arg Gly Asp Val Phe Thr Cys Ser Val Met His Glu Ala Leu His Asn
        435                 440                 445

His Tyr Thr Gln Lys Ser Ile Ser Arg Ser Pro Gly Lys
    450                 455                 460
```

<210> SEQ ID NO 16
<211> LENGTH: 235
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
            20                  25                  30

Val Ser Ala Ala Val Gly Gly Thr Val Thr Ile Ser Cys Gln Ser Ser
        35                  40                  45

Gln Ser Val Tyr Asn Asn Asn Tyr Leu Ala Trp Tyr Gln Gln Lys Pro
    50                  55                  60

Gly Gln Pro Pro Lys Arg Leu Ile Tyr Glu Ala Ser Lys Leu Ala Ser
65                  70                  75                  80

Gly Val Pro Ser Arg Phe Arg Gly Ser Gly Ser Gly Thr His Phe Thr
                85                  90                  95

Leu Thr Ile Ser Gly Val Gln Cys Asp Asp Ala Ala Thr Tyr Tyr Cys
            100                 105                 110

Leu Gly Ala Tyr Phe Thr Thr Ile Val Phe Gly Gly Gly Thr Glu Val
        115                 120                 125

Val Val Arg Gly Asp Pro Val Ala Pro Thr Val Leu Ile Phe Pro Pro
    130                 135                 140

Ala Ala Asp Gln Val Ala Thr Gly Thr Val Thr Ile Val Cys Val Ala
145                 150                 155                 160

Asn Lys Tyr Phe Pro Asp Val Thr Val Thr Trp Glu Val Asp Gly Thr
                165                 170                 175

Thr Gln Thr Thr Gly Ile Glu Asn Ser Lys Thr Pro Gln Asn Ser Ala
            180                 185                 190

Asp Cys Thr Tyr Asn Leu Ser Ser Thr Leu Thr Leu Thr Ser Thr Gln
        195                 200                 205

Tyr Asn Ser His Lys Glu Tyr Thr Cys Lys Val Thr Gln Gly Thr Thr
    210                 215                 220

Ser Val Val Gln Ser Phe Asn Arg Gly Asp Cys
225                 230                 235
```

<210> SEQ ID NO 17
<211> LENGTH: 458
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

-continued

```
Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Gln
            20                  25                  30

Pro Glu Gly Ser Leu Thr Leu Thr Cys Lys Ala Ser Gly Phe Ser Phe
        35                  40                  45

Ser Ser Ser Tyr Trp Ile Cys Trp Val Arg Gln Ala Pro Gly Lys Gly
    50                  55                  60

Pro Glu Trp Ile Ala Cys Ile Tyr Ile Gly Ala Gly Ser Thr Tyr Tyr
65                  70                  75                  80

Ala Asn Trp Ala Lys Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Phe Cys Ser Arg Gly Ile Ala Gly Val Ala Leu Trp Gly Pro Gly
        115                 120                 125

Thr Leu Val Thr Val Ser Ser Gly Gln Pro Lys Ala Pro Ser Val Phe
    130                 135                 140

Pro Leu Ala Pro Cys Cys Gly Asp Thr Pro Ser Ser Thr Val Thr Leu
145                 150                 155                 160

Gly Cys Leu Val Lys Gly Tyr Leu Pro Glu Pro Val Thr Val Thr Trp
                165                 170                 175

Asn Ser Gly Thr Leu Thr Asn Gly Val Arg Thr Phe Pro Ser Val Arg
            180                 185                 190

Gln Ser Ser Gly Leu Tyr Ser Leu Ser Ser Val Val Ser Val Thr Ser
        195                 200                 205

Ser Ser Gln Pro Val Thr Cys Asn Val Ala His Pro Ala Thr Asn Thr
    210                 215                 220

Lys Val Asp Lys Thr Val Ala Pro Ser Thr Cys Ser Lys Pro Met Cys
225                 230                 235                 240

Pro Pro Pro Glu Leu Pro Gly Gly Pro Ser Val Phe Ile Phe Pro Pro
                245                 250                 255

Lys Pro Lys Asp Thr Leu Met Ile Ser Arg Thr Pro Glu Val Thr Cys
            260                 265                 270

Val Val Val Asp Val Ser Gln Asp Asp Pro Glu Val Gln Phe Thr Trp
        275                 280                 285

Tyr Ile Asn Asn Glu Gln Val Arg Thr Ala Arg Pro Pro Leu Arg Glu
    290                 295                 300

Gln Gln Phe Asn Ser Thr Ile Arg Val Val Ser Thr Leu Pro Ile Ala
305                 310                 315                 320

His Gln Asp Trp Leu Arg Gly Lys Glu Phe Lys Cys Lys Val His Asn
                325                 330                 335

Lys Ala Leu Pro Ala Pro Ile Glu Lys Thr Ile Ser Lys Ala Arg Gly
            340                 345                 350

Gln Pro Leu Glu Pro Lys Val Tyr Thr Met Gly Pro Pro Arg Glu Glu
        355                 360                 365

Leu Ser Ser Arg Ser Val Ser Leu Thr Cys Met Ile Asn Gly Phe Tyr
    370                 375                 380

Pro Ser Asp Ile Ser Val Glu Trp Glu Lys Asn Gly Lys Ala Glu Asp
385                 390                 395                 400

Asn Tyr Lys Thr Thr Pro Thr Val Leu Asp Ser Asp Gly Ser Tyr Phe
                405                 410                 415

Leu Tyr Ser Lys Leu Ser Val Pro Thr Ser Glu Trp Gln Arg Gly Asp
```

-continued

```
            420                 425                 430

Val Phe Thr Cys Ser Val Met His Glu Ala Leu His Asn His Tyr Thr
        435                 440                 445

Gln Lys Ser Ile Ser Arg Ser Pro Gly Lys
    450                 455


<210> SEQ ID NO 18
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Ser Thr Val Thr Ile Asn Cys Gln Ala Ser
        35                  40                  45

Gln Ser Val Tyr Lys Asn Asn Tyr Leu Ala Trp Tyr Gln Gln Lys Pro
    50                  55                  60

Gly Gln Pro Pro Lys Gln Leu Ile Tyr Asp Ala Ser Thr Leu Ala Ser
65                  70                  75                  80

Gly Val Pro Thr Arg Phe Lys Gly Ser Gly Ser Gly Thr Gln Phe Thr
                85                  90                  95

Leu Thr Ile Ser Asp Val Gln Cys Asp Asp Ala Ala Thr Tyr Tyr Cys
            100                 105                 110

Ala Gly Ala Tyr Ser Thr Val Val Val Phe Gly Gly Gly Thr Glu Val
        115                 120                 125

Val Val Lys Gly Asp Pro Val Ala Pro Thr Val Leu Ile Phe Pro Pro
    130                 135                 140

Ala Ala Asp Gln Val Ala Thr Gly Thr Val Thr Ile Val Cys Val Ala
145                 150                 155                 160

Asn Lys Tyr Phe Pro Asp Val Thr Val Thr Trp Glu Val Asp Gly Thr
                165                 170                 175

Thr Gln Thr Thr Gly Ile Glu Asn Ser Lys Thr Pro Gln Asn Ser Ala
            180                 185                 190

Asp Cys Thr Tyr Asn Leu Ser Ser Thr Leu Thr Leu Thr Ser Thr Gln
        195                 200                 205

Tyr Asn Ser His Lys Glu Tyr Thr Cys Lys Val Thr Gln Gly Thr Thr
    210                 215                 220

Ser Val Val Gln Ser Phe Asn Arg Gly Asp Cys
225                 230                 235


<210> SEQ ID NO 19
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Glu Thr Gly Leu Arg Trp Leu Leu Leu Val Ala Val Leu Lys Gly
1               5                   10                  15

Val Gln Cys Gln Gln Gln Leu Glu Glu Ser Gly Gly Gly Leu Val Lys
```

-continued

```
            20                  25                  30

Pro Gly Gly Thr Leu Thr Leu Thr Cys Arg Ala Ser Gly Ile Asp Phe
        35                  40                  45

Ser Ser Tyr Tyr Tyr Met Cys Trp Val Arg Gln Ala Pro Gly Arg Gly
    50                  55                  60

Leu Glu Leu Val Ala Cys Ile Glu Pro Ser Thr Val Ser Thr Trp Tyr
65                  70                  75                  80

Ala Asn Trp Val Ile Gly Arg Phe Thr Ile Ser Arg Thr Ser Ser Thr
                85                  90                  95

Thr Val Thr Leu Gln Met Thr Ser Leu Thr Ala Ala Asp Thr Ala Thr
            100                 105                 110

Tyr Phe Cys Ala Thr Ser Tyr Ser Tyr Gly Arg Ser Gly Tyr Ala Ser
        115                 120                 125

Thr Thr Thr Arg Leu Asp Leu Trp Gly Gln Gly Thr Leu Val Thr Val
    130                 135                 140

Ser Ser Gly Gln Pro Lys Ala Pro Ser Val Phe Pro Leu Ala Pro Cys
145                 150                 155                 160

Cys Gly Asp Thr Pro Ser Ser Thr Val Thr Leu Gly Cys Leu Val Lys
                165                 170                 175

Gly Tyr Leu Pro Glu Pro Val Thr Val Thr Trp Asn Ser Gly Thr Leu
            180                 185                 190

Thr Asn Gly Val Arg Thr Phe Pro Ser Val Arg Gln Ser Ser Gly Leu
        195                 200                 205

Tyr Ser Leu Ser Ser Val Val Ser Val Thr Ser Ser Ser Gln Pro Val
    210                 215                 220

Thr Cys Asn Val Ala His Pro Ala Thr Asn Thr Lys Val Asp Lys Thr
225                 230                 235                 240

Val Ala Pro Ser Thr Cys Ser Lys Pro Met Cys Pro Pro Pro Glu Leu
                245                 250                 255

Pro Gly Gly Pro Ser Val Phe Ile Phe Pro Pro Lys Pro Lys Asp Thr
            260                 265                 270

Leu Met Ile Ser Arg Thr Pro Glu Val Thr Cys Val Val Val Asp Val
        275                 280                 285

Ser Gln Asp Asp Pro Glu Val Gln Phe Thr Trp Tyr Ile Asn Asn Glu
    290                 295                 300

Gln Val Arg Thr Ala Arg Pro Pro Leu Arg Glu Gln Gln Phe Asn Ser
305                 310                 315                 320

Thr Ile Arg Val Val Ser Thr Leu Pro Ile Ala His Gln Asp Trp Leu
                325                 330                 335

Arg Gly Lys Glu Phe Lys Cys Lys Val His Asn Lys Ala Leu Pro Ala
            340                 345                 350

Pro Ile Glu Lys Thr Ile Ser Lys Ala Arg Gly Gln Pro Leu Glu Pro
        355                 360                 365

Lys Val Tyr Thr Met Gly Pro Pro Arg Glu Glu Leu Ser Ser Arg Ser
    370                 375                 380

Val Ser Leu Thr Cys Met Ile Asn Gly Phe Tyr Pro Ser Asp Ile Ser
385                 390                 395                 400

Val Glu Trp Glu Lys Asn Gly Lys Ala Glu Asp Asn Tyr Lys Thr Thr
                405                 410                 415

Pro Thr Val Leu Asp Ser Asp Gly Ser Tyr Phe Leu Tyr Ser Lys Leu
            420                 425                 430

Ser Val Pro Thr Ser Glu Trp Gln Arg Gly Asp Val Phe Thr Cys Ser
        435                 440                 445
```

```
Val Met His Glu Ala Leu His Asn His Tyr Thr Gln Lys Ser Ile Ser
    450                 455                 460

Arg Ser Pro Gly Lys
465


<210> SEQ ID NO 20
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Gly Ala Val Thr Ile Asn Cys Gln Ser Ser
        35                  40                  45

Lys Ser Val Tyr Asn Asn Asn Glu Leu Ser Trp Tyr Gln Gln Lys Pro
    50                  55                  60

Gly Gln Pro Pro Lys Leu Leu Ile Tyr Leu Ala Ser Asn Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Val Gln Cys Asp Asp Ala Ala Thr Tyr Tyr Cys
            100                 105                 110

Ile Gly Gly Trp Ser Ser Ser Ser Asp Gln Asn Gly Phe Gly Gly Gly
        115                 120                 125

Thr Glu Val Val Val Lys Gly Asp Pro Val Ala Pro Thr Val Leu Ile
    130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235


<210> SEQ ID NO 21
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Lys
            20                  25                  30
```

-continued

```
Pro Gly Ala Ser Leu Ala Leu Thr Cys Lys Ala Ser Gly Ile Asp Phe
        35                  40                  45

Asn Ser Gly Tyr Tyr Ile Cys Trp Val Arg Gln Ala Pro Gly Lys Gly
    50                  55                  60

Leu Glu Trp Ile Ala Cys Ile Asp Thr Gly Thr Ala Asp Thr Ala Tyr
65                  70                  75                  80

Ala Thr Trp Ala Lys Gly Arg Phe Thr Ile Ser Lys Thr Ser Ser Thr
                85                  90                  95

Thr Val Thr Leu Gln Met Thr Ser Leu Thr Gly Ala Asp Thr Ala Thr
            100                 105                 110

Tyr Phe Cys Ser Arg Asp Leu Gly Gly Gly Gly Tyr Asp Pro Asp Leu
        115                 120                 125

Trp Gly Pro Gly Thr Leu Val Thr Val Ser Ser Gly Gln Pro Lys Ala
    130                 135                 140

Pro Ser Val Phe Pro Leu Ala Pro Cys Cys Gly Asp Thr Pro Ser Ser
145                 150                 155                 160

Thr Val Thr Leu Gly Cys Leu Val Lys Gly Tyr Leu Pro Glu Pro Val
                165                 170                 175

Thr Val Thr Trp Asn Ser Gly Thr Leu Thr Asn Gly Val Arg Thr Phe
            180                 185                 190

Pro Ser Val Arg Gln Ser Ser Gly Leu Tyr Ser Leu Ser Ser Val Val
        195                 200                 205

Ser Val Thr Ser Ser Ser Gln Pro Val Thr Cys Asn Val Ala His Pro
    210                 215                 220

Ala Thr Asn Thr Lys Val Asp Lys Thr Val Ala Pro Ser Thr Cys Ser
225                 230                 235                 240

Lys Pro Met Cys Pro Pro Pro Glu Leu Pro Gly Gly Pro Ser Val Phe
                245                 250                 255

Ile Phe Pro Pro Lys Pro Lys Asp Thr Leu Met Ile Ser Arg Thr Pro
            260                 265                 270

Glu Val Thr Cys Val Val Val Asp Val Ser Gln Asp Asp Pro Glu Val
        275                 280                 285

Gln Phe Thr Trp Tyr Ile Asn Asn Glu Gln Val Arg Thr Ala Arg Pro
    290                 295                 300

Pro Leu Arg Glu Gln Gln Phe Asn Ser Thr Ile Arg Val Val Ser Thr
305                 310                 315                 320

Leu Pro Ile Ala His Gln Asp Trp Leu Arg Gly Lys Glu Phe Lys Cys
                325                 330                 335

Lys Val His Asn Lys Ala Leu Pro Ala Pro Ile Glu Lys Thr Ile Ser
            340                 345                 350

Lys Ala Arg Gly Gln Pro Leu Glu Pro Lys Val Tyr Thr Met Gly Pro
        355                 360                 365

Pro Arg Glu Glu Leu Ser Ser Arg Ser Val Ser Leu Thr Cys Met Ile
    370                 375                 380

Asn Gly Phe Tyr Pro Ser Asp Ile Ser Val Glu Trp Glu Lys Asn Gly
385                 390                 395                 400

Lys Ala Glu Asp Asn Tyr Lys Thr Thr Pro Thr Val Leu Asp Ser Asp
                405                 410                 415

Gly Ser Tyr Phe Leu Tyr Ser Lys Leu Ser Val Pro Thr Ser Glu Trp
            420                 425                 430

Gln Arg Gly Asp Val Phe Thr Cys Ser Val Met His Glu Ala Leu His
        435                 440                 445
```

-continued

```
Asn His Tyr Thr Gln Lys Ser Ile Ser Arg Ser Pro Gly Lys
    450                 455                 460


<210> SEQ ID NO 22
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Asp Thr Arg Ala Pro Thr Gln Leu Leu Gly Leu Leu Leu Leu Trp
1               5                   10                  15

Leu Pro Gly Ala Arg Cys Ala Ala Asp Met Thr Gln Thr Pro Ser Ser
            20                  25                  30

Val Ser Pro Thr Val Gly Gly Thr Val Thr Ile Asn Cys Gln Ser Ser
        35                  40                  45

Pro Ser Val Trp Asn Asn Tyr Leu Ser Trp Phe Gln Gln Lys Pro Gly
    50                  55                  60

Gln Pro Pro Lys Leu Leu Ile Tyr Gly Ala Ser Thr Leu Ala Ser Gly
65                  70                  75                  80

Val Pro Ser Arg Phe Gln Gly Ser Gly Ser Gly Thr Gln Phe Thr Leu
                85                  90                  95

Thr Ile Ser Asp Val Gln Cys Asp Asp Ala Ala Thr Tyr Tyr Cys Ala
            100                 105                 110

Gly Gly Tyr Arg Ser Tyr Thr Asp Thr Phe Val Phe Gly Gly Gly Thr
        115                 120                 125

Glu Val Val Val Lys Gly Asp Pro Val Ala Pro Thr Val Leu Ile Phe
    130                 135                 140

Pro Pro Ala Ala Asp Gln Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235


<210> SEQ ID NO 23
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Gly Leu Val Gln Pro
            20                  25                  30

Glu Gly Ser Leu Thr Leu Thr Cys Thr Ala Ser Gly Phe Ser Phe Thr
        35                  40                  45
```

-continued

```
Met Tyr Gly Ile Ile Trp Val Arg Gln Ala Pro Gly Lys Gly Leu Glu
    50                  55                  60

Trp Ile Ala Cys Ile Asp Ala Gly Arg Ser Gly Ser Thr Tyr Tyr Ala
65                  70                  75                  80

Ser Trp Ala Lys Gly Arg Phe Thr Ile Ser Lys Thr Ser Ser Thr Thr
                85                  90                  95

Val Thr Leu Gln Met Thr Ser Leu Thr Ala Ala Asp Thr Ala Thr Tyr
            100                 105                 110

Phe Cys Ala Arg Gly Gly Ala Gly Phe Thr Leu Trp Gly Pro Gly Thr
        115                 120                 125

Leu Val Thr Val Ser Ser Gly Gln Pro Lys Ala Pro Ser Val Phe Pro
    130                 135                 140

Leu Ala Pro Cys Cys Gly Asp Thr Pro Ser Ser Thr Val Thr Leu Gly
145                 150                 155                 160

Cys Leu Val Lys Gly Tyr Leu Pro Glu Pro Val Thr Val Thr Trp Asn
                165                 170                 175

Ser Gly Thr Leu Thr Asn Gly Val Arg Thr Phe Pro Ser Val Arg Gln
            180                 185                 190

Ser Ser Gly Leu Tyr Ser Leu Ser Ser Val Val Ser Val Thr Ser Ser
        195                 200                 205

Ser Gln Pro Val Thr Cys Asn Val Ala His Pro Ala Thr Asn Thr Lys
    210                 215                 220

Val Asp Lys Thr Val Ala Pro Ser Thr Cys Ser Lys Pro Met Cys Pro
225                 230                 235                 240

Pro Pro Glu Leu Pro Gly Gly Pro Ser Val Phe Ile Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Asp Asp Pro Glu Val Gln Phe Thr Trp Tyr
        275                 280                 285

Ile Asn Asn Glu Gln Val Arg Thr Ala Arg Pro Pro Leu Arg Glu Gln
    290                 295                 300

Gln Phe Asn Ser Thr Ile Arg Val Val Ser Thr Leu Pro Ile Ala His
305                 310                 315                 320

Gln Asp Trp Leu Arg Gly Lys Glu Phe Lys Cys Lys Val His Asn Lys
                325                 330                 335

Ala Leu Pro Ala Pro Ile Glu Lys Thr Ile Ser Lys Ala Arg Gly Gln
            340                 345                 350

Pro Leu Glu Pro Lys Val Tyr Thr Met Gly Pro Pro Arg Glu Glu Leu
        355                 360                 365

Ser Ser Arg Ser Val Ser Leu Thr Cys Met Ile Asn Gly Phe Tyr Pro
    370                 375                 380

Ser Asp Ile Ser Val Glu Trp Glu Lys Asn Gly Lys Ala Glu Asp Asn
385                 390                 395                 400

Tyr Lys Thr Thr Pro Thr Val Leu Asp Ser Asp Gly Ser Tyr Phe Leu
                405                 410                 415

Tyr Ser Lys Leu Ser Val Pro Thr Ser Glu Trp Gln Arg Gly Asp Val
            420                 425                 430

Phe Thr Cys Ser Val Met His Glu Ala Leu His Asn His Tyr Thr Gln
        435                 440                 445

Lys Ser Ile Ser Arg Ser Pro Gly Lys
    450                 455
```

<210> SEQ ID NO 24
<211> LENGTH: 238
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Met Asp Thr Arg Ala Pro Thr Gln Leu Leu Gly Leu Leu Leu Leu Trp
1               5                   10                  15

Leu Pro Gly Ala Thr Phe Ala Ile Val Met Thr Gln Thr Pro Ala Ser
            20                  25                  30

Val Ser Ala Ala Val Gly Gly Thr Val Ser Ile Ser Cys Gln Ser Ser
        35                  40                  45

Glu Ser Val Tyr Lys Asn Asn Tyr Leu Ser Trp Tyr Gln Gln Lys Pro
    50                  55                  60

Gly Gln Pro Pro Lys Arg Leu Ile Tyr Asp Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Val Val Cys Asp Asp Ala Ala Thr Tyr Tyr Cys
            100                 105                 110

Ala Gly Tyr Lys Ser Ser Ala Thr Asp Gly Ile Ala Phe Gly Gly Gly
        115                 120                 125

Thr Glu Val Val Val Lys Gly Asp Pro Val Ala Pro Thr Val Leu Ile
    130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235
```

<210> SEQ ID NO 25
<211> LENGTH: 457
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Gln
            20                  25                  30

Pro Glu Gly Ser Leu Thr Leu Thr Cys Lys Ala Ser Gly Leu Asp Phe
        35                  40                  45

Leu Ser Asn Tyr Trp Ile Cys Trp Val Arg Gln Ala Pro Gly Lys Gly
    50                  55                  60

Leu Glu Trp Ile Ala Cys Ile Tyr Ile Asp Asp Gly Thr Thr Tyr Tyr
```

```
65                  70                  75                  80

Ala Asn Trp Ala Lys Gly Arg Phe Thr Ile Ser Arg Thr Ser Ser Thr
                85                  90                  95

Thr Val Thr Leu Gln Met Ala Ser Leu Thr Ala Ala Asp Thr Ala Thr
            100                 105                 110

Tyr Phe Cys Ala Arg Gly Asn Pro Phe Thr Leu Trp Gly Pro Gly Thr
        115                 120                 125

Leu Val Thr Val Ser Ser Gly Gln Pro Lys Ala Pro Ser Val Phe Pro
    130                 135                 140

Leu Ala Pro Cys Cys Gly Asp Thr Pro Ser Ser Thr Val Thr Leu Gly
145                 150                 155                 160

Cys Leu Val Lys Gly Tyr Leu Pro Glu Pro Val Thr Val Thr Trp Asn
                165                 170                 175

Ser Gly Thr Leu Thr Asn Gly Val Arg Thr Phe Pro Ser Val Arg Gln
            180                 185                 190

Ser Ser Gly Leu Tyr Ser Leu Ser Ser Val Val Ser Val Thr Ser Ser
        195                 200                 205

Ser Gln Pro Val Thr Cys Asn Val Ala His Pro Ala Thr Asn Thr Lys
    210                 215                 220

Val Asp Lys Thr Val Ala Pro Ser Thr Cys Ser Lys Pro Met Cys Pro
225                 230                 235                 240

Pro Pro Glu Leu Pro Gly Gly Pro Ser Val Phe Ile Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Asp Asp Pro Glu Val Gln Phe Thr Trp Tyr
        275                 280                 285

Ile Asn Asn Glu Gln Val Arg Thr Ala Arg Pro Pro Leu Arg Glu Gln
    290                 295                 300

Gln Phe Asn Ser Thr Ile Arg Val Val Ser Thr Leu Pro Ile Ala His
305                 310                 315                 320

Gln Asp Trp Leu Arg Gly Lys Glu Phe Lys Cys Lys Val His Asn Lys
                325                 330                 335

Ala Leu Pro Ala Pro Ile Glu Lys Thr Ile Ser Lys Ala Arg Gly Gln
            340                 345                 350

Pro Leu Glu Pro Lys Val Tyr Thr Met Gly Pro Pro Arg Glu Glu Leu
        355                 360                 365

Ser Ser Arg Ser Val Ser Leu Thr Cys Met Ile Asn Gly Phe Tyr Pro
    370                 375                 380

Ser Asp Ile Ser Val Glu Trp Glu Lys Asn Gly Lys Ala Glu Asp Asn
385                 390                 395                 400

Tyr Lys Thr Thr Pro Thr Val Leu Asp Ser Asp Gly Ser Tyr Phe Leu
                405                 410                 415

Tyr Ser Lys Leu Ser Val Pro Thr Ser Glu Trp Gln Arg Gly Asp Val
            420                 425                 430

Phe Thr Cys Ser Val Met His Glu Ala Leu His Asn His Tyr Thr Gln
        435                 440                 445

Lys Ser Ile Ser Arg Ser Pro Gly Lys
    450                 455

<210> SEQ ID NO 26
<211> LENGTH: 237
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 26

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
            20                  25                  30

Val Ser Ala Ala Val Gly Gly Thr Val Thr Ile Asn Cys Gln Ser Ser
        35                  40                  45

Pro Ser Val Tyr Arg Asn Tyr Leu Ser Trp Tyr Gln Gln Lys Pro Gly
    50                  55                  60

Gln Arg Pro Lys Leu Leu Ile Tyr His Ala Ser Thr Leu Ala Ser Gly
65                  70                  75                  80

Val Pro Ser Arg Phe Ser Ala Ser Gly Ser Gly Thr Gln Phe Ser Leu
                85                  90                  95

Thr Ile Ser Asp Ala His Cys Asp Asp Ala Ala Thr Tyr Tyr Cys Ala
            100                 105                 110

Gly Gly Tyr Ile Gly Ser Ser Asp Ala Trp Ala Phe Gly Gly Gly Thr
        115                 120                 125

Glu Val Val Val Arg Gly Asp Pro Val Ala Pro Thr Val Leu Ile Phe
    130                 135                 140

Pro Pro Ala Ala Asp Gln Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235
```

<210> SEQ ID NO 27
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Met Glu Thr Gly Leu Arg Trp Leu Leu Leu Val Ala Val Leu Lys Gly
1               5                   10                  15

Val Gln Cys Gln Glu Gln Leu Lys Glu Ser Gly Gly Asp Leu Val Thr
            20                  25                  30

Pro Gly Thr Pro Leu Thr Leu Thr Cys Thr Val Ser Gly Phe Ser Leu
        35                  40                  45

Ser Ser Ser Tyr Met Ser Trp Val Arg Gln Ala Pro Gly Lys Gly Leu
    50                  55                  60

Glu Trp Ile Gly Ile Ile Phe Ala Ser Gly Ser Thr Tyr Tyr Ala Thr
65                  70                  75                  80

Trp Ala Lys Gly Arg Phe Thr Ile Ser Arg Thr Ser Thr Thr Val Asp
                85                  90                  95
```

-continued

```
Leu Lys Met Thr Ser Leu Thr Thr Glu Asp Thr Ala Thr Tyr Phe Cys
            100                 105                 110

Ala Arg Asn Ser Pro Gly Tyr Gly Ser Asp Ile Trp Gly Pro Gly Thr
        115                 120                 125

Leu Val Thr Val Ser Leu Gly Gln Pro Lys Ala Pro Ser Val Phe Pro
    130                 135                 140

Leu Ala Pro Cys Cys Gly Asp Thr Pro Ser Ser Thr Val Thr Leu Gly
145                 150                 155                 160

Cys Leu Val Lys Gly Tyr Leu Pro Glu Pro Val Thr Val Thr Trp Asn
                165                 170                 175

Ser Gly Thr Leu Thr Asn Gly Val Arg Thr Phe Pro Ser Val Arg Gln
            180                 185                 190

Ser Ser Gly Leu Tyr Ser Leu Ser Ser Val Val Ser Val Thr Ser Ser
        195                 200                 205

Ser Gln Pro Val Thr Cys Asn Val Ala His Pro Ala Thr Asn Thr Lys
    210                 215                 220

Val Asp Lys Thr Val Ala Pro Ser Thr Cys Ser Lys Pro Met Cys Pro
225                 230                 235                 240

Pro Pro Glu Leu Pro Gly Gly Pro Ser Val Phe Ile Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Asp Asp Pro Glu Val Gln Phe Thr Trp Tyr
        275                 280                 285

Ile Asn Asn Glu Gln Val Arg Thr Ala Arg Pro Pro Leu Arg Glu Gln
    290                 295                 300

Gln Phe Asn Ser Thr Ile Arg Val Val Ser Thr Leu Pro Ile Ala His
305                 310                 315                 320

Gln Asp Trp Leu Arg Gly Lys Glu Phe Lys Cys Lys Val His Asn Lys
                325                 330                 335

Ala Leu Pro Ala Pro Ile Glu Lys Thr Ile Ser Lys Ala Arg Gly Gln
            340                 345                 350

Pro Leu Glu Pro Lys Val Tyr Thr Met Gly Pro Pro Arg Glu Glu Leu
        355                 360                 365

Ser Ser Arg Ser Val Ser Leu Thr Cys Met Ile Asn Gly Phe Tyr Pro
    370                 375                 380

Ser Asp Ile Ser Val Glu Trp Glu Lys Asn Gly Lys Ala Glu Asp Asn
385                 390                 395                 400

Tyr Lys Thr Thr Pro Thr Val Leu Asp Ser Asp Gly Ser Tyr Phe Leu
                405                 410                 415

Tyr Ser Lys Leu Ser Val Pro Thr Ser Glu Trp Gln Arg Gly Asp Val
            420                 425                 430

Phe Thr Cys Ser Val Met His Glu Ala Leu His Asn His Tyr Thr Gln
        435                 440                 445

Lys Ser Ile Ser Arg Ser Pro Gly Lys
    450                 455
```

<210> SEQ ID NO 28
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Asp Thr Arg Ala Pro Thr Gln Leu Leu Gly Leu Leu Leu Leu Trp
1 5 10 15

Leu Pro Gly Ala Thr Phe Ala Gln Val Leu Thr Gln Thr Pro Ser Ser
20 25 30

Val Ser Ala Ala Val Gly Gly Thr Val Thr Ile Asn Cys Gln Ser Ser
35 40 45

Gln Ser Val Tyr Ala Asn Asn His Leu Ser Trp Tyr Gln Gln Lys Pro
50 55 60

Gly Gln Pro Pro Lys Leu Leu Val Tyr Arg Ala Ser Asn Leu Glu Thr
65 70 75 80

Gly Val Pro Ser Arg Phe Ser Gly Ser Gly Ser Gly Thr Gln Phe Ser
85 90 95

Leu Thr Ile Ser Gly Val Gln Cys Asp Asp Ala Ala Ala Tyr Tyr Cys
100 105 110

Gly Gly Asp Val Ser Ala Ser Thr Gly Gly Phe Gly Gly Gly Thr Glu
115 120 125

Val Val Val Lys Gly Asp Pro Val Ala Pro Thr Val Leu Ile Phe Pro
130 135 140

Pro Ala Ala Asp Gln Val Ala Thr Gly Thr Val Thr Ile Val Cys Val
145 150 155 160

Ala Asn Lys Tyr Phe Pro Asp Val Thr Val Thr Trp Glu Val Asp Gly
165 170 175

Thr Thr Gln Thr Thr Gly Ile Glu Asn Ser Lys Thr Pro Gln Asn Ser
180 185 190

Ala Asp Cys Thr Tyr Asn Leu Ser Ser Thr Leu Thr Leu Thr Ser Thr
195 200 205

Gln Tyr Asn Ser His Lys Glu Tyr Thr Cys Lys Val Thr Gln Gly Thr
210 215 220

Thr Ser Val Val Gln Ser Phe Asn Arg Gly Asp Cys
225 230 235

<210> SEQ ID NO 29
<211> LENGTH: 463
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Met Glu Thr Gly Leu Arg Trp Leu Leu Leu Val Ala Val Leu Lys Gly
1 5 10 15

Val Gln Cys Gln Ser Leu Glu Glu Ser Gly Gly Asp Leu Val Lys Pro
20 25 30

Gly Ala Ser Leu Thr Leu Thr Cys Lys Ala Ser Gly Phe Asp Leu Ser
35 40 45

Ser Ser Tyr Phe Met Cys Trp Val Arg Gln Ala Pro Gly Arg Gly Leu
50 55 60

Glu Trp Ile Ala Cys Ile Asp Thr Arg Asn Ile Asp Thr Ala Tyr Ala
65 70 75 80

Thr Trp Ala Lys Gly Arg Phe Thr Ile Ser Lys Thr Ser Ser Thr Thr
85 90 95

Val Thr Leu Gln Met Thr Ser Leu Thr Ala Ala Asp Thr Ala Lys Tyr
100 105 110

```
Phe Cys Gly Arg Gly Gly Asn Ile Asn Gly Leu Ala Thr Gly Phe Ala
        115                 120                 125

Leu Trp Gly Pro Gly Thr Leu Val Thr Val Ser Ser Gly Gln Pro Lys
    130                 135                 140

Ala Pro Ser Val Phe Pro Leu Ala Pro Cys Cys Gly Asp Thr Pro Ser
145                 150                 155                 160

Ser Thr Val Thr Leu Gly Cys Leu Val Lys Gly Tyr Leu Pro Glu Pro
                165                 170                 175

Val Thr Val Thr Trp Asn Ser Gly Thr Leu Thr Asn Gly Val Arg Thr
            180                 185                 190

Phe Pro Ser Val Arg Gln Ser Ser Gly Leu Tyr Ser Leu Ser Ser Val
        195                 200                 205

Val Ser Val Thr Ser Ser Ser Gln Pro Val Thr Cys Asn Val Ala His
    210                 215                 220

Pro Ala Thr Asn Thr Lys Val Asp Lys Thr Val Ala Pro Ser Thr Cys
225                 230                 235                 240

Ser Lys Pro Met Cys Pro Pro Pro Glu Leu Pro Gly Gly Pro Ser Val
                245                 250                 255

Phe Ile Phe Pro Pro Lys Pro Lys Asp Thr Leu Met Ile Ser Arg Thr
            260                 265                 270

Pro Glu Val Thr Cys Val Val Val Asp Val Ser Gln Asp Asp Pro Glu
        275                 280                 285

Val Gln Phe Thr Trp Tyr Ile Asn Asn Glu Gln Val Arg Thr Ala Arg
    290                 295                 300

Pro Pro Leu Arg Glu Gln Gln Phe Asn Ser Thr Ile Arg Val Val Ser
305                 310                 315                 320

Thr Leu Pro Ile Ala His Gln Asp Trp Leu Arg Gly Lys Glu Phe Lys
                325                 330                 335

Cys Lys Val His Asn Lys Ala Leu Pro Ala Pro Ile Glu Lys Thr Ile
            340                 345                 350

Ser Lys Ala Arg Gly Gln Pro Leu Glu Pro Lys Val Tyr Thr Met Gly
        355                 360                 365

Pro Pro Arg Glu Glu Leu Ser Ser Arg Ser Val Ser Leu Thr Cys Met
    370                 375                 380

Ile Asn Gly Phe Tyr Pro Ser Asp Ile Ser Val Glu Trp Glu Lys Asn
385                 390                 395                 400

Gly Lys Ala Glu Asp Asn Tyr Lys Thr Thr Pro Thr Val Leu Asp Ser
                405                 410                 415

Asp Gly Ser Tyr Phe Leu Tyr Ser Lys Leu Ser Val Pro Thr Ser Glu
            420                 425                 430

Trp Gln Arg Gly Asp Val Phe Thr Cys Ser Val Met His Glu Ala Leu
        435                 440                 445

His Asn His Tyr Thr Gln Lys Ser Ile Ser Arg Ser Pro Gly Lys
    450                 455                 460
```

<210> SEQ ID NO 30
<211> LENGTH: 238
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Met Asp Thr Arg Ala Pro Thr Gln Leu Leu Gly Leu Leu Leu Leu Trp
1               5                   10                  15
```

```
Leu Pro Gly Ala Thr Phe Ala Ala Val Leu Thr Gln Thr Pro Ser Pro
            20                  25                  30

Val Ser Ala Ala Val Gly Gly Thr Val Thr Ile Ser Cys Gln Ala Ser
        35                  40                  45

Gln Ser Val Tyr Asn Asn Asn Trp Leu Ala Trp Tyr Gln Gln Lys Pro
    50                  55                  60

Gly Gln Pro Pro Lys Leu Leu Ile Tyr Trp Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Gln Gly Gly Tyr Phe Arg Arg Val Asp Ser Phe Pro Phe Gly Gly Gly
        115                 120                 125

Thr Glu Val Val Val Lys Gly Asp Pro Val Ala Pro Thr Val Leu Ile
    130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235


<210> SEQ ID NO 31
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Lys Ala Ser Gly Phe Asp Leu Ser
        35                  40                  45

Ser Ser Tyr Phe Met Cys Trp Val Arg Gln Ala Pro Gly Arg Gly Leu
    50                  55                  60

Glu Trp Ile Ala Cys Ile Asp Thr Arg Asn Ile Asp Thr Ala Tyr Ala
65                  70                  75                  80

Ser Trp Ala Lys Gly Arg Phe Thr Ile Ser Lys Thr Ser Ser Thr Thr
                85                  90                  95

Val Thr Leu Gln Met Thr Ser Leu Thr Ala Ala Asp Thr Ala Arg Tyr
            100                 105                 110

Phe Cys Gly Arg Gly Gly Asn Ile Asn Gly Leu Ala Thr Gly Phe Asn
        115                 120                 125

Leu Trp Gly Pro Gly Thr Leu Val Thr Val Ser Ser Gly Gln Pro Lys
```

-continued

```
    130                 135                 140

Ala Pro Ser Val Phe Pro Leu Ala Pro Cys Cys Gly Asp Thr Pro Ser
145                 150                 155                 160

Ser Thr Val Thr Leu Gly Cys Leu Val Lys Gly Tyr Leu Pro Glu Pro
                165                 170                 175

Val Thr Val Thr Trp Asn Ser Gly Thr Leu Thr Asn Gly Val Arg Thr
            180                 185                 190

Phe Pro Ser Val Arg Gln Ser Ser Gly Leu Tyr Ser Leu Ser Ser Val
        195                 200                 205

Val Ser Val Thr Ser Ser Ser Gln Pro Val Thr Cys Asn Val Ala His
    210                 215                 220

Pro Ala Thr Asn Thr Lys Val Asp Lys Thr Val Ala Pro Ser Thr Cys
225                 230                 235                 240

Ser Lys Pro Met Cys Pro Pro Pro Glu Leu Pro Gly Gly Pro Ser Val
                245                 250                 255

Phe Ile Phe Pro Pro Lys Pro Lys Asp Thr Leu Met Ile Ser Arg Thr
            260                 265                 270

Pro Glu Val Thr Cys Val Val Val Asp Val Ser Gln Asp Asp Pro Glu
        275                 280                 285

Val Gln Phe Thr Trp Tyr Ile Asn Asn Glu Gln Val Arg Thr Ala Arg
    290                 295                 300

Pro Pro Leu Arg Glu Gln Gln Phe Asn Ser Thr Ile Arg Val Val Ser
305                 310                 315                 320

Thr Leu Pro Ile Ala His Gln Asp Trp Leu Arg Gly Lys Glu Phe Lys
                325                 330                 335

Cys Lys Val His Asn Lys Ala Leu Pro Ala Pro Ile Glu Lys Thr Ile
            340                 345                 350

Ser Lys Ala Arg Gly Gln Pro Leu Glu Pro Lys Val Tyr Thr Met Gly
        355                 360                 365

Pro Pro Arg Glu Glu Leu Ser Ser Arg Ser Val Ser Leu Thr Cys Met
    370                 375                 380

Ile Asn Gly Phe Tyr Pro Ser Asp Ile Ser Val Glu Trp Glu Lys Asn
385                 390                 395                 400

Gly Lys Ala Glu Asp Asn Tyr Lys Thr Thr Pro Thr Val Leu Asp Ser
                405                 410                 415

Asp Gly Ser Tyr Phe Leu Tyr Ser Lys Leu Ser Val Pro Thr Ser Glu
            420                 425                 430

Trp Gln Arg Gly Asp Val Phe Thr Cys Ser Val Met His Glu Ala Leu
        435                 440                 445

His Asn His Tyr Thr Gln Lys Ser Ile Ser Arg Ser Pro Gly Lys
    450                 455                 460


<210> SEQ ID NO 32
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Asp Thr Arg Ala Pro Thr Gln Leu Leu Gly Leu Leu Leu Leu Trp
1               5                   10                  15

Leu Pro Gly Ala Thr Phe Ala Val Val Leu Thr Gln Thr Pro Ser Pro
            20                  25                  30
```

```
Val Ser Ala Ala Val Gly Gly Thr Val Thr Ile Ser Cys Gln Ala Ser
        35                  40                  45

Gln Ser Val Tyr Asn Asn Asp Trp Leu Ala Trp Tyr Gln Gln Lys Pro
    50                  55                  60

Gly Gln Pro Pro Lys Leu Leu Ile Tyr Trp Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Gln Gly Gly Tyr Phe Arg Arg Val Asp Ser Phe Pro Phe Gly Gly Gly
        115                 120                 125

Thr Glu Val Val Val Lys Gly Asp Pro Val Ala Pro Thr Val Leu Ile
    130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235


<210> SEQ ID NO 33
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Pro Thr Tyr Met Ile Trp Val Arg Gln Ala Pro Gly Lys Gly Leu Glu
    50                  55                  60

Trp Ile Gly Val Ile Tyr Pro Asn Gly Ile Pro Tyr Tyr Ala Thr Trp
65                  70                  75                  80

Ala Lys Gly Arg Phe Thr Ile Ser Lys Thr Ser Thr Thr Val Asp Leu
                85                  90                  95

Arg Ile Thr Ser Pro Thr Thr Glu Asp Thr Ala Thr Tyr Phe Cys Gly
            100                 105                 110

Arg Asn Ser Pro Gly Trp Gly Thr Asp Met Trp Gly Pro Gly Thr Leu
        115                 120                 125

Val Thr Val Ser Phe Gly Gln Pro Lys Ala Pro Ser Val Phe Pro Leu
    130                 135                 140

Ala Pro Cys Cys Gly Asp Thr Pro Ser Ser Thr Val Thr Leu Gly Cys
145                 150                 155                 160
```

-continued

```
Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Met Cys Pro Pro
225                 230                 235                 240

Pro Glu Leu Pro Gly Gly Pro Ser Val Phe Ile Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Asp Asp Pro Glu Val Gln Phe Thr Trp Tyr Ile
        275                 280                 285

Asn Asn Glu Gln Val Arg Thr Ala Arg Pro Pro Leu Arg Glu Gln Gln
    290                 295                 300

Phe Asn Ser Thr Ile Arg Val Val Ser Thr Leu Pro Ile Ala His Gln
305                 310                 315                 320

Asp Trp Leu Arg Gly Lys Glu Phe Lys Cys Lys Val His Asn Lys Ala
                325                 330                 335

Leu Pro Ala Pro Ile Glu Lys Thr Ile Ser Lys Ala Arg Gly Gln Pro
            340                 345                 350

Leu Glu Pro Lys Val Tyr Thr Met Gly Pro Pro Arg Glu Glu Leu Ser
        355                 360                 365

Ser Arg Ser Val Ser Leu Thr Cys Met Ile Asn Gly Phe Tyr Pro Ser
    370                 375                 380

Asp Ile Ser Val Glu Trp Glu Lys Asn Gly Lys Ala Glu Asp Asn Tyr
385                 390                 395                 400

Lys Thr Thr Pro Thr Val Leu Asp Ser Asp Gly Ser Tyr Phe Leu Tyr
                405                 410                 415

Ser Lys Leu Ser Val Pro Thr Ser Glu Trp Gln Arg Gly Asp Val Phe
            420                 425                 430

Thr Cys Ser Val Met His Glu Ala Leu His Asn His Tyr Thr Gln Lys
        435                 440                 445

Ser Ile Ser Arg Ser Pro Gly Lys
    450                 455


<210> SEQ ID NO 34
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Asp Thr Arg Ala Pro Thr Gln Leu Leu Gly Leu Leu Leu Leu Trp
1               5                   10                  15

Leu Pro Gly Ala Ile Cys Asp Pro Val Leu Thr Gln Thr Pro Ser Ser
            20                  25                  30

Val Ser Ala Val Val Gly Gly Thr Val Thr Ile Asn Cys Gln Ala Ser
        35                  40                  45

Gln Ser Val Tyr Asn Asn Asn His Leu Ser Trp Tyr Gln Gln Lys Ala
```

-continued

```
    50                  55                  60

Gly Gln Pro Pro Asn Leu Leu Ile Tyr Lys Ile Ser Thr Leu Ala Ser
65                  70                  75                  80

Gly Val Pro Ser Arg Phe Ser Gly Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Gly Gly Asp Phe Gly Val Asp Val Ala Ser Tyr Gly Gly Gly Thr Glu
        115                 120                 125

Val Val Val Lys Gly Asp Pro Val Ala Pro Thr Val Leu Ile Phe Pro
    130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235


<210> SEQ ID NO 35
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Glu Thr Gly Leu Arg Trp Leu Leu Leu Val Ala Val Leu Lys Asp
1               5                   10                  15

Ile Gln Cys Gln Glu Gln Leu Val Glu Ser Gly Gly Gly Leu Val Gln
            20                  25                  30

Pro Glu Gly Ser Leu Thr Leu Thr Cys Thr Ala Ser Gly Phe Ser Phe
        35                  40                  45

Ser Ser Ser His Trp Ile Cys Trp Val Arg Gln Ala Pro Gly Lys Gly
    50                  55                  60

Leu Glu Trp Ile Gly Cys Ile Tyr Ile Gly Asn Gly Arg Thr Tyr Tyr
65                  70                  75                  80

Ala Ser Trp Ala Lys Gly Arg Phe Thr Ile Ser Lys Thr Ser Ser Thr
                85                  90                  95

Thr Met Thr Leu Gln Ile Ser Ser Leu Thr Asp Ala Asp Thr Ala Thr
            100                 105                 110

Tyr Phe Ser Val Arg Asp Pro Thr Ala Gly Trp Gly Gly Gly Leu Trp
        115                 120                 125

Gly Pro Gly Thr Leu Val Thr Val Ser Ser Gly Gln Pro Lys Ala Pro
    130                 135                 140

Ser Val Phe Pro Leu Ala Pro Cys Cys Gly Asp Thr Pro Ser Ser Thr
145                 150                 155                 160

Val Thr Leu Gly Cys Leu Val Lys Gly Tyr Leu Pro Glu Pro Val Thr
                165                 170                 175
```

-continued

```
Val Thr Trp Asn Ser Gly Thr Leu Thr Asn Gly Val Arg Thr Phe Pro
            180                 185                 190

Ser Val Arg Gln Ser Ser Gly Leu Tyr Ser Leu Ser Ser Val Val Ser
        195                 200                 205

Val Thr Ser Ser Ser Gln Pro Val Thr Cys Asn Val Ala His Pro Ala
    210                 215                 220

Thr Asn Thr Lys Val Asp Lys Thr Val Ala Pro Ser Thr Cys Ser Lys
225                 230                 235                 240

Pro Met Cys Pro Pro Pro Glu Leu Pro Gly Gly Pro Ser Val Phe Ile
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Asp Asp Pro Glu Val Gln
        275                 280                 285

Phe Thr Trp Tyr Ile Asn Asn Glu Gln Val Arg Thr Ala Arg Pro Pro
    290                 295                 300

Leu Arg Glu Gln Gln Phe Asn Ser Thr Ile Arg Val Val Ser Thr Leu
305                 310                 315                 320

Pro Ile Ala His Gln Asp Trp Leu Arg Gly Lys Glu Phe Lys Cys Lys
                325                 330                 335

Val His Asn Lys Ala Leu Pro Ala Pro Ile Glu Lys Thr Ile Ser Lys
            340                 345                 350

Ala Arg Gly Gln Pro Leu Glu Pro Lys Val Tyr Thr Met Gly Pro Pro
        355                 360                 365

Arg Glu Glu Leu Ser Ser Arg Ser Val Ser Leu Thr Cys Met Ile Asn
    370                 375                 380

Gly Phe Tyr Pro Ser Asp Ile Ser Val Glu Trp Glu Lys Asn Gly Lys
385                 390                 395                 400

Ala Glu Asp Asn Tyr Lys Thr Thr Pro Thr Val Leu Asp Ser Asp Gly
                405                 410                 415

Ser Tyr Phe Leu Tyr Ser Lys Leu Ser Val Pro Thr Ser Glu Trp Gln
            420                 425                 430

Arg Gly Asp Val Phe Thr Cys Ser Val Met His Glu Ala Leu His Asn
        435                 440                 445

His Tyr Thr Gln Lys Ser Ile Ser Arg Ser Pro Gly Lys
    450                 455                 460


<210> SEQ ID NO 36
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Asp Thr Arg Ala Pro Thr Gln Leu Leu Gly Leu Leu Leu Leu Trp
1               5                   10                  15

Leu Pro Gly Ala Ile Cys Asp Pro Val Met Thr Gln Thr Pro Ser Ser
            20                  25                  30

Thr Ser Ala Ala Val Gly Gly Thr Val Thr Ile Ser Cys Gln Ser Ser
        35                  40                  45

Gln Ser Val Tyr Asn Asn Asn Tyr Leu Ala Trp Tyr Gln Gln Lys Pro
    50                  55                  60

Gly Gln Pro Pro Lys Arg Leu Ile Tyr Glu Ala Ser Ser Leu Ala Ser
65                  70                  75                  80
```

```
Gly Val Pro Ser Arg Phe Lys Gly Ser Gly Ser Gly Ala Gln Phe Ala
                85                  90                  95

Leu Thr Ile Ser Gly Val Gln Cys Asp Asp Ala Ala Thr Tyr Tyr Cys
            100                 105                 110

Leu Gly Ala Tyr Tyr Thr Thr Leu Val Phe Gly Gly Gly Thr Glu Val
        115                 120                 125

Val Val Arg Gly Asp Pro Val Ala Pro Thr Val Leu Ile Phe Pro Pro
    130                 135                 140

Ala Ala Asp Gln Val Ala Thr Gly Thr Val Thr Ile Val Cys Val Ala
145                 150                 155                 160

Asn Lys Tyr Phe Pro Asp Val Thr Val Thr Trp Glu Val Asp Gly Thr
                165                 170                 175

Thr Gln Thr Thr Gly Ile Glu Asn Ser Lys Thr Pro Gln Asn Ser Ala
            180                 185                 190

Asp Cys Thr Tyr Asn Leu Ser Ser Thr Leu Thr Leu Thr Ser Thr Gln
        195                 200                 205

Tyr Asn Ser His Lys Glu Tyr Thr Cys Lys Val Thr Gln Gly Thr Thr
    210                 215                 220

Ser Val Val Gln Ser Phe Asn Arg Gly Asp Cys
225                 230                 235


<210> SEQ ID NO 37
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Phe Ser Ser
1


<210> SEQ ID NO 38
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Phe Asn Ser
1


<210> SEQ ID NO 39
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Met Tyr
1


<210> SEQ ID NO 40
<211> LENGTH: 3
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 40

Phe Leu Ser
1

<210> SEQ ID NO 41
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Gly Tyr
1

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Val Ala Cys Ile Glu Pro Ser Thr Val Ser
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Ala Cys Ile Asp Thr Gly Thr Ala Asp
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Cys Ile Asp Ala Gly Arg Ser Gly Ser Thr
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ile Ala Cys Ile Tyr Ile Asp Asp Gly Thr
1               5                   10

```
<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Ile Asp Arg Gly Ser Tyr Gly Thr Thr
1               5                   10


<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ile Ala Cys Ile Tyr His Phe Ser Gly Arg
1               5                   10


<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Phe Cys Ala Thr Ser Tyr Ser Tyr
1               5


<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Phe Cys Ser Arg Asp Leu Gly Gly
1               5


<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Cys Ala Arg Gly Gly Ala Gly Phe
1               5


<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51
```

Phe Cys Ala Arg Gly Asn Pro Phe
1 5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Cys Val Arg Gly Gly Ala Gly Phe
1 5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Phe Cys Ala Arg Asp Gly Ile Gly
1 5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Val Tyr Asn Asn Asn Glu Leu Ser
1 5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Val Trp Asn Asn Tyr Leu Ser Trp
1 5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Val Tyr Lys Asn Asn Tyr Leu Ser
1 5

<210> SEQ ID NO 57
<211> LENGTH: 8
<212> TYPE: PRT
<213> ORGANISM: Artificial Sequence -continued
<220> FEATURE:
<223> OTHER INFORMATION: Description of Artificial Sequence: Synthetic
peptide

<400> SEQUENCE: 57

Val Tyr Arg Asn Tyr Leu Ser Trp
1 5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Val Tyr Asn Asn Tyr Leu Ser Trp
1 5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 59

Leu Tyr Asn Tyr Asn Gln Leu Ser
1 5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Ile Tyr Leu Ala Ser Asn Leu Ala
1 5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Tyr Gly Ala Ser Thr Leu Ala Ser
1 5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Ile Tyr Asp Ala Ser Thr Leu Ala
1 5

-continued

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Tyr His Ala Ser Thr Leu Ala Ser
1 5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Tyr Asp Thr Ser Thr Leu Ala Ser
1 5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Ile Tyr Ser Ala Ser Thr Leu Ala
1 5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Gly Gly Trp Ser Ser Ser Ser Asp
1 5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Gly Tyr Arg Ser Tyr Thr Asp Thr
1 5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Gly Tyr Lys Ser Ser Ala Thr Asp
1 5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Gly Tyr Ile Gly Ser Ser Asp Ala
1 5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Tyr Lys Ser Ser Thr Thr Asp Gly
1 5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Gly Thr Tyr Ile Thr Ser His Asn
1 5

<210> SEQ ID NO 72
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Ser Asn Asn
1

<210> SEQ ID NO 73
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Ser Ser Arg
1

<210> SEQ ID NO 74
<211> LENGTH: 10
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 74

Ile Ala Cys Ile Tyr Gly Gly Ser Ser Gly
1 5 10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 75

Ile Ala Cys Ile Tyr Gly Gly Ala Ser Gly
1 5 10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 76

Ile Ala Cys Ile Tyr Leu Ser Ser Gly Ser
1 5 10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 77

Ser Ala Cys Ile Asp Thr Gly Ser Gly Ser
1 5 10

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Ala Cys Ile Asn Thr Gly Val Tyr Asp Thr
1 5 10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Ala Cys Ile Tyr Thr Gly Val Gly Ser Thr
1 5 10

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Tyr Phe Cys Met Arg Gly Ala Asn
1 5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Tyr Phe Cys Ala Arg Gly Gly Phe
1 5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Tyr Phe Cys Ala Arg Glu Tyr Ser
1 5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Phe Cys Ala Arg Asp Leu Thr His
1 5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Cys Ala Arg Asp Tyr Asp Leu Trp
1 5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Val Tyr Ser Asn Tyr Leu Ser Trp
1 5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 86

Ile Asp Ser Tyr Leu Ala Trp Tyr
1 5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 87

Ile Ser Thr Ala Leu Ala Trp Tyr
1 5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Ile Tyr Asn His Asn Tyr Leu Ser
1 5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 89

Val Tyr Asn Asn Asn Phe Ser Trp
1 5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 90

Tyr Ser Ala Ser Thr Leu Ala Ser
1 5

<210> SEQ ID NO 91
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Ala Ser Thr Leu Ala Ser Gly
1               5


<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asp Ala Ser Arg Leu Ala Ser Gly
1               5


<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ile Tyr His Ala Ser Thr Leu Ala
1               5


<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Tyr Lys Pro Ser Thr Leu Ala Ser
1               5


<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Tyr Thr Tyr Thr Ser Asp Ser
1               5


<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Tyr Tyr Ser Ser Asn Pro Glu Gly
```

1 5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 97

Phe Gly Ala Ser Asn Val Asp Asn
1 5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 98

Gly Ala Tyr Ala Asn Thr Tyr Ser
1 5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 99

Ser Ser Ser Thr Asp Ser Ala Phe
1 5

<210> SEQ ID NO 100
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

Phe Ser Asp
1

<210> SEQ ID NO 101
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Ser Ser Ser
1

<210> SEQ ID NO 102
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Phe Ile Ser
1

<210> SEQ ID NO 103
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Phe Ser Ala
1

<210> SEQ ID NO 104
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Phe Ser Arg
1

<210> SEQ ID NO 105
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 105

Phe Ser Asn
1

<210> SEQ ID NO 106
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 106

Ile Ser Ser
1

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 107

```
Ile Gly Cys Ile Tyr Ile Gly Ser Ser Ser
1               5                   10
```

<210> SEQ ID NO 108

<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 108

Ala Cys Ile Asp Thr Gly Ser Ser Gly Ser
1 5 10

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 109

Ile Ala Cys Ile Tyr Ile Gly Gly His Thr
1 5 10

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 110

Val Gly Cys Ile Tyr Ile Gly Ser Gly Asn
1 5 10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 111

Ile Ala Cys Ile Tyr Ile Gly Ala Gly Ser
1 5 10

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 112

Ile Gly Cys Ile Tyr Ile Gly Asn Gly Arg
1 5 10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 113

```
Ile Gly Cys Leu Tyr Val Gly Ser Gly Arg
1               5                   10


<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ile Gly Cys Ile Tyr Ile Gly Ser Ser Gly
1               5                   10


<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ile Gly Cys Ile Tyr Ile Gly Ser Val Arg
1               5                   10


<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ile Gly Cys Ile Trp Ile Gly Gly Gly Gly
1               5                   10


<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ile Gly Cys Ile Tyr Thr Gly Ser Gly Arg
1               5                   10


<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Phe Cys Gly Arg Asp Pro Thr Ala
1               5


<210> SEQ ID NO 119
<211> LENGTH: 8
<212> TYPE: PRT
<213> ORGANISM: Artificial Sequence
<220> FEATURE:
```

<223> OTHER INFORMATION: Description of Artificial Sequence: Synthetic
peptide

<400> SEQUENCE: 119

Phe Cys Ala Arg Lys Gly Asp Gly
1 5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 120

Phe Cys Ala Arg Gly Ile Ala Gly
1 5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 121

Phe Cys Ser Arg Gly Ile Ala Gly
1 5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 122

Phe Ser Val Arg Asp Pro Thr Ala
1 5

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Tyr Phe Cys Gly Arg Asp Pro Thr
1 5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Ser Val Tyr Asn Asn Asn Tyr Leu
1 5

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Ser Ile Ser Ser Tyr Leu Asn Trp
1 5

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Ser Val Phe Arg Asn Asn Tyr Leu
1 5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Ser Val Tyr Lys Asn Asn Tyr Leu
1 5

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

Ser Leu Phe Asn Asn Asn Tyr Leu
1 5

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 129

Ser Val Tyr Asn Val Asn Tyr Leu
1 5

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 130

-continued

Asn Val Tyr Ser Asn Asn Tyr Leu
1 5

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

Ser Val Tyr Val Asn Asn Tyr Leu
1 5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Leu Ile Tyr Glu Ser Ser Lys Leu
1 5

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

Tyr Arg Ala Ser Thr Leu Ala Ser
1 5

<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 134

Leu Ile Tyr Leu Ala Ser Thr Leu
1 5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 135

Leu Ile Tyr Glu Ala Ser Lys Leu
1 5

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 136

Leu Ile Tyr Asp Ala Ser Thr Leu
1 5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 137

Leu Ile Tyr Glu Ala Ser Ser Leu
1 5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 138

Leu Ile Tyr Glu Ala Ser Arg Leu
1 5

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 139

Leu Ile Tyr Glu Thr Ser Lys Leu
1 5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 140

Leu Gly Ala Tyr Tyr Thr Thr Leu
1 5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 141

Tyr Gly Gly Tyr Ser Ile Tyr Gly
1 5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 142

Ala Gly Ala Thr Ser Ser Ile Ile
1 5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 143

Leu Gly Ala Tyr Phe Thr Thr Ile
1 5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 144

Ala Gly Ala Tyr Ser Thr Val Val
1 5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 145

Leu Gly Ala Phe Tyr Thr Thr Leu
1 5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 146

Leu Gly Ala Tyr Tyr Ser Thr Leu
1 5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 147

Ala Gly Ala Tyr Tyr Thr Thr Ile
1 5

<210> SEQ ID NO 148
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 148

Leu Ser Ser
1

<210> SEQ ID NO 149
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 149

Ser Pro Thr
1

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 150

Gly Ile Ile Phe Ala Ser Gly Ser Thr Tyr
1 5 10

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 151

Ala Cys Ile Asp Thr Arg Asn Ile Asp Thr
1 5 10

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 152

Val Ile Tyr Pro Asn Gly Ile Pro Tyr Tyr
1 5 10

<210> SEQ ID NO 153
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 153

Arg Asn Ser Pro Gly Tyr Gly Ser
1               5


<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Cys Gly Arg Gly Gly Asn Ile Asn
1               5


<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asn Ser Pro Gly Trp Gly Thr Asp
1               5


<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Val Tyr Ala Asn Asn His Leu Ser
1               5


<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Val Tyr Asn Asn Asn Trp Leu Ala
1               5


<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Val Tyr Asn Asn Asp Trp Leu Ala
1               5
```

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 159

Val Tyr Asn Asn Asn His Leu Ser
1 5

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 160

Val Tyr Arg Ala Ser Asn Leu Glu
1 5

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 161

Ile Tyr Trp Ala Ser Thr Leu Ala
1 5

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 162

Ile Tyr Lys Ile Ser Thr Leu Ala
1 5

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 163

Gly Asp Val Ser Ala Ser Thr Gly
1 5

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
peptide -continued

<400> SEQUENCE: 164

```
Gly Gly Tyr Phe Arg Arg Val Asp
1               5
```

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 165

```
Gly Asp Phe Gly Val Asp Val Ala
1               5
```